US012797450B2

(12) United States Patent
Chene et al.

(10) Patent No.: US 12,797,450 B2
(45) Date of Patent: Nov. 17, 2026

(54) ANTIGENIC PEPTIDES FOR TREATMENT OF B-CELL MALIGNANCY

(71) Applicant: ENTEROME S.A., Paris (FR)

(72) Inventors: Laurent Chene, Neuville aux Bois (FR); Francesco Strozzi, Paris (FR); Joao Gamelas Magalhaes, Corbeil-Essonnes (FR); Guillaume Kulakowski, Le Kremlin Bicetre (FR)

(73) Assignee: ENTEROME S.A., Paris (FR)

( * ) Notice: Subject to any disclaimer, the term of this patent is extended or adjusted under 35 U.S.C. 154(b) by 692 days.

(21) Appl. No.: 18/354,966

(22) Filed: Jul. 19, 2023

(65) Prior Publication Data

US 2024/0033335 A1 Feb. 1, 2024

Related U.S. Application Data

(60) Division of application No. 17/734,694, filed on May 2, 2022, now Pat. No. 11,759,508, which is a continuation of application No. PCT/EP2020/082101, filed on Nov. 13, 2020.

(30) Foreign Application Priority Data

Nov. 15, 2019 (EP) .................................... 19306475
Oct. 16, 2020 (WO) ................. PCT/EP2020/079257

(51) Int. Cl.
*A61K 39/00* (2006.01)
*A61P 35/00* (2006.01)

(52) U.S. Cl.
CPC ................. *A61K 39/001124* (2018.08); *A61K 39/001112* (2018.08); *A61K 39/001113* (2018.08); *A61K 39/001117* (2018.08); *A61K 39/001129* (2018.08); *A61P 35/00* (2018.01); *A61K 2039/55516* (2013.01); *A61K 2039/55566* (2013.01)

(58) Field of Classification Search
CPC .... A61K 39/001124; A61K 39/001112; A61K 39/001113; A61K 39/001117; A61K 39/001129; A61P 35/00
See application file for complete search history.

(56) References Cited

U.S. PATENT DOCUMENTS

2022/0323561 A1 10/2022 Chene et al.

FOREIGN PATENT DOCUMENTS

| | | | |
|---|---|---|---|
| CN | 106008695 | A | 10/2016 |
| CN | 110022893 | A | 7/2019 |
| EA | 029831 | | 5/2018 |
| EP | 2030984 | A1 | 3/2009 |
| RU | 2451521 | C2 | 5/2012 |
| WO | WO-2005007673 | A2 | 1/2005 |
| WO | 2009015843 | A1 | 2/2009 |
| WO | WO-2013040142 | A2 | 3/2013 |
| WO | WO-2017184590 | A1 | 10/2017 |
| WO | WO-2019051001 | A1 | 3/2019 |
| WO | WO-2019072871 | A2 | 4/2019 |
| WO | WO-2019197567 | A2 | 10/2019 |
| WO | WO-2020072700 | A1 | 4/2020 |

OTHER PUBLICATIONS

Office Action and Search Report from Chinese Application No. 202080083161.5 dated Apr. 27, 2025.
Extract of database GenBank: ADS74153.1, referring to SEQ ID 39 of U.S. Pat. No. 7,811,828.
Extract of data base GenBank: AOB77384.1, referring to SEQ ID 13081 of U.S. Pat. No. 9,115,368.
Extract of database GenBank AEI22253.1, referring to SEQ ID 449 of U.S. Pat. No. 7,960,534.
Extract of database GenBank AED49091.1, referring to SEQ ID 26 of U.S. Pat. No. 7,893,197.
Extract of database GenBank AKX79603.1, referring to SEQ ID 584 of U.S. Pat. No. 8,999,654.
International Search Report from corresponding PCT Application No. PCT/EP2020/082101 dated Aug. 30, 2021.
Written Opinion from corresponding PCT Application No. PCT/EP2020/082101 dated Aug. 30, 2021.
Database UniProt, "Database accession No. UniParc—UPI000197B4B6", XP002803181, Sep. 18, 2013.
Database UniProt, "Database accession No. UniParc—UPI0009BFB842", XP055810403, Dec. 5, 2018.
Office Action from corresponding U.S. Appl. No. 17/734,694 dated Jan. 30, 2023.

*Primary Examiner* — Elly-Gerald Stoica
(74) *Attorney, Agent, or Firm* — Harness, Dickey & Pierce, P.L.C.

(57) ABSTRACT

The present invention relates to antigen-based immunotherapy, in particular cancer immunotherapy. In particular, the present invention provides antigenic peptides, which are distinct from, but have amino acid similarity to, especially share the same core sequence with epitopes of human tumor antigens. The present invention further provides immunogenic compounds, nanoparticles, cells and pharmaceutical compositions comprising such antigenic peptides and nucleic acids encoding such antigenic peptides.

13 Claims, 15 Drawing Sheets

Specification includes a Sequence Listing.

CD19-B1
HHD-DR1 mice

CD22-B1
HHD-DR3 mice

C

D

ANTIGENIC PEPTIDES FOR TREATMENT OF B-CELL MALIGNANCY

This application is a divisional of U.S. application Ser. No. 17/734,694 filed on 2 May 2022, which is a continuation of International Patent Application No. PCT/EP2020/082101, which has an international filing date of 13 Nov. 2020 and claims foreign priority to International Patent Application No. PCT/EP2020/079257 filed on 16 Oct. 2020 and European Patent Application No. 19306475.5 filed on 15 Nov. 2019. Each patent application recited above is hereby incorporated by reference in its entirety.

This application contains references to amino acid sequences and/or nucleic acid sequences which have been submitted concurrently herewith as the sequence listing .xml file entitled "ST26_SL_amendment_3_Oct_2023", file size 699 KiloBytes (KB), created on 3 Oct. 2023. The aforementioned sequence listing is hereby incorporated by reference in its entirety.

The present invention relates to the field of cancer therapy, more particularly by immunotherapeutic methods. In particular, the present invention provides various peptides, which are useful in cancer immunotherapy, especially for preventing and treating B-cell malignancy.

Amongst all B-cell malignancies, such as B-cell lymphomas, non-Hodgkin's lymphoma (NHL) is the seventh leading cause of new cancer cases and accounts for approximately 3% of cancer-related deaths in the United States. Among all NHLs, diffuse large B-cell lymphoma (DLBCL) is the most common lymphoma subtype comprising 32.5% of all newly diagnosed cases, followed by follicular lymphoma (FL) with 17.1%, and mantle-cell lymphoma (MCL) representing 3-5%. Over 25,000 new cases of DLBCL are diagnosed annually in the United States, representing an incidence rate of 6.9 per 100,000. Addition of the anti-CD20 monoclonal antibody, namely rituximab, to the standard chemotherapy, R-CHOP, resulted in significant improvement in complete response (CR) rates, event-free (EFS) and overall (OS) survival in DLBCL. Unfortunately, approximately 30-40% of cases relapse or progress after R-CHOP. There are specific subgroups of patients who will have poor responses and outcomes to standard R-CHOP such as MYC-rearranged DLBCL, high-grade B-cell lymphomas with MYC, BCL2 or BCL rearrangements, activated B-cell (ABC) DLBCL that could benefit from novel approaches (Chavez et al., CAR T-cell therapy for B-cell lymphomas: clinical trial results of available products; Ther Adv Hematol. 2019).

Amongst new approaches, chimeric antigen receptor (CAR) T-cells, such as CD19-targeted CAR T-cells, represent the new standard of care for patients with DLBCL that are refractory to at least two prior lines of therapy. Two CAR T-cell products [axicabtagene ciloleucel (axi-cel) (KTE-019) and tisagenlecleucel (CTL019) have obtained US Food and Drug Administration approval for the treatment of refractory DLBCL after two lines of therapy. While this represents a significant addition to the treatment armamentarium of DLBCL, approximately 50% of cases will continue to succumb to their disease. As a result, future research must focus on identifying disease-, treatment- or patient-related factors that can help successfully predict treatment outcomes.

Tumor antigen-based vaccination thus represents a unique approach to cancer therapy that has gained considerable interest as it can enlist the patient's own immune system to recognize, attack and destroy tumors, in a specific and durable manner. Tumor cells are indeed known to express a large number of peptide antigens susceptible to be recognized by the immune system. Vaccines based on such antigens thus provide great opportunities not only to improve patient's overall survival but also for the monitoring of immune responses and the preparation of GMP-grade product thanks to the low toxicity and low molecular weight of tumor antigens. Examples of tumor antigens include, among others, by-products of proteins transcribed from normally silent genes or overexpressed genes and from proteins expressed by oncovirus (Kvistborg et al., Human cancer regression antigens. Curr Opin Immunol. 2013 April; 25(2):284-90), and neo-antigens, resulting from point mutations of cellular proteins. However, most of the tumor-associated antigens (TAAs) and tumor-specific antigens (TSAs) are (existing) human proteins and are, thus, considered as self-antigens. During thymic selection process, T cells that recognize peptide/self MHC complexes with sufficient affinity are clonally depleted. By offering a protection against auto-immune disease, this mechanism of T cell repertoire selection also reduce the possibility to develop immunity against TAAs and TSAs. This is exemplified by the fact that cancer-reactive TCRs are generally of weak affinity. Furthermore, until now, most of the vaccine trials performed with selected TAAs and TSAs with high binding affinity for MHC have not been shown to elicit strong immunity, probably reflecting the consequence of thymic selection. A potent anti-tumoral response will thus depend on the presentation of immunoreactive peptides and the presence of a sufficient number of reactive cells "trained" to recognize these antigens. There is thus a need in the art to identify alternative antigenic peptides, which can overcome the limitations encountered in this field.

The invention has for objective to meet the aforementioned needs. This object is achieved by means of the subject-matter set out below, in particular in the items provided by the present invention and in the appended claims.

The invention is described in more detail below.

Definitions

Unless otherwise defined herein, scientific and technical terms used in the present application shall have the meanings that are commonly understood by those of ordinary skill in the art. Further, unless otherwise required by context, nomenclatures used herein, and techniques of cell and tissue culture are those well-known and commonly used in the art.

Such techniques are fully explained in the literature, such as Owen et al. (Kuby Immunology, $7^{th}$, edition, 2013—W. H. Freeman) and Sambrook et al. (Molecular cloning: A laboratory manual 4th edition, Cold Spring Harbor Laboratory Press—Cold Spring Harbor, NY, USA, 2012).

Nevertheless, with respect to the use of different terms throughout the current specification, the following definitions more particularly apply.

The terms "peptide", "polypeptide", "protein" and variations of these terms refer to peptides, oligopeptides, polypeptides, or proteins comprising at least two amino acids joined to each other preferably by a normal peptide bond, or, alternatively, by a modified peptide bond, such as for example in the cases of isosteric peptides. The term "(poly) peptide" refers to a peptide and/or to a polypeptide. In particular, the terms "peptide", "polypeptide" and "protein" refer to a sequential chain of amino acids of any length linked together via peptide bonds (—NHCO—). Peptides, polypeptides and proteins can play a structural and/or functional role in a cell in vitro and/or in vivo. The terms "peptide", "polypeptide", "protein" preferably encompass amino acids chains in size ranging from 2 to at least about 1000 amino acid residues. The term "peptide" preferably encompasses herein amino acid chains in size of less than about 30 amino acids, while the terms "polypeptide" and "protein" preferably encompass amino acid chains in size of at least 30 amino acids. The terms "polypeptide" and "protein" are used herein interchangeably. In a preferred embodiment, the terms "peptide", "polypeptide", "protein" also include "peptidomimetics" which are defined as peptide analogs containing non-peptidic structural elements, which peptides are capable of mimicking or antagonizing the biological action(s) of a natural parent peptide. A peptidomimetic lacks classical peptide characteristics such as enzymatically scissile peptide bonds. In particular, a peptide, polypeptide or protein can comprise amino acids other than the 20 amino acids defined by the genetic code in addition to these amino acids, or it can be composed of amino acids other than the 20 amino acids defined by the genetic code. In particular, a peptide, polypeptide or protein in the context of the present invention can equally be composed of amino acids modified by natural processes, such as post-translational maturation processes or by chemical processes, which are well known to a person skilled in the art. Such modifications are fully detailed in the literature. These modifications can appear anywhere in the polypeptide: in the peptide skeleton, in the amino acid chain or even at the carboxy- or amino-terminal ends. In particular, a peptide or polypeptide can be branched following an ubiquitination or be cyclic with or without branching. This type of modification can be the result of natural or synthetic post-translational processes that are well known to a person skilled in the art. The terms "peptide", "polypeptide", "protein" in the context of the present invention in particular also include modified peptides, polypeptides and proteins. For example, peptide, polypeptide or protein modifications can include acetylation, acylation, ADP-ribosylation, amidation, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, glycosylation including pegylation, hydroxylation, iodization, methylation, myristoylation, oxidation, proteolytic processes, phosphorylation, prenylation, racemization, seneloylation, sulfatation, amino acid addition such as arginylation or ubiquitination. Such modifications are fully detailed in the literature (Proteins Structure and Molecular Properties (1993) 2nd Ed., T. E. Creighton, New York; Post-translational Covalent Modifications of Proteins (1983) B. C. Johnson, Ed., Academic Press, New York; Seifter et al. (1990) Analysis for protein modifications and nonprotein cofactors, Meth. Enzymol. 182: 626-646 and Rattan et al., (1992) Protein Synthesis: Post-translational Modifications and Aging, Ann NY Acad Sci, 663: 48-62). Accordingly, the terms "peptide", "polypeptide", "protein" preferably include for example lipopeptides, lipoproteins, glycopeptides, glycoproteins and the like.

In a preferred embodiment, a (poly)peptide or protein is a "classical" (poly)peptide or protein, whereby a "classical" (poly)peptide or protein is typically composed of amino acids selected from the 20 amino acids defined by the genetic code, linked to each other by a normal peptide bond.

As well-known in the art, peptides, polypeptides and proteins can be encoded by nucleic acids. The terms "nucleic acid", "nucleic acid molecule", "nucleic acid sequence", "polynucleotide", "nucleotide sequence" are used herein interchangeable and refer to a precise succession of natural nucleotides (e.g., A, T, G, C and U), or synthetic nucleotides, i.e. to a chain of at least two nucleotides. In particular, the terms "nucleic acid", "nucleic acid molecule", "nucleic acid sequence", "polynucleotide", "nucleotide sequence" refer to DNA or RNA. Nucleic acids preferably comprise single stranded, double stranded or partially double stranded DNA or RNA, preferably selected from genomic DNA (gDNA), complementary DNA (cDNA), ribosomal DNA (rDNA), and the transcription product of said DNA, such as RNA. Preferred examples of nucleic acids include ribosomal RNA (rRNA), messenger RNA (mRNA); antisense DNA, antisense RNA; complementary RNA and/or DNA sequences, ribozyme, (complementary) RNA/DNA sequences with or without expression elements, a vector; a mini-gene, gene fragments, regulatory elements, promoters, and combinations thereof. Further preferred examples of nucleic acid (molecules) and/or polynucleotides include, e.g., a recombinant polynucleotide, a vector, an oligonucleotide, an RNA molecule such as an rRNA, an mRNA, or a transfer RNA (tRNA), or a DNA molecule as described above. It is thus preferred that the nucleic acid (molecule) is a DNA molecule or an RNA molecule; preferably selected from gDNA; cDNA; rRNA; mRNA; antisense DNA; antisense RNA; complementary RNA and/or DNA sequences; RNA and/or DNA sequences with or without expression elements, regulatory elements, and/or promoters; a vector; and combinations thereof. It is within the skill of the person in the art to determine nucleotide sequences which can encode a specific amino acid sequence.

The (poly)peptides and/or nucleic acids according to the invention may be prepared by any known method in the art including, but not limited to, any synthetic method, any recombinant method, any ex vivo generation method and the like, and any combination thereof. Such techniques are fully explained in the literature as mentioned above.

The term "antigenic peptide" as used herein refers to a peptide, which is prone to induce/elicit, increase, prolong or maintain an immune response in a subject to whom it is administered. In particular, the antigenic peptide is a sequence variant of (a fragment/epitope of) a (human) tumor antigen. In other words, the antigenic peptide is preferably distinct from (a fragment/epitope of) a (human) tumor antigen, but it has preferably amino acid similarity with (a fragment/epitope of) the (human) tumor antigen. Importantly, the antigenic peptide shares the same core sequence with the respective (fragment/epitope of) a (human) tumor antigen. Preferably, the immune response induced/elicited, increased, prolonged or maintained by the antigenic peptide (also) targets the respective (fragment/epitope of) a (human) tumor antigen.

As used herein, the term "tumor antigen" comprises tumor-specific antigens (TSAs) and tumor-associated antigens (TAAs). In general, the term "tumor antigen" or "tumor protein" designates herein an antigenic substance produced in tumor cells, and sometimes also in normal cells, and which can trigger an immune response upon administration in a subject. In humans, those have been classified according to their expression pattern, function or genetic origin, and include without limitation, overexpressed self-antigens (such as BIRC5); cancer-testis (CT) antigens (such as MAGE-1); mutational antigens, also known as neo-antigens (such as mutants from p53); tissue-specific differentiation antigens (such as the melanoma antigens Melan A/MART-1); viral antigens which are expressed by oncoviruses (such as HPV, EBV); oncofetal antigens (such as alpha-fetoprotein AFP and carcinoembryonic antigen CEA); and universal antigens (telomerase).

The term "B-cell tumor antigen", as used herein, refers to an antigen associated with and/or involved in the etiology of the B-cell malignancy, e.g. is involved or expressed in the B-cell malignancy. In other words, the antigen is expressed by or on B cells, including human B cells, such as any of a number of known B cell marker. Preferably, the B-cell tumor antigen is highly expressed (overexpressed) in B-cell lymphomas such as CD19, CD20, CD22, CD37 or TNFRSF13C. An antigenic peptide "derived from" a B-cell tumor antigen usually shares the same core sequence as an epitope (the "reference epitope") of said B-cell tumor antigen.

The term "core sequence", as used herein, refers to the amino acids in the middle of the sequence (also referred as the "central amino acids" of the sequence), e.g. in the middle of an antigenic peptide and/or a (reference) epitope. Accordingly, the core sequence consists of all amino acids except the two most N-terminal and the two most C-terminal amino acids. For example, in a peptide of nine amino acids (e.g. an antigenic peptide according to the present invention or the respective (fragment/epitope of) a (human) tumor antigen), the five middle amino acids represent the core sequence and alterations may only occur at any of the two N-terminal and the two C-terminal amino acid positions. Accordingly, a "shared core sequence" (or a "maintained" core sequence) usually means that mutations/differences are allowed only in the two most N-terminal and in the two most C-terminal amino acids of the (reference) epitope/sequence.

The term "prevalence", as used herein, refers to the cumulative frequency of each protein of the human microbiota wherein the core sequence shared with the respective (fragment/epitope of) a (human) tumor antigen) is found and present in an antigenic peptide. Indeed, a core sequence of interest may be present in one or several distinct antigenic peptides, each of such antigenic peptides may be present in one or distinct proteins expressed in the human microbiota. Accordingly, a global prevalence of a core sequence is derived from the frequency of each protein of the human microbiota wherein the core sequence shared with the respective (fragment/epitope of) a (human) tumor antigen) is found and by considering the frequencies of each protein of the human microbiota where similar peptides (i.e. distinct antigenic peptides) sharing the same core sequence were found.

The term "microbiota", as used herein, refers to commensal microorganisms found in and on all multicellular organisms studied to date from plants to animals. In particular, microbiota have been found to be crucial for immunologic, hormonal and metabolic homeostasis of their host. Microbiota include bacteria, archaea, protists, fungi and viruses. Accordingly, a "microbiota sequence variant" (or "microbiota variant") is a sequence variant of a (human) reference sequence (in particular an epitope/a fragment of a human tumor antigen), which occurs in microbiota, such as bacteria (e.g., it may be contained in a microbiota protein, such as a bacterial protein). Preferably, the antigenic peptide of the invention is a microbiota sequence variant (of a reference epitope/fragment of a human B-cell tumor antigen). Accordingly, the antigenic peptide is preferably present (e.g. comprised in) in at least one protein expressed by the human microbiota.

A "sequence variant" typically shares, in particular over the whole length of the sequence, at least 50% sequence identity with a reference sequence, namely, a fragment/epitope of a (reference) tumor antigen. Preferably, the sequence variant shares at least 60%, preferably at least 70%, preferably at least 75%, more preferably at least 80%, even more preferably at least 85%, still more preferably at least 90%, particularly preferably at least 95%, and most preferably at least 99% sequence identity with the reference sequence, namely, a fragment/epitope of a (reference) tumor antigen. Sequence identity may be calculated as known in the art, in particular as described below. Preferably, a sequence variant preserves the specific function of the reference sequence, for example its function as tumor epitope and/or its ability to elicit or maintain an immune response. The microbiota sequence variant is preferably selected from the group consisting of bacterial sequence variants, archaea sequence variants, protist sequence variants, fungi sequence variants and viral sequence variants. More preferably, the microbiota sequence variant is a bacterial sequence variant.

Anatomically, microbiota reside on or within any of a number of tissues and biofluids, including the skin, conjunctiva, mammary glands, vagina, placenta, seminal fluid, uterus, ovarian follicles, lung, saliva, oral cavity (in particular oral mucosa), and the gastrointestinal tract, in particular the gut. In the context of the present invention the microbiota sequence variant is preferably a sequence variant of microbiota of the gastrointestinal tract (microorganisms residing in the gastrointestinal tract), more preferably a sequence variant of microbiota of the gut (microorganisms residing in the gut). Accordingly, it is most preferred that the microbiota sequence variant is a (human) gut bacterial sequence variant (i.e. a sequence variant of bacteria residing in the (human) gut).

While microbiota can be found in and on many multicellular organisms (all multicellular organisms studied to date from plants to animals), microbiota found in and on human are preferred. Such microbiota are referred to herein as "human microbiota" (wherein the term human refers specifically to the localization/residence of the microbiota). Within the context of the present invention, the microbiota sequence variant is a human microbiota sequence variant.

The term "immunogenic compound" refers to a compound comprising an antigenic peptide according to the present invention. An "immunogenic compound" is able to induce/elicit, increase, prolong or maintain an immune response against said antigenic peptide in a subject to whom it is administered. In some embodiments, immunogenic compounds comprise at least one antigenic peptide, or alternatively at least one compound comprising such an antigenic peptide, linked to a protein, such as a carrier protein.

A "carrier protein" is usually a protein, which is able to transport a cargo, such as the antigenic peptide according to the present invention. For example, the carrier protein may transport its cargo across a membrane. In the context of the present invention, a carrier protein in particular (also) encompasses a peptide or a polypeptide that is able to elicit an immune response against the antigenic peptide that is linked thereto. Carrier proteins are known in the art.

Alternatively, such carrier peptide or polypeptide may be co-administered in the form of immune adjuvant.

Preferably, the antigenic peptide as described herein may be co-administrated or linked, for example by covalent or non-covalent bond, to a protein/peptide having immuno-adjuvant properties, such as providing stimulation of CD4+ Th1 cells. While the antigenic peptide as described herein preferably binds to MHC class I, CD4+ helper epitopes may be additionally used to provide an efficient immune response. Th1 helper cells are able to sustain efficient dendritic cell (DC) activation and specific CTL activation by secreting interferon-gamma (IFN-γ), tumor necrosis factor-alpha (TNF-α) and interleukin-2 (IL-2) and enhancing expression of costimulatory signal on DCs and T cells (Galaine et al., Interest of Tumor-Specific CD4 T Helper 1 Cells for Therapeutic Anticancer Vaccine. Vaccines (Basel). 2015 Jun. 30; 3(3):490-502).

For example, the adjuvant peptide/protein may preferably be distinct from the antigenic peptide according to the present invention. Preferably, the adjuvant peptide/protein is capable of recalling immune memory or provides a non-specific help or could be a specific helper peptide. Several helper peptides have been described in the literature for providing a nonspecific T cell help, such as tetanus helper peptide, keyhole limpet hemocyanin peptide or PADRE peptide (Adotévi et al., Targeting antitumor CD4 helper T cells with universal tumor-reactive helper peptides derived from telomerase for cancer vaccine. Hum Vaccin Immunother. 2013 May; 9(5):1073-7, Slingluff C L, The present and future of peptide vaccines for cancer: single or multiple, long or short, alone or in combination? Cancer J. 2011 September-October; 17(5):343-50). Accordingly, tetanus helper peptide, keyhole limpet hemocyanin peptide and PADRE peptide are preferred examples of such adjuvant peptide/proteins. The HHD-DR3 peptide of sequence MAKTIAYDEEARRGLERGLN (SEQ ID NO: 473). This peptide represents another example of a helper peptide (having immuno-adjuvant properties), which is preferred in the context of the present invention. Another preferred example is h-pAg T13L (sequence: TPPAYRPPNAPIL; SEQ ID NO: 474; Bhasin M, Singh H, Raghava G P (2003) MHCBN: a comprehensive database of MHC binding and non-binding peptides. Bioinformatics 19: 665-666). Further examples of preferred helper peptides include the UCP2 peptide (for example as described in WO 2013/135553 A1 or in Dosset M, Godet Y, Vauchy C, Beziaud L, Lone Y C, Sedlik C, Liard C, Levionnois E, Clerc B, Sandoval F, Daguindau E, Wain-Hobson S, Tartour E, Langlade-Demoyen P, Borg C, Adotévi O: Universal cancer peptide-based therapeutic vaccine breaks tolerance against telomerase and eradicates established tumor. Clin Cancer Res. 2012 Nov. 15; 18(22): 6284-95. doi: 10.1158/1078-0432.CCR-12-0896. Epub 2012 Oct. 2) and the BIRC5 peptide (for example as described in EP2119726 A1 or in Widenmeyer M, Griesemann H, Stevanović S, Feyerabend S, Klein R, Attig S, Hennenlotter J, Wernet D, Kuprash D V, Sazykin A Y, Pascolo S, Stenzl A, Gouttefangeas C, Rammensee H G: Promiscuous survivin peptide induces robust CD4+ T-cell responses in the majority of vaccinated cancer patients. Int J Cancer. 2012 Jul. 1; 131(1):140-9. doi: 10.1002/ijc.26365. Epub 2011 Sep. 14). The most preferred helper peptide is the UCP2 peptide (amino acid sequence: KSVWSKLQSIGIRQH; SEQ ID NO: 475, for example as described in WO 2013/135553 A1 or in Dosset et al., Clin Cancer Res. 2012 Nov. 15; 18(22):6284-95. In particular, the antigenic peptide as described herein, or a polypeptide comprising the said antigenic peptide, may be linked, for example by covalent or non-covalent bond, to the helper peptide.

As used herein, the term "immunogenic composition" refers to a composition that is able to elicit, induce, increase, prolong or maintain an immune response, in particular which elicits, induces, increases, prolongs or maintains an immune response, when it is administered to a mammal, and especially when it is administered to a human individual. Preferably, an immunogenic composition further comprises one or more immuno-adjuvant substances.

By "pharmaceutically acceptable excipient or carrier", it is meant herein a compound of pharmaceutical grade which improves the delivery, stability or bioavailability of an active agent, and can be metabolized by, and is non-toxic to, a subject to whom it is administered. Preferred excipients and carriers according to the invention include any of the excipients or carriers commonly used in pharmaceutical products, such as, for example, water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable excipients or carriers may further comprise minor amounts of auxiliary substances such as wetting or emulsifying agents, or preservatives.

By "vaccine", it is meant herein a composition capable of stimulating the immune system of a living organism so that protection against a harmful antigen is provided, either through prophylaxis or through therapy. Prophylactic vaccines are preferred. Preferably, a vaccine or a vaccine composition further comprises one or more immuno-adjuvant substances.

According to the different aspects and embodiments of the invention described herein, a "subject" or "host" preferably refers to a mammal, and most preferably to a human being. Said subject may have, been suspected of having, or be at risk of developing B-cell malignancy.

The term "B cell malignancy" refers to diseases associated with transformation of B cells. It encompasses, among others, B-cell lymphomas, acute lymphocytic (or lymphoblastic) leukemia (ALL), chronic lymphocytic leukemia (CLL, Richter's). In the context of the present invention, B-cell lymphomas are preferred such as non-Hodgkin lymphoma (NHL). For instance, NHL is selected from the group consisting of indolent (slow-growing) NHL, aggressive NHL, diffuse large B cell lymphoma (DLBCL), NOS (de novo and transformed from indolent), primary mediastinal large B cell lymphoma (PMBCL), T cell/histiocyte-rich large B cell lymphoma (TCHRBCL), Burkitt's lymphoma, mantle cell lymphoma (MCL), and/or follicular lymphoma (FL), optionally, follicular lymphoma Grade 3B (FL3B).

As used herein, the terms "preventing", "prevention", "prophylaxis" or "prevent" generally mean to avoid or minimize the onset or development of a disease or condition before its onset, while the terms "treating, "treatment" or "treat" encompass reducing, ameliorating or curing a disease or condition (or symptoms of a disease or condition) after its onset. The term "preventing" encompasses "reducing the likelihood of" occurrence of or "reducing the likelihood of reoccurrence".

An "effective amount" or "effective dose" as used herein is an amount which provides the desired effect. For therapeutic purposes, an effective amount is an amount sufficient to provide a beneficial or desired clinical result. The preferred effective amount for a given application can be easily determined by the skilled person taking into consideration, for example, the size, age, weight of the subject, the type of disease/disorder to be prevented or treated, and the amount of time since the disease/disorder began. In the context of the present invention, in terms of prevention or treatment, an effective amount of the composition is an amount that is sufficient to induce a humoral and/or cell-mediated immune response directed against the disease/disorder.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term “comprise” encompasses the term “consist of”. The term “comprising” thus encompasses “including” as well as “consisting” e.g., a composition “comprising” X may consist exclusively of X or may include something additional e.g., X+Y.

The terms “a” and “an” and “the” and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word “substantially” does not exclude “completely” e.g., a composition which is “substantially free” from Y may be completely free from Y. Where necessary, the word “substantially” may be omitted from the definition of the invention.

The term “about” in relation to a numerical value x means x±10%.

Additional definitions are provided throughout the specification.

The present invention may be understood more readily by reference to the following detailed description, including preferred embodiments of the invention, and examples included herein.

DETAILED DESCRIPTION

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Antigenic Peptides According to the Present Invention

In a first aspect, the present invention provides an antigenic peptide derived from a tumor antigen, especially a B-cell tumor antigen, wherein the antigenic peptide shares the same core sequence with the reference epitope of a tumor antigen, and wherein the shared core sequence has a high prevalence in the human microbiota.

The present invention also provides an antigenic peptide comprising or consisting of an amino acid sequence as set forth in any one of SEQ ID NOs 316, 304-315, 317-472, and 501-509. Preferably, the antigenic peptide may comprise or consist of an amino acid sequence as set forth in any one of SEQ ID NOs 316, 304-315 and 317-326.

Furthermore, the present invention provides an antigenic peptide comprising or consisting of an amino acid sequence as set forth in any one of SEQ ID NOs 1-257 and 476-500, wherein, optionally, one or two amino acid residues may be substituted, deleted or added. Preferably, the core sequence (of SEQ ID NOs 1-257 and 476-500) is maintained, if one or two amino acid residues are substituted, deleted or added. More preferably, the antigenic peptide comprises or consists of an amino acid sequence as set forth in any one of SEQ ID NOs 1-257 and 476-500 (without mutations) Amino acid sequences according to SEQ ID NOs 1-257 and 476-500 are microbiota sequence variants (microbiota variants, in particular bacterial sequence variants) of human tumor epitopes, in particular of reference epitopes/fragments of human B-cell tumor antigens. In other words, amino acid sequences according to SEQ ID NOs 1-257 and 476-500 can be found in bacterial proteins and show sequence similarity to reference epitopes/fragments of human B-cell tumor antigens, as illustrated in detail in Table 1A.

The present inventors have identified a set of antigenic peptides that can be used to induce a specific immune response against tumor cells. Those antigenic peptides are distinct from, but have amino acid similarity to, (fragments of) human tumor antigens, especially tumor antigens highly expressed in B-cell lymphomas such as CD19, CD20, CD22, CD37 or TNFRSF13C, as shown in Table 1A, Table 1B and Table 1C. Importantly, the antigenic peptides according to the present invention have a core sequence identical with the core sequence of the sequence of the epitope (fragment) of the reference tumor antigen. Moreover, the core sequence displays a high prevalence based on the frequency of the proteins present in the human microbiota where the core sequence is found.

In particular, the antigenic peptides according to the present invention are comprised in polypeptides and proteins produced by commensal bacteria from the human gut. Accordingly, the antigenic peptides according to the present invention are not human sequences, but bacterial sequences. Without wishing to be bound by any particular theory, the inventors believe that the human immune repertoire contains T-cell clones that are reactive against bacterial peptides (comprised in proteins produced by commensal bacteria from the gut), which have amino acid similarity to fragments of human tumor antigens. In particular, the antigenic peptides according to the present invention can elicit a stronger immune response than the corresponding human peptides, since T cells able to recognize strictly human peptides have been depleted as recognizing self-antigens during maturation, which is not the case for the antigenic peptides according to the present invention. This may explain why the antigenic peptides described herein are able to induce an immune response, and especially a T-cell response, when these peptides are administered to a (human) individual.

Accordingly, without being bound to any theory the inventors assume that proteins produced by commensal bacteria from the gut are able to “mimic” tumor antigens, and can be used for triggering a specific immune response against tumor cells. These findings provide further evidence that commensal bacteria may contribute to tumor cells eradication.

The antigenic peptides disclosed herein can be prepared using well known techniques. For example, the peptides can be prepared synthetically, by recombinant DNA technology or chemical synthesis. Peptides disclosed herein can be synthesized individually or as longer polypeptides comprising two or more peptides (e.g., two or more peptides or a peptide and a non-peptide). The antigenic peptides can be isolated i.e., purified to be substantially free of other naturally occurring host cell proteins and fragments thereof, e.g., at least about 70%, 80% or 90% purified. Preferably, the antigenic peptides according to the present invention are isolated antigenic peptides.

Therefore, the core sequence represents a major feature of the antigenic peptides according to the present invention. The inventors have thus identified core sequences of highly interest with high prevalence since they are present in several sequence variants of a fragment of a (reference) tumor antigen and/or in several human microbiota proteins with high frequency in a significant portion of the general human population. The inventors have selected the antigenic peptides of the invention liable to trigger the best cross-reactive tumor-specific cytotoxic T cell immune response in order to prevent and treat B-cell malignancy.

In general, the shared core sequence has a high prevalence in the human microbiota, when the prevalence is higher than 30%, preferably higher than 40%, preferably higher than 50%, more preferably higher than 60%, even more preferably higher than 70%, still more preferably higher than 80%, particularly preferably higher than 90%, and most preferably higher than 95%.

The prevalence of a core sequence is derived from the frequency of each protein of the human microbiota wherein the core sequence shared with the respective (fragment/epitope of) a (human) tumor antigen) is found and by considering the frequencies of each protein of the human microbiota where similar peptides (i.e. distinct antigenic peptides) sharing the same core sequence were found. For example, to assess whether a core sequence has high prevalence, the frequency of each protein present in the human microbiota wherein said core sequence is found is calculated from a microbiota sequence database. The prevalence is then derived from the cumulative frequency calculated for each protein of the human microbiota where the core sequence of interest is found and present in an antigenic peptide. Such database may preferably comprise microbiota (sequence) data of multiple individuals (subjects). An example of such a database is the "Integrated reference catalog of the human gut microbiome" (version 1.0, March 2014; Li et al. MetaHIT Consortium. An integrated catalog of reference genes in the human gut microbiome. Nat Biotechnol. 2014 August; 32(8):834-41 URL: http://meta.genomics.cn/meta/home), which includes data from the major human microbiome profiling efforts, the American National Institutes of Health Human Microbiome Project (NIH-HMP) and the European Metagenomics of the Human Intestinal Tract Initiative (MetaHIT).

Accordingly, the invention relates to antigenic peptides having amino acid similarity with a tumor antigen since they are derived from this tumor antigen (or tumor epitope). The expression "having amino acid similarity with a tumor antigen" as used herein, refers in particular to a sequence variant of fragments of a (reference) human tumor antigen, such as CD22 or the other exemplified human tumor antigens described below in Tables 1A, 1B and 1C. A "sequence variant" typically shares, in particular over the whole length of the sequence, at least 50% sequence identity with a reference sequence, namely, a fragment of a (reference) tumor antigen. Preferably, the sequence variant shares at least 55%, preferably at least 60%, preferably 66%, preferably at least 70%, preferably at least 77%, more preferably at least 80%, even more preferably at least 88%, still more preferably at least 90% sequence identity with the reference sequence, namely, a fragment of a (reference) tumor antigen. Sequence identity may be calculated as known in the art, in particular as described below. Preferably, a sequence variant preserves the specific function of the reference sequence, for example its function as tumor epitope and/or its ability to elicit or maintain an immune response. In particular, an amino acid sequence variant has an altered sequence in which one or more of the amino acids in the reference sequence is mutated, e.g. deleted or substituted, or one or more amino acids are inserted into the sequence of the reference amino acid sequence. For example, variant sequences which are at least 90% identical have no more than 10 alterations, i.e. any combination of deletions, insertions or substitutions, per 100 amino acids of the reference sequence.

Methods for comparing the identity (similarity) of two or more sequences are well known in the art. The percentage to which two sequences are identical can, e.g., be determined using a mathematical algorithm. A preferred, but not limiting, example of a mathematical algorithm which can be used is the algorithm of Karlin et al. (1993), PNAS USA, 90:5873-5877. Such an algorithm is integrated in the BLAST family of programs, e.g. BLAST or NBLAST program (see also Altschul et al., 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 183, 63-98; Pearson and Lipman (1988), Proc. Natl. Acad. Sci. U.S.A 85, 2444-2448). Sequences which are identical to other sequences to a certain extent can be identified by these programmes. Furthermore, programs available in the Wisconsin Sequence Analysis Package, version 9.1 (Devereux et al., 1984, Nucleic Acids Res., 387-395), for example the programs BESTFIT and GAP, may also be used to determine the % identity between two polynucleotides and the % identity between two (poly)peptide sequences. BESTFIT uses the "local homology" algorithm of Smith and Waterman (1981), J. Mol. Biol. 147, 195-197 and finds the best single region of similarity between two sequences.

In general, the antigenic peptide according to the present invention binds to MHC class I (major histocompatibility complex class I, MHC I) molecules.

MHC class I molecules present epitopes to killer T cells, also called cytotoxic T lymphocytes (CTLs). A CTL expresses CD8 receptors, in addition to TCRs (T-cell receptors). When a CTL's CD8 receptor docks to a MHC class I molecule, if the CTL's TCR fits the epitope within the MHC class I molecule, the CTL triggers the cell to undergo programmed cell death by apoptosis. This route is particularly useful in prevention and/or treatment of cancer, since cancer cells are directly attacked. In humans, MHC class I comprises HLA-A, HLA-B, and HLA-C molecules. Typically, peptides (epitopes) having a length of 8-10, amino acids are presented by MHC I.

In general, the antigenic peptide according to the present invention may be of any length. Preferably, the length of the antigenic peptide according to the present invention does not exceed 350 amino acids. For example, the maximum length of the antigenic peptide according to the present invention may be 300 or 250 amino acids. More preferably, the maximum length of the antigenic peptide according to the present invention does not exceed 200 amino acids, e.g., not more than 190, 180, 170, 160, 150, 140, 130, 120, 110, 100, 95, 90, 85, 80, 75, 70, 65, 60, 55, 50, 45, 40, 35, 30, 29, 28, 27, 26, 25, 24, 23, 22, 21, 20, 19, 18, 17, 16, 15, 14 or 13 amino acids. In particular, the length of the antigenic peptides according to the present invention is preferably at most 30 or 25 amino acids, more preferably at most 20 or 15 amino acids, even more preferably at most 10 amino acids. Particularly preferably, the antigenic peptide according to the present invention comprises at least 8 or 9 amino acids, such as 10 amino acids. Still more preferably, the antigenic peptide has a length of 9 or 10 amino acids. In particular, the antigenic peptides are not the full-length proteins produced by human microbiota (from which the antigenic peptides may be derived from). In other words, the antigenic peptide of the invention is preferably a fragment of a full-length protein (produced by human microbiota).

Similarly, the "fragment/epitope" of the (reference) tumor antigen, which typically serves as reference sequence, preferably comprises consecutive 9 amino acids of the tumor antigen and eventually 10 amino acids. It is understood that the "fragment/epitope" of the (reference) tumor antigen is not the full-length tumor antigen (protein).

A "fragment" (of a protein or nucleic acid (sequence)), as used herein, has preferably a maximum length of 95%, 90%, 85%, 80%, 75%, 70%, 65%, 60%, 55%, 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2% or 1% of the full-length (reference) protein/nucleic acid/sequence. In some embodiments, the length of the fragment does not exceed 50% of the length of the (full-length) (reference) protein/nucleic acid. In other embodiments, the length of the fragment of the (reference) protein/nucleic acid does not exceed 20% or 10% of the length of the (full-length) (reference) protein/nucleic acid.

In more general, the present invention provides an antigenic peptide, which comprises or consists of a sequence variant of a fragment/epitope of a human (reference) tumor antigen, especially a microbiota sequence variant of a fragment/epitope of a human tumor antigen. The human tumor antigen may be selected from the group consisting of CD19, CD20, CD22, CD37 and TNFRSF13C. The fragment/epitope of the human (reference) tumor antigen may be selected from the group consisting of any one of SEQ ID 258-280.

Preferably, the antigenic peptide comprises or consists of a microbiota variant of a human reference peptide according to any one of SEQ ID NOs 258-280. In particular, SEQ ID NOs 258-280 refer to human tumor epitopes, in particular reference epitopes/fragments of human B-cell tumor antigens. Examples of microbiota variants of human reference peptides according to any one of SEQ ID NOs 258-280 are peptides according to SEQ ID NOs 1-257 and 476-500 (as illustrated in Table 1A below). Preferred microbiota sequence variants (microbiota variants) are bacterial sequence variants. In other words, amino acid sequences according to SEQ ID NOs 1-257 and 476-500 can be found in bacterial proteins and show sequence similarity to reference epitopes/fragments of human B-cell tumor antigens, as illustrated in detail in Table 1A. More preferably, the antigenic peptide comprises or consists of a microbiota variant of a human reference peptide according to any one of SEQ ID NOs 258, 260-266, 270, 271, 279 and 280. Even more preferably, the antigenic peptide comprises or consists of a microbiota variant of a human reference peptide according to any one of SEQ ID NOs 260, 264, 270, 271, 279 and 280. Still more preferably, the antigenic peptide comprises or consists of a microbiota variant of a human reference peptide according to any one of SEQ ID NOs 264, 270, 271 and 279.

Accordingly, the present invention also provides an antigenic peptide comprising or consisting of a microbiota variant of a human reference peptide according to any one of SEQ ID NOs 258-280; preferably according to any one of SEQ ID NOs 258, 260-266, 270, 271, 279 and 280; more preferably according to any one of SEQ ID NOs 260, 264, 270, 271, 279 and 280; even more preferably according to any one of SEQ ID NOs 264, 270, 271 and 279.

In a particular embodiment, the present invention provides an antigenic peptide derived from CD19, CD20, CD22, CD37 or TNFRSF13C, wherein the antigenic peptide shares the same core sequence with a fragment/epitope of a (reference) tumor antigen; and wherein the shared core sequence has a high prevalence in the human microbiota. Such prevalence is derived from the frequency of the at least one protein present in the human microbiota wherein said core sequence is found. Preferably, the antigenic peptide according to the invention comprises or consists of any one of SEQ ID Nos 304-326 (MHC I Consensus Sequences).

In one embodiment, the antigenic peptide binds moderately, strongly or very strongly to MHC class I (major histocompatibility complex class I, MHC I) molecules.

Binding of the at least one antigenic peptide to MHC class I (major histocompatibility complex class I) molecules, may be tested by the MHC I in silico or in vitro binding tests as described herein. Accordingly, strong and very strong binders may be selected as described above. Preferably, binding to MHC I is tested (in silico and/or in vitro as described herein) for the at least one antigenic peptide to MHC I molecules and, additionally, for the (respective reference) tumor antigen (the fragment/epitope of a (reference) tumor antigen) to MHC I molecules, and binding affinities are preferably obtained for both (the fragment/epitope of tumor antigen and the antigenic peptide).

After the binding test, preferably only such antigenic peptides are selected, which bind moderately, strongly or very strongly to MHC I. More preferably only strong and very strong binders are selected and most preferably, only such antigenic peptides are selected, which bind very strongly to MHC I. More preferably, only such antigenic peptides are selected, which bind strongly or very strongly to MHC I molecule, and wherein the epitope/fragment of a (reference) tumor antigen (the "corresponding" tumor antigenic epitope sequence) binds weaker (e.g. weakly or moderately) to MHC I molecule. Even more preferably, only such microbiota sequence variants are selected, which bind very strongly to MHC I, and wherein the epitope/fragment of a (reference) tumor antigen binds weakly MHC I.

Accordingly, the antigenic peptide of the invention binds preferably stronger (i.e., has a higher binding affinity) to an MHC I molecule than the respective human reference epitope of the B-cell tumor antigen (which shares the same core sequence). In other words, the reference epitope of the human B-cell tumor antigen, which shares the same core sequence, binds preferably weaker to MHC I molecules (i.e., has lower binding affinity) than the respective antigenic peptide.

Prediction of MHC class I binding (MHC in silico binding test) may be performed using publicly available tools, such as "NetMHCpan", for example the "NetMHCpan 3.0 Server" or the "NetMHCpan 4.0 Server" (Center for biological sequence analysis, Technical University of Denmark DTU; URL: http://www.cbs.dtu.dk/services/NetMHCpan/). The NetMHCpan method, in particular NetMHCpan 3.0 or a higher version, is trained on more than 180000 quantitative binding data covering 172 MHC molecules from human (HLA-A, B, C, E) and other species. In general, the affinity may be predicted by leaving default thresholds for strong and weak binders. For example, for HLA-A*0201 a calculated affinity below 50 nM may indicate "strong binders", and an affinity between 50 and 300 nM may indicate "moderate binders". In NetMHCpan, for example in NetMHCpan 3.0 or in NetMHCpan 4.0, the rank of the predicted affinity may be compared to a set of 400000 random natural peptides, which may be used as a measure of the % rank binding affinity. This value is not affected by inherent bias of certain molecules towards higher or lower mean predicted affinities. For example (e.g., for HLA-A*020), very strong binders may be defined as having % rank <0.5, strong binders may be defined as having % rank <1.0, moderate binders may be defined as having % rank from 1.0 to 2.0, and weak binders may be defined as having a % rank >2.0. A method for in vitro testing is well-known to the skilled person. For example, the skilled person may use the experimental protocol as validated for peptides presented by HLA-A*0201 in Tourdot et al., A general strategy to enhance immunogenicity of low-affinity HLA-A2.1—associated peptides: implication in the identification of cryptic tumor epitopes. Eur J Immunol. 2000 December; 30(1 2):341 1-21. In this context, a reference peptide, such as HIV pol 589-597, may be additionally used in the test. This enables calculation of the in vitro affinity relative to the binding observed with the reference peptide, e.g. by the following equation: Relative affinity=concentration of each peptide inducing 20% of expression of HLA-A*0201/concentration of the reference peptide inducing 20% of expression of HLA-A*020 (where 100% is the level of HLA-A*0201 expression detected with the reference peptide, e.g. HIV pol 589-597, for example used at a 100 μM concentration). For example, a peptide displaying a relative affinity below 1 may be considered as a "strong binder", a peptide displaying relative affinity between 1 and 2 may be considered as a "moderate binder" and a peptide displaying relative affinity more than 3 may be considered as a "weak binder".

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, HLA-A*24 and HLA-B*07 are examples of different MHC class I alleles that can be expressed from these loci. For instance, the antigenic peptide according to the invention may bind to HLA-A*01, HLA-A*02, HLA-A*24 and HLA-B*07 molecules. In particular, the antigenic peptide according to the invention binds to HLA-A*02.

In one embodiment, the antigenic peptide according to the invention is a microbiota sequence variant of an epitope of a human tumor antigen.

In particular, the microbiota sequence variant of an epitope of a human tumor antigen is identified in at least one protein expressed in the human microbiota. Preferably, the at least one protein present in the human microbiota is secreted or comprises a transmembrane domain.

Cellular localization, in particular whether a protein is secreted or comprises a transmembrane domain, can be tested in silico or in vitro by methods well-known to the skilled person. For example, "SignalP 4.1 Server" (Center for biological sequence analysis, Technical University of Denmark DTU; URL: www.cbs.dtu.dk/services/SignalP) and/or "Phobius" (A combined transmembrane topology and signal peptide predictor, Stockholm Bioinformatics Centre; URL: phobius.sbc.su.se) may be used. Preferably, two prediction tools (e.g., SignalP 4.1 Server and Phobius) may be combined.

For example, to test whether a protein is secreted, presence of a signal peptide may be assessed. Signal peptides are ubiquitous protein-sorting signals that target their passenger (cargo) protein for translocation across the cytoplasmic membrane in prokaryotes. To test presence of a signal peptide, for example "SignalP 4.1 Server" (Center for biological sequence analysis, Technical University of Denmark DTU; URL: www.cbs.dtu.dk/services/SignalP) and/or "Phobius" (A combined transmembrane topology and signal peptide predictor, Stockholm Bioinformatics Centre; URL: phobius.sbc.su.se) may be used. Preferably, two prediction tools (e.g., SignalP 4.1 Server and Phobius) may be combined.

Moreover, it may be determined whether a protein comprises a transmembrane domain. Both, signal peptides and transmembrane domains are hydrophobic, but transmembrane helices typically have longer hydrophobic regions. For example, SignalP 4.1 Server and Phobius have the capacity to differentiate signal peptides from transmembrane domains. Preferably, a minimum number of two predicted transmembrane helices is set to differentiate between membrane and cytoplasmic proteins to deliver the final consensus list.

In one embodiment, the microbiota sequence variant of a fragment/epitope of a human tumor antigen is presented in its entirety after the cleavage of the bacterial protein expressed in the human microbiota. In this context, the term "cleavage" refers to the processing of the peptide for MHC presentation, in particular to MHC-I processing. For example, cleavage prediction score and/or affinity can be used to predict antigenic cleavage for proper MHC binding (for presentation to CD8 T cells). Such "cleavage probability score" may be calculated with software (preferably such score is higher than 70%, preferably higher than 80%, more preferably higher than 90%). For example, "IEDB" (Immune Epitope Database and Analysis Resource, IEDB Analysis Resource, supported by a contract from the National Institute of Allergy and Infectious Diseases, a component of the National Institutes of Health in the Department of Health and Human Services), which provides, for example, MHC-I processing predictions (URL: http://tools.iedb.org/mhcnp/) may be used. In another example, NetChop3 (The role of the proteasome in generating cytotoxic T cell epitopes: Insights obtained from improved predictions of proteasomal cleavage. M. Nielsen, C. Lundegaard, O. Lund, and C. Kesmir. Immunogenetics, 57(1-2):33-41, 2005; Prediction of proteasome cleavage motifs by neural networks. C. Kesmir, A. Nussbaum, Hansjorg Schild, Vincent Detours, and S. Brunak, Prot. Eng., 15(4): 287-296, 2002; URL: http://www.cbs.dtu.dk/services/NetChop/) may be used for cleavage prediction. This algorithm is based on a neural network trained on experimental data on proteasome cleavage in vitro and known HLA ligands. The output of the network was a score between 0.0 and 1.0. A random predictor would score 0.5 and a perfect predictor would score 1. Accordingly, a high score for a peptide (e.g. above 0.7, preferably above 0.8, more preferably above 0.9, as described above) suggests that it is effectively cleaved at its N- and/or C-terminus (and not its center), while a low score is associated with peptides cleaved in their center. Thereby, information regarding proteasomal cleavage, TAP transport, and MHC class 1 analysis tools can be combined for prediction of peptide presentation.

In one embodiment, the antigenic peptide induces T-cell cross-reactivity against the human epitope of a (reference) tumor antigen. T-cell cross-reactivity is a phenomenon of the immune system defined as the recognition of two or more peptide-MHC complexes (pMHCs) by the T-cell receptor (TCR).

Epitope mimicry relates to the concept of sequence and structure similarity between foreign antigens and self-antigens as a trigger mechanism to elicit a cross reactive immune response against the self-antigens. Interestingly, such epitope mimicry offers a possible way to bypass the repertoire restriction of human T cells due to clonal depletion of T cells recognizing self-antigens.

In particular, antigens (i.e. the antigenic peptides according to the present invention) distinct from self-antigens (e.g. human epitope of a tumor antigen), but sharing sequence similarity with the self-antigen, (i) can still be recognized due to the cross-reactivity of the T-cell receptor and (ii) it is expected that such antigens are recognized by T cell/TCR that have not been depleted during T cell education process. Accordingly, such antigens are able to elicit a strong immune response leading to clonal expansion of T cell harboring potential cross reactivity with self-antigens.

T cell receptor cross-reactivity with the epitope of a human (reference) tumor antigen may be measured as shown in the section EXAMPLES by ELISPOT-IFNγ assay. Briefly HLA-A2 transgenic mice (e.g. HHD DR1 mice expressing human HLA-A2 and HLA-DR1 MHC and lacking the murine H-2 class I and class II MHCs and/or HHD DR3 mice expressing human HLA-A2 and HLA-DR3 MHC) are immunized on day 0 (d0) with a prime injection, and on d14 with a boost injection with an antigenic peptide of the present invention and the epitope of a human (reference) tumor antigen. Seven days after the boost injection (i.e. on d21), the mice are euthanized and splenocytes are stimulated in vitro with the antigenic peptide of the present invention to assess their capacity to secrete IFN-gamma as assessed by ELISPOT.

In particular, the present invention provides an antigenic peptide, which is a microbiota sequence variant of a fragment/epitope of a human tumor antigen, wherein the epitope of a human tumor antigen may comprise or consist of any one of SEQ ID Nos 1-257 and 476-500.

Table 1A below provides an overview over the antigenic peptides according to the present inventions with their amino acid sequences and SEQ ID NOs and with the corresponding fragment/epitope of a human tumor antigen (also referred to herein as "human reference peptide"). Table 1A also provides information to which tumor antigen each antigenic peptide according to the present invention relates. SEQ ID NOs 1 to 257 and 476-500 refer to HLA-A*02 antigenic peptides according to the present invention.

TABLE 1A

HLA-A*02 Antigenic peptides according to the invention.

| Tumor antigen | Sequence human reference peptide | SEQ ID NO. human reference peptide | Sequence antigenic peptide | SEQ ID NO. antigenic peptide |
|---|---|---|---|---|
| CD19 | FLLFLTPME | 258 | FLLFLTPIL | 1 |
| CD19 | FLLFLTPME | 258 | FLLFLTPLL | 2 |
| CD19 | FLLFLTPME | 258 | FMLFLTPRI | 3 |
| CD19 | FLLFLTPME | 258 | GLLFLTPLA | 4 |
| CD19 | FLLFLTPME | 258 | GLLFLTPLL | 5 |
| CD19 | FLLFLTPME | 258 | GLLFLTPLM | 6 |
| CD19 | FLLFLTPME | 258 | ILLFLIPLL | 7 |
| CD19 | FLLFLTPME | 258 | SLLFLTPLL | 8 |
| CD19 | FLLFLTPME | 258 | TLLFLTPLI | 9 |
| CD19 | FLLFLTPME | 258 | TLLFLTPML | 10 |
| CD19 | FLLFLTPME | 258 | VLLFLTPML | 11 |
| CD19 | FLLFLTPME | 258 | YLLFLTPVL | 12 |
| CD19 | KLSLGLPGL | 259 | ALSLGLPGL | 13 |
| CD19 | KLSLGLPGL | 259 | ALSLGLPLL | 14 |
| CD19 | KLSLGLPGL | 259 | ALSLGLPML | 15 |
| CD19 | KLSLGLPGL | 259 | ALSLGLPQL | 16 |
| CD19 | KLSLGLPGL | 259 | ALSLGLPRL | 17 |
| CD19 | KLSLGLPGL | 259 | AMSLGLPCL | 18 |
| CD19 | KLSLGLPGL | 259 | AMSLGLPML | 19 |
| CD19 | KLSLGLPGL | 259 | FLSLGLPIL | 20 |
| CD19 | KLSLGLPGL | 259 | FLSLGLPKL | 21 |
| CD19 | KLSLGLPGL | 259 | ILSLGLPIL | 22 |
| CD19 | KLSLGLPGL | 259 | KLSLGLPVL | 23 |
| CD19 | KLSLGLPGL | 259 | LLSLGLPFL | 24 |
| CD19 | KLSLGLPGL | 259 | LLSLGLPGL | 25 |
| CD19 | KLSLGLPGL | 259 | MLSLGLPIL | 26 |
| CD19 | KLSLGLPGL | 259 | RLSLGLPGL | 27 |
| CD19 | KLSLGLPGL | 259 | SLSLGLPIL | 28 |
| CD19 | KLSLGLPGL | 259 | SLSLGLPKL | 29 |
| CD19 | KLSLGLPGL | 259 | VLSLGLPLL | 30 |
| CD19 | KLSLGLPGL | 259 | VLSLGLPTA | 31 |
| CD19 | KLSLGLPGL | 259 | VLSLGLPTV | 32 |
| CD19 | KLSLGLPGL | 259 | YLSLGLPIL | 33 |
| CD19 | SLVGILHLQ | 260 | LLVGILHLV | 34 |
| CD19 | SLVGILHLQ | 260 | SLVGILHII | 35 |
| CD19 | TLAYLIFCL | 261 | FLAYLIFGL | 36 |
| CD19 | TLAYLIFCL | 261 | FLAYLIFTL | 37 |
| CD19 | TLAYLIFCL | 261 | RLAYLIFLL | 38 |
| CD19 | TLAYLIFCL | 261 | YLAYLIFEL | 39 |

TABLE 1A-continued

HLA-A*02 Antigenic peptides according to the invention.

| Tumor antigen | Sequence human reference peptide | SEQ ID NO. human reference peptide | Sequence antigenic peptide | SEQ ID NO. antigenic peptide |
|---|---|---|---|---|
| CD19 | QQMGGFYLC | 262 | LQMGGFYLL | 40 |
| CD20 | IALGGLLMI | 263 | AILGGLLLI | 41 |
| CD20 | IALGGLLMI | 263 | ALLGGLLLI | 42 |
| CD20 | IALGGLLMI | 263 | ALLGGLLML | 43 |
| CD20 | IALGGLLMI | 263 | FALGGLLTV | 44 |
| CD20 | IALGGLLMI | 263 | FLLGGLLLI | 45 |
| CD20 | IALGGLLMI | 263 | FLLGGLLMV | 46 |
| CD20 | IALGGLLMI | 263 | GMLGGLLLI | 47 |
| CD20 | IALGGLLMI | 263 | GMLGGLLML | 48 |
| CD20 | IALGGLLMI | 263 | HILGGLLMV | 49 |
| CD20 | IALGGLLMI | 263 | IILGGLLVV | 50 |
| CD20 | IALGGLLMI | 263 | ILLGGLLLI | 51 |
| CD20 | IALGGLLMI | 263 | LLLGGLLLI | 52 |
| CD20 | IALGGLLMI | 263 | LLLGGLLMI | 53 |
| CD20 | IALGGLLMI | 263 | NLLGGLLLI | 54 |
| CD20 | IALGGLLMI | 263 | SILGGLLLI | 55 |
| CD20 | IALGGLLMI | 263 | SLLGGLLLI | 56 |
| CD20 | IALGGLLMI | 263 | SLLGGLLML | 57 |
| CD20 | IALGGLLMI | 263 | SMLGGLLLI | 58 |
| CD20 | IALGGLLMI | 263 | TLLGGLLMI | 59 |
| CD20 | IALGGLLMI | 263 | YALGGLLEV | 60 |
| CD20 | IALGGLLMI | 263 | YILGGLLMV | 61 |
| CD20 | IALGGLLMI | 263 | YMLGGLLLI | 62 |
| CD20 | IALGGLLMI | 263 | YVLGGLLMI | 63 |
| CD20 | IALGGLLMI | 263 | YVLGGLLMV | 64 |
| CD20 | IMNSLSLFA | 264 | AMNSLSLLL | 476 |
| CD20 | IMNSLSLFA | 264 | AMNSLSLTV | 477 |
| CD20 | IMNSLSLFA | 264 | AMNSLSLYI | 65 |
| CD20 | IMNSLSLFA | 264 | GMNSLSLLV | 478 |
| CD20 | IMNSLSLFA | 264 | ILNSLSLDI | 479 |
| CD20 | IMNSLSLFA | 264 | ILNSLSLKI | 66 |
| CD20 | IMNSLSLFA | 264 | ILNSLSLKL | 67 |
| CD20 | IMNSLSLFA | 264 | ILNSLSLLL | 68 |
| CD20 | IMNSLSLFA | 264 | ILNSLSLTA | 480 |
| CD20 | IMNSLSLFA | 264 | LLNSLSLFL | 69 |
| CD20 | IMNSLSLFA | 264 | QMNSLSLFL | 481 |

TABLE 1A-continued

HLA-A*02 Antigenic peptides according to the invention.

| Tumor antigen | Sequence human reference peptide | SEQ ID NO. human reference peptide | Sequence antigenic peptide | SEQ ID NO. antigenic peptide |
|---|---|---|---|---|
| CD20 | IMNSLSLFA | 264 | VLNSLSLYA | 482 |
| CD20 | IMNSLSLFA | 264 | VMNSLSLLI | 483 |
| CD20 | IMNSLSLFA | 264 | YINSLSLFI | 484 |
| CD20 | IMNSLSLFA | 264 | YMNSLSLAL | 70 |
| CD20 | LMIPAGIYA | 265 | FLIPAGIFL | 71 |
| CD20 | LMIPAGIYA | 265 | ILIPAGIYL | 72 |
| CD20 | LMIPAGIYA | 265 | LLIPAGIAV | 73 |
| CD20 | LMIPAGIYA | 265 | LLIPAGIEL | 74 |
| CD20 | LMIPAGIYA | 265 | LLIPAGIGL | 75 |
| CD20 | LMIPAGIYA | 265 | LLIPAGILI | 76 |
| CD20 | LMIPAGIYA | 265 | LLIPAGILL | 77 |
| CD20 | LMIPAGIYA | 265 | MLIPAGIPA | 78 |
| CD20 | LMIPAGIYA | 265 | MMIPAGIAV | 79 |
| CD20 | LMIPAGIYA | 265 | VMIPAGIFL | 80 |
| CD20 | SLFLGILSV | 266 | FLFLGILGL | 81 |
| CD20 | SLFLGILSV | 266 | FLFLGILPL | 82 |
| CD20 | SLFLGILSV | 266 | MLFLGILSV | 83 |
| CD20 | SLFLGILSV | 266 | YLFLGILGI | 84 |
| CD20 | SLFLGILSV | 266 | YLFLGILGL | 85 |
| CD20 | SLFLGILSV | 266 | YLFLGILSL | 86 |
| CD20 | SLFLGILSV | 266 | YLFLGILYL | 87 |
| CD22 | FLSNDTVQL | 267 | FLSNDTVLL | 88 |
| CD22 | FLSNDTVQL | 267 | FLSNDTVPL | 89 |
| CD22 | FLSNDTVQL | 267 | FLSNDTVSA | 90 |
| CD22 | FLSNDTVQL | 267 | FMSNDTVKV | 91 |
| CD22 | FLSNDTVQL | 267 | ILSNDTVWL | 92 |
| CD22 | FLSNDTVQL | 267 | KMSNDTVVL | 93 |
| CD22 | FLSNDTVQL | 267 | RLSNDTVGL | 94 |
| CD22 | FLSNDTVQL | 267 | RMSNDTVEI | 95 |
| CD22 | FLSNDTVQL | 267 | TLSNDTVWL | 96 |
| CD22 | HLLGPWLLL | 268 | ALLGPWLIV | 97 |
| CD22 | HLLGPWLLL | 268 | FLLGPWLCL | 98 |
| CD22 | HLLGPWLLL | 268 | KLLGPWLSV | 99 |
| CD22 | HLLGPWLLL | 268 | LLLGPWLLL | 100 |
| CD22 | HLLGPWLLL | 268 | YLLGPWLLV | 101 |
| CD22 | ILILAICGL | 269 | ILILAICGV | 102 |

TABLE 1A-continued

HLA-A*02 Antigenic peptides according to the invention.

| Tumor antigen | Sequence human reference peptide | SEQ ID NO. human reference peptide | Sequence antigenic peptide | SEQ ID NO. antigenic peptide |
|---|---|---|---|---|
| CD22 | ILILAICGL | 269 | IMILAICLV | 103 |
| CD22 | ILILAICGL | 269 | RLILAICGL | 104 |
| CD22 | ILILAICGL | 269 | YLILAICGV | 105 |
| CD22 | WVFEHPETL | 270 | FLFEHPETE | 485 |
| CD22 | WVFEHPETL | 270 | HIFEHPEHL | 486 |
| CD22 | WVFEHPETL | 270 | KIFEHPELL | 106 |
| CD22 | WVFEHPETL | 270 | LIFEHPERV | 107 |
| CD22 | WVFEHPETL | 270 | RVFEHPELV | 108 |
| CD22 | WVFEHPETL | 270 | RVFEHPERV | 487 |
| CD22 | WVFEHPETL | 270 | YTFEHPETI | 488 |
| CD22 | WVFEHPETL | 270 | YVFEHPELL | 109 |
| CD22 | WVFEHPETL | 270 | YIFEHPETA | 110 |
| CD37 | GLAFVPLQI | 271 | ALAFVPLAV | 111 |
| CD37 | GLAFVPLQI | 271 | ALAFVPLSV | 112 |
| CD37 | GLAFVPLQI | 271 | ALAFVPLWL | 489 |
| CD37 | GLAFVPLQI | 271 | AMAFVPLAL | 490 |
| CD37 | GLAFVPLQI | 271 | FLAFVPLDV | 491 |
| CD37 | GLAFVPLQI | 271 | FLAFVPLIL | 113 |
| CD37 | GLAFVPLQI | 271 | FLAFVPLQL | 114 |
| CD37 | GLAFVPLQI | 271 | FLAFVPLVL | 115 |
| CD37 | GLAFVPLQI | 271 | FMAFVPLQL | 116 |
| CD37 | GLAFVPLQI | 271 | GMAFVPLLL | 117 |
| CD37 | GLAFVPLQI | 271 | HLAFVPLLV | 118 |
| CD37 | GLAFVPLQI | 271 | ILAFVPLYL | 119 |
| CD37 | GLAFVPLQI | 271 | IMAFVPLAV | 120 |
| CD37 | GLAFVPLQI | 271 | IMAFVPLIV | 121 |
| CD37 | GLAFVPLQI | 271 | IMAFVPLVV | 122 |
| CD37 | GLAFVPLQI | 271 | LLAFVPLAL | 123 |
| CD37 | GLAFVPLQI | 271 | LLAFVPLDV | 124 |
| CD37 | GLAFVPLQI | 271 | LLAFVPLML | 125 |
| CD37 | GLAFVPLQI | 271 | LLAFVPLPL | 492 |
| CD37 | GLAFVPLQI | 271 | LLAFVPLSL | 126 |
| CD37 | GLAFVPLQI | 271 | LMAFVPLTL | 127 |
| CD37 | GLAFVPLQI | 271 | TLAFVPLAV | 128 |
| CD37 | GLAFVPLQI | 271 | VLAFVPLGV | 493 |
| CD37 | GLAFVPLQI | 271 | VLAFVPLLV | 129 |

TABLE 1A-continued

HLA-A*02 Antigenic peptides according to the invention.

| Tumor antigen | Sequence human reference peptide | SEQ ID NO. human reference peptide | Sequence antigenic peptide | SEQ ID NO. antigenic peptide |
|---|---|---|---|---|
| CD37 | GLAFVPLQI | 271 | VMAFVPLVV | 130 |
| CD37 | GLYFGMLLL | 272 | FLYFGMLLL | 131 |
| CD37 | GLYFGMLLL | 272 | GLYFGMLHM | 132 |
| CD37 | GLYFGMLLL | 272 | LLYFGMLGL | 133 |
| CD37 | GLYFGMLLL | 272 | LLYFGMLLL | 134 |
| CD37 | GLYFGMLLL | 272 | TMYFGMLYL | 135 |
| CD37 | GLYFGMLLL | 272 | VLYFGMLLI | 136 |
| CD37 | ILIDKTSFV | 273 | CLIDKTSVV | 137 |
| CD37 | ILIDKTSFV | 273 | FLIDKTSAA | 138 |
| CD37 | ILIDKTSFV | 273 | ILIDKTSGA | 139 |
| CD37 | ILIDKTSFV | 273 | ILIDKTSGV | 140 |
| CD37 | ILIDKTSFV | 273 | IMIDKTSTV | 141 |
| CD37 | ILIDKTSFV | 273 | VIIDKTSSV | 142 |
| CD37 | ILIDKTSFV | 273 | VLIDKTSQL | 143 |
| CD37 | ILIDKISFV | 273 | VLIDKTSSV | 144 |
| CD37 | ILIDKTSFV | 273 | YLIDKISNI | 145 |
| CD37 | ILIDKTSFV | 273 | YLIDKTSNL | 146 |
| CD37 | ILIDKTSFV | 273 | YLIDKTSTV | 147 |
| CD37 | LLLLFATQI | 274 | FILLFATHV | 148 |
| CD37 | LLLLFATQI | 274 | FLLLFATSV | 149 |
| CD37 | LLLLFATQI | 274 | LLLLFATAV | 150 |
| CD37 | LLLLFATQI | 274 | LLLLFATSV | 151 |
| CD37 | LLLLFATQI | 274 | LMLLFATSV | 152 |
| CD37 | LLLLFATQI | 274 | MMLLFATLL | 153 |
| CD37 | LLLLFATQI | 274 | YLLLFATNV | 154 |
| CD37 | LLLLFATQI | 274 | YLLLFATYL | 155 |
| CD37 | SIVGICLGV | 275 | ILVGICLGV | 156 |
| CD37 | SIVGICLGV | 275 | SIVGICLNV | 157 |
| CD37 | SLIKYFLFV | 276 | KLIKYFLKV | 158 |
| CD37 | SLIKYFLFV | 276 | KLIKYFLVV | 159 |
| CD37 | SLIKYFLFV | 276 | MMIKYFLCV | 160 |
| CD37 | SLIKYFLFV | 276 | NLIKYFLYV | 161 |
| CD37 | SLIKYFLFV | 276 | SLIKYFLSI | 162 |
| TNFRSF13C | ALVLALVLV | 277 | ALVLALVGV | 163 |
| TNFRSF13C | ALVLALVLV | 277 | ALVLALVPV | 164 |
| TNFRSF13C | ALVLALVLV | 277 | GLVLALVGV | 165 |

TABLE 1A-continued

HLA-A*02 Antigenic peptides according to the invention.

| Tumor antigen | Sequence human reference peptide | SEQ ID NO. human reference peptide | Sequence antigenic peptide | SEQ ID NO. antigenic peptide |
|---|---|---|---|---|
| TNFRSF13C | ALVLALVLV | 277 | NLVLALVEV | 166 |
| TNFRSF13C | ALVLALVLV | 277 | SLVLALVGV | 167 |
| TNFRSF13C | ALVLALVLV | 277 | SLVLALVSV | 168 |
| TNFRSF13C | ALVLALVLV | 277 | SLVLALVYV | 169 |
| TNFRSF13C | ALVLALVLV | 277 | TLVLALVSV | 170 |
| TNFRSF13C | GLALVLALV | 278 | ALALVLALL | 171 |
| TNFRSF13C | GLALVLALV | 278 | ALALVLAML | 172 |
| TNFRSF13C | GLALVLALV | 278 | ALALVLATV | 173 |
| TNFRSF13C | GLALVLALV | 278 | FLALVLAAA | 174 |
| TNFRSF13C | GLALVLALV | 278 | FLALVLAAL | 175 |
| TNFRSF13C | GLALVLALV | 278 | FLALVLAGL | 176 |
| TNFRSF13C | GLALVLALV | 278 | FLALVLAGV | 177 |
| TNFRSF13C | GLALVLALV | 278 | FLALVLALL | 178 |
| TNFRSF13C | GLALVLALV | 278 | FLALVLAML | 179 |
| TNFRSF13C | GLALVLALV | 278 | FLALVLATL | 180 |
| TNFRSF13C | GLALVLALV | 278 | GLALVLAAI | 181 |
| TNFRSF13C | GLALVLALV | 278 | GLALVLAAL | 182 |
| TNFRSF13C | GLALVLALV | 278 | GLALVLAAV | 183 |
| TNFRSF13C | GLALVLALV | 278 | GLALVLALL | 184 |
| TNFRSF13C | GLALVLALV | 278 | GLALVLALV | 185 |
| TNFRSF13C | GLALVLALV | 278 | GLALVLANI | 186 |
| TNFRSF13C | GLALVLALV | 278 | GLALVLATL | 187 |
| TNFRSF13C | GLALVLALV | 278 | GLALVLATV | 188 |
| TNFRSF13C | GLALVLALV | 278 | GLALVLAVV | 189 |
| TNFRSF13C | GLALVLALV | 278 | GMALVLAAV | 190 |
| TNFRSF13C | GLALVLALV | 278 | ILALVLAMV | 191 |
| TNFRSF13C | GLALVLALV | 278 | ILALVLARV | 192 |
| TNFRSF13C | GLALVLALV | 278 | ILALVLAYL | 193 |
| TNFRSF13C | GLALVLALV | 278 | KLALVLAML | 194 |
| TNFRSF13C | GLALVLALV | 278 | LLALVLAEV | 195 |
| TNFRSF13C | GLALVLALV | 278 | MLALVLAGL | 196 |
| TNFRSF13C | GLALVLALV | 278 | SLALVLALL | 197 |
| TNFRSF13C | GLALVLALV | 278 | SLALVLALV | 198 |
| TNFRSF13C | GLALVLALV | 278 | SLALVLAML | 199 |
| TNFRSF13C | GLALVLALV | 278 | VLALVLAEL | 200 |
| TNFRSF13C | GLALVLALV | 278 | VLALVLAEV | 201 |
| TNFRSF13C | GLALVLALV | 278 | VLALVLAGV | 202 |
| TNFRSF13C | GLALVLALV | 278 | VLALVLALV | 203 |
| TNFRSF13C | GLALVLALV | 278 | VLALVLAMV | 204 |
| TNFRSF13C | GLALVLALV | 278 | VLALVLATV | 205 |
| TNFRSF13C | GLALVLALV | 278 | YLALVLAFL | 206 |
| TNFRSF13C | GLALVLALV | 278 | YLALVLALI | 207 |
| TNFRSF13C | GLALVLALV | 278 | YLALVLALL | 208 |
| TNFRSF13C | GLALVLALV | 278 | YLALVLAML | 209 |
| TNFRSF13C | LLFGAPALL | 279 | ALFGAPAAA | 494 |
| TNFRSF13C | LLFGAPALL | 279 | ALFGAPAAV | 210 |
| TNFRSF13C | LLFGAPALL | 279 | ALFGAPAKL | 211 |
| TNFRSF13C | LLFGAPALL | 279 | FLFGAPASA | 212 |
| TNFRSF13C | LLFGAPALL | 279 | GLFGAPAFI | 213 |
| TNFRSF13C | LLFGAPALL | 279 | ILFGAPAGA | 495 |
| TNFRSF13C | LLFGAPALL | 279 | LLFGAPAAL | 214 |
| TNFRSF13C | LLFGAPALL | 279 | LLFGAPAGI | 215 |
| TNFRSF13C | LLFGAPALL | 279 | LLFGAPAGL | 216 |
| TNFRSF13C | LLFGAPALL | 279 | LLFGAPAGV | 217 |
| TNFRSF13C | LLFGAPALL | 279 | LLFGAPALL | 218 |
| TNFRSF13C | LLFGAPALL | 279 | LMFGAPAFV | 219 |
| TNFRSF13C | LLFGAPALL | 279 | LMFGAPALV | 220 |
| TNFRSF13C | LLFGAPALL | 279 | MLFGAPAEA | 221 |
| TNFRSF13C | LLFGAPALL | 279 | NMFGAPAQV | 496 |
| TNFRSF13C | LLFGAPALL | 279 | SLFGAPATA | 497 |
| TNFRSF13C | LLFGAPALL | 279 | SMFGAPAHV | 222 |
| TNFRSF13C | LLFGAPALL | 279 | TLFGAPAAA | 498 |
| TNFRSF13C | LLFGAPALL | 279 | VIFGAPALV | 499 |
| TNFRSF13C | LLFGAPALL | 279 | VLFGAPAGI | 500 |
| TNFRSF13C | LLFGAPALL | 279 | VLFGAPANL | 223 |
| TNFRSF13C | LLFGAPALL | 279 | VLFGAPAYL | 224 |
| TNFRSF13C | LLFGAPALL | 279 | YLFGAPAAA | 225 |
| TNFRSF13C | PLPGLLFGA | 280 | FLPGLLFSV | 226 |
| TNFRSF13C | PLPGLLFGA | 280 | FMPGLLEGA | 227 |
| TNFRSF13C | PLPGLLFGA | 280 | FVPGLLFGV | 228 |
| TNFRSF13C | PLPGLLFGA | 280 | GLPGLLFEL | 229 |
| TNFRSF13C | PLPGLLFGA | 280 | ILPGLLFAI | 230 |

TABLE 1A-continued

HLA-A*02 Antigenic peptides according to the invention.

| Tumor antigen | Sequence human reference peptide | SEQ ID NO. human reference peptide | Sequence antigenic peptide | SEQ ID NO. antigenic peptide |
|---|---|---|---|---|
| TNFRSF13C | PLPGLLFGA | 280 | ILPGLLFGL | 231 |
| TNFRSF13C | PLPGLLFGA | 280 | ILPGLLFLI | 232 |
| TNFRSF13C | PLPGLLFGA | 280 | ILPGLLFSL | 233 |
| TNFRSF13C | PLPGLLFGA | 280 | ILPGLLFYI | 234 |
| TNFRSF13C | PLPGLLFGA | 280 | ILPGLLFYM | 235 |
| TNFRSF13C | PLPGLLFGA | 280 | IMPGLLFHI | 236 |
| TNFRSF13C | PLPGLLFGA | 280 | IMPGLLFQV | 237 |
| TNFRSF13C | PLPGLLFGA | 280 | IMPGLLFYV | 238 |
| TNFRSF13C | PLPGLLFGA | 280 | KLPGLLFHA | 239 |
| TNFRSF13C | PLPGLLFGA | 280 | KLPGLLFSV | 240 |
| TNFRSF13C | PLPGLLFGA | 280 | LLPGLLFGL | 241 |
| TNFRSF13C | PLPGLLFGA | 280 | LLPGLLFTL | 242 |
| TNFRSF13C | PLPGLLFGA | 280 | LLPGLLFVV | 243 |
| TNFRSF13C | PLPGLLFGA | 280 | MLPGLLFAL | 244 |
| TNFRSF13C | PLPGLLFGA | 280 | MLPGLLFGL | 245 |
| TNFRSF13C | PLPGLLFGA | 280 | MLPGLLFKV | 246 |

TABLE 1A-continued

HLA-A*02 Antigenic peptides according to the invention.

| Tumor antigen | Sequence human reference peptide | SEQ ID NO. human reference peptide | Sequence antigenic peptide | SEQ ID NO. antigenic peptide |
|---|---|---|---|---|
| TNFRSF13C | PLPGLLFGA | 280 | MLPGLLFVV | 247 |
| TNFRSF13C | PLPGLLFGA | 280 | PLPGLLFSV | 248 |
| TNFRSF13C | PLPGLLFGA | 280 | RMPGLLFKV | 249 |
| TNFRSF13C | PLPGLLFGA | 280 | SLPGLLFFL | 250 |
| TNFRSF13C | PLPGLLFGA | 280 | SLPGLLFTL | 251 |
| TNFRSF13C | PLPGLLFGA | 280 | SLPGLLFVV | 252 |
| TNFRSF13C | PLPGLLFGA | 280 | TLPGLLFPA | 253 |
| TNFRSF13C | PLPGLLFGA | 280 | TLPGLLFPV | 254 |
| TNFRSF13C | PLPGLLFGA | 280 | VLPGLLFGV | 255 |
| TNFRSF13C | PLPGLLFGA | 280 | VLPGLLFYV | 256 |
| TNFRSF13C | PLPGLLFGA | 280 | YLPGLLFLM | 257 |

Table 1B below provides an overview over the consensus sequences (MHC Class I Consensus Sequence) of the antigenic peptides according to the present inventions with their amino acid sequences and SEQ ID NOs and with the corresponding fragment/epitope of a human tumor antigen (also referred to herein as "human reference peptide") as well as to their core sequence.

TABLE 1B

MHC Class I Consensus Sequences of the antigenic peptides according to the invention.

| Tumor antigen | Sequence human reference peptide | SEQ ID NO. human reference peptide | Core sequence | SEQ ID NO. core sequence | MHC Class I consensus sequence | SEQ ID NO. consensus sequence |
|---|---|---|---|---|---|---|
| CD19 | FLLFLTPME | 258 | LFLTP | 281 | XXLFLTPXX | 304 |
| CD19 | KLSLGLPGL | 259 | SLGLP | 282 | XXSLGLPXX | 305 |
| CD19 | SLVGILHLQ | 260 | VGILH | 283 | XXVGILHXX | 306 |
| CD19 | TLAYLIFCL | 261 | AYLIF | 284 | XXAYLIFXX | 307 |
| CD19 | QQMGGFYLC | 262 | MGGFY | 285 | XXMGGFYXX | 308 |
| CD20 | IALGGLLMI | 263 | LGGLL | 286 | XXLGGLLXX | 309 |
| CD20 | IMNSLSLFA | 264 | NSLSL | 287 | XXNSLSLXX | 310 |
| CD20 | LMIPAGIYA | 265 | IPAGI | 288 | XXIPAGIXX | 311 |
| CD20 | SLFLGILSV | 266 | FLGIL | 289 | XXFLGILXX | 312 |
| CD22 | FLSNDTVQL | 267 | SNDTV | 290 | XXSNDTVXX | 313 |
| CD22 | HLLGPWLLL | 268 | LGPWL | 291 | XXLGPWLXX | 314 |
| CD22 | ILILAICGL | 269 | ILAIC | 292 | XXILAICXX | 315 |
| CD22 | WVFEHPETL | 270 | FEHPE | 293 | XXFEHPEXX | 316 |
| CD37 | GLAFVPLQI | 271 | AFVPL | 294 | XXAFVPLXX | 317 |

TABLE 1B-continued

MHC Class I Consensus Sequences of the antigenic peptides according to the invention.

| Tumor antigen | Sequence human reference peptide | SEQ ID NO. human reference peptide | Core sequence | SEQ ID NO. core sequence | MHC Class I consensus sequence | SEQ ID NO. consensus sequence |
|---|---|---|---|---|---|---|
| CD37 | GLYFGMLLL | 272 | YFGML | 295 | XXYFGMLXX | 318 |
| CD37 | ILIDKTSFV | 273 | IDKTS | 296 | XXIDKTSXX | 319 |
| CD37 | LLLLFATQI | 274 | LLFAT | 297 | XXLLFATXX | 320 |
| CD37 | SIVGICLGV | 275 | VGICL | 298 | XXVGICLXX | 321 |
| CD37 | SLIKYFLFV | 276 | IKYFL | 299 | XXIKYFLXX | 322 |
| TNFRSF13C | ALVLALVLV | 277 | VLALV | 300 | XXVLALVXX | 323 |
| TNFRSF13C | GLALVLALV | 278 | ALVLA | 301 | XXALVLAXX | 324 |
| TNFRSF13C | LLFGAPALL | 279 | FGAPA | 302 | XXFGAPAXX | 325 |
| TNFRSF13C | PLPGLLFGA | 280 | PGLLF | 303 | XXPGLLFXX | 326 |

Table 1C below provides an overview over the HLA-A*02 consensus sequences of the antigenic peptides according to the present inventions with their amino acid sequences and SEQ ID NOs and with the corresponding core sequence of a human tumor antigen. Table 1C also provides information to which core sequence and HLA-A*02 consensus sequence each antigenic peptide according to the present invention relates.

Accordingly, the antigenic peptide may comprise or consist of an amino acid sequence as set forth in any one of SEQ ID NOs 309-326. In some embodiments, the antigenic peptide comprises or consists of an amino acid sequence as set forth in any one of SEQ ID Nos 316, 304-315 and 317-472 and 501-509, preferably as set forth in any one of SEQ ID Nos 316, 304-315 and 317-326.

TABLE 1C

HLA-A*02 Consensus Sequences of the antigenic peptides according to the invention.

| Tumor antigen | Core sequence | SEQ ID NO. core sequence | HLA-A*02 consensus sequence | SEQ ID NO. consensus sequence | SEQ ID NO. antigenic peptide |
|---|---|---|---|---|---|
| CD19 | LFLTP | 281 | FLLFLTPXL | 327 | 1-2 |
| CD19 | LFLTP | 281 | FXLFLTPXX | 328 | 1-3 |
| CD19 | LFLTP | 281 | GLLFLTPXX | 329 | 4-6 |
| CD19 | LFLTP | 281 | TLLFLTPXX | 330 | 9-10 |
| CD19 | LFLTP | 281 | XLLFLTPLL | 331 | 2, 5, 7-8 |
| CD19 | LFLTP | 281 | XLLFLTPML | 332 | 10-11 |
| CD19 | LFLTP | 281 | XLLFLTPXL | 333 | 1-2, 5, 7-8, 10-12 |
| CD19 | SLGLP | 282 | ALSLGLPXL | 334 | 13-17 |
| CD19 | SLGLP | 282 | AMSLGLPXL | 335 | 18-19 |
| CD19 | SLGLP | 282 | FLSLGLPXL | 336 | 20-21 |
| CD19 | SLGLP | 282 | LLSLGLPXL | 337 | 24-25 |
| CD19 | SLGLP | 282 | SLSLGLPXL | 338 | 28-29 |
| CD19 | SLGLP | 282 | VLSLGLPXX | 339 | 30-32 |
| CD19 | SLGLP | 282 | XLSLGLPGL | 340 | 13, 25, 27 |
| CD19 | SLGLP | 282 | XLSLGLPIL | 341 | 20, 22, 26, 28, 33 |

TABLE 1C-continued

HLA-A*02 Consensus Sequences of the antigenic peptides according to the invention.

| Tumor antigen | Core sequence | SEQ ID NO. core sequence | HLA-A*02 consensus sequence | SEQ ID NO. consensus sequence | SEQ ID NO. antigenic peptide |
|---|---|---|---|---|---|
| CD19 | SLGLP | 282 | XLSLGLPKL | 342 | 21, 29 |
| CD19 | SLGLP | 282 | XLSLGLPXL | 343 | 13-17, 20-30, 33 |
| CD19 | VGILH | 283 | XLVGILHXX | 344 | 34-35 |
| CD19 | AYLIF | 284 | FLAYLIFXL | 345 | 36-37 |
| CD19 | AYLIF | 284 | XLAYLIFXL | 346 | 36-39 |
| CD20 | LGGLL | 286 | ALLGGLLXX | 347 | 42-43 |
| CD20 | LGGLL | 286 | AXLGGLLLI | 348 | 41, 43 |
| CD20 | LGGLL | 286 | FXLGGLLXV | 349 | 44, 46 |
| CD20 | LGGLL | 286 | GMLGGLLXX | 350 | 47-48 |
| CD20 | LGGLL | 286 | XLLGGLLXI | 351 | 51-52 |
| CD20 | LGGLL | 286 | SLLGGLLXX | 352 | 56-57 |
| CD20 | LGGLL | 286 | SXLGGLLLI | 353 | 55-56, 58 |
| CD20 | LGGLL | 286 | YXLGGLLMV | 354 | 61, 64 |
| CD20 | LGGLL | 286 | YXLGGLLXV | 355 | 60-61, 64 |
| CD20 | LGGLL | 286 | XLLGGLLLI | 356 | 42, 45, 51-52, 54 |
| CD20 | LGGLL | 286 | XMLGGLLLI | 357 | 47, 58, 62 |
| CD20 | LGGLL | 286 | XXLGGLLMI | 358 | 53, 59, 63 |
| CD20 | LGGLL | 286 | XXLGGLLML | 359 | 43, 48, 57 |
| CD20 | LGGLL | 286 | XXLGGLLMV | 360 | 46, 49, 61, 64 |
| CD20 | NSLSL | 287 | AMNSLSLXX | 501 | 65, 476-477 |
| CD20 | NSLSL | 287 | ILNSLSLXX | 361 | 66-68, 479-480 |
| CD20 | NSLSL | 287 | XLNSLSLXL | 362 | 67-69 |
| CD20 | NSLSL | 287 | XMNSLSLLX | 502 | 476, 478, 483 |
| CD20 | NSLSL | 287 | XMNSLSLXI | 503 | 65, 483 |
| CD20 | NSLSL | 287 | XMNSLSLXI | 504 | 70, 476, 479 |
| CD20 | NSLSL | 287 | XMNSLSLXX | 363 | 65, 70, 476-477 |
| CD20 | NSLSL | 287 | XXNSLSLXI | 364 | 65-66, 479, 483-484 |
| CD20 | IPAGI | 288 | LLIPAGIXX | 365 | 73-77 |
| CD20 | IPAGI | 288 | MXIPAGIXX | 366 | 78-79 |
| CD20 | IPAGI | 288 | XLIPAGIXL | 367 | 71-72, 75, 77 |
| CD20 | IPAGI | 288 | XMIPAGIXX | 368 | 79-80 |
| CD20 | IPAGI | 288 | XXIPAGIAV | 369 | 73, 79 |
| CD20 | FLGIL | 289 | FLFLGILXL | 370 | 81-82 |
| CD20 | FLGIL | 289 | YLFLGILXL | 371 | 85-87 |
| CD20 | FLGIL | 289 | YLFLGILXX | 372 | 84-87 |
| CD20 | FLGIL | 289 | XLFLGILGL | 373 | 81, 85 |

TABLE 1C-continued

HLA-A*02 Consensus Sequences of the antigenic peptides according to the invention.

| Tumor antigen | Core sequence | SEQ ID NO. core sequence | HLA-A*02 consensus sequence | SEQ ID NO. consensus sequence | SEQ ID NO. antigenic peptide |
|---|---|---|---|---|---|
| CD20 | FLGIL | 289 | XLFLGILSX | 374 | 83, 86 |
| CD22 | SNDTV | 290 | FLSNDTVXL | 375 | 88-89 |
| CD22 | SNDTV | 290 | FLSNDTVXX | 376 | 88-90 |
| CD22 | SNDTV | 290 | FXSNDTVXX | 377 | 88-91 |
| CD22 | SNDTV | 290 | XMSNDTVXX | 378 | 91, 93, 95 |
| CD22 | SNDTV | 290 | XLSNDTVWL | 379 | 92, 96 |
| CD22 | SNDTV | 290 | XLSNDTVXL | 380 | 88-89, 92, 94, 96 |
| CD22 | LGPWL | 291 | XLLGPWLXL | 381 | 98, 100 |
| CD22 | LGPWL | 291 | XLLGPWLXV | 382 | 97, 99, 101 |
| CD22 | LGPWL | 291 | XLLGPWLXX | 383 | 97-101 |
| CD22 | ILAIC | 292 | IXILAICXV | 384 | 102-103 |
| CD22 | ILAIC | 292 | XLILAICGV | 385 | 102, 105 |
| CD22 | ILAIC | 292 | XLILAICGX | 386 | 102, 104-105 |
| CD22 | FEHPE | 293 | XIFEHPEXX | 387 | 106-107, 110, 486 |
| CD22 | FEHPE | 293 | XXFEHPELL | 388 | 106, 109 |
| CD22 | FEHPE | 293 | XXFEHPELX | 389 | 108-109 |
| CD22 | FEHPE | 293 | YXFEHPETX | 505 | 110, 488 |
| CD22 | FEHPE | 293 | YXFEHPEXX | 390 | 109-110, 488 |
| CD37 | AFVPL | 294 | ALAFVPLXV | 391 | 111-112 |
| CD37 | AFVPL | 294 | FLAFVPLXL | 392 | 113-115 |
| CD37 | AFVPL | 294 | FXAFVPLQL | 393 | 115-116 |
| CD37 | AFVPL | 294 | IMAFVPLXV | 394 | 120-122 |
| CD37 | AFVPL | 294 | LLAFVPLXL | 395 | 123, 125-126 |
| CD37 | AFVPL | 294 | LLAFVPLXX | 396 | 123-126 |
| CD37 | AFVPL | 294 | XMAFVPLXV | 397 | 120, 130 |
| CD37 | AFVPL | 294 | XMAFVPLXL | 398 | 116-117 |
| CD37 | AFVPL | 294 | XLAFVPLAV | 399 | 111, 128 |
| CD37 | AFVPL | 294 | XLAFVPLXV | 400 | 111-112, 118, 124, 128-129 |
| CD37 | AFVPL | 294 | XXAFVPLAV | 401 | 111, 120, 128 |
| CD37 | AFVPL | 294 | XXAFVPLXL | 402 | 114, 116-117, 119, 127 |
| CD37 | YFGML | 295 | LLYFGMLXL | 403 | 133-134 |
| CD37 | YFGML | 295 | XLYFGMLXL | 404 | 131, 133-134 |
| CD37 | YFGML | 295 | XLYFGMLXX | 405 | 131-134, 136 |
| CD37 | YFGML | 295 | XXLYFGMLXL | 406 | 131, 133-134, 136 |

TABLE 1C-continued

HLA-A*02 Consensus Sequences of the antigenic peptides according to the invention.

| Tumor antigen | Core sequence | SEQ ID NO. core sequence | HLA-A*02 consensus sequence | SEQ ID NO. consensus sequence | SEQ ID NO. antigenic peptide |
|---|---|---|---|---|---|
| CD37 | IDKTS | 296 | ILIDKTSGX | 407 | 139-140 |
| CD37 | IDKTS | 296 | IXIDKTSXV | 408 | 140-141 |
| CD37 | IDKTS | 296 | VLIDKTSXX | 409 | 143-144 |
| CD37 | IDKTS | 296 | VXIDKTSSV | 410 | 142, 144 |
| CD37 | IDKTS | 296 | YLIDKTSXX | 411 | 145-146 |
| CD37 | IDKTS | 296 | XLIDKTSXA | 412 | 138-139 |
| CD37 | IDKTS | 296 | XLIDKTSXV | 413 | 137, 147 |
| CD37 | IDKTS | 296 | XLIDKTSXX | 414 | 137-139, 143-146 |
| CD37 | LLFAT | 297 | FXLLFATXV | 415 | 148-149 |
| CD37 | LLFAT | 297 | LLLLFATXV | 416 | 150-151 |
| CD37 | LLFAT | 297 | LXLLFATXV | 417 | 150-152 |
| CD37 | LLFAT | 297 | YLLLFATXX | 418 | 154-155 |
| CD37 | LLFAT | 297 | XXLLFATSV | 419 | 149, 152 |
| CD37 | LLFAT | 297 | XMLLFATXX | 420 | 152-153 |
| CD37 | VGICL | 298 | XXVGICLXV | 421 | 156-157 |
| CD37 | IKYFL | 299 | KLIKYFLXV | 422 | 158-159 |
| CD37 | IKYFL | 299 | XLIKYFLXV | 423 | 158-159, 161 |
| CD37 | IKYFL | 299 | XLIKYFLXX | 424 | 158-159, 161-162 |
| CD37 | IKYFL | 299 | XXIKYFLXV | 425 | 158-161 |
| TNFRSF13C | VLALV | 300 | ALVLALVXV | 426 | 163-164 |
| TNFRSF13C | VLALV | 300 | SLVLALVXV | 427 | 167-169 |
| TNFRSF13C | VLALV | 300 | XLVLALVXV | 428 | 163-170 |
| TNFRSF13C | ALVLA | 301 | ALALVLAXL | 429 | 171-172 |
| TNFRSF13C | ALVLA | 301 | ALALVLAXX | 430 | 171-173 |
| TNFRSF13C | ALVLA | 301 | FLALVLAAX | 431 | 174-175 |
| TNFRSF13C | ALVLA | 301 | FLALVLAXL | 432 | 175-176, 178-180 |
| TNFRSF13C | ALVLA | 301 | GLALVLAXI | 433 | 181, 186 |
| TNFRSF13C | ALVLA | 301 | GLALVLAXL | 434 | 182, 184, 187 |
| TNFRSF13C | ALVLA | 301 | GLALVLAXV | 435 | 183, 185, 188-190 |
| TNFRSF13C | ALVLA | 301 | GXALVLAVV | 436 | 189-190 |
| TNFRSF13C | ALVLA | 301 | SLALVLALX | 437 | 197-198 |
| TNFRSF13C | ALVLA | 301 | VLALVLAEX | 438 | 200-201 |
| TNFRSF13C | ALVLA | 301 | VLALVLAXV | 439 | 201-205 |
| TNFRSF13C | ALVLA | 301 | YLALVLAXL | 440 | 206, 208-209 |
| TNFRSF13C | ALVLA | 301 | XLALVLAEV | 441 | 195, 201 |
| TNFRSF13C | ALVLA | 301 | XLALVLALL | 442 | 171, 178, 184 |

TABLE 1C-continued

HLA-A*02 Consensus Sequences of the antigenic peptides according to the invention.

| Tumor antigen | Core sequence | SEQ ID NO. core sequence | HLA-A*02 consensus sequence | SEQ ID NO. consensus sequence | SEQ ID NO. antigenic peptide |
|---|---|---|---|---|---|
| TNFRSF13C | ALVLA | 301 | XLALVLAML | 443 | 172, 179, 194 |
| TNFRSF13C | ALVLA | 301 | XLALVLAXL | 444 | 171-172, 175-176, 178-180, 187, 208-209 |
| TNFRSF13C | ALVLA | 301 | XLALVLAXI | 445 | 181, 186, 207 |
| TNFRSF13C | ALVLA | 301 | XLALVLAXV | 446 | 173, 191-192, 198, 201-204 |
| TNFRSF13C | FGAPA | 302 | ALFGAPAAX | 506 | 210, 494 |
| TNFRSF13C | FGAPA | 302 | ALFGAPAXX | 447 | 210-211, 494 |
| TNFRSF13C | FGAPA | 302 | LLFGAPAXL | 448 | 214, 216, 218 |
| TNFRSF13C | FGAPA | 302 | LLFGAPAGX | 449 | 215-217 |
| TNFRSF13C | FGAPA | 302 | LMFGAPAXV | 450 | 219-220 |
| TNFRSF13C | FGAPA | 302 | VLFGAPAXL | 451 | 223-224 |
| TNFRSF13C | FGAPA | 302 | VLFGAPAXX | 507 | 223-224, 500 |
| TNFRSF13C | FGAPA | 302 | XLFGAPAAA | 508 | 225, 494, 498 |
| TNFRSF13C | FGAPA | 302 | XLFGAPAXA | 452 | 212, 221, 225, 494, 498 |
| TNFRSF13C | FGAPA | 302 | XLFGAPAXI | 453 | 213, 215 |
| TNFRSF13C | FGAPA | 302 | XMFGAPAXV | 454 | 219-220, 222, 496 |
| TNFRSF13C | FGAPA | 302 | XMFGAPALV | 509 | 220, 496 |
| TNFRSF13C | FGAPA | 302 | XXFGAPAXV | 455 | 210, 217, 219-220, 222 |
| TNFRSF13C | PGLLF | 303 | FXPGLLFXV | 456 | 226, 228 |
| TNFRSF13C | PGLLF | 303 | ILPGLLFYX | 457 | 234-325 |
| TNFRSF13C | PGLLF | 303 | ILPGLLFXI | 458 | 230, 232, 234 |
| TNFRSF13C | PGLLF | 303 | ILPGLLFXL | 459 | 231, 233 |
| TNFRSF13C | PGLLF | 303 | IMPGLLFXX | 460 | 236-238 |
| TNFRSF13C | PGLLF | 303 | KLPGLLFXX | 461 | 239-240 |
| TNFRSF13C | PGLLF | 303 | LLPGLLFXX | 462 | 241-243 |
| TNFRSF13C | PGLLF | 303 | MLPGLLFXX | 463 | 244-247 |
| TNFRSF13C | PGLLF | 303 | SLPGLLFXX | 464 | 250-252 |
| TNFRSF13C | PGLLF | 303 | TLPGLLFPX | 465 | 253-254 |
| TNFRSF13C | PGLLF | 303 | VLPGLLFXV | 466 | 255-256 |
| TNFRSF13C | PGLLF | 303 | XMPGLLFXX | 467 | 227, 236-238, 249 |
| TNFRSF13C | PGLLF | 303 | XLPGLLFSV | 468 | 226, 240, 248 |
| TNFRSF13C | PGLLF | 303 | XLPGLLFVV | 469 | 243, 247, 252 |
| TNFRSF13C | PGLLF | 303 | XLPGLLFXM | 470 | 235, 257 |

TABLE 1C-continued

| HLA-A*02 Consensus Sequences of the antigenic peptides according to the invention. | | | | | |
|---|---|---|---|---|---|
| Tumor antigen | Core sequence | SEQ ID NO. core sequence | HLA-A*02 consensus sequence | SEQ ID NO. consensus sequence | SEQ ID NO. antigenic peptide |
| TNFRSF13C | PGLLF | 303 | XLPGLLFXL | 471 | 229, 231, 241-242, 250-251 |
| TNFRSF13C | PGLLF | 303 | XLPGLLFXV | 472 | 226, 240, 246-248, 252, 254-256 |

As can be retrieved from Tables 1A-1C the antigenic peptides according to the present invention can be categorized according to the respective human tumor antigen, to the respective core sequence and to the respective MHC Class I and/or HLA-A*02 Consensus Sequences.

Accordingly, the antigenic peptide may comprise a (core) sequence according to any one of SEQ ID NOs 281-303. Preferably, the antigenic peptide comprises a (core) sequence according to any one of SEQ ID NOs 281, 283-289, 293, 294, 302 and 303. More preferably, the antigenic peptide comprises a (core) sequence according to any one of SEQ ID NOs 283, 287, 293, 294, 302 and 303. Even more preferably, the antigenic peptide comprises a (core) sequence according to any one of SEQ ID NOs 287, 293, 294 and 302.

In one embodiment, the antigenic peptide according to the present invention is a sequence variant of a fragment of the tumor antigen CD19 (human reference peptide), such as "FLLFLTPME" (SEQ ID NO: 258), "KLSLGLPGL" (SEQ ID NO: 259), "SLVGILHLQ" (SEQ ID NO: 260), "TLAYLIFCL" (SEQ ID NO: 261) or "QQMGGFYLC" (SEQ ID NO: 262). In a preferred embodiment, the antigenic peptide according to the present invention is a sequence variant of a fragment of the tumor antigen CD19, such as antigenic peptides having a core sequence consisting of an amino acid sequence as set forth in any one of SEQ ID NOs 281-285. Accordingly, the antigenic peptide according to the present invention is a sequence variant of a fragment of the tumor antigen CD19 comprising or consisting of an MHC Class I Consensus Sequence as set forth in any one of SEQ ID Nos 304-308. In a particular embodiment, the antigenic peptide according to the present invention is a sequence variant of a fragment of the tumor antigen CD19 that bind to a particular HLA molecule (HLA-A2*02), such as an antigenic peptide comprising or consisting of an HLA-A2*02 Consensus Sequence as set forth in any one of SEQ ID Nos 327-346. More preferably, the antigenic peptide according to the present invention is a microbiota sequence variant of a fragment of the tumor antigen CD19, such as antigenic peptides comprising or consisting of an amino acid sequence as set forth in any one of SEQ ID NOs 1-40. More preferably, the antigenic peptide according to the present invention is a sequence variant of the CD19 fragment (human reference peptide) "FLLFLTPME" (SEQ ID NO: 258), such as an antigenic peptide comprising or consisting of an amino acid sequence as set forth in SEQ ID NO: 1-12, 304, and 327-333, e.g. an antigenic peptide comprising or consisting of an amino acid sequence as set forth in SEQ ID NO: 10. It is also more preferred that the antigenic peptide according to the present invention is a sequence variant of the CD19 fragment (human reference peptide) "KLSLGLPGL" (SEQ ID NO: 259), such as an antigenic peptide comprising or consisting of an amino acid sequence as set forth in SEQ ID NO: 13-33, 305 and 334-343. It is also more preferred that the antigenic peptide according to the present invention is a sequence variant of the CD19 fragment (human reference peptide) "SLVGILHLQ" (SEQ ID NO: 260), such as an antigenic peptide comprising or consisting of an amino acid sequence as set forth in SEQ ID NO: 34-35, 306 and 344, e.g. an antigenic peptide comprising or consisting of an amino acid sequence as set forth in SEQ ID NO: 34 or 35. It is also more preferred that the antigenic peptide according to the present invention is a sequence variant of the CD19 fragment (human reference peptide) "TLAYLIFCL" (SEQ ID NO: 261), such as an antigenic peptide comprising or consisting of an amino acid sequence as set forth in SEQ ID NO: 36-39, 307 and 345-346, e.g. an antigenic peptide comprising or consisting of an amino acid sequence as set forth in SEQ ID NO: 39. It is also more preferred that the antigenic peptide according to the present invention is a sequence variant of the CD19 fragment (human reference peptide) "QQMGGFYLC" (SEQ ID NO: 262), such as an antigenic peptide comprising or consisting of an amino acid sequence as set forth in SEQ ID NO: 40 and 308, e.g. an antigenic peptide comprising or consisting of an amino acid sequence as set forth in SEQ ID NO: 40.

In one embodiment, the antigenic peptide according to the present invention is a sequence variant of a fragment of the tumor antigen CD20 (MS4A1; human reference peptide), such as "IALGGLLMI" (SEQ ID NO: 263), "IMNSLSLFA" (SEQ ID NO: 264), "LMIPAGIYA" (SEQ ID NO: 265) or "SLFLGILSV" (SEQ ID NO: 266). In a preferred embodiment, the antigenic peptide according to the present invention is a sequence variant of a fragment of the tumor antigen CD20, such as antigenic peptides having a core sequence consisting of an amino acid sequence as set forth in any one of SEQ ID NOs 286-289. Accordingly, the antigenic peptide according to the present invention is a sequence variant of a fragment of the tumor antigen CD20 comprising or consisting of an MHC Class I Consensus Sequence as set forth in any one of SEQ ID Nos 309-312. In a particular embodiment, the antigenic peptide according to the present invention is a sequence variant of a fragment of the tumor antigen CD20 that bind to a particular HLA molecule (HLA-A2*02), such as an antigenic peptide comprising or consisting of an HLA-A2*02 Consensus Sequence as set forth in any one of SEQ ID Nos 347-374. More preferably, the antigenic peptide according to the present invention is a microbiota sequence variant of a fragment of the tumor antigen CD20, such as antigenic peptides comprising or consisting of an amino acid sequence as set forth in any one of SEQ ID NOs 41-87. More preferably, the antigenic peptide according to the present invention is a sequence variant of the CD20 fragment (human reference peptide) “IALGGLLMI” (SEQ ID NO: 263), such as an antigenic peptide comprising or consisting of an amino acid sequence as set forth in SEQ ID NO: 41-64, 309, and 347-360, e.g. an antigenic peptide comprising or consisting of an amino acid sequence as set forth in SEQ ID NO: 61. It is also more preferred that the antigenic peptide according to the present invention is a sequence variant of the CD20 fragment (human reference peptide) “IMNSLSLFA” (SEQ ID NO: 264), such as an antigenic peptide comprising or consisting of an amino acid sequence as set forth in SEQ ID NO: 65-70, 310 and 361-364 and 476-484, e.g. an antigenic peptide comprising or consisting of an amino acid sequence as set forth in any one of SEQ ID NO: 65, 68, 70 and 477. It is also more preferred that the antigenic peptide according to the present invention is a sequence variant of the CD20 fragment (human reference peptide) “LMIPAGIYA” (SEQ ID NO: 265), such as an antigenic peptide comprising or consisting of an amino acid sequence as set forth in SEQ ID NO: 71-80, 311 and 365-369, e.g. an antigenic peptide comprising or consisting of an amino acid sequence as set forth in SEQ ID NO: 72. It is also more preferred that the antigenic peptide according to the present invention is a sequence variant of the CD20 fragment (human reference peptide) “SLFLGILSV” (SEQ ID NO: 266), such as an antigenic peptide comprising or consisting of an amino acid sequence as set forth in SEQ ID NO: 81-87, 312 and 370-374, e.g. an antigenic peptide comprising or consisting of an amino acid sequence as set forth in SEQ ID NO: 86.

In one embodiment, the antigenic peptide according to the present invention is a sequence variant of a fragment of the tumor antigen CD22 (human reference peptide), such as “FLSNDTVQL” (SEQ ID NO: 267), “HLLGPWLLL” (SEQ ID NO: 268), “ILILAICGL” (SEQ ID NO: 269) or “WVFEHPETL” (SEQ ID NO: 270). In a preferred embodiment, the antigenic peptide according to the present invention is a sequence variant of a fragment of the tumor antigen CD22, such as antigenic peptides having a core sequence consisting of an amino acid sequence as set forth in any one of SEQ ID NOs 290-293. Accordingly, the antigenic peptide according to the present invention is a sequence variant of a fragment of the tumor antigen CD22 comprising or consisting of an MHC Class I Consensus Sequence as set forth in any one of SEQ ID Nos 313-316. In a particular embodiment, the antigenic peptide according to the present invention is a sequence variant of a fragment of the tumor antigen CD22 that bind to a particular HLA molecule (HLA-A2*02), such as an antigenic peptide comprising or consisting of an HLA-A2*02 Consensus Sequence as set forth in any one of SEQ ID Nos 375-390. More preferably, the antigenic peptide according to the present invention is a microbiota sequence variant of a fragment of the tumor antigen CD22, such as antigenic peptides comprising or consisting of an amino acid sequence as set forth in any one of SEQ ID NOs 88-110. More preferably, the antigenic peptide according to the present invention is a sequence variant of the CD22 fragment (human reference peptide) FLSNDTVQL" (SEQ ID NO: 267), such as an antigenic peptide comprising or consisting of an amino acid sequence as set forth in SEQ ID NO: 88-96, 313, and 375-380. It is also more preferred that the antigenic peptide according to the present invention is a sequence variant of the CD22 fragment (human reference peptide) “HLLGPWLLL” (SEQ ID NO: 268), such as an antigenic peptide comprising or consisting of an amino acid sequence as set forth in SEQ ID NO: 97-101, 314 and 381-383. It is also more preferred that the antigenic peptide according to the present invention is a sequence variant of the CD22 fragment (human reference peptide) “ILILAICGL” (SEQ ID NO: 269), such as an antigenic peptide comprising or consisting of an amino acid sequence as set forth in SEQ ID NO: 102-105, 315 and 384-386. It is also more preferred that the antigenic peptide according to the present invention is a sequence variant of the CD22 fragment (human reference peptide) “WVFEHPETL” (SEQ ID NO: 270), such as an antigenic peptide comprising or consisting of an amino acid sequence as set forth in SEQ ID NO: 106-110, 316 and 387-390 and 485-488, e.g. an antigenic peptide comprising or consisting of an amino acid sequence as set forth in any one of SEQ ID NO: 107, 108, 109 and 110.

In one embodiment, the antigenic peptide according to the present invention is a sequence variant of a fragment of the tumor antigen CD37 (human reference peptide), such as “GLAFVPLQI” (SEQ ID NO: 271), “GLYFGMLLL” (SEQ ID NO: 272), “ILILAICGL” (SEQ ID NO: 273), “LLLLFATQI” (SEQ ID NO: 274), “SIVGICLGV” (SEQ ID NO: 275) or “SLIKYFLFV” (SEQ ID NO: 276). In a preferred embodiment, the antigenic peptide according to the present invention is a sequence variant of a fragment of the tumor antigen CD37, such as antigenic peptides having a core sequence consisting of an amino acid sequence as set forth in any one of SEQ ID NOs 294-299. Accordingly, the antigenic peptide according to the present invention is a sequence variant of a fragment of the tumor antigen CD37 comprising or consisting of an MHC Class I Consensus Sequence as set forth in any one of SEQ ID Nos 317-322. In a particular embodiment, the antigenic peptide according to the present invention is a sequence variant of a fragment of the tumor antigen CD37 that bind to a particular HLA molecule (HLA-A2*02), such as an antigenic peptide comprising or consisting of an HLA-A2*02 Consensus Sequence as set forth in any one of SEQ ID Nos 391-425. More preferably, the antigenic peptide according to the present invention is a microbiota sequence variant of a fragment of the tumor antigen CD37, such as antigenic peptides comprising or consisting of an amino acid sequence as set forth in any one of SEQ ID NOs 111-162. More preferably, the antigenic peptide according to the present invention is a sequence variant of the CD37 fragment (human reference peptide) “GLAFVPLQI” (SEQ ID NO: 271), such as an antigenic peptide comprising or consisting of an amino acid sequence as set forth in SEQ ID NO: 111-130, 317, and 391-402 and 489-493, e.g. an antigenic peptide comprising or consisting of an amino acid sequence as set forth in any one of SEQ ID NO: 114, 117, 119, 120, 491 and 493. It is also more preferred that the antigenic peptide according to the present invention is a sequence variant of the CD37 fragment (human reference peptide) “GLYFGMLLL” (SEQ ID NO: 272), such as an antigenic peptide comprising or consisting of an amino acid sequence as set forth in SEQ ID NO: 131-136, 318 and 403-406. It is also more preferred that the antigenic peptide according to the present invention is a sequence variant of the CD37 fragment (human reference peptide) “ILILAICGL” (SEQ ID NO: 273), such as an antigenic peptide comprising or consisting of an amino acid sequence as set forth in SEQ ID NO: 137-147, 319 and 407-414. It is also more preferred that the antigenic peptide according to the present invention is a sequence variant of the CD37 fragment (human reference peptide) “LLLLFATQI” (SEQ ID NO: 274), such as an antigenic peptide comprising or consisting of an amino acid sequence as set forth in SEQ ID NO: 148-155, 320 and 415-420. It is also more preferred that the antigenic peptide according to the present invention is a sequence variant of the CD37 fragment (human reference peptide) "SIVGI-CLGV" (SEQ ID NO: 275), such as an antigenic peptide comprising or consisting of an amino acid sequence as set forth in SEQ ID NO: 156-157, 321 and 421. It is also more preferred that the antigenic peptide according to the present invention is a sequence variant of the CD37 fragment (human reference peptide) "SLIKYFLFV" (SEQ ID NO: 276), such as an antigenic peptide comprising or consisting of an amino acid sequence as set forth in SEQ ID NO: 158-162, 322 and 422-425.

In one embodiment, the antigenic peptide according to the present invention is a sequence variant of a fragment of the tumor antigen TNFRSF13C (human reference peptide), such as "GLAFVPLQI" (SEQ ID NO: 277), "GLALVLALV" (SEQ ID NO: 278), "LLFGAPALL" (SEQ ID NO: 279), "PLPGLLFGA" or (SEQ ID NO: 280). In a preferred embodiment, the antigenic peptide according to the present invention is a sequence variant of a fragment of the tumor antigen TNFRSF13C, such as antigenic peptides having a core sequence consisting of an amino acid sequence as set forth in any one of SEQ ID NOs 300-303. Accordingly, the antigenic peptide according to the present invention is a sequence variant of a fragment of the tumor antigen TNFRSF13C comprising or consisting of an MHC Class I Consensus Sequence as set forth in any one of SEQ ID Nos 323-326. In a particular embodiment, the antigenic peptide according to the present invention is a sequence variant of a fragment of the tumor antigen TNFRSF13C that bind to a particular HLA molecule (HLA-A2*02), such as an antigenic peptide comprising or consisting of an HLA-A2*02 Consensus Sequence as set forth in any one of SEQ ID Nos 426-472. More preferably, the antigenic peptide according to the present invention is a microbiota sequence variant of a fragment of the tumor antigen TNFRSF13C, such as antigenic peptides comprising or consisting of an amino acid sequence as set forth in any one of SEQ ID NOs 163-257. More preferably, the antigenic peptide according to the present invention is a sequence variant of the TNFRSF13C fragment (human reference peptide) "GLAFVPLQI" (SEQ ID NO: 277), such as an antigenic peptide comprising or consisting of an amino acid sequence as set forth in SEQ ID NO: 163-170, 323, and 426-428. It is also more preferred that the antigenic peptide according to the present invention is a sequence variant of the TNFRSF13C fragment (human reference peptide) "GLALVLALV" (SEQ ID NO: 278), such as an antigenic peptide comprising or consisting of an amino acid sequence as set forth in SEQ ID NO: 171-209, 324 and 429-446. It is also more preferred that the antigenic peptide according to the present invention is a sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 210-225, 325 and 447-455 and 494-500, e.g. an antigenic peptide comprising or consisting of an amino acid sequence as set forth in any one of SEQ ID NO: 212, 217, 220 and 224. It is also more preferred that the antigenic peptide according to the present invention is a sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 226-257, 326 and 456-472, e.g. an antigenic peptide comprising or consisting of an amino acid sequence as set forth in SEQ ID NO: 227.

Preferably, the antigenic peptide according to the present invention comprises or consists of an MHC Class I Consensus Sequence as set forth in any one of SEQ ID Nos 304-312, 315-316 and 325. More preferably, the antigenic peptide according to the present invention comprises or consists of an HLA-A*02 Consensus Sequence as set forth in any one of SEQ ID Nos. 330, 332-333, 336, 341-344, 346, 354-355, 360, 363-364, 367, 371-372, 374,387, 390, 392-393, 402 and 450.

In some embodiments, the antigenic peptide comprises or consists of an amino acid sequence as set forth in any one of SEQ ID NOs 1-12, 34-35, 36-39, 40, 41-64, 65-70, 476-484, 71-80, 81-87, 106-110, 485-488, 111-130, 489-493, 210-225, 494-500 and 226-257; preferably the antigenic peptide comprises or consists of an amino acid sequence as set forth in any one of SEQ ID NOs 34-35, 65-70, 476-484, 106-110, 485-488, 111-130, 489-493, 210-225, 494-500 and 226-257; more preferably the antigenic peptide comprises or consists of an amino acid sequence as set forth in any one of SEQ ID NOs 65-70, 476-484, 106-110, 485-488, 111-130, 489-493, 210-225 and 494-500.

In some embodiments, the antigenic peptide comprises or consists of an amino acid sequence as set forth in any one of SEQ ID NOs 10, 34, 35, 39, 40, 61, 68, 70, 72, 86, 107-110, 114, 117, 119, 120, 212, 217, 220, 224, 227, 231, 477, 491 and 493. Even more preferably, the antigenic peptide according to the present invention comprises or consists of an amino acid sequence as set forth in any one of SEQ ID NOs 10, 21, 33, 35, 39, 40, 61, 65, 68, 72, 86, 110, 114 and 220. Still more preferably, the antigenic peptide according to the present invention comprises or consists of an amino acid sequence as set forth in any one of SEQ ID NOs 10, 21, 33, 35, 39, 40, 110, 114 and 220. Most preferably, the antigenic peptide according to the present invention comprises or consists of an amino acid sequence as set forth in any one of SEQ ID NOs 10, 110, 114 and 220. Still more preferably, the antigenic peptides according to the present invention comprises or consists of an amino acid sequence as set forth in any one of SEQ ID NOs 65, 110, 114 and 220. In some embodiments, the antigenic peptide comprises or consists of an amino acid sequence as set forth in SEQ ID NO: 65. In some embodiments, the antigenic peptide comprises or consists of an amino acid sequence as set forth in SEQ ID NO: 110. In some embodiments, the antigenic peptide comprises or consists of an amino acid sequence as set forth in SEQ ID NO: 114. In some embodiments, the antigenic peptide comprises or consists of an amino acid sequence as set forth in SEQ ID NO: 220.

As shown in the examples herein, the specific antigenic peptides according to the present invention allow the raise of a strong immune response against themselves, and most importantly, allow the raise of a strong immune response against peptides having amino acid similarity therewith which are comprised in the tumor antigen, even if the human reference peptides comprised in the tumor antigen may be tolerogenic.

Advantageously, the antigenic peptides according to the present invention may be in the form of immunogenic compounds, in particular for use in the prevention or in the treatment of B-cell malignancy.

Immunogenic Compounds Comprising the Antigenic Peptide According to the Invention In a further aspect, the present invention also provides an immunogenic compound comprising an antigenic peptide according to the present invention as described above. In particular, preferred embodiments of the antigenic peptide as described above also apply for the immunogenic compound according to the present invention. For example, the antigenic peptide comprised in the immunogenic compound preferably comprises or consists of MHC Class I Consensus Sequence as set forth in any one of SEQ ID Nos 304-326, such as an antigenic peptide comprising or consisting of an amino acid sequence as set forth in any one of SEQ ID NOs 1 to 247 and 476-500. For example, antigenic peptides according to the present invention comprising or consisting of an amino acid sequence as set forth in any one of SEQ ID NOs 10, 21, 33, 35, 39, 40, 61, 65, 68, 72, 86, 110, 114 and 220 are even more preferred. For example, antigenic peptides according to the present invention comprising or consisting of an amino acid sequence as set forth in any one of SEQ ID NOs 10, 21, 33, 35, 39, 40, 110, 114 and 220 are still more preferred. For example, antigenic peptides according to the present invention comprising or consisting of an amino acid sequence as set forth in any one of SEQ ID NOs 10, 110, 114 and 220 are still more preferred. For example, antigenic peptides according to the present invention comprising or consisting of an amino acid sequence as set forth in any one of SEQ ID NOs 65, 110, 114 and 220 are still more preferred. Also combinations thereof are preferred, namely, immunogenic compound comprising distinct antigenic peptides according to the present invention.

As used herein, the term "immunogenic compound" refers to a compound that is able to induce, increase, prolong or maintain an immune response, in particular which induces, increases, prolongs or maintains an immune response, when it is administered to a mammal, and especially when it is administered to a human individual.

In general, the term "immunogenic compound" includes all kinds of compounds comprising the antigenic peptide according to the present invention. For example, the antigenic peptide according to the present invention may be linked to a carrier molecule or the antigenic peptide according to the present invention may be comprised in a polypeptide or protein (which polypeptide or protein may occur "separately", i.e. not linked to any other compound, or the polypeptide or protein comprising the antigenic peptide may be linked to a carrier molecule).

Preferably, the immunogenic compound according to present invention comprises the antigenic peptide and a carrier molecule, in particular wherein the antigenic peptide (or a polypeptide or protein comprising the antigenic peptide) is linked to a carrier molecule. A preferred carrier molecule is a carrier protein or a carrier peptide. According to a preferred embodiment, the antigenic peptide as above defined, or a polypeptide/protein comprising said antigenic peptide, is linked to a carrier protein or a carrier peptide, for example by a covalent or non-covalent bond. Alternatively, such a carrier protein or carrier peptide as described herein) may be (separately) co-administered in the form of immune adjuvant (i.e., not as an "immunogenic compound", but as co-administration/combination therapy as described herein below).

The carrier molecule may also be a lipid or a lipid-like moiety. In this case, the immunogenic compound may be a lipopeptide. As used herein, the term "lipopeptide" refers to a molecule that comprises a lipid or a lipid-like moiety covalently linked to a peptide moiety. In general, a "lipid" is soluble in nonpolar solvents, but usually a "lipid" does not (or does not easily) dissolve in water. Examples of a lipid or a lipid-like moiety include, but are not limited to, fatty acids, waxes, sterols, monoglycerides, diglycerides, triglycerides and phospolipids. The lipid may be a fatty acid, a glycerolipid, a gylcerophospholipid, a sphingolipid, a sterol lipid, a prenol lipid, a saccharolipid, or a polyketide. Preferably, the lipid is a fatty acid or a derivative thereof (including monoglycerides, diglycerides, triglycerides and phospolipids). Fatty acids typically contain a hydrocarbon chain that terminates with a carboxylic group. Fatty acids may be saturated or unsaturated. Fatty acids may be attached to functional groups, e.g., containing oxygens, halogens, nitrogen or sulfur. Preferred fatty acids are saturated or unsaturated long-chain fatty acids, such as myristic acid with 14 carbon atoms ($CH_3(CH_2)_{12}COOH$) or palmitic acid with 16 carbon atoms ($CH_3(CH_2)_{14}COOH$), as well as phospholipids, such as phosphatidylglycerol (PG).

Preferably, the antigenic peptide as described herein, or a polypeptide/protein comprising the antigenic peptide, may be co-administrated or linked, for example by covalent or non-covalent bond, to a protein/peptide having immuno-adjuvant properties, such as providing stimulation of CD4+ Th1 cells. While the antigenic peptide as described herein preferably binds to MHC class I, CD4+ helper epitopes may be additionally used to provide an efficient immune response. Th1 helper cells are able to sustain efficient dendritic cell (DC) activation and specific CTL activation by secreting interferon-gamma (IFN-γ), tumor necrosis factor-alpha (TNF-α) and interleukin-2 (IL-2) and enhancing expression of costimulatory signal on DCs and T cells (Galaine et al., Interest of Tumor-Specific CD4 T Helper 1 Cells for Therapeutic Anticancer Vaccine. Vaccines (Basel). 2015 Jun. 30; 3(3):490-502).

For example, the adjuvant peptide/protein may preferably be a non-tumor antigen that recalls immune memory or provides a non-specific help or could be a specific tumor-derived helper peptide. Several helper peptides have been described in the literature for providing a nonspecific T cell help, such as tetanus helper peptide, keyhole limpet hemocyanin peptide or PADRE peptide (Adotévi et al., Targeting antitumor CD4 helper T cells with universal tumor-reactive helper peptides derived from telomerase for cancer vaccine. Hum Vaccin Immunother. 2013 May; 9(5):1073-7, Slingluff C L, The present and future of peptide vaccines for cancer: single or multiple, long or short, alone or in combination? Cancer J. 2011 September-October; 17(5):343-50). Accordingly, tetanus helper peptide, keyhole limpet hemocyanin peptide and PADRE peptide are preferred examples of such adjuvant peptide/proteins. Moreover, specific tumor derived helper peptides are preferred. Specific tumor derived helper peptides are typically presented by MHC class II, in particular by HLA-DR, HLA-DP or HLA-DQ. Specific tumor derived helper peptides may be fragments of sequences of shared overexpressed tumor antigens, such as HER2, NY-ESO-1, hTERT or IL13RA2. Such fragments have preferably a length of at least 10 amino acids, more preferably of at least 11 amino acids, even more preferably of at least 12 amino acids and most preferably of at least 13 amino acids. In particular, fragments of shared overexpressed tumor antigens, such as HER2, NY-ESO-1, hTERT, having a length of 13 to 24 amino acids are preferred. Preferred fragments bind to MHC class II and may, thus, be identified using, for example, the MHC class II binding prediction tools of IEDB (Immune epitope database and analysis resource; Supported by a contract from the National Institute of Allergy and Infectious Diseases, a component of the National Institutes of Health in the Department of Health and Human Services; URL: http://www.iedb.org/; http://tools.iedb.org/mhcii/). Preferably, the adjuvant peptide/protein may be the HHD-DR3 peptide of sequence MAKTIAYDEEARRGLERGLN (SEQ ID NO: 473). Another preferred example is h-pAg T13L (sequence: TPPAYRPPNAPIL; SEQ ID NO: 474; Bhasin M, Singh H, Raghava G P (2003) MHCBN: a comprehensive database of MHC binding and non-binding peptides. Bioinformatics 19: 665-

666). Further examples of preferred adjuvant peptides/proteins, in particular of helper peptides, include the UCP2 peptide (for example as described in WO 2013/135553 A1 or in Dosset et al. Clin Cancer Res. 2012 Nov. 15; 18(22): 6284-95) and the BIRC5 peptide (for example as described in EP2119726 A1 or in Widenmeyer et al. Int J Cancer. 2012 Jul. 1; 131(1): 140-9). The most preferred helper peptide is the UCP2 peptide (amino acid sequence: KSVWSKLQSIGIRQH; SEQ ID NO: 475, for example as described in WO 2013/135553 A1 or in Dosset et al., Clin Cancer Res. 2012 Nov. 15; 18 (246284-95).

It is also preferred that the immunogenic compound according to the present invention is a polypeptide or a protein comprising the antigenic peptide according to the present invention. Preferably, such a protein or polypeptide is a recombinant protein or polypeptide, for example a fusion protein. The term "recombinant" means that it does not occur in nature.

In a preferred embodiment, the immunogenic compound according to the present invention comprises or consists of a polypeptide of formula (I)

PepNt-CORE-PepCt (I)

wherein:

"PepNt" consists of a polypeptide having a length varying from 0 to 500 amino acid residues and is located at the N-terminal end of the polypeptide of formula (I);

"CORE" consists of an antigenic peptide according to the present invention as defined above; and "PepCt" consists of a polypeptide having a length varying from 0 to 500 amino acid residues and is located at the C-terminal end of the polypeptide of formula (I).

For example, the immunogenic compound may comprise or consist of a polypeptide of formula (Ia) or (Ib):

PepNt-CORE (Ia); or

CORE-PepCt (Ib)

wherein "PepNt" and "PepCt" and "CORE" are as defined above.

Preferably, the polypeptide of formula (I), (Ia) or (Ib) is a fusion peptide or fusion protein, in particular a recombinant fusion peptide or protein.

It is also preferred that the polypeptide or the immunogenic compound as defined above, comprises from 9 to 1000 amino acids; which includes 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67? 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 600, 700, 800, 900 and 1000 amino acids. Accordingly, the length of "PepNt" and "PepCt", if applicable, may be defined accordingly.

Thus, "PepNt" and "PepCt", as defined above, may comprise from 0 to 500 amino acid residues; which includes 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, and 500 amino acid residues.

The types of carrier molecules used for generating an immunogenic compound of the invention, such as an immunogenic compound comprising or consisting of a polypeptide of formula (I) linked to a carrier molecule, are well in the general knowledge of the one skilled in the art. In particular, the function of the carrier molecule is to provide cytokine help (or T-cell help) in order to enhance the immune response against tumor antigen.

Preferably, the antigenic peptide is linked to a carrier molecule, in particular to a carrier protein, preferably by covalent or non-covalent bond. The carrier molecule to which the peptide is optionally bound can be selected from a wide variety of known carriers. Examples of carrier molecules for vaccine purposes encompass proteins such as human or bovine serum albumin and keyhole limpet haemocyanin (KLH) and fatty acids. Other embodiments of carrier molecules to which an antigenic peptide of formula (I) may be covalently linked include bacterial toxins or toxoids, such as diphtheria, cholera, *E. coli* heat labile or tetanus toxoids, the *N. meningitidis* outer membrane protein (European patent application no EP0372501), synthetic peptides (European patent applications no EP0378881 and no EP0427347), heat shock proteins (PCT application no WO93/17712), Pertussis proteins (PCT application no WO98/58668), protein D from *H. influenzae* (PCT application no WO00/56360.) and toxin A or B from *C. difficile* (International patent application WO00/61761).

More preferably, the carrier protein or carrier peptide is a protein/peptide having immuno-adjuvant properties, such as providing stimulation of CD4+ Th1 cells as described herein. A preferred example thereof is a non-tumor antigen that recalls immune memory or provides a non-specific help or could be a specific tumor-derived helper peptide, such as tetanus helper peptide, keyhole limpet hemocyanin peptide or PADRE peptide. Another preferred example is a specific tumor derived helper peptide, which may be presented by MHC II, in particular by HLA-DR, HLA-DP or HLA-DQ, such as fragments of shared overexpressed tumor antigens, e.g. HER2, NY-ESO-1, or hTERT. In a preferred embodiment, the carrier protein or carrier peptide is a protein/peptide having immuno-adjuvant properties may be a HHD-DR3 carrier peptide MAKTIAYDEEARRGLERGLN (SEQ ID NO: 473). In particular, "PepNt" and/or "PepCt" may correspond to a carrier protein or carrier peptide, such as the HHD-DR3 carrier peptide MAKTIAYDEEARRGLERGLN (SEQ ID NO: 473). Another preferred example is h-pAg T13L (sequence: TPPAYRPPNAPIL; SEQ ID NO: 474; Bhasin M, Singh H, Raghava G P (2003) MHCBN: a comprehensive database of MHC binding and non-binding peptides. Bioinformatics 19: 665-666). Further examples of preferred carrier proteins/peptides, in particular of helper peptides, include the UCP2 peptide (for example as described in WO 2013/135553 A1 or in Dosset et al., Clin Cancer Res. 2012 Nov. 15; 18(22):6284-95) and the BIRC5 peptide (for example as described in EP2119726 A1 or in Widenmeyer et al., Int J Cancer. 2012 Jul. 1; 131(1):140-9). The most preferred helper peptide is the UCP2 peptide (amino acid sequence: KSVWSKLQSIGIRQH; SEQ ID NO: 475).

Moreover, in the polypeptide according to formula (I), (Ia) or (Ib), "PepNt" and/or "PepCt" may preferably correspond to such a protein/peptide having immuno-adjuvant properties, such as providing stimulation of CD4+ Th1 cells as described herein.

Moreover, the immunogenic compound may comprise or consist of such a protein/peptide having immuno-adjuvant properties, such as providing stimulation of CD4+ Th1 cells as described herein, linked covalently to the N-terminus of the antigenic peptide according to the present invention or to the N-Terminus of a polypeptide/protein comprising said antigenic peptide.

Preferably, the antigenic peptide according to the present invention (or the polypeptide/protein comprising said antigenic peptide) is covalently bound to the carrier molecule through a linker moiety.

Preferred linker agents encompass the linker agents named GMBS, sulfo-GMBS, SMPB and sulfo-SMPB.

In some embodiments of an immunogenic compound as defined above, the linker agent is selected from the group consisting of GMBS (N-[γ-maleimidobutyryl-oxy]succinimide ester), Sulfo-GMBS (N-[γ-maleimidobutyryl-oxy] sulfosuccinimide ester), SMPB (succinimidyl 4-[p-maleimidophenyl]butyrate) and Sulfo-SMPB (sulfosuccinimidyl 4-[p-maleimidophenyl]butyrate).

Methods for conjugating two proteins with a linker agent in general, and more particularly with a linker agent selected from the group consisting of GMBS, Sulfo-GMBS, SMPB and Sulfo-SMPB, are well known by the one skilled in the art. Illustratively, such protocols are disclosed in the leaflets that are made publicly available by the Pierce Company (Illinois, USA).GMBS, Sulfo-GMBS, SMPB and Sulfo-SMPB consist of heterobifunctional linker agents that contain both a N-hydroxysuccinimide (NHS) ester group and a maleimide group. Conjugation using GMBS, Sulfo-GMBS, SMPB or Sulfo-SMPB is usually performed by a two-step procedure. In a first step, the amine-containing protein is reacted with a several-fold molar excess of the linker agent at pH 7-9 to form amide bonds, followed by removal of excess non-reacted linker agent, usually by desalting or dialysis. In a second step, the sulfhydryl-containing molecule (e.g. peptide of formula (I)) is added to react with the maleimide groups already attached to the first protein at pH 6.5-7.5 to form stable thioether bonds.

Using SMPB or Sulfo-SMPB as linker agents for covalently linking the antigenic peptide according to the present invention (or the polypeptide/protein comprising said antigenic peptide, such as the polypeptide of formula (I)) to the amine-containing carrier protein, leads to a conjugate of formula (II) below:

(II)

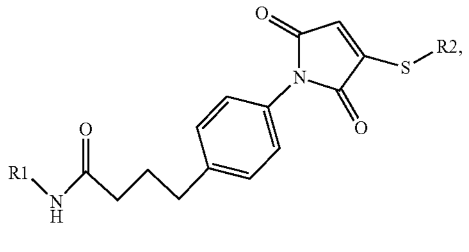

wherein:

R1 consists of one reactive group of the amine-containing carrier protein, and wherein the NH group attached thereto derives from (i) the alpha amino group located at the N-terminal end of the amine-containing carrier protein or (ii) a lateral chain amino group from a Lysine (K) amino acid residue of the amine-containing carrier protein; and R2 consists of the antigenic peptide according to the present invention (or the polypeptide/protein comprising said antigenic peptide, such as a polypeptide of formula (I)), and wherein the sulphur (S) atom attached thereto derives from a sulfhydryl (SH) group of a cysteine residue located at the N-terminal end or at the C-terminal end of a peptide of formula (I). In some embodiments, the sulfhydryl moiety could be part of an unnatural amino acid, or any other molecule present at the end of the peptide of formula (I).

Using GMBS or Sulfo-GMBS as linker agents for covalently linking the antigenic peptide according to the present invention (or the polypeptide/protein comprising said antigenic peptide, such as a polypeptide of formula (I)) to the amine-containing carrier protein, in particular the CRM197 carrier, protein leads to a conjugate of formula (III) below:

(III)

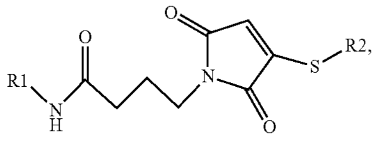

wherein:

R1 consists of one reactive group of the amine-containing carrier protein, and wherein the NH group attached thereto derives from (i) the alpha amino group located at the N-terminal end of the amine-containing carrier protein or (ii) a lateral chain amino group from a Lysine (K) amino acid residue of the amine-containing carrier protein; and R2 consists of the antigenic peptide according to the present invention (or the polypeptide/protein comprising said antigenic peptide, such as a polypeptide of formula (I)), and wherein the sulphur (S) atom attached thereto derives from a sulfhydryl (SH) group of a cysteine residue located at the N-terminal end or at the C-terminal end of a peptide of formula (I). In some embodiments, the sulfhydryl moiety could be part of an unnatural amino acid, or any other molecule present at the end of the peptide of formula (I).

Peptide-MHC (pMHC) Multimers Comprising the Antigenic Peptide

In a further aspect, the present invention also provides a Peptide-MHC (pMHC) multimer comprising an antigenic peptide according to the present invention.

As used herein, the term "peptide-MHC multimer" (pMHC) refers to a stable multimeric complex composed of major histocompatibility complex (MHC) protein subunits loaded with an antigenic peptide of the invention. In general, "MHC multimers" are oligomeric forms of MHC molecules. The main function of an MHC molecule is to bind to an antigen. According to the invention, said antigen is the antigenic peptide according to the invention. Accordingly, a complex of MHC proteins "loaded" with the antigenic peptide of the invention typically means that the antigenic peptide of the invention is bound to one or more of the MHC proteins. The "peptide-MHC multimers" (pMHC) of the invention include, but are not limited to, a peptide-MHC dimer, trimer, tetramer, pentamer, hexamer, heptamer or octamer. MHC tetramers and pentamers are preferred. The term "Major Histocompatibility Complex" (MHC) is a generic designation meant to encompass the histo-compatibility antigen systems described in different species including the human leucocyte antigens (HLA). In humans there are three major different genetic loci that encode MHC class I molecules: HLA-A, HLA-B, and HLA-C. HLA-A*01, HLA-A*02, and HLA-A*11 are examples of different MHC class I alleles that can be expressed from these loci.

In one embodiment of the invention, the pMHC multimer is a peptide/MHC class I multimer. In another particular embodiment, the pMHC multimer is a HLA corresponding to MHC class I/peptide multimer. Accordingly, the pMHC multimer may be a HLA-peptide multimer selected from the group consisting of HLA-A-peptide multimer, HLA-B-peptide multimer, HLA-C-peptide multimer, HLA-E-peptide multimer, MICA-peptide multimer and MICB-peptide multimer.

Methods for obtaining pMHC multimers are known in the art and described, for example, in WO96/26962 and WO01/18053, which are incorporated herein by reference.

In addition to the MHC molecule and the antigenic peptide of the invention, the pMHC may contain further components, such as a multimerization agent and/or a label (e.g., for visualization). Examples of labels include, but are not limited to, fluorescent labels, e.g. fluorescently labelled proteins, such as streptavidin. Fluorescent labels include allophycocyanin (APC), phycoerythrin (PE), R-phycoerythrin (R-PE) and fluorescein isothiocyanate (FITC). A preferred label is biotin.

In one embodiment of the invention, said pMHC multimer can be used to visualize T cell populations that are specific for the MHC class I peptide complex or a HLAs corresponding to MHC class I/peptide complex as described here above. For example, the pMHC multimer may be a multimer where the heavy chain of the MHC is biotinylated, which allows combination as a tetramer with streptavidin. Such pMHC tetramer has an increased avidity for the appropriate TCR-carrier T lymphocytes and can therefore be used to visualize reactive populations by immunofluorescence. In another embodiment of the invention, said pMHC multimer can be used for the detection and/or isolation by screening (in flow cytometry or by immunomagnetic screening) of T cell populations that are specific for a pMHC complex as described here above.

Antigenic Peptide-Specific Cytotoxic T Lymphocytes (CTL)

In a further aspect, the present invention also provides a cytotoxic T lymphocyte (CTL) specific for an antigenic peptide according to the invention, in particular an activated cytotoxic T lymphocyte (CTL) specific for an antigenic peptide according to the invention.

The present invention further provides a method for producing cytotoxic T lymphocytes (CTL) specific for an antigenic peptide according to the invention, in particular activated cytotoxic T lymphocytes (CTL) specific for an antigenic peptide according to the invention, the method comprising contacting in vitro a CTL with an antigen-loaded human class I or II MHC molecule expressed on the surface of an antigen-presenting cell or an artificial construct mimicking an antigen-presenting cell, wherein said antigen is an antigenic peptide according to the invention. Preferred antigen-presenting cells include dendritic cells. An artificial construct mimicking an antigen-presenting cell may be, for instance, a peptide-MHC multimer according to the invention. The step of contacting the CTL with the antigen-loaded human class I or II MHC molecule expressed on the surface of the antigen-presenting cell or the artificial construct mimicking an antigen-presenting cell may be carried out for a period of time sufficient to activate said CTL in an antigen specific manner. Preferably, the antigenic peptide is a preferred antigenic peptide as described above, such as an antigenic peptide comprising or consisting of an amino acid sequence as set forth in any one of SEQ ID NOs 65, 110, 114 and 220.

The (activated) T cells that are directed against the antigenic peptides of the invention are useful in therapy. In particular, activated T cells, which are produced by the above method, selectively recognize a cell that aberrantly expresses a polypeptide that comprises an amino acid sequence of SEQ ID NO: 258-280 (i.e., a tumor antigen), for example, a polypeptide that comprises an amino acid sequence of as set forth in any one of SEQ ID NOs 264, 270, 271 and 279.

Preferably, the (activated) cytotoxic T lymphocytes (CTL) according to the present invention, which are specific for an antigenic peptide of the invention, may have (exhibit/express) memory markers. Such memory markers are preferably memory markers of gut memory cells, such as CCR9, CXCR3, CD103, CX3CR1 and $\alpha4\beta7+$.

The (activated) cytotoxic T lymphocytes (CTL) according to the present invention, which are specific for an antigenic peptide of the invention, are preferably more/stronger amplified after vaccination with antigenic peptide of the invention (derived from human microbiota sequences) as compared to vaccination with peptides not derived from microbiota sequences, such as the human (reference) sequence and/or a synthetic peptide (e.g., including mutations, which were, e.g., artificially introduced). In other words, vaccination of subjects with the antigenic peptide of the invention preferably increases the number of (activated) cytotoxic T lymphocytes (CTL) according to the present invention, which are specific for said antigenic peptide of the invention, more than vaccination with respective human peptides or synthetic peptides (not derived from microbiota), which relate to the same reference epitope.

The (activated) cytotoxic T lymphocytes (CTL) according to the present invention, which are specific for an antigenic peptide of the invention, are preferably more/stronger and/or faster amplified after vaccination in subjects having said peptide in the gut (expressed by the subject's microbiota), e.g., the peptide can be found in a stool sample of the subject, as compared to subjects not having said peptide in the gut (not expressed by the subject's microbiota), e.g. subjects where said peptide is not detectable in stool samples. In particular, subjects having said peptide in the gut (expressed by the subject's microbiota), may respond faster (faster T cell expansion) and/or have T cells from the desired type Tc 1.

Cells Loaded with the Antigenic Peptide or the Immunogenic Compound

In a further aspect, the present invention also provides a cell loaded with an antigenic peptide according to the present invention or with the immunogenic compound comprising an antigenic peptide according to the present invention as described above. In particular, preferred embodiments of the antigenic peptide as described above also apply for such a cell according to the present invention. For example, the antigenic peptide loaded to the cell or comprised in the immunogenic compound loaded to the cell preferably comprises or consists of MHC Class I Consensus Sequence as set forth in any one of SEQ ID Nos 304-326, such as an antigenic peptide comprising or consisting of an amino acid sequence as set forth in any one of SEQ ID NOs 1 to 247 and 476-500. For example, antigenic peptides according to the present invention comprising or consisting of an amino acid sequence as set forth in any one of SEQ ID NOs 10, 21, 33, 35, 39, 40, 61, 65, 68, 72, 86, 110, 114 and 220 are even more preferred. For example, antigenic peptides according to the present invention comprising or consisting of an amino acid sequence as set forth in any one of SEQ ID NOs 10, 21, 33, 35, 39, 40, 110, 114 and 220 are still more preferred. For example, antigenic peptides according to the present invention comprising or consisting of an amino acid sequence as set forth in any one of SEQ ID NOs 10, 110, 114 and 220 are still more preferred. For example, antigenic peptides according to the present invention comprising or consisting of an amino acid sequence as set forth in any one of SEQ ID NOs 65, 110, 114 and 220 are still more preferred. Also combinations thereof are preferred, namely, cells loaded with distinct antigenic peptides according to the present invention (or with the respective immunogenic compound(s)).

A preferred cell loaded with the antigenic peptide according to the present invention or with the immunogenic compound according to the present invention is an antigen presenting cell (APC), more preferably a dendritic cell (DC).

APCs are of particular interest, as their main function is to process antigens and present it on the cell surface to the T cells of the immune system, so as to initiate and modulate T-cell responses in vivo. In the context of the present invention, it is preferred that the APCs are loaded with the antigenic peptide(s) and/or immunogenic compound(s) according to the invention. This may be done by exposing APCs in vitro with said antigenic peptide(s) and/or immunogenic compound(s) (as described in Rizzo M M, Alaniz L, Mazzolini G. Ex vivo loading of autologous dendritic cells with tumor antigens. Methods Mol Biol. 2014; 1139:41-4; Rolinski J, Hus I. Breaking immunotolerance of tumors: a new perspective for dendritic cell therapy. J Immunotoxicol. 2014 October; 11(4):311-8).

Preferred APCs according to the invention are dendritic cells (DCs). It can indeed be advantageous to combine at least one antigenic peptide or immunogenic compound according to the invention with DCs, as those are the most potent APCs and have been reported to be frequently functionally defective in cancer patients. DCs can be easily obtained by the skilled person in the art from either healthy compatible donors (i.e. the DCs are HLA-related) or from the patient himself provided that they are functional (i.e. the DCs are autologous), for example by direct isolation from the peripheral blood, or by derivation from peripheral blood cells such as CD14+ monocytes or CD34+ hematopoietic precursors (Figdor C G, de Vries I J, Lesterhuis W J, Melief C J. Dendritic cell immunotherapy: mapping the way. Nat Med. 2004 May; 10(5):475-80). DCs can indeed be distinguished from other cells of peripheral blood by their surface markers, such as S100, p55, CD83, and/or OX62, and may thus be isolated and purified based on said markers using cell cultures techniques well-known in the art.

Nucleic Acids Encoding the Antigenic Peptides and Host Cells Comprising Nucleic Acids In a further aspect, the present invention also provides a nucleic acid encoding the antigenic peptide according to the present invention, the polypeptide of formula (I) as defined above, or the immunogenic compound according to the present invention, wherein the immunogenic compound is a peptide or a protein. In particular, preferred embodiments of the antigenic peptide as described above also apply for such a nucleic acid according to the present invention. For example, the antigenic peptide encoded by the nucleic acid preferably comprises or consists of MHC Class I Consensus Sequence as set forth in any one of SEQ ID Nos 304-326, such as an antigenic peptide comprising or consisting of an amino acid sequence as set forth in any one of SEQ ID NOs 1 to 247 and 476-500. For example, antigenic peptides according to the present invention comprising or consisting of an amino acid sequence as set forth in any one of SEQ ID NOs 10, 21, 33, 35, 39, 40, 61, 65, 68, 72, 86, 110, 114 and 220 are even more preferred. For example, antigenic peptides according to the present invention comprising or consisting of an amino acid sequence as set forth in any one of SEQ ID NOs 10, 21, 33, 35, 39, 40, 110, 114 and 220 are still more preferred. For example, antigenic peptides according to the present invention comprising or consisting of an amino acid sequence as set forth in any one of SEQ ID NOs 10, 110, 114 and 220 are still more preferred. For example, antigenic peptides according to the present invention comprising or consisting of an amino acid sequence as set forth in any one of SEQ ID NOs 65, 110, 114 and 220 are still more preferred. Also combinations thereof are preferred, namely, nucleic acids encoding distinct antigenic peptides according to the present invention.

Nucleic acids preferably comprise single stranded, double stranded or partially double stranded nucleic acids, preferably selected from gDNA, cDNA, RNA, antisense DNA, antisense RNA, complementary RNA/DNA sequences with or without expression elements, a mini-gene, gene fragments, regulatory elements, promoters, and combinations thereof. Further preferred examples of nucleic acid (molecules) and/or polynucleotides include, e.g., a recombinant polynucleotide, a vector, an oligonucleotide, an RNA molecule such as an rRNA, an mRNA, or a tRNA, or a DNA molecule as described above. It is thus preferred that the nucleic acid (molecule) is a DNA molecule or an RNA molecule; preferably selected from gDNA; cDNA; rRNA; mRNA; antisense DNA; antisense RNA; complementary RNA and/or DNA sequences; RNA and/or DNA sequences with or without expression elements, regulatory elements, and/or promoters; a vector; and combinations thereof.

It is of great interest in the fields of therapeutics, diagnostics, reagents and for biological assays to be able to deliver a nucleic acid, e.g., a ribonucleic acid (RNA) inside a cell, whether in vitro, in vivo, in situ or ex vivo, such as to cause intracellular translation of the nucleic acid and production of an encoded peptide of interest. Of particular importance is the delivery and function of a non-integrative polynucleotide. Accordingly, nucleic acids, which do not integrate into the chromosomes of the host, are preferred, such as mRNA. In general, nucleic acids, such as mRNA, may be optimized for expression of the antigenic peptide of the invention, e.g. by methods known in the art, such as codon optimization. In addition, the nucleic acid may be modified, for example, in order to enhance its stability, prolong its lifetime and/or to increase the expression of the antigenic peptide of the invention. Accordingly, optimized or modified mRNA (mmRNA), which encodes an antigenic peptide according to the present invention, is preferred. The mmRNA are distinguished from wild type mRNA in their functional and/or structural design features for optimal delivery of the mRNA and/or for optimal expression of the antigenic peptide of the invention (for example as described in WO 2013/151672 A2, WO 2013/101690 A1, WO2013/052523 A, which are incorporated herein by reference). In general, nucleic acids may be delivered "naked" or associated with a carrier, e.g., a cationic carrier. Cationic carriers (positively charged) typically associate easily with nucleic acids, which are negatively charged. The carrier may be any of any kind including, for example, polymers, proteins, lipids and nanoparticles. Cationic lipids and nanoparticles (in particular lipid nanoparticles, LNPs) are preferred for nucleic acid delivery. Accordingly, the present invention also provides a nucleic acid as described herein associated with a carrier (e.g., a lipid, in particular a cationic lipid or an LNP).

In some embodiments, the nucleic acid molecule may be a vector. The term "vector", as used in the context of the present invention, refers to a nucleic acid molecule, preferably to an artificial nucleic acid molecule, i.e. a nucleic acid molecule which does not occur in nature. A vector in the context of the present invention is suitable for incorporating or harboring a desired nucleic acid sequence. Such vectors may be storage vectors, expression vectors, cloning vectors, transfer vectors etc. A storage vector is a vector which allows the convenient storage of a nucleic acid molecule. Thus, the vector may comprise a sequence corresponding, e.g., to a desired antigenic peptide according to the present invention. An expression vector may be used for production of expression products such as RNA, e.g. mRNA, or peptides, polypeptides or proteins. For example, an expression vector may comprise sequences needed for transcription of a sequence stretch of the vector, such as a promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule. For example, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector. Preferably, a vector in the context of the present application is an expression vector. A preferred vector is a vector for expression in bacterial cells. More preferably, the vector is useful for expression in so-called "live bacterial vaccine vectors", wherein live bacterial cells (such as bacteria or bacterial spores, e.g., endospores, exospores or microbial cysts) can serve as vaccines. Preferred examples thereof are described in da Silva et al., Live bacterial vaccine vectors: an overview; Braz J Microbiol. 2015 Mar. 4; 45(4):1117-29.

Nucleic acids encoding antigenic peptides according to the invention may be in the form of naked nucleic acids, or nucleic acids cloned into plasmids or viral vectors (Tregoning and Kinnear, Using Plasmids as DNA Vaccines for Infectious Diseases. Microbiol Spectr. 2014 December; 2(6). doi: 10.1128/microbiolspec.PLAS-0028-2014), the latter being particularly preferred. Examples of suitable viral vectors according to the invention include, without limitation, retrovirus, adenovirus, adeno-associated virus (AAV), herpes virus and poxvirus vectors. It is within the skill of the person in the art to clone a nucleic acid into a plasmid or viral vector, using standard recombinant techniques in the art.

In a further aspect, the present invention also provides a host cell comprising the nucleic acid according to the present invention. Also combinations thereof are preferred, namely, host cells comprising distinct nucleic acids according to the present invention, for example encoding distinct antigenic peptides according to the present invention.

Preferably, the nucleic acid comprised in the host cell is preferably a vector. Preferably, the host cell is a bacterial cell. Such a host cell may be preferably used for production of the antigenic peptide according to the present invention or the immunogenic compound according to the present invention. Moreover, such a host cell may also be an active component in a vaccine.

Preferably, the host cell is a bacterial cell, more preferably a gut bacterial cell. The term "gut bacterial cell" refers to bacteria residing in the (human) gut.

Such a bacterial host cell may serve as "live bacterial vaccine vector", wherein live bacterial cells (such as bacteria or bacterial spores, e.g., endospores, exospores or microbial cysts) can serve as vaccines. Preferred examples thereof are described in da Silva et al., Live bacterial vaccine vectors: an overview; Braz J Microbiol. 2015 Mar. 4; 45(4):1117-29.

Bacterial cells (such as bacteria or bacterial spores, e.g., endospores, exospores or microbial cysts), in particular (entire) gut bacterial species, can be advantageous, as they have the potential to trigger a greater immune response than the (poly)peptides or nucleic acids they contain.

Alternatively, bacterial cells, in particular gut bacteria, according to the invention may be in the form of probiotics, i.e. of live gut bacterium, which can thus be used as food additive due to the health benefits it can provide. Those can be for example lyophilized in granules, pills or capsules, or directly mixed with dairy products for consumption.

Nanoparticles Comprising the Antigenic Peptide or the Immunogenic Compound

In a further aspect, the present invention also provides a nanoparticle comprising, in particular a nanoparticle loaded with,

- at least one of the antigenic peptides according to the present invention, or
- at least one of the immunogenic compounds according to the present invention;

and, optionally, with an adjuvant.

In particular, preferred embodiments of the antigenic peptide as described above also apply for such a nanoparticle according to the present invention. For example, the antigenic peptide loaded to the nanoparticle or comprised in the immunogenic compound loaded to the nanoparticle preferably comprises or consists of MHC Class I Consensus Sequence as set forth in any one of SEQ ID Nos 304-326, such as an antigenic peptide comprising or consisting of an amino acid sequence as set forth in any one of SEQ ID NOs 1 to 247 and 476-500. For example, antigenic peptides according to the present invention comprising or consisting of an amino acid sequence as set forth in any one of SEQ ID NOs 10, 21, 33, 35, 39, 40, 61, 65, 68, 72, 86, 110, 114 and 220 are even more preferred. For example, antigenic peptides according to the present invention comprising or consisting of an amino acid sequence as set forth in any one of SEQ ID NOs 10, 21, 33, 35, 39, 40, 110, 114 and 220 are still more preferred. For example, antigenic peptides according to the present invention comprising or consisting of an amino acid sequence as set forth in any one of SEQ ID NOs 10, 110, 114 and 220 are still more preferred. For example, antigenic peptides according to the present invention comprising or consisting of an amino acid sequence as set forth in any one of SEQ ID NOs 65, 110, 114 and 220 are still more preferred. Also combinations thereof are preferred, namely, nanoparticles loaded with distinct antigenic peptides according to the present invention (or with the respective immunogenic compound(s)).

Nanoparticles, in particular for use as vaccines, are known in the art and described, for example, in Shao et al., Nanoparticle-based immunotherapy for cancer, ACS Nano 2015, 9(1):16-30; Zhao et al., Nanoparticle vaccines, Vaccine 2014, 32(3):327-37; and Gregory et al., Vaccine delivery using nanoparticles, Front Cell Infect Microbiol. 2013, 3:13, doi: 10.3389/fcimb.2013.00013. eCollection 2013, Review. In particular, the nanoparticle is used for delivery of the antigenic peptide (or the immunogenic compound/polypeptide/protein/nucleic acid comprising the antigenic peptide) and may optionally also act as an adjuvant. The antigenic peptide (the immunogenic compound/polypeptide/ protein/nucleic acid comprising the antigenic peptide) is typically either encapsulated within the nanoparticle or linked/bound to (decorated onto) the surface of the nanoparticle ("coating"). Compared to conventional approaches, nanoparticles can protect the payload (antigen/adjuvant) from the surrounding biological milieu, increase the half-life, minimize the systemic toxicity, promote the delivery to APCs, or even directly trigger the activation of TAA-specific T-cells. Preferably, the nanoparticle has a size (diameter) of no more than 300 nm, more preferably of no more than 200 nm and most preferably of no more than 100 nm. Such nanoparticles are adequately sheltered from phagocyte uptake, with high structural integrity in the circulation and long circulation times, capable of accumulating at sites of tumor growth, and able to penetrate deep into the tumor mass.

Examples of nanoparticles include polymeric nanoparticles such as poly(ethylene glycol) (PEG) and poly (D,L-lactic-coglycolic acid) (PLGA); inorganic nanoparticles such as gold nanoparticles, iron oxide beads, iron-oxide zinc-oxide nanoparticles, carbon nanotubes and mesoporous silica nanoparticles; liposomes, such as cationic liposomes; immunostimulating complexes (ISCOM); virus-like particles (VLP); and self-assembled proteins.

Polymeric nanoparticles are nanoparticles based on/comprising polymers, such as poly(D,L-lactide-co-glycolide) (PLG), poly(D,L-lactic-coglycolic acid)(PLGA), poly(γ-glutamic acid) (γ-PGA), poly(ethylene glycol) (PEG), and polystyrene. Polymeric nanoparticles may entrap an antigen (e.g., the antigenic peptide or a (poly)peptide comprising the same) or bind to/conjugate to an antigen (e.g., the antigenic peptide or a (poly)peptide comprising the same). Polymeric nanoparticles may be used for delivery, e.g. to certain cells, or sustain antigen release by virtue of their slow biodegradation rate. For example, g-PGA nanoparticles may be used to encapsulate hydrophobic antigens. Polystyrene nanoparticles can conjugate to a variety of antigens as they can be surface-modified with various functional groups. Polymers, such as Poly(L-lactic acid) (PLA), PLGA, PEG, and natural polymers such as polysaccharides may also be used to synthesize hydrogel nanoparticles, which are a type of nano-sized hydrophilic three-dimensional polymer network. Nanogels have favorable properties including flexible mesh size, large surface area for multivalent conjugation, high water content, and high loading capacity for antigens. Accordingly, a preferred nanoparticle is a nanogel, such as a chitosan nanogel. Preferred polymeric nanoparticles are nanoparticles based on/comprising PEG and PLGA.

Inorganic nanoparticles are nanoparticles based on/comprising inorganic substances, and examples of such nanoparticles include gold nanoparticles, iron oxide beads, iron-oxide zinc-oxide nanoparticles, carbon nanoparticles (e.g., carbon nanotubes) and mesoporous silica nanoparticles.

Inorganic nanoparticles provide a rigid structure and controllable synthesis. For example, gold nanoparticles can be easily produced in different shapes, such as spheres, rods, cubes. Inorganic nanoparticles may be surface-modified, e.g. with carbohydrates. Carbon nanoparticles provide good biocompatibility and may be produced, for example, as nanotubes or (mesoporous) spheres. For example, multiple copies of the antigenic peptide according to the present invention (or a (poly)peptide comprising the same) may be conjugated onto carbon nanoparticles, e.g. carbon nanotubes. Mesoporous carbon nanoparticles are preferred for oral administration. Silica-based nanoparticles (SiNPs) are also preferred. SiNPs are biocompatible and show excellent properties in selective tumor targeting and vaccine delivery. The abundant silanol groups on the surface of SiNPs may be used for further modification to introduce additional functionality, such as cell recognition, absorption of specific biomolecules, improvement of interaction with cells, and enhancement of cellular uptake. Mesoporous silica nanoparticles are particularly preferred.

Liposomes are typically formed by phospholipids, such as 1,2-dioleoyl-3-trimethylammonium propane (DOTAP). In general, cationic liposomes are preferred. Liposomes are self-assembling with a phospholipid bilayer shell and an aqueous core. Liposomes can be generated as unilamellar vesicles (having a single phospholipid bilayer) or as multilamellar vesicles (having several concentric phospholipid shells separated by layers of water). Accordingly, antigens can be encapsulated in the core or between different layers/shells. Preferred liposome systems are those approved for human use, such as Inflexal® V and Epaxal®.

Immunostimulating complexes (ISCOM) are cage like particles of about 40 nm (diameter), which are colloidal saponin containing micelles, for example made of the saponin adjuvant Quil-A, cholesterol, phospholipids, and the (poly)peptide antigen (such as the antigenic peptide or a polypeptide comprising the same). These spherical particles can trap the antigen by apolar interactions. Two types of ISCOMs have been described, both of which consist of cholesterol, phospholipid (typically either phosphatidylethanolamine or phosphatidylcholine) and saponin (such as Quil-A).

Virus-like particles (VLP) are self-assembling nanoparticles formed by self-assembly of biocompatible capsid proteins. Due to the naturally-optimized nanoparticle size and repetitive structural order VLPs can induce potent immune responses. VLPs can be derived from a variety of viruses with sizes ranging from 20 nm to 800 nm, typically in the range of 20-150 nm. VLPs can be engineered to express additional peptides or proteins either by fusing these peptides/proteins to the particle or by expressing multiple antigens. Moreover, antigens can be chemically coupled onto the viral surface to produce bioconjugate VLPs.

Examples of self-assembled proteins include ferritin and major vault protein (MVP). Ferritin is a protein that can self-assemble into nearly-spherical 10 nm structure. Ninety-six units of MVP can self-assemble into a barrel-shaped vault nanoparticle, with a size of approximately 40 nm wide and 70 nm long. Antigens that are genetically fused with a minimal interaction domain can be packaged inside vault nanoparticles by self-assembling process when mixed with MVPs. Accordingly, the antigen (such as the antigenic peptide according to the present invention of a polypeptide comprising the same) may be fused to a self-assembling protein or to a fragment/domain thereof, such as the minimal interaction domain of MVP. Accordingly, the present invention also provides a fusion protein comprising a self-assembling protein (or a fragment/domain thereof) and the antigenic peptide according to the present invention.

In general, preferred examples of nanoparticles (NPs) include iron oxide beads, polystyrene microspheres, poly(γ-glutamic acid) (γ-PGA) NPs, iron oxide-zinc oxide NPs, cationized gelatin NPs, pluronic-stabilized poly(propylene sulfide) (PPS) NPs, PLGA NPs, (cationic) liposomes, (pH-responsive) polymeric micelles, PLGA, cancer cell membrane coated PLGA, lipid-calcium-phosphate (LCP) NPs, liposome-protamine-hyaluronic acid (LPH) NPs, polystyrene latex beads, magnetic beads, iron-dextran particles and quantum dot nanocrystals.

Preferably, the nanoparticle further comprises an adjuvant, for example a toll-like receptor (TLR) agonist.

Thereby, the antigenic peptide (the immunogenic compound/polypeptide/protein/nucleic acid comprising the antigenic peptide) can be delivered together with an adjuvant, for example to antigen-presenting cells (APCs), such as dendritic cells (DCs). The adjuvant may be encapsulated by the nanoparticle or bound to/conjugated to the surface of the nanoparticle, preferably similarly to the antigenic peptide.

Particularly preferred adjuvants are polyinosinic: polycytidylic acid (also referred to as "poly I:C") and/or its derivative poly-ICLC. Poly I:C is a mismatched double-stranded RNA with one strand being a polymer of inosinic acid, the other a polymer of cytidylic acid. Poly I:C is an immunostimulant known to interact with toll-like receptor 3 (TLR3). Poly I:C is structurally similar to double-stranded RNA, which is the "natural" stimulant of TLR3. Accordingly, poly I:C may be considered a synthetic analog of double-stranded RNA. Poly-ICLC is a synthetic complex of carboxymethylcellulose, polyinosinic-polycytidylic acid, and poly-L-lysine double-stranded RNA. Similar to poly I:C, also poly-ICLC is a ligand for TLR3. Poly I:C and poly-ICLC typically stimulate the release of cytotoxic cytokines. A preferred example of poly-ICLC is Hiltonol®.

Pharmaceutical Compositions

In a further aspect, the present invention also provides a pharmaceutical composition comprising at least one of the following:

- the antigenic peptide according to the present invention as described herein,
- the immunogenic compound according to the present invention as described herein,
- the nanoparticle according to the present invention as described herein,
- the cell according to the present invention as described herein,
- the nucleic acid according to the present invention as described herein,
- the host cell according to the present invention as described herein, and/or
- the cytotoxic T lymphocyte according to the present invention as described herein, and, optionally, one or more pharmaceutically acceptable excipients or carriers.

Accordingly, the present invention provides a pharmaceutical composition comprising (at least) one antigenic peptide according to the present invention as described herein. Moreover, the present invention also provides a pharmaceutical composition comprising (at least) one immunogenic compound according to the present invention as described herein. Moreover, the present invention also provides a pharmaceutical composition comprising (at least) one nanoparticle according to the present invention as described herein. Moreover, the present invention also provides a pharmaceutical composition comprising (at least) one cell according to the present invention as described herein. Moreover, the present invention also provides a pharmaceutical composition comprising (at least) one nucleic acid according to the present invention as described herein. Moreover, the present invention also provides a pharmaceutical composition comprising (at least) one host cell according to the present invention as described herein. Moreover, the present invention also provides a pharmaceutical composition comprising (at least) one cytotoxic T lymphocyte according to the present invention as described herein.

In particular, preferred embodiments of the antigenic peptide as described above also apply for such a pharmaceutical composition according to the present invention. For example, the antigenic peptide comprised in the pharmaceutical composition or the antigenic peptide comprised in any of the immunogenic compound, the nanoparticle, the cell, the nucleic acid or the host cell comprised by the pharmaceutical composition preferably comprises or consists of an amino acid sequence as set forth in any one of SEQ ID NOs 1 to 247 and 476-500. For example, antigenic peptides according to the present invention comprising or consisting of an amino acid sequence as set forth in any one of SEQ ID NOs 10, 21, 33, 35, 39, 40, 61, 65, 68, 72, 86, 110, 114 and 220 are even more preferred. For example, antigenic peptides according to the present invention comprising or consisting of an amino acid sequence as set forth in any one of SEQ ID NOs 10, 21, 33, 35, 39, 40, 110, 114 and 220 are still more preferred. For example, antigenic peptides according to the present invention comprising or consisting of an amino acid sequence as set forth in any one of SEQ ID NOs 10, 110, 114 and 220 are still more preferred. For example, antigenic peptides according to the present invention comprising or consisting of an amino acid sequence as set forth in any one of SEQ ID NOs 65, 110, 114 and 220 are still more preferred.

Also combinations thereof are preferred, namely, pharmaceutical compositions comprising distinct antigenic peptides according to the present invention. For example, the pharmaceutical composition may comprise (i) at least two distinct antigenic peptides according to the present invention;
(ii) at least two distinct immunogenic compounds according to the present invention;
(iii) at least two distinct nanoparticles according to the present invention;
(iv) at least two distinct nucleic acids according to the present invention; and/or
(v) at least two distinct cytotoxic T lymphocytes according to the present invention.

Accordingly, the pharmaceutical composition may comprise at least "two distinct components" (of a pharmaceutical composition according to the present invention), preferably three or four distinct components. In general, the expression "distinct components", as used herein, refers to (1) a first component, such as the antigenic peptide according to the present invention as described herein, the immunogenic compound according to the present invention as described herein, the nanoparticle according to the present invention as described herein, the cell according to the present invention as described herein, the nucleic acid according to the present invention as described herein, the host cell according to the present invention as described herein, or the cytotoxic T lymphocyte according to the present invention as described herein; and
(2) at least one other component (which is distinct from the first component; while in the case of more than two distinct components each component is distinct from each other component), such as the anti-cancer therapeutic agent as described above, a distinct antigenic peptide according to the present invention as described herein, a distinct immunogenic compound according to the present invention as described herein, a distinct nanoparticle according to the present invention as described herein, a distinct cell according to the present invention as described herein, a distinct nucleic acid according to the present invention as described herein, a distinct host cell according to the present invention as described herein, a distinct cytotoxic T lymphocyte according to the present invention as described herein, or one or more (fragments of) human tumor antigens in any form ("naked", as immunogenic compound as described herein, as nanoparticle as described herein, as (host) cell as described herein, or as nucleic acid as described herein).

Accordingly, the "distinct components" are preferably active components (as described above) in the context of a disease (B-cell malignancy) to be prevented and/or treated. In other words, each of the distinct components may also be useful for preventing and/or treating said cancer, if administered separately (not in combination as described herein)—although the combination (i.e. combined administration) typically potentiates their preventive and/or therapeutic effect (such as the immune response), preferably in a synergistic manner.

Preferably, the "distinct components" are of the same type (e.g., distinct antigenic peptides, distinct immunogenic compounds, distinct nanoparticles, distinct cells, distinct nucleic acids, distinct host cells, or distinct cytotoxic T lymphocytes) and differ from each other only in that they relate to distinct antigenic peptides of the present invention as described herein.

For example, the at least three or four distinct active components are preferably of the same type, but differ (only) in that each of them relates to a distinct antigenic peptide. More preferably

- a first component relates to the antigenic peptide comprising or consisting of a (microbiota) sequence variant of a fragment of the human tumor antigen CD22;
- a (distinct) second component relates to the antigenic peptide comprising or consisting of a (microbiota) sequence variant of a fragment of the human tumor antigen CD37;
- a (distinct) third component relates to the antigenic peptide comprising or consisting of a (microbiota) sequence variant of a fragment of the human tumor antigen TNFRSF13C; and
- optionally, a (distinct) fourth component relates to the antigenic peptide comprising or consisting of a (microbiota) sequence variant of a fragment of the human tumor antigen MS4A1 (CD20).

Even more preferably

- a first component relates to the antigenic peptide comprising or consisting of a (microbiota) sequence variant of SEQ ID NO: 270;
- a (distinct) second component relates to the antigenic peptide comprising or consisting of a (microbiota) sequence variant of SEQ ID NO: 271;
- a (distinct) third component relates to the antigenic peptide comprising or consisting of a (microbiota) sequence variant of SEQ ID NO: 279; and
- optionally, a (distinct) fourth component relates to the antigenic peptide comprising or consisting of a (microbiota) sequence variant of SEQ ID NO: 264.

Still more preferably

- a first component relates to the antigenic peptide comprising or consisting of an amino acid sequence as set forth in SEQ ID NO: 110;
- a (distinct) second component relates to the antigenic peptide comprising or consisting of an amino acid sequence as set forth in SEQ ID NO: 114;
- a (distinct) third component relates to the antigenic peptide comprising or consisting of an amino acid sequence as set forth in SEQ ID NO: 220; and
- optionally, a (distinct) fourth component relates to the antigenic peptide comprising or consisting of an amino acid sequence as set forth in SEQ ID NO: 65.

Preferably, the pharmaceutical composition comprises at least two distinct antigenic peptides according to the present invention.

Preferably, the pharmaceutical composition comprises a first antigenic peptide according to the present invention, which comprises or consists of a (microbiota) sequence variant of a fragment of the human tumor antigen CD22, and a second antigenic peptide according to the present invention, which comprises or consists of a (microbiota) sequence variant of a fragment of the human tumor antigen TNFRSF13C. Preferably, the first antigenic peptide comprises or consists of a (microbiota) sequence variant of the CD22 fragment (human reference peptide) "WVFEHPETL" (SEQ ID NO: 270), such as an antigenic peptide comprising or consisting of an amino acid sequence as set forth in SEQ ID NO: 106-110, 316 and 387-390 and 485-488, e.g. an antigenic peptide comprising or consisting of an amino acid sequence as set forth in any one of SEQ ID NO: 107, 108, 109 and 110, and the second antigenic peptide comprises or consists of a (microbiota) sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 210-225, 325 and 447-455 and 494-500, e.g. an antigenic peptide comprising or consisting of an amino acid sequence as set forth in any one of SEQ ID NO: 212, 217, 220 and 224, in particular as set forth in SEQ ID NO: 220, 325 and 450. More preferably, the first antigenic peptide comprises or consists of an amino acid sequence as set forth in SEQ ID NO: 110, 387 and 390 and the second antigenic peptide comprises or consists of an amino acid sequence as set forth in SEQ ID NO: 220, and 450. Even more preferably, the pharmaceutical composition comprises an antigenic peptide comprising or consisting of SEQ ID NO: 110 and an antigenic peptide comprising or consisting of SEQ ID NO: 220.

More preferably, the pharmaceutical composition comprises at least three distinct antigenic peptides according to the present invention.

In particular, the pharmaceutical composition may comprise a first antigenic peptide according to the present invention, which comprises or consists of a (microbiota) sequence variant of a fragment of the human tumor antigen CD22, a second antigenic peptide according to the present invention, which comprises or consists of a (microbiota) sequence variant of a fragment of the human tumor antigen TNFRSF13C and a third antigenic peptide according to the present invention, which comprises or consists of a (microbiota) sequence variant of a fragment of the human tumor antigen CD37. Preferably, the pharmaceutical composition comprises a first antigenic peptide comprising or consisting of a (microbiota) sequence variant of the CD22 fragment (human reference peptide) "WVFEHPETL" (SEQ ID NO: 270), such as an antigenic peptide comprising or consisting of an amino acid sequence as set forth in SEQ ID NO: 106-110, 316 and 387-390 and 485-488, e.g. an antigenic peptide comprising or consisting of an amino acid sequence as set forth in any one of SEQ ID NO: 107, 108, 109 and 110, a second antigenic peptide comprising or consisting of a (microbiota) sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 210-225, 325 and 447-455 and 494-500, e.g. an antigenic peptide comprising or consisting of an amino acid sequence as set forth in any one of SEQ ID NO: 212, 217, 220 and 224, in particular as set forth in SEQ ID NO: 220, 325 and 450 and a third antigenic peptide comprising or consisting of a (microbiota) sequence variant of the CD37 fragment (human reference peptide) "GLAFVPLQI" (SEQ ID NO: 271), such as an antigenic peptide comprising or consisting of an amino acid sequence as set forth in SEQ ID NO: 111-130, 317, and 391-402 and 489-493, e.g. an antigenic peptide comprising or consisting of an amino acid sequence as set forth in any one of SEQ ID NO: 114, 117, 119, 120, 491 and 493, in particular as set forth in SEQ ID NO: 113-116, 324 and 392-393.

Still more preferably, the pharmaceutical composition comprises at least four distinct antigenic peptides according to the present invention.

In particular, the pharmaceutical composition may comprise a first antigenic peptide according to the present invention, which comprises or consists of a (microbiota) sequence variant of a fragment of the human tumor antigen CD22, a second antigenic peptide according to the present invention, which comprises or consists of a (microbiota) sequence variant of a fragment of the human tumor antigen TNFRSF13C, a third antigenic peptide according to the present invention, which comprises or consists of a (microbiota) sequence variant of a fragment of the human tumor antigen CD37, a fourth antigenic peptide according to the present invention, which comprises or consists of a (microbiota) sequence variant of a fragment of the human tumor antigen CD19 or CD20. Preferably, the pharmaceutical composition comprises a first antigenic peptide comprising or consisting of a (microbiota) sequence variant of the CD22 fragment (human reference peptide) "WVFEHPETL" (SEQ ID NO: 270), such as an antigenic peptide comprising or consisting of an amino acid sequence as set forth in SEQ ID NO: 106-110, 316 and 387-390 and 485-488, e.g. an antigenic peptide comprising or consisting of an amino acid sequence as set forth in any one of SEQ ID NO: 107, 108, 109 and 110; a second antigenic peptide comprising or consisting of a (microbiota) sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 210-225, 325 and 447-455 and 494-500, e.g. an antigenic peptide comprising or consisting of an amino acid sequence as set forth in any one of SEQ ID NO: 212, 217, 220 and 224, in particular as set forth in SEQ ID NO: 220, 325 and 450; a third antigenic peptide comprising or consisting of a (microbiota) sequence variant of the CD37 fragment (human reference peptide) "GLAFVPLQI" (SEQ ID NO: 271), such as an antigenic peptide comprising or consisting of an amino acid sequence as set forth in SEQ ID NO: 111-130, 317, and 391-402 and 489-493, e.g. an antigenic peptide comprising or consisting of an amino acid sequence as set forth in any one of SEQ ID NO: 114, 117, 119, 120, 491 and 493, in particular as set forth in SEQ ID NO: 113-116, 324 and 392-393; and a fourth antigenic peptide comprising or consisting of a (microbiota) sequence variant of the CD20 (MS4A1) fragment (human reference peptide) "IMNSLSLFA" (SEQ ID NO: 264), such as an antigenic peptide comprising or consisting of an amino acid sequence as set forth in SEQ ID NO: 65-70, 310 and 361-364 and 476-484, e.g. an antigenic peptide comprising or consisting of an amino acid sequence as set forth in any one of SEQ ID NO: 65, 68, 70 and 477.

Preferably, the pharmaceutical composition comprises:

- a first antigenic peptide according to the present invention, which comprises or consists of a (microbiota) sequence variant of a fragment of the human tumor antigen CD22,
- a second antigenic peptide according to the present invention, which comprises or consists of a (microbiota) sequence variant of a fragment of the human tumor antigen TNFRSF13C,
- a third antigenic peptide according to the present invention, which comprises or consists of a (microbiota) sequence variant of a fragment of the human tumor antigen CD37, and
- optionally, a fourth antigenic peptide according to the present invention, which comprises or consists of a (microbiota) sequence variant of a fragment of the human tumor antigen CD20.

More preferably, the pharmaceutical composition comprises:

- a first antigenic peptide comprising or consisting of a (microbiota) sequence variant of the CD22 fragment (human reference peptide) "WVFEHPETL" (SEQ ID NO: 270), such as an antigenic peptide comprising or consisting of an amino acid sequence as set forth in SEQ ID NO: 106-110, 316 and 387-390,
- a second antigenic peptide comprising or consisting of a (microbiota) sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 220, 325 and 450,
- a third antigenic peptide comprising or consisting of a (microbiota) sequence variant of the CD37 fragment (human reference peptide) "GLAFVPLQI" (SEQ ID NO: 271), such as an antigenic peptide comprising or consisting of an amino acid sequence as set forth in SEQ ID NO: 113-116, 324 and 392-393, and
- optionally, a fourth antigenic peptide comprising or consisting of a (microbiota) sequence variant of the CD20 fragment (human reference peptide) "IMNSLSLFA" (SEQ ID NO: 264), such as an antigenic peptide comprising or consisting of an amino acid sequence as set forth in SEQ ID NO: 65-70, 310 and 361-364.

Even more preferably, the pharmaceutical composition comprises antigenic peptides according to the present invention comprising or consisting of an amino acid sequence as set forth in SEQ ID NOs 110, 114, 220 and, optionally, 65.

In some embodiments, the pharmaceutical composition does not comprise further antigenic peptides (in addition to the antigenic peptides of the invention as described above).

It is understood that the pharmaceutical composition may also contain—instead of the above-described preferred combinations of antigenic peptides—a respective combination of immunogenic compounds of the invention, a respective combination of nanoparticles of the invention or a respective combination of nucleic acids of the invention.

Preferably, the pharmaceutical composition further comprises one or more pharmaceutically acceptable excipients or carriers.

The pharmaceutical composition of the invention may be in any form suitable for the purposes of the invention. For example, said composition may be in a form suitable for parenteral, enteral or topical administration, such as a liquid suspension, a solid dosage form (granules, pills, capsules or tablets), or a paste or gel. It is within the skill of the person in the art to select the appropriate form of the composition for the intended purpose.

The composition according to the invention can further comprise other active agents, for example such, which can enhance the effects of the antigenic peptide or immunogenic compound. Alternatively, the composition may not comprise any other active agents (i.e., other than the antigenic peptide according to the present invention, the immunogenic compound according to the present invention, the nanoparticle according to the present invention, the cell according to the present invention, the nucleic acid according to the present invention, and/or the host cell according to the present invention).

The pharmaceutical composition as defined herein is preferably an immunogenic composition, i.e. a composition that is able to induce, increase, prolong or maintain an immune response. This may be achieved by an antigenic peptide according to the present invention or by an immunogenic compound according to the present invention comprised in said composition. Preferably, the pharmaceutical composition further comprises one or more immuno-adjuvant substances. A pharmaceutical composition, in particular an immunogenic composition, may also be termed "vaccine composition" in the present specification.

Preferably, the pharmaceutical composition further comprises at least one immunostimulatory agent, in particular so as to increase, potentiate, prolong or maintain the immune response mediated by the antigenic peptide. Preferred immunostimulatory agents according to the invention include, without limitation, immune adjuvants, antigen-presenting cells, and combinations thereof. Preferably, the immunostimulatory agent is an immune adjuvant or an antigen-presenting cell (APC).

Preferably, the immunostimulatory agent is an immune adjuvant. Some immune adjuvants are capable of favoring and prolonging the duration of interaction between an antigen and the immune system, while others are capable of recruiting and activating cells of the natural immunity so as to induce an adaptive response. The adjuvants belonging to the former category include, without limitation, mineral compounds such as alum, aluminum hydroxide, aluminum phosphate, calcium phosphate hydroxide; and oil-based emulsions such as paraffin oil, starch oil, Freund's complete/incomplete adjuvant (FCA/FIA), saponins (e.g. from the plants *Quillaja*, Soybean, *Polygala senega*). The adjuvants of belonging to the latter category include, without limitation, immunostimulatory complexes (ISCOMs) such as cytokines (e.g. GM-CSF; Interleukins such as IL-1, IL-2, IL6, IL8, or IL12; Tumor necrosis factors (TNFs) such as TNFα or TNFβ; Interferons IFNS such as IFNα, IFNβ, IFNγ or IFNδ, etc); ligands of toll-like receptors (TLRs) such as imiquimod, resiquimod or MPL; exosomes such as exosomes derived from dendritic cells (DCs) or from tumor cells; bacterial products such as heat-shock proteins (HSPS such as gp96, hsp90, hsp70, calreticulin, hsp110, hsp170), pathogen-associated molecular patterns (PAMPs), trehalose dimicolate (TDM), muramyldipeptide (MDP), polysaccharide (PLS) such as polysaccharide-K.

More preferably, the immune adjuvant is a protein/peptide having immuno-adjuvant properties, such as providing stimulation of CD4+ Th1 cells, as described herein ("helper" peptides). A preferred example thereof is a non-tumor antigen that recalls immune memory or provides a non-specific help or could be a specific tumor-derived helper peptide, such as tetanus helper peptide, keyhole limpet hemocyanin peptide or PADRE peptide, as described herein. Another preferred example is a specific tumor derived helper peptide, which may be presented by MHC II, in particular by HLA-DR, HLA-DP or HLA-DQ, such as fragments of shared overexpressed tumor antigens, e.g. HER2, NY-ESO-1, hTERT or IL13RA2, as described above. In particular, the immune adjuvant may be the HHD-DR3 peptide of sequence MAKTIAYDEEARRGLERGLN (SEQ ID NO: 473). This peptide represents another example of a helper peptide (having immuno-adjuvant properties), which is preferred in the context of the present invention. Another preferred example is h-pAg T13L (sequence: TPPAYRPPNAPIL; SEQ ID NO: 474; Bhasin M, Singh H, Raghava G P (2003) MHCBN: a comprehensive database of MHC binding and non-binding peptides. Bioinformatics 19: 665-666). Further examples of preferred immune adjuvants, in particular of helper peptides, include the UCP2 peptide (for example as described in WO 2013/135553 A1 or in Dosset et al., Clin Cancer Res. 2012 Nov. 15; 18(22):6284-95) and the BIRC5 peptide (for example as described in EP2119726 A1 or in Widenmeyer et al., Int J Cancer. 2012 Jul. 1,131 (1):140-9). The most preferred helper peptide is the UCP2 peptide (amino acid sequence: KSVWSKLQSIGIRQH; SEQ ID NO: 475).

Preferably, the pharmaceutical composition comprises at least two distinct antigenic peptides according to the present invention and a helper peptide, preferably the UCP2 peptide (SEQ ID NO: 475).

In particular, the pharmaceutical composition may comprise a first antigenic peptide according to the present invention, which comprises or consists of a sequence variant of a fragment of the human tumor antigen CD22, a second antigenic peptide according to the present invention, which comprises or consists of a sequence variant of a fragment of the human tumor antigen TNFRSF13C and a helper peptide, preferably the UCP2 peptide (SEQ ID NO: 475). Preferably, the pharmaceutical composition comprises a first antigenic peptide comprising or consisting of a sequence variant of the CD22 fragment (human reference peptide) "WVFEHPETL" (SEQ ID NO: 270), such as an antigenic peptide comprising or consisting of an amino acid sequence as set forth in SEQ ID NO: 106-110, 316 and 387-390, a second antigenic peptide comprising or consisting of a sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 220, 325 and 450 and a helper peptide, preferably the UCP2 peptide (SEQ ID NO: 475). More preferably, the first antigenic peptide comprises or consists of an amino acid sequence as set forth in SEQ ID NO: 110, 387 and 390 and the second antigenic peptide comprises or consists of an amino acid sequence as set forth in SEQ ID NO: 220, and 450. Even more preferably, the pharmaceutical composition comprises an antigenic peptide comprising or consisting of SEQ ID NO: 110, an antigenic peptide comprising or consisting of SEQ ID NO: 220 and the UCP2 helper peptide (SEQ ID NO: 475).

Still more preferably, the pharmaceutical composition comprises at least three distinct antigenic peptides according to the present invention and a helper peptide, preferably the UCP2 peptide (SEQ ID NO: 475).

In particular, the pharmaceutical composition may comprise a first antigenic peptide according to the present invention, which comprises or consists of a (microbiota) sequence variant of a fragment of the human tumor antigen CD22, a second antigenic peptide according to the present invention, which comprises or consists of a (microbiota) sequence variant of a fragment of the human tumor antigen TNFRSF13C, a third antigenic peptide according to the present invention, which comprises or consists of a (microbiota) sequence variant of a fragment of the human tumor antigen CD37 and a helper peptide, preferably the UCP2 peptide (SEQ ID NO: 475). Preferably, the pharmaceutical composition comprises a first antigenic peptide comprising or consisting of a (microbiota) sequence variant of the CD22 fragment (human reference peptide) "WVFEHPETL" (SEQ ID NO: 270), such as an antigenic peptide comprising or consisting of an amino acid sequence as set forth in SEQ ID NO: 106-110, 316 and 387-390, a second antigenic peptide comprising or consisting of a (microbiota) sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 220, 325 and 450, a third antigenic peptide comprising or consisting of a (microbiota) sequence variant of the CD37 fragment (human reference peptide) "GLAFVPLQI" (SEQ ID NO: 271), such as an antigenic peptide comprising or consisting of an amino acid sequence as set forth in SEQ ID NO: 113-116, 324 and 392-393, and a helper peptide, preferably the UCP2 peptide (SEQ ID NO: 475).

Most preferably, the pharmaceutical composition comprises at least four distinct antigenic peptides according to the present invention and a helper peptide, preferably the UCP2 peptide (SEQ ID NO: 475).

In particular, the pharmaceutical composition may comprise a first antigenic peptide according to the present invention, which comprises or consists of a (microbiota) sequence variant of a fragment of the human tumor antigen CD22, a second antigenic peptide according to the present invention, which comprises or consists of a (microbiota) sequence variant of a fragment of the human tumor antigen TNFRSF13C, a third antigenic peptide according to the present invention, which comprises or consists of a (microbiota) sequence variant of a fragment of the human tumor antigen CD37, a fourth antigenic peptide according to the present invention, which comprises or consists of a (microbiota) sequence variant of a fragment of the human tumor antigen CD19 or CD20 and a helper peptide, preferably the UCP2 peptide (SEQ ID NO: 475).

Preferably, the pharmaceutical composition comprises a first antigenic peptide according to the present invention, which comprises or consists of a (microbiota) sequence variant of a fragment of the human tumor antigen CD22, a second antigenic peptide according to the present invention, which comprises or consists of a (microbiota) sequence variant of a fragment of the human tumor antigen TNFRSF13C, a third antigenic peptide according to the present invention, which comprises or consists of a (microbiota) sequence variant of a fragment of the human tumor antigen CD37, (optionally) a fourth antigenic peptide according to the present invention, which comprises or consists of a (microbiota) sequence variant of a fragment of the human tumor antigen CD20, and a helper peptide, preferably the UCP2 peptide (SEQ ID NO: 475). More preferably, the pharmaceutical composition comprises a first antigenic peptide comprising or consisting of a (microbiota) sequence variant of the CD22 fragment (human reference peptide) "WVFEHPETL" (SEQ ID NO: 270), such as an antigenic peptide comprising or consisting of an amino acid sequence as set forth in SEQ ID NO: 106-110, 316 and 387-390, a second antigenic peptide comprising or consisting of a (microbiota) sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 220, 325 and 450, a third antigenic peptide comprising or consisting of a (microbiota) sequence variant of the CD37 fragment (human reference peptide) "GLAFVPLQI" (SEQ ID NO: 271), such as an antigenic peptide comprising or consisting of an amino acid sequence as set forth in SEQ ID NO: 113-116, 324 and 392-393, (optionally) a fourth antigenic peptide comprising or consisting of a (microbiota) sequence variant of the CD20 fragment (human reference peptide) "IMNSLSLFA" (SEQ ID NO: 264), such as an antigenic peptide comprising or consisting of an amino acid sequence as set forth in SEQ ID NO: 65-70, 310 and 361-364, and a helper peptide, preferably the UCP2 peptide (SEQ ID NO: 475).

Particularly preferred immune adjuvants are polyinosinic: polycytidylic acid (also referred to as "poly I:C") and/or its derivative poly-ICLC. Poly I:C is a mismatched double-stranded RNA with one strand being a polymer of inosinic acid, the other a polymer of cytidylic acid. Poly I:C is an immunostimulant known to interact with toll-like receptor 3 (TLR3). Poly I:C is structurally similar to double-stranded RNA, which is the "natural" stimulant of TLR3. Accordingly, poly I:C may be considered a synthetic analog of double-stranded RNA. Poly-ICLC is a synthetic complex of carboxymethylcellulose, polyinosinic-polycytidylic acid, and poly-L-lysine double-stranded RNA. Similar to poly I:C, also poly-ICLC is a ligand for TLR3. Poly I:C and poly-ICLC typically stimulate the release of cytotoxic cytokines. A preferred example of poly-ICLC is Hiltonol®.

Most preferably, the adjuvant is Montanide, such as Montanide ISA 51 VG and/or Montanide ISA 720 VG. Those adjuvants are rendering stable water-in-oil emulsions when mixed with water based antigenic media. Montanide ISA 51 VG is based on a blend of mannide monooleate surfactant and mineral oil, whereas Montanide ISA 720 VG uses a non-mineral oil (Aucouturier J, Dupuis L, Deville S, Ascarateil S, Ganne V. Montanide ISA 720 and 51: a new generation of water in oil emulsions as adjuvants for human vaccines. Expert Rev Vaccines. 2002 June; 1(1): 111-8; Ascarateil S, Puget A, Koziol M-E. Safety data of Montanide ISA 51 VG and Montanide ISA 720 VG, two adjuvants dedicated to human therapeutic vaccines. Journal for Immunotherapy of Cancer. 2015; 3(Suppl 2):P428. doi:10.1186/2031-1426-3-S2-P428).

It is also preferred that the immunostimulatory agent is an antigen-presenting cell (APC). APCs are also of particular interest, as their main function is to process antigens and present it on the cell surface to the T cells of the immune system, so as to initiate and modulate T-cell responses in vivo. In the present composition, it is preferred that the APCs are loaded with the antigenic peptide(s) and/or immunogenic compound(s) according to the invention, which can be done by exposing APCs in vitro with said antigenic peptide(s) and/or immunogenic compound(s) (Rizzo et al., Methods Mol Biol. 2014; 1139:41-4; Rolinski and Hus, J Immunotoxicol. 2014 October; 11(4):311-8).

Preferably, the APC is a dendritic cell (DC). DCs are the most potent APCs and have been reported to be frequently functionally defective in cancer patients. DCs can be easily obtained by the skilled person in the art from either healthy compatible donors (i.e. the dendritic cells are HLA-related) or from the patient himself provided that they are functional (i.e. the DCs are autologous), for example by direct isolation from the peripheral blood, or by derivation from peripheral blood cells such as CD14+ monocytes or CD34+ hematopoietic precursors (Emens et al., 2008). DCs can indeed be distinguished from other cells of peripheral blood by their surface markers, such as S100, p55, CD83, and/or OX62, and may thus be isolated and purified based on said markers using cell cultures techniques well-known in the art.

According to a preferred embodiment, the pharmaceutical composition may further comprise at least one anti-cancer therapeutic agent. Said therapeutic agent is thus preferably capable of preventing and/or treating the same type of cancer than the one for which the antigenic peptide according to the invention is used. Preferably, the anti-cancer therapeutic agent is selected from antibodies, CAR-T cells, tumor cell lysates, chemotherapeutic agents, radiotherapeutic agents, immune checkpoint modulators and combinations thereof.

Antibodies are particularly advantageous in cancer therapy as they can either bind to specific antigens on cancer cell surfaces, thereby directing the therapy to the tumor (i.e. these are referred as tumor-targeting antibodies), or block immune checkpoints that are dysregulated in cancer (i.e. these are referred herein as immunomodulatory antibodies). The purpose of the later type of antibodies is to inhibit cancer immune resistance, which can notably be observed against T cells that are specific for tumor antigens. Indeed, as well-known in the art, under normal physiological conditions, immune checkpoints are crucial for the maintenance of self-tolerance (i.e. prevention of autoimmunity) and protect tissues from damage when the immune system is responding to pathogenic infection. However, in cancer, immune-checkpoints expression can be dysregulated as an important mechanism of immune resistance. Said resistance has notably been observed in melanoma, ovarian, lung, glioblastoma, breast, and pancreatic cancers with regard to the PD-L1 checkpoint (Konishi et al., B7-H1 expression on non-small cell lung cancer cells and its relationship with tumor-infiltrating lymphocytes and their PD-1 expression. Clin Cancer Res. 2004 Aug. 1; 10(13):3094-100; Ghebeh et al., The B7-H1 (PD-L1) T lymphocyte-inhibitory molecule is expressed in breast cancer patients with infiltrating ductal carcinoma: correlation with important high-risk prognostic factors. Neoplasia. 2006 March; 8(3):190-8; Hino et al., Tumor cell expression of programmed cell death-1 ligand 1 is a prognostic factor for malignant melanoma. Cancer. 2010 Apr. 1; 116(7):1757-66). Other examples of immune checkpoints include, without limitation, PD-L2, PD-1, CD80, CD86, CTLA-4, B7H3, B7H4, PVR, TIGIT, GALS, LAG-3, GITR, CD137, TIM3, VISTA, VISTA-R (Pico de Coaña et al., Checkpoint blockade for cancer therapy: revitalizing a suppressed immune system. Trends Mol Med. 2015 August; 21(8):482-91; Pardoll D M. The blockade of immune checkpoints in cancer immunotherapy. Nat Rev Cancer. 2012 Mar. 22; 12(4):252-64).

Antibodies are usually employed for the above purposes either in the form of naked monoclonal antibodies (i.e. non-conjugated), or conjugated to another molecule which can be toxic to cells or radioactive.

Examples of well-known monoclonal tumor-targeting antibodies used in cancer immunotherapy include, without limitation, alemtuzumab (chronic lymphocytic leukemia), bevacizumab (colorectal cancer, glioblastoma multiforme, cervical cancer, lung cancer, renal cancer), brentuximab/vedotin (lymphomas), blinatumomab (acute lymphoblastic leukemia), catumaxomab (malignant ascites in EPCAM+ cancers), cetuximab (head and neck cancer, colorectal cancer), denosumab (breast, prostate and bone cancers), Gemtuzumab/ozogamicin (acute myeloid leukemia), ibritumomab/tiuxetan (non-Hodgkin lymphoma), panitumumab (colorectal cancer), pertuzumab (breast cancer), obinutuzumab (chronic lymphocytic leukemia), ofatumumab (chronic lymphocytic leukemia), opilimumab (melanoma), ramucirumab (gastric and gastro-oeasophageal cancers), rituximab (chronic lymphocytic leukemia and non-Hodgkin lymphoma), siltuximab (multicentric's Catsleman's disease), tositumomab (non-Hodgkin lymphoma), and trastuzumab (breast, gastric and gastro-oeasophageal cancers); while examples of immunomodulatory antibodies include, without limitation, ipilimumab (melanoma) which blocks the CTLA4-dependent immune checkpoint, nivolumab (melanoma, lung cancer) and prembrolizubmab (melanoma) which both block the PDCD1-dependent immune checkpoint, as well as MPDL3280A, MED14736, MEDI0680, and MSB0010718C which all block the PD-L1-dependent immune checkpoint (Sharma and Allison, The future of immune checkpoint therapy. Science. 2015 Apr. 3; 348(6230):56-61).

Other antibodies for cancer immunotherapy have been described in Buqué et al., Trial Watch: Immunomodulatory monoclonal antibodies for oncological indications. Oncoimmunology. 2015 Mar. 2; 4(4):e1008814. eCollection 2015 April; Redman et al., Mechanisms of action of therapeutic antibodies for cancer. Mol Immunol. 2015 October; 67(2 Pt A):28-45; Simpson and Caballero, Monoclonal antibodies for the therapy of cancer MC Proc. 2014; 8(Suppl 4): 06 as well as on the antibody society website (list of therapeutic monoclonal antibodies approved or in review in the European Union or United States available on the weblink http://www.antibodysociety.org/news/approved_mabs.php).

Adoptive cellular immunotherapy with chimeric antigen receptor (CAR) T cells has changed the treatment landscape of B-cell non-Hodgkin's lymphoma (NHL), especially for aggressive B-cell lymphomas. For instance, CD19-targeted CAR T-cells, represent the new standard of care for patients with DLBCL that are refractory to at least two prior lines of therapy. Two CAR T-cell products axicabtagene ciloleucel (axi-cel) (KTE-019) (YESCARTA™) and tisagenlecleucel (CTL019) (KYMRIAH™) have obtained US Food and Drug Administration approval for the treatment of refractory DLBCL after two lines of therapy. A third product, lisocabtagene maraleucel (liso-cel) (JCAR017), is currently being evaluated in clinical trials. Other CAR T-cells include CD20-CAR-T cells.

Tumor cell lysates may also be combined with the antigenic peptide(s) according to the invention. Tumor cells are indeed capable of priming the immune response, by presenting endogenous peptides-MHC complexes, as well as via dendritic cells (DCs) of the host which can process and present the antigen delivered by said lysates. The range of antigens against which an immune response can be induced is thereby increased. Tumor cell lysates can be easily obtained by treating tumor cells with a heat shock and/or a chemical treatment, and can be autologous (i.e. isolated from the patient), or allogeneic (i.e. isolated from another subject).

Standard chemotherapeutic drugs and radiotherapeutic agents need not be further described herein as they have been extensively described in the literature, notably by Baskar et al. (Baskar et al., Cancer and radiation therapy: current advances and future directions. Int J Med Sci. 2012; 9(3):193-9), Paci et al., (Paci et al., Review of therapeutic drug monitoring of anticancer drugs part 1—cytotoxics. Eur J Cancer. 2014 August; 50(12):2010-9) and Widmer et al. (Widmer et al., Review of therapeutic drug monitoring of anticancer drugs part two—targeted therapies. Eur J Cancer. 2014 August; 50(12):2020-36). A list of such drugs and agents is also available on the cancer.gov website (http://www.cancer.gov/about-cancer/treatment/drugs).

Preferably, the immune checkpoint modulator for combination with the antigenic peptide as defined herein is an activator or an inhibitor of one or more immune checkpoint point molecule(s) selected from CD27, CD28, CD40, CD122, CD137, OX40, GITR, ICOS, A2AR, B7-H3, B7-H4, BTLA, CD40, CTLA-4, IDO, KIR, LAG3, PD-1, TIM-3, VISTA, CEACAM1, GARP, PS, CSF1R, CD94/

NKG2A, TDO, GITR, TNFR and/or FasR/DcR3; or an activator or an inhibitor of one or more ligands thereof.

More preferably, the immune checkpoint modulator is an activator of a (co-)stimulatory checkpoint molecule or an inhibitor of an inhibitory checkpoint molecule or a combination thereof.

Accordingly, the immune checkpoint modulator is more preferably (i) an activator of CD27, CD28, CD40, CD122, CD137, OX40, GITR and/or ICOS or (ii) an inhibitor of A2AR, B7-H3, B7-H4, BTLA, CD40, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or FasR/DcR3.

Even more preferably, the immune checkpoint modulator is an inhibitor of an inhibitory checkpoint molecule (but preferably no inhibitor of a stimulatory checkpoint molecule). Accordingly, the immune checkpoint modulator is even more preferably an inhibitor of A2AR, B7-H3, B7-H4, BTLA, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or DcR3 or of a ligand thereof.

It is also preferred that the immune checkpoint modulator is an activator of a stimulatory or costimulatory checkpoint molecule (but preferably no activator of an inhibitory checkpoint molecule). Accordingly, the immune checkpoint modulator is more preferably an activator of CD27, CD28, CD40, CD122, CD137, OX40, GITR and/or ICOS or of a ligand thereof.

It is even more preferred that the immune checkpoint modulator is a modulator of the CD40 pathway, of the IDO pathway, of the LAG3 pathway, of the CTLA-4 pathway and/or of the PD-1 pathway. In particular, the immune checkpoint modulator is preferably a modulator of CD40, LAG3, CTLA-4, PD-L1, PD-L2, PD-1 and/or IDO, more preferably the immune checkpoint modulator is an inhibitor of CTLA-4, PD-L1, PD-L2, PD-1, LAG3, and/or IDO or an activator of CD40, even more preferably the immune checkpoint modulator is an inhibitor of CTLA-4, PD-L1, PD-1, LAG3 and/or IDO, even more preferably the immune checkpoint modulator is an inhibitor of LAG3, CTLA-4 and/or PD-1, and most preferably the immune checkpoint modulator is an inhibitor of CTLA-4 and/or PD-1.

Accordingly, the checkpoint modulator for combination with the antigenic peptide may be selected from known modulators of the CTLA-4 pathway or the PD-1 pathway. Preferably, the checkpoint modulator for combination with the antigenic peptide as defined herein may be selected from known modulators of the CTLA-4 pathway or the PD-1 pathway. Particularly preferably, the immune checkpoint modulator is a PD-1 inhibitor. Preferred inhibitors of the CTLA-4 pathway and of the PD-1 pathway include the monoclonal antibodies Yervoy® (Ipilimumab; Bristol Myers Squibb) and Tremelimumab (Pfizer/MedImmune) as well as Opdivo® (Nivolumab; Bristol Myers Squibb), Keytruda® (Pembrolizumab, also known as Lambrolizumab or MK-3475; Merck), Imfinzi® (Durvalumab, also known as MEDI4736; MedImmune/AstraZeneca), Tecentriq® (Atezolizumab, also known as MPDL3280A; Roche/Genentech), Pidilizumab (CT-011; CureTech), MEDI0680 (AMP-514; AstraZeneca), Bavencio® (Avelumab; Merck KGaA/Pfizer, also known as MSB-0010718C), MIH1 (Affymetrix), LY3300054 (Eli Lilly) and Spartalizumab (also known as PDR001; Novartis). More preferred checkpoint inhibitors include the CTLA-4 inhibitors Yervoy® (Ipilimumab; Bristol Myers Squibb) and Tremelimumab (Pfizer/MedImmune) as well as the PD-1 inhibitors Opdivo® (Nivolumab; Bristol Myers Squibb), Keytruda® (Pembrolizumab; Merck), Pidilizumab (CT-011; CureTech), MEDI0680 (AMP-514; AstraZeneca), AMP-224 (a PD-L2 Fc fusion protein; MedImmune).

It is also preferred that the immune checkpoint modulator for combination with the antigenic peptide as defined herein is selected from the group consisting of Pembrolizumab, Ipilimumab, Nivolumab, Atezolizumab, Durvalumab, Tremelimumab, Avelumab, Spartalizumab, LAG525 (an anti-LAG-3 monoclonal antibody), Epacadostat (also known as INCB24360; an IDO inhibitor), Varlilumab (an anti-CD27 monoclonal antibody), Urelumab (an anti-CD137 monoclonal antibody), AMP-224 and CM-24 (an anti-CEACAM1 monoclonal antibody).

It is within the skill of ordinary person in the art to select the appropriate immune anti-cancer therapeutic agent for the purposes of the invention. For example, should one wish to prevent or treat melanoma, a lysate from melanoma cells and/or the antibody Ipilimumab can preferably be used, along with an appropriate antigenic peptide. Appropriate antigenic peptides may be selected by (i) selecting an appropriate tumor antigen for a certain type of cancer as known in the art and/or as described herein in Table 1B and (ii) selecting an appropriate antigenic peptide according to the invention for the selected tumor antigen, as described above, e.g. in Table 1A.

The anti-cancer therapeutic agent can also be administered in combination with the composition of the invention, either simultaneously, separately, or sequentially. Should the composition and the therapeutic agent be administered in a separate or sequential manner, those may be administered in distinct pharmaceutical forms.

Thus, in another aspect, the invention relates to a composition of the invention and at least one anti-cancer therapeutic agent as described above, as a combined preparation for a simultaneous, separate, or sequential administration. In other terms, the invention proposes a combined use of the composition the invention and least one anti-cancer therapeutic agent as described above, for a simultaneous, separate, or sequential administration.

Kits-of-Parts

In a further aspect, the present invention also provides a kit-of-parts (also referred to herein as "kit") comprising at least one of the following:

- the antigenic peptide according to the present invention as described herein,
- the immunogenic compound according to the present invention as described herein,
- the nanoparticle according to the present invention as described herein,
- the cell according to the present invention as described herein,
- the nucleic acid according to the present invention as described herein,
- the host cell according to the present invention as described herein,
- the cytotoxic T lymphocyte according to the present invention as described herein, and/or
- the pharmaceutical composition according to the present invention as described herein.

In particular, preferred embodiments of the antigenic peptide as described above also apply for such a kit according to the present invention. For example, the antigenic peptide comprised in the kit or the antigenic peptide comprised in any of the immunogenic compound, the nanoparticle, the cell, the nucleic acid, the host cell or the pharmaceutical composition comprised in the kit preferably comprises or consists of an amino acid sequence as set forth in any one of SEQ ID NOs 1 to 247 and 476-500. For example, antigenic peptides according to the present invention comprising or consisting of an amino acid sequence as set forth in any one of SEQ ID NOs 10, 21, 33, 35, 39, 40, 61, 65, 68, 72, 86, 110, 114 and 220 are even more preferred. For example, antigenic peptides according to the present invention comprising or consisting of an amino acid sequence as set forth in any one of SEQ ID NOs 10, 21, 33, 35, 39, 40, 110, 114 and 220 are still more preferred. For example, antigenic peptides according to the present invention comprising or consisting of an amino acid sequence as set forth in any one of SEQ ID NOs 10, 110, 114 and 220 are still more preferred. For example, antigenic peptides according to the present invention comprising or consisting of an amino acid sequence as set forth in any one of SEQ ID NOs 65, 110, 114 and 220 are still more preferred.

Also combinations thereof are preferred, namely, kits comprising distinct antigenic peptides according to the present invention. In particular, the kit-of-parts of the invention may comprise more than one of the above described components, e.g. 2, 3, 4, 5, 6, 7, 8, 9, or 10 distinct components. For example, the kit-of-parts according to the present invention may comprise at least two (e.g. 2, 3, 4, 5, 6, 7, 8, 9, or 10) different immunogenic compounds, at least two (e.g. 2, 3, 4, 5, 6, 7, 8, 9, or 10) different antigenic peptides, at least two (e.g. 2, 3, 4, 5, 6, 7, 8, 9, or 10) different nanoparticles, at least two (e.g. 2, 3, 4, 5, 6, 7, 8, 9, or 10) different cells, at least two (e.g. 2, 3, 4, 5, 6, 7, 8, 9, or 10) different nucleic acids, at least two (e.g. 2, 3, 4, 5, 6, 7, 8, 9, or 10) different host cells, and/or at least two (e.g. 2, 3, 4, 5, 6, 7, 8, 9, or 10) different pharmaceutical compositions. Preferably, such different components comprised by the kit-of-parts as described above differ in the antigenic peptides according to the present invention, for example one component relating to a first antigenic peptide, and one component relating to a second antigenic peptide (distinct from the first antigenic peptide). For example, the kit may comprise at least two distinct immunogenic compounds according to the present invention. For example, the kit may comprise at least two distinct antigenic peptides according to the present invention. For example, the kit may comprise at least two distinct nanoparticles according to the present invention. For example, the kit may comprise at least two distinct nucleic acids according to the present invention. For example, the kit may comprise at least two distinct cytotoxic T lymphocytes according to the present invention.

Preferred combinations of components, such as antigenic peptides, according to the present invention included in the kit correspond to the preferred combinations of components, such as antigenic peptides, according to the present invention included in the pharmaceutical composition as described above.

Accordingly, the present invention provides a kit comprising (at least one) antigenic peptide according to the present invention as described herein. Moreover, the present invention also provides a kit comprising (at least one) immunogenic compound according to the present invention as described herein. Moreover, the present invention also provides a kit comprising (at least one) nanoparticle according to the present invention as described herein. Moreover, the present invention also provides a kit comprising (at least one) cell according to the present invention as described herein. Moreover, the present invention also provides a kit comprising (at least one) nucleic acid according to the present invention as described herein. Moreover, the present invention also provides a kit comprising (at least one) host cell according to the present invention as described herein.

The various components of the kit-of-parts may be packaged in one or more containers. The above components may be provided in a lyophilized or dry form or dissolved in a suitable buffer. The kit may also comprise additional reagents including, for instance, preservatives, growth media, and/or buffers for storage and/or reconstitution of the above-referenced components, washing solutions, and the like.

Accordingly, the present invention provides a kit comprising at least two, preferably three distinct antigenic peptides according to the present invention as described herein (or immunogenic compounds, nanoparticles, nucleic acids, cells, etc. as described above, which differ regarding the antigenic peptide), and, optionally, a helper peptide, such as the UCP2 peptide, and/or an adjuvant, such as MONTANIDE ISA 51. Distinct antigenic peptides (or immunogenic compounds, nanoparticles, nucleic acids, cells, etc. as described above, which differ regarding the antigenic peptide) may be contained in the same or in distinct containers. For example, the kit may comprise a (single) container containing a first antigenic peptide as described herein and a second antigenic peptide as described herein. Said (single) container may additionally also comprise a helper peptide, such as UCP2. Optionally, the first and second antigenic peptide (and optionally the helper peptide) contained in the (single) container may be formulated together, e.g. in water for injection and/or Dimethyl sulfoxide (DMSO). Additionally, the kit may comprise a further container (distinct from the container containing the antigenic peptides), which contains the adjuvant, e.g. MONTANIDE ISA 51.

It is thus preferred that the kit comprises (i) a first vial comprising one or more antigenic peptides of the invention (e.g., at least 200 or 300 μg of each antigenic peptide), and, optionally, a helper peptide, such as UCP2 (e.g., at least 200 or 300 μg of the helper peptide), optionally formulated in water for injection and dimethyl sulfoxide (DMSO); and (ii) a second vial comprising MONTANIDE ISA 51 (e.g., at least 0.4 or 0.5 ml).

In addition, the kit may comprise one or more (e.g., 2 or 3) syringes, for example silicon- and rubber-free syringes. The kit may also comprise a connector, such as an I-connector.

Non-limiting examples of such connectors are:

the I-connector developed by Green Peptide (Japan), the connector of reference DIDRACDLLFT from Didanorm (France), the I-connector (ref: ODG0015ST) from Promepla (Monaco), and the I-connector (ref: MX494) from Smiths medical (US).

The syringes are preferably suitable for MONTANIDE, i.e., silicon-free and rubber free (i.e., without any rubber tip free on the plunger), and preferably also latex-free. Non-limiting examples of such syringes are:

2 ml INKJET (Ref: 4606701V from B-Braun, Germany), 5 ml INKJET (Ref: 4606710V from B-Braun, Germany), 2 ml Norm-Ject (Ref: 4020.000V0 from Henke Sass Wolf GMBH, Germany), and 5 ml Norm-Ject (Ref: 4050.000V0 from Henke Sass Wolf GMBH, Germany).

For example, the kit may comprise (i) a first vial comprising at least 300 μg of an antigenic peptide of the invention (or two or three antigenic peptides, at least 300 μg of each), and optionally at least 300 μg of UCP2, formulated in water for Injection and Dimethyl sulfoxide (DMSO), (ii)

a second vial comprising at least 0.5 ml of MONTANIDE ISA 51, (iii) two silicon- and rubber-free syringes, and (iv) an I-connector.

Optionally, the kit can also comprise a vial of water for injection and/or a vial adapter. A sterile needle can also be comprised, e.g. for vaccinating the patient after obtaining the emulsion. The syringes in the kit can be, for example, 2 ml syringes.

In addition, the kit-of-parts according to the present invention may optionally contain instructions of use. Accordingly, it is preferred that the kit comprises a package insert or instruction leaflet with directions to prevent or to treat B-cell malignancy by using the immunogenic compound according to the present invention, the antigenic peptide according to the present invention, the nanoparticle according to the present invention, the cell according to the present invention, the nucleic acid according to the present invention, the host cell according to the present invention, or the pharmaceutical composition according to the present invention.

It is also preferred that, in addition to any of components as described above, the kit comprises an anti-cancer therapeutic agent as described herein.

Moreover, the present invention also provides a vaccination kit for treating, preventing and/or stabilizing B-cell malignancy, comprising the pharmaceutical composition as described herein or a vaccine as described herein and instructions for use of said pharmaceutical composition or of said vaccine in the prevention and/or treatment of B-cell malignancy.

Medical Treatment and Uses

As stated above, the composition of the invention can be particularly useful for therapeutic purposes (as medicament), notably for triggering a specific immune response towards a particular tumor antigen/protein, for example to prevent or treat B-cell malignancy (such as B-cell lymphomas) in a patient in need thereof.

In view thereof, the present invention provides

- the antigenic peptide according to the present invention as described herein,
- the immunogenic compound according to the present invention as described herein,
- the nanoparticle according to the present invention as described herein,
- the cytotoxic T lymphocyte (CTL) according to the invention as described herein,
- the cell according to the present invention as described herein,
- the nucleic acid according to the present invention as described herein,
- the host cell according to the present invention as described herein,
- the pharmaceutical composition according to the present invention as described herein,
- the kit according to the present invention as described herein, or
- the combination according to the present invention as described herein for use in medicine, in particular in the prevention and/or in the treatment of a B-cell malignancy.

In particular, preferred embodiments of the antigenic peptide as described above also apply for the use according to the present invention in the prevention and/or in the treatment of a B-cell malignancy. For example, the antigenic peptide used in the prevention and/or in the treatment of B-cell malignancy or the antigenic peptide comprised in any of the immunogenic compound, the nanoparticle, the cell, the nucleic acid, the host cell or the pharmaceutical composition used in the prevention and/or in the treatment of a cancer preferably comprises or consists of an amino acid sequence as set forth in any one of SEQ ID NOs SEQ ID NOs 1 to 257 and 476-500. In some embodiments, antigenic peptides according to the present invention comprise or consist of an amino acid sequence as set forth in any one of SEQ ID NOs 1-12, 34-35, 36-39, 40, 41-64, 60-70, 476-484, 71-80, 81-87, 106-110, 485-488, 111-130, 489-493, 210-225, 494-500 and 226-257; preferably the antigenic peptide comprises or consists of an amino acid sequence as set forth in any one of SEQ ID NOs 34-35, 65-70, 476-484, 106-110, 485-488, 111-130, 489-493, 210-225, 494-500 and 226-257; more preferably the antigenic peptide comprises or consists of an amino acid sequence as set forth in any one of SEQ ID NOs 65-70, 476-484, 106-110, 485-488, 111-130, 489-493, 210-225 and 494-500. More preferably, the antigenic peptide comprises or consists of an amino acid sequence as set forth in any one of SEQ ID NOs 10, 34, 35, 39, 40, 61, 68, 70, 72, 86, 107-110, 114, 117, 119, 120, 212, 217, 220, 224, 227, 231, 477, 491 and 493. For example, antigenic peptides according to the present invention comprising or consisting of an amino acid sequence as set forth in any one of SEQ ID NOs 10, 21, 33, 35, 39, 40, 61, 65, 68, 72, 86, 110, 114 and 220 are even more preferred. For example, antigenic peptides according to the present invention comprising or consisting of an amino acid sequence as set forth in any one of SEQ ID NOs 10, 21, 33, 35, 39, 40, 110, 114 and 220 are still more preferred. For example, antigenic peptides according to the present invention comprising or consisting of an amino acid sequence as set forth in any one of SEQ ID NOs 10, 110, 114 and 220 are still more preferred. For example, antigenic peptides according to the present invention comprising or consisting of an amino acid sequence as set forth in any one of SEQ ID NOs 65, 110, 114 and 220 are still more preferred.

Also combinations thereof are preferred, namely, distinct antigenic peptides according to the present invention for use in the prevention and/or in the treatment of B-cell malignancy. In particular, more than one of the above described components may be used in the prevention and/or in the treatment of B-cell malignancy. For example, at least two different antigenic peptides, at least two different immunogenic compounds, at least two different nanoparticles, at least two different cells, at least two different nucleic acids, at least two different host cells, and/or at least two different pharmaceutical compositions may be used in the prevention and/or in the treatment of B-cell malignancy. Preferably, such different components used in the prevention and/or in the treatment of B-cell malignancy as described above differ in the antigenic peptides according to the present invention, for example one component relating to a first antigenic peptide, and one component relating to a second antigenic peptide (distinct from the first antigenic peptide). For example, at least two distinct immunogenic compounds according to the present invention may be used in the prevention and/or in the treatment of B-cell malignancy. For example, at least two distinct antigenic peptides according to the present invention may be used in the prevention and/or in the treatment of B-cell malignancy. For example, at least two distinct nanoparticles according to the present invention may be used in the prevention and/or in the treatment of B-cell malignancy. For example, at least two distinct nucleic acids according to the present invention may be used in the prevention and/or in the treatment of B-cell malignancy.

Accordingly, the present invention provides (at least one) antigenic peptide according to the present invention as described herein for use in the prevention and/or in the treatment of B-cell malignancy. Moreover, the present invention also provides (at least one) immunogenic compound according to the present invention as described herein for use in the prevention and/or in the treatment of B-cell malignancy. Moreover, the present invention also provides (at least one) nanoparticle according to the present invention as described herein for use in the prevention and/or in the treatment of B-cell malignancy. Moreover, the present invention also provides (at least one) cell according to the present invention as described herein for use in the prevention and/or in the treatment of B-cell malignancy. Moreover, the present invention also provides (at least one) nucleic acid according to the present invention as described herein for use in the prevention and/or in the treatment of B-cell malignancy. Moreover, the present invention also provides (at least one) host cell according to the present invention as described herein for use in the prevention and/or in the treatment of B-cell malignancy. Moreover, the present invention also provides (at least one) pharmaceutical composition according to the present invention as described herein for use in the prevention and/or in the treatment of B-cell malignancy. Moreover, the present invention also provides a kit according to the present invention as described herein for use in the prevention and/or in the treatment of B-cell malignancy.

Accordingly, the present invention also provides a method for preventing (reducing occurrence of) and/or treating a B-cell malignancy or initiating, enhancing or prolonging an anti-tumor-response against a B-cell malignancy in a subject in need thereof comprising administering to the subject

- the antigenic peptide according to the present invention,
- the immunogenic compound according to the present invention,
- the nanoparticle according to the present invention,
- the cell according to the present invention,
- the cytotoxic T lymphocyte (CTL) according to the invention as described herein,
- the nucleic acid according to the present invention,
- the host cell according to the present invention,
- the pharmaceutical composition according to the present invention,
- the kit according to the present invention, or
- the combination according to the present invention as described herein.

Preferably, the B cell malignancy to be treated include leukemia and lymphoma, e.g., acute myeloid (or myelogenous) leukemia (AML), chronic myeloid (or myelogenous) leukemia (CML), acute lymphocytic (or lymphoblastic) leukemia (ALL), B-chronic lymphocytic leukemia (BCLL), chronic lymphocytic leukemia (CLL, Richter's), hairy cell leukemia (HCL), lymphoplasmacytic lymphoma (LPC) or Waldenstrom's macroglobulinemia, prolymphocytic leukemia (PLL), small lymphocytic lymphoma (SLL), mantle cell lymphoma (MCL), marginal zone lymphoma (MZL), Burkitt lymphoma (BL), Hodgkin lymphoma (HL), non-Hodgkin lymphoma (NHL), anaplastic large cell lymphoma (ALCL), follicular lymphoma (FL), refractory follicular lymphoma, diffuse large B-cell lymphoma (DLBCL) and multiple myeloma (MM). In some embodiments, the B cell malignancy is selected from among acute lymphoblastic leukemia (ALL), adult ALL, chronic lymphoblastic leukemia (CLL), non-Hodgkin lymphoma (NHL), and Diffuse Large B-Cell Lymphoma (DLBCL). In some embodiments, the disease or condition is NHL and the NHL is selected from the group consisting of indolent (slow-growing) NHL, aggressive NHL, diffuse large B cell lymphoma (DLBCL), NOS (de novo and transformed from indolent), primary mediastinal large B cell lymphoma (PMBCL), T cell/histiocyte-rich large B cell lymphoma (TCHRBCL), Burkitt's lymphoma, mantle cell lymphoma (MCL), and/or follicular lymphoma (FL), optionally, follicular lymphoma Grade 3B (FL3B).

Moreover, the present invention provides a method for eliciting or improving, in a subject, an immune response against one or multiple epitopes that is dependent on $CD8^+$ cytotoxic T cells, wherein said method comprises administering to said subject any one of:

- the antigenic peptide according to the present invention,
- the immunogenic compound according to the present invention,
- the nanoparticle according to the present invention,
- the cytotoxic T lymphocyte (CTL) according to the invention,
- the cell according to the present invention,
- the nucleic acid according to the present invention,
- the host cell according to the present invention,
- the pharmaceutical composition according to the present invention,
- the kit according to the present invention, or
- the combination according to the present invention as described herein.

An immune response that is dependent on $CD8^+$ response can be determined by evaluating an inflammatory response, a pro-inflammatory cytokine response, including an increase in the expression of one or more of IFN-γ, TNF-α and IL-2 mRNA or protein relative to the level before administration of the compounds of the invention. It can also be measured by an increase in the frequency or absolute number of antigen-specific T cells after administration of the compounds of the invention, measured by HLA-peptide multimer staining, ELISPOT assays, and delayed type hypersensitivity tests. It can also be indirectly measured by an increase in antigen-specific serum antibodies that are dependent on antigen-specific T helper cells.

The present invention also provides a method for eliciting or improving, in a subject, an immune response against one or multiple antigens or antigenic epitopes that is restricted by multiple MHC class I molecules, wherein said method comprises administering to said subject any one of:

- the antigenic peptide according to the present invention,
- the immunogenic compound according to the present invention,
- the nanoparticle according to the present invention,
- the cytotoxic T lymphocyte (CTL) according to the invention,
- the cell according to the present invention,
- the nucleic acid according to the present invention,
- the host cell according to the present invention,
- the pharmaceutical composition according to the present invention,
- the kit according to the present invention, or
- the combination according to the present invention as described herein.

A method for eliciting or improving, in a subject, an immune response against multiple epitopes as described herein, that is restricted by multiple MHC class I molecules can be determined by evaluating a cytokine response, including an increase in the expression of one or more of IFN-γ, TNF-α and IL-2 mRNA or protein relative to the level before administration of the compounds of the invention, after in vitro stimulation of T cells with individual peptides binding to discrete MHC class I molecules on antigen presenting cells. Restriction to MHC class I molecules can also be validated by using antigen presenting cells expressing MHC class I molecules, or by using MHC class I blocking antibodies. It can also be measured by an increase in the frequency or absolute number of antigen-specific T cells after administration of the compounds of the invention, measured by HLA-peptide multimer staining, using multimers assembled with MHC class I molecules.

Thus, in another aspect, the present invention also provides

- the antigenic peptide according to the present invention,
- the immunogenic compound according to the present invention,
- the nanoparticle according to the present invention,
- the cytotoxic T lymphocyte (CTL) according to the invention,
- the cell according to the present invention,
- the nucleic acid according to the present invention,
- the host cell according to the present invention,
- the pharmaceutical composition according to the present invention,
- the kit according to the present invention, or
- the combination according to the present invention as described herein.

for use as a medicament.

The invention relates more particularly to a composition as defined above, for use as a vaccine for immunotherapy. Moreover,

- the antigenic peptide according to the present invention,
- the immunogenic compound according to the present invention,
- the nanoparticle according to the present invention,
- the cytotoxic T lymphocyte (CTL) according to the invention,
- the cell according to the present invention,
- the nucleic acid according to the present invention,
- the host cell according to the present invention,
- the pharmaceutical composition according to the present invention,
- the kit according to the present invention, or
- the combination according to the present invention as described herein may be used as vaccine, in particular for (cancer) immunotherapy.

As used in the context of the present invention, the term "vaccine" refers to a (biological) preparation that provides innate and/or adaptive immunity, typically to a particular disease, preferably B-cell malignancy. Thus, a vaccine supports in particular an innate and/or an adaptive immune response of the immune system of a subject to be treated. For example, the antigenic peptide according to the present invention typically leads to or supports an adaptive immune response in the patient to be treated.

In the context of the present invention, the vaccine (composition) can induce a specific immune response against a tumor antigen, and is thus preferably used to prevent or treat B-cell malignancy.

Accordingly, in a preferred embodiment, the invention relates to a composition as defined above, for use in the prevention and/or treatment of cancer in a subject in need thereof. More preferably, the invention relates to the use of the composition of the invention for manufacturing a medicament to prevent or treat cancer in a subject in need thereof. In other words, the invention relates to a method for preventing or treating cancer in a subject in need thereof, comprising administering an effective amount of the composition of the invention, to said subject.

Preferably the cancer to be prevented and/or treated by

- the antigenic peptide according to the present invention,
- the immunogenic compound according to the present invention,
- the nanoparticle according to the present invention,
- the cytotoxic T lymphocyte (CTL) according to the invention,
- the cell according to the present invention,
- the nucleic acid according to the present invention,
- the host cell according to the present invention,
- the pharmaceutical composition according to the present invention,
- the kit according to the present invention, or
- the combination according to the present invention as described herein relates to the (reference) tumor antigen of the antigenic peptide as described herein. Namely, appropriate antigenic peptides may be selected by (i) selecting an appropriate tumor antigen for a certain type of cancer as known in the art and (ii) selecting an appropriate antigenic peptide according to the invention for the selected tumor antigen, as described above, e.g. in Table 1A. One skilled in the art will readily understand that an antigenic peptide of the invention can be selected based upon the nature of the B-cell malignancy to be prevented or treated, and/or on the human gene/human tumor antigen involved in said B-cell malignancy.

In general, antigenic peptides of the invention may be administered "naked" or in the form of immunogenic compounds according to the present invention, cells loaded therewith according to the present invention, nanoparticles according to the present invention, nucleic acids according to the present invention, host cells according to the present invention and/or pharmaceutical compositions according to the present invention.

In a preferred embodiment, they may be administered in the form of a micro-organism such as a gut bacterial species. Entire gut bacterial species can also be advantageous as they have the potential to trigger a greater immune response than the (poly)peptides or nucleic acids they contain. Alternatively, gut bacteria according to the invention may be in the form of probiotics, i.e. of live gut bacterium, which can thus be used as food additive thanks to the health benefits it can provide. Those can be for example lyophilized in granules, pills or capsules, or directly mixed with dairy products for consumption.

Methods of administration are well-known to the skilled person in the art. With regard to the composition of the invention, it can be directly administered into the subject, into the affected organ (i.e. local administration) or systemically (i.e. enteral or parenteral administration), or even applied ex vivo to cells derived from the subject or a human cell line which are subsequently administered to the subject, or even used in vitro to select a subpopulation of immune cells derived from the subject, which are then re-administered to the said subject. Enteral administrations include oral and rectal administrations, as well as administrations via gastric feeding tubes, duodenal feeding tubes or gastrostomy, while parenteral administrations include, among others, subcutaneous, intravenous, intramuscular, intra-arterial, intradermal, intraosseous, intracerebral, and intrathecal injections. The administration method will often depend upon the antigenic peptide(s) and/or immunogenic compound(s) present in the composition, and the type of cancer to be treated and other active agents that may be contained in said composition. For example, the administration is preferably an intramuscular or an intradermal injection if the immunogenic compound is a nucleic acid as defined above, the oral/nasal administration being particularly preferred if said nucleic acid is cloned into a viral vector. Alternatively, the administration is preferably an intramuscular, an intradermal or an oral administration if the antigenic peptide and/or immunogenic compound is a (poly)peptide as defined above or if it is loaded in/on a nanoparticle as described herein. Yet, still alternatively, the administration is preferably an oral administration if the antigenic peptide and/or immunogenic compound is delivered in the form of a gut bacterium as defined above, notably if the gut bacterium is in the form of probiotics.

The antigenic peptides, the immunogenic compounds and the nucleic acids according to the invention can further be encapsulated so as to facilitate their administration to the subject in need thereof. For example, those may be encapsulated into peptide nanocarriers (preferable if the immunogenic compound is a nucleic acid or a (poly)peptide), into virosomes (preferable if the immunogenic compound is a nucleic acid or a (poly)peptide), or into lipid-based carrier systems such as liposome-polycation-DNA complex (preferable if the immunogen is a nucleic acid or a (poly)peptide) (Trovato M, De Berardinis P. Novel antigen delivery systems. World J Virol. 2015 Aug. 12; 4(3):156-68; Saade F, Petrovsky N. Technologies for enhanced efficacy of DNA vaccines. Expert Rev Vaccines. 2012 February; 11(2):189-209; Li et al., Peptide Vaccine: Progress and Challenges. Vaccines (Basel). 2014 Jul. 2; 2(3):515-36).

The composition may also be administered more than once so as to achieve the desired effect. In a preferred embodiment, said composition is administered repeatedly, at least twice, and preferably more than twice. This can be done over an extended period of time, such as weekly, every other week, monthly, yearly, or even several years after the first administration to ensure that the subject is properly immunized.

Combination Therapy

The administration of the antigenic peptide according to the present invention, the immunogenic compound according to the present invention, the nanoparticle according to the present invention, the cell according to the present invention, the nucleic acid according to the present invention, the host cell according to the present invention, and the pharmaceutical composition according to the present invention, in particular in the methods and uses according to the invention, can be carried out alone or in combination with a co-agent useful for treating and/or preventing cancer, such as an anti-cancer therapeutic agent.

Said therapeutic agent is thus preferably capable of preventing and/or treating the same type of cancer as the one for which the antigenic peptide according to the invention is used. Particularly preferred anti-cancer therapeutic agents according to the invention include, without limitation, antibodies, CAR-T cells, tumor cell lysates, chemotherapeutic agents, radiotherapeutic agents, immune checkpoint modulators and combinations thereof.

Antibodies are particularly advantageous in cancer therapy as they can either bind to specific antigens on cancer cell surfaces, thereby directing the therapy to the tumor (i.e. these are referred as tumor-targeting antibodies), or block immune checkpoints that are dysregulated in cancer (i.e. these are referred herein as immunomodulatory antibodies). The purpose of the later type of antibodies is to inhibit cancer immune resistance, which can notably be observed against T cells that are specific for tumour antigens. Indeed, as well-known in the art, under normal physiological conditions, immune checkpoints are crucial for the maintenance of self-tolerance (i.e. prevention of autoimmunity) and protect tissues from damage when the immune system is responding to pathogenic infection. However, in cancer, immune-checkpoints expression can be dysregulated as an important mechanism of immune resistance. Said resistance has notably been observed in melanoma, ovarian, lung, glioblastoma, breast, and pancreatic cancers with regard to the PD-L1 checkpoint (Konishi et al., B7-H1 expression on non-small cell lung cancer cells and its relationship with tumor-infiltrating lymphocytes and their PD-1 expression. Clin Cancer Res. 2004 Aug. 1; 10(15):5094-100; Ghebeh et al., The B7-H1 (PD-L1) T lymphocyte-inhibitory molecule is expressed in breast cancer patients with infiltrating ductal carcinoma: correlation with important high-risk prognostic factors. Neoplasia. 2006 March; 8(3):190-8; Hino et al., Tumor cell expression of programmed cell death-1 ligand 1 is a prognostic factor for malignant melanoma. Cancer. 2010 Apr. 1; 116(7):1757-66). Other examples of immune checkpoints include, without limitation, PD-L2, PD-1, CD80, CD86, CTLA4, B7H3, B7H4, PVR, TIGIT, GALS, LAG-3, GITR, CD137, TIM3, VISTA, VISTA-R (Pico de Coaña et al., Checkpoint blockade for cancer therapy: revitalizing a suppressed immune system. Trends Mol Med. 2015 August; 21(8):482-91; Pardon DM1. The blockade of immune checkpoints in cancer immunotherapy. Nat Rev Cancer. 2012 Mar. 22; 12(4):252-64).

Antibodies are usually employed for the above purposes either in the form of naked monoclonal antibodies (i.e. non-conjugated), or conjugated to another molecule which can be toxic to cells or radioactive.

Examples of well-known monoclonal tumor-targeting antibodies used in cancer immunotherapy include, without limitation, alemtuzumab (chronic lymphocytic leukemia), bevacizumab (colorectal cancer, glioblastoma multiforme, cervical cancer, lung cancer, renal cancer), brentuximab/vedotin (lymphomas), blinatumomab (acute lymphoblastic leukemia), catumaxomab (malignant ascites in EPCAM+ cancers), cetuximab (head and neck cancer, colorectal cancer), denosumab (breast, prostate and bone cancers), Gemtuzumab/ozogamicin (acute myeloid leukemia), ibritumomab/tiuxetan (non-Hodgkin lymphoma), panitumumab (colorectal cancer), pertuzumab (breast cancer), obinutuzumab (chronic lymphocytic leukemia), ofatumumab (chronic lymphocytic leukemia), opilimumab (melanoma), ramucirumab (gastric and gastro-oeasophageal cancers), rituximab (chronic lymphocytic leukemia and non-Hodgkin lymphoma), siltuximab (multicentric's Catsleman's disease), tositumomab (non-Hodgkin lymphoma), and trastuzumab (breast, gastric and gastro-oeasophageal cancers); while examples of immunomodulatory antibodies include, without limitation, ipilimumab (melanoma) which blocks the CTLA4-dependent immune checkpoint, nivolumab (melanoma, lung cancer) and prembrolizubmab (melanoma) which both block the PDCD1-dependent immune checkpoint, as well as MPDL3280A, MEDI4736, MEDI0680, and MSB0010718C which all block the PD-L1-dependent immune checkpoint (Sharma and Allison, The future of immune checkpoint therapy. Science. 2015 Apr. 3; 348(6230):56-61).

Other antibodies for cancer immunotherapy have been described in Buqué et al. (Buqué et al., Trial Watch: Immunomodulatory monoclonal antibodies for oncological indications. Oncoimmunology. 2015 Mar. 2; 4(4):e1008814. eCollection 2015 April), Redman et al. (Redman et al., Mechanisms of action of therapeutic antibodies for cancer. Mol Immunol. 2015 October; 67(2 Pt A):28-45), and in Simpson and Caballero, Monoclonal antibodies for the therapy of cancer MC Proc. 2014; 8(Suppl 4): 06 as well as on the antibody society website (list of therapeutic monoclonal antibodies approved or in review in the European Union or United States available on the weblink http://www.antibodysociety.org/news/approved_mabs.php).

Adoptive cellular immunotherapy with chimeric antigen receptor (CAR) T cells has changed the treatment landscape of B-cell non-Hodgkin's lymphoma (NHL), especially for aggressive B-cell lymphomas. For instance, CD19-targeted CAR T-cells, represent the new standard of care for patients with DLBCL that are refractory to at least two prior lines of therapy. Two CAR T-cell products axicabtagene ciloleucel (axi-cel) (KTE-019) (YESCARTA™) and tisagenlecleucel (CTL019) (KYMRIAH™) have obtained US Food and Drug Administration approval for the treatment of refractory DLBCL after two lines of therapy. A third product, lisocabtagene maraleucel (liso-cel) (JCAR017), is currently being evaluated in clinical trials. Other CAR T-cells include CD20-CAR-T cells.

Tumor cell lysates may also be combined with the antigenic peptide(s) according to the invention. Tumor cells are indeed capable of priming the immune response, by presenting endogenous peptides-MHC complexes, as well as via dendritic cells (DCs) of the host which can process and present the antigen delivered by said lysates. The range of antigens against which an immune response can be induced is thereby increased. Tumor cell lysates can be easily obtained by treating tumor cells with a heat shock and/or a chemical treatment, and can be autologous (i.e. isolated from the patient), or allogeneic (i.e. isolated from another subject).

Standard chemotherapeutic drugs and radiotherapeutic agents need not be further described herein as they have been extensively described in the literature, notably by Baskar et al. (Baskar et al., Cancer and radiation therapy: current advances and future directions. Int J Med Sci. 2012; 9(3):193-9), Paci et al. (Paci et al., Review of therapeutic drug monitoring of anticancer drugs part 1—cytotoxics. Eur J Cancer. 2014 August; 50(12):2010-9) and Widmer et al. (Widmer et al., Review of therapeutic drug monitoring of anticancer drugs part two—targeted therapies. Eur J Cancer. 2014 August; 50(12):2020-36). A list of such drugs and agents is also available on the cancer.gov website (http://www.cancer.gov/about-cancer/treatment/drugs).

Preferably, the immune checkpoint modulator for combination with the antigenic peptide as defined herein is an activator or an inhibitor of one or more immune checkpoint point molecule(s) selected from CD27, CD28, CD40, CD122, CD137, OX40, GITR, ICOS, A2AR, B7-H3, B7-H4, BTLA, CD40, CTLA-4, IDO, KIR, LAG3, PD-1, TIM-3, VISTA, CEACAM1, GARP, PS, CSF1R, CD94/NKG2A, TDO, GITR, TNFR and/or FasR/DcR3; or an activator or an inhibitor of one or more ligands thereof.

More preferably, the immune checkpoint modulator is an activator of a (co-)stimulatory checkpoint molecule or an inhibitor of an inhibitory checkpoint molecule or a combination thereof. Accordingly, the immune checkpoint modulator is more preferably (i) an activator of CD27, CD28, CD40, CD122, CD137, OX40, GITR and/or ICOS or (ii) an inhibitor of A2AR, B7-H3, B7-H4, BTLA, CD40, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or FasR/DcR3.

Even more preferably, the immune checkpoint modulator is an inhibitor of an inhibitory checkpoint molecule (but preferably no inhibitor of a stimulatory checkpoint molecule). Accordingly, the immune checkpoint modulator is even more preferably an inhibitor of A2AR, B7-H3, B7-H4, BTLA, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or DcR3 or of a ligand thereof.

It is also preferred that the immune checkpoint modulator is an activator of a stimulatory or costimulatory checkpoint molecule (but preferably no activator of an inhibitory checkpoint molecule). Accordingly, the immune checkpoint modulator is more preferably an activator of CD27, CD28, CD40, CD122, CD137, OX40, GITR and/or ICOS or of a ligand thereof.

It is even more preferred that the immune checkpoint modulator is a modulator of the CD40 pathway, of the IDO pathway, of the LAG3 pathway, of the CTLA-4 pathway and/or of the PD-1 pathway. In particular, the immune checkpoint modulator is preferably a modulator of CD40, LAG3, CTLA-4, PD-L1, PD-L2, PD-1 and/or IDO, more preferably the immune checkpoint modulator is an inhibitor of CTLA-4, PD-LL PD-L2, PD-1, LAG3, and/or IDO or an activator of CD40, even more preferably the immune checkpoint modulator is an inhibitor of CTLA-4, PD-LL PD-1, LAG3 and/or IDO, even more preferably the immune checkpoint modulator is an inhibitor of LAG3, CTLA-4 and/or PD-1, and most preferably the immune checkpoint modulator is an inhibitor of CTLA-4 and/or PD-1.

Accordingly, the checkpoint modulator for combination with the antigenic peptide may be selected from known modulators of the CTLA-4 pathway or the PD-1 pathway. Preferably, the checkpoint modulator for combination with the antigenic peptide as defined herein may be selected from known modulators of the CTLA-4 pathway or the PD-1 pathway. Particularly preferably, the immune checkpoint modulator is a PD-1 inhibitor. Preferred inhibitors of the CTLA-4 pathway and of the PD-1 pathway include the monoclonal antibodies Yervoy® (Ipilimumab; Bristol Myers Squibb) and Tremelimumab (Pfizer/MedImmune) as well as Opdivo® (Nivolumab; Bristol Myers Squibb), Keytruda® (Pembrolizumab; also known as Lambrolizumab or MK-3475; Merck), Imfinzi® (Durvalumab also known as MEDI4736; MedImmune/AstraZeneca), Tecentriq® (Atezolizumab also known as MPDL3280A; Roche/Genentech), Pidilizumab (CT-011; CureTech), MEDI0680 (AMP-514; AstraZeneca), Bavencio® (Avelumab; Merck KGaA/Pfizer also known as MSB-0010718C), M1H1 (Affymetrix), LY3300054 (Eli Lilly) and Spartalizumab (also known as PDR001; Novartis). More preferred checkpoint inhibitors include the CTLA-4 inhibitors Yervoy® (Ipilimumab; Bristol Myers Squibb) and Tremelimumab (Pfizer/MedImmune) as well as the PD-1 inhibitors Opdivo® (Nivolumab; Bristol Myers Squibb), Keytruda® (Pembrolizumab; Merck), Pidilizumab (CT-011; CureTech), MEDI0680 (AMP-514; AstraZeneca), AMP-224 (a PD-L2 Fc fusion protein; MedImmune).

It is also preferred that the immune checkpoint modulator for combination with the antigenic peptide as defined herein is selected from the group consisting of Pembrolizumab, Ipilimumab, Nivolumab, Atezolizumab, MEDI4736, Tremelimumab, Avelumab, Spartalizumab, LAG525 (an anti-LAG3 monoclonal antibody), Epacadostat (formerly INCB24360; an IDO inhibitor), Varlilumab (an anti-CD27 monoclonal antibody), Urelumab (an anti-CD137 monoclonal antibody), AMP-224 and CM-24 (an anti-CEACAM1 monoclonal antibody).

It is within the skill of ordinary person in the art to select the appropriate immune anti-cancer therapeutic agent for the purposes of the invention.

The anti-cancer therapeutic agent can also be administered in association with the antigenic peptide according to the present invention, the immunogenic compound according to the present invention, the nanoparticle according to the present invention, the cell according to the present invention, the nucleic acid according to the present invention, the host cell according to the present invention, or the pharmaceutical composition according to the present invention, either at about the same time or consecutively as described herein and in the same or distinct pharmaceutical forms. Thus, the invention proposes a combined use of the composition the invention and least one anti-cancer therapeutic agent as described above, for a simultaneous, separate, or sequential administration as described herein.

Furthermore, the present invention also relates to a combination of at least two distinct antigenic peptides according to the present invention, e.g. for use in the prevention and/or treatment of B-cell malignancy. Furthermore, the present invention also relates to a combination of at least two distinct immunogenic compounds according to the present invention, e.g. for use in the prevention and/or treatment of B-cell malignancy. Furthermore, the present invention also relates to a combination of at least two distinct nanoparticles according to the present invention, e.g. for use in the prevention and/or treatment of B-cell malignancy. Furthermore, the present invention also relates to a combination of at least two distinct nucleic acids according to the present invention, e.g. for use in the prevention and/or treatment of B-cell malignancy.

Thus, according to a preferred embodiment, at least two antigenic peptides according to the present invention may be administered in combination, for example in the same pharmaceutical composition. For example, at least 3 antigenic peptides, at least 4 antigenic peptides, at least 5 antigenic peptides, at least 6 antigenic peptides, at least 7 antigenic peptides, at least 8 antigenic peptides, at least 9 antigenic peptides, at least 10 antigenic peptides, at least 11 antigenic peptides, at least 12 antigenic peptides, at least 13 antigenic peptides, at least 14 antigenic peptides, at least 15 antigenic peptides, at least 20 antigenic peptides, at least 25 antigenic peptides, at least 50 antigenic peptides, at least 100 antigenic peptides are administered in combination, for example in the same pharmaceutical composition. It is within the skill of the person in the art to select the combination of antigenic peptides that is suitable for the intended purpose.

In a particularly preferred embodiment two distinct antigenic peptides according to the present invention (e.g., relating to the same type of B-cell malignancy and/or to the same reference antigen) are combined. For example, (i) at least two distinct immunogenic compounds according to the present invention;
(ii) at least two distinct antigenic peptides according to the present invention;
(iii) at least two distinct nanoparticles according to the present invention; or
(iv) at least two distinct nucleic acids according to the present invention may be combined.

For example, the present invention provides a combination of at least two distinct antigenic peptides according to the present invention, in particular (i) a first antigenic peptide according to the present invention, and
(ii) a second antigenic peptide according to the present invention (distinct from the first) preferably for use in the prevention and/or treatment of B-cell malignancy.

For example, the present invention provides a combination of at least two distinct immunogenic compounds according to the present invention, in particular (i) an immunogenic compound according to the present invention comprising a first antigenic peptide according to the present invention, and
(ii) an immunogenic compound according to the present invention comprising a second antigenic peptide according to the present invention (distinct from the first)

preferably for use in the prevention and/or treatment of B-cell malignancy.

For example, the present invention provides a combination of at least two distinct nanoparticles according to the present invention, in particular (i) a nanoparticle according to the present invention comprising a first antigenic peptide according to the present invention, and
(ii) a nanoparticle according to the present invention comprising a second antigenic peptide according to the present invention (distinct from the first)

preferably for use in the prevention and/or treatment of B-cell malignancy.

For example, the present invention provides a combination of at least two distinct nucleic acids according to the present invention, in particular (i) a nucleic acid according to the present invention comprising a polynucleotide encoding a first antigenic peptide according to the present invention and
(ii) a nucleic acid according to the present invention comprising a polynucleotide encoding a second antigenic peptide according to the present invention (distinct from the first)

preferably for use in the prevention and/or treatment of B-cell malignancy.

For example, the present invention provides a combination of at least two distinct cytotoxic T lymphocytes according to the present invention, in particular (i) a cytotoxic T lymphocyte according to the present invention specific for a first antigenic peptide according to the present invention and
(ii) a cytotoxic T lymphocyte according to the present invention specific for a second antigenic peptide according to the present invention (distinct from the first)

preferably for use in the prevention and/or treatment of B-cell malignancy.

In the combinations according to the present invention, such combinations of components, such as antigenic peptides, according to the present invention are preferred, which correspond to the preferred combinations of components, such as antigenic peptides, according to the present invention included in the pharmaceutical composition as described above.

Moreover, the antigenic peptide according to the present invention may also be combined with the corresponding (human) tumor antigen epitope (as described above regarding the peptide “families”). Thereby, selection of T-cell clones, which are very efficient against the tumor, is obtained/supported. In particular, the antigenic peptide according to the present invention and the corresponding (human) tumor antigen epitope may be co-administered. Such co-administration may be at about the same time (simultaneously) or consecutively, whereby in consecutive administration it is preferred that the antigenic peptide according to the present invention is administered first and the corresponding (human) tumor antigen epitope is administered thereafter. In particular, the antigenic peptide according to the present invention may be administered first, and the corresponding (human) tumor antigen epitope may be used as (re)boost. For example, the antigenic peptide according to SEQ ID NO: 10 may be combined with the reference peptide according to SEQ ID NO: 258. In another example, the antigenic peptide according to SEQ ID NO: 110 may be combined with the reference peptide according to SEQ ID NO: 270. In another example, the antigenic peptide according to SEQ ID NO: 114 may be combined with the reference peptide according to SEQ ID NO: 271. In another example, the antigenic peptide according to SEQ ID NO: 220 may be combined with the reference peptide according to SEQ ID NO: 279.

The peptides, which are to be combined, such as (a) the antigenic peptide according to the present invention and the corresponding (human) tumor antigen epitope or (b) two distinct antigenic peptides according to the present invention, may be administered

- in the same immunogenic compound according to the present invention or in distinct immunogenic compounds according to the present invention,
- (loaded) in the same nanoparticle according to the present invention or in distinct nanoparticles according to the present invention,
- (loaded) in the same cell according to the present invention or in distinct cells according to the present invention,
- (encoded by) the same nucleic acid according to the present invention or by distinct nucleic acids according to the present invention,
- (expressed by) the same host cell according to the present invention or by distinct host cells according to the present invention, or
- (comprised) in the same pharmaceutical composition according to the present invention or in distinct pharmaceutical composition according to the present invention.

In general, the expression "two distinct components" in the context of a combination, e.g. for use according to the present invention (a combination therapy), is defined as above (in the context of the pharmaceutical composition). In particular, it refers to (1) a first component, such as the antigenic peptide according to the present invention as described herein, the immunogenic compound according to the present invention as described herein, the nanoparticle according to the present invention as described herein, the cell according to the present invention as described herein, the nucleic acid according to the present invention as described herein, the host cell according to the present invention as described herein, or the pharmaceutical composition according to the present invention as described herein; and (2) a second component (which is distinct from the first component), such as the anti-cancer therapeutic agent as described above, a distinct antigenic peptide according to the present invention as described herein, a distinct immunogenic compound according to the present invention as described herein, a distinct nanoparticle according to the present invention as described herein, a distinct cell according to the present invention as described herein, a distinct nucleic acid according to the present invention as described herein, a distinct host cell according to the present invention as described herein, a distinct pharmaceutical composition according to the present invention as described herein, or one or more (fragments of) human tumor antigens in any form ("naked", as immunogenic compound as described herein, as nanoparticle as described herein, as (host) cell as described herein, as nucleic acid as described herein or as pharmaceutical composition as described herein).

Accordingly, the "two distinct components", as referred to herein in the context of a combination for use according to the present invention (a combination therapy), are preferably active components in the context of the disease (B-cell malignancy) to be prevented and/or treated. In other words, each of the at least two distinct components may also be useful for preventing and/or treating said cancer, if administered separately (not in combination as described herein)—although the combination (i.e. combined administration) typically potentiates their preventive and/or therapeutic effect (such as the immune response), in particular in a synergistic manner.

Accordingly, the present invention also provides the combination of (at least) two distinct antigenic peptides according to the present invention as described herein. In this context, the (at least) two distinct antigenic peptides may be in any form, e.g., "naked", comprised in immunogenic compounds, nanoparticles, (pharmaceutical) compositions or cells loaded therewith, or encoded by nucleic acids (e.g., vectors). Accordingly, the (at least) two distinct antigenic peptides may be comprised in (at least) two distinct components (to be combined). In a preferred embodiment, the at least two distinct components of the combination according to the present invention are at least distinct antigenic peptides according to the present invention (in any form, e.g. comprised in immunogenic compounds, nanoparticles, cells, pharmaceutical compositions, encoded by the nucleic acids, etc.).

Preferably, the at least two distinct components of the combination for use according to the present invention relate to the same type of cancer, for example to the same or distinct antigens associated with this cancer and/or to the same or distinct (reference) epitopes within an antigen associated with this cancer. More preferably, the at least two distinct components relate to the same tumor antigen.

In certain embodiments, the at least two distinct components of the combination for use according to the present invention are comprised in the same or distinct compositions. In certain embodiments, the at least two distinct components of the combination for use according to the present invention are administered via the same or distinct routes of administration. In certain embodiments, the at least two distinct components of the combination for use according to the present invention are administered at about the same time (simultaneously) or consecutively.

Preferably, the at least two distinct components of the combination for use according to the present invention are administered at about the same time. In more general, it is preferred that the first component is administered at about the same time as the second component, wherein the at least two distinct components of the combination for use according to the present invention are preferably administered in the same form (i.e., in the same type of formulation, e.g., as nanoparticles, as pharmaceutical compositions, etc.).

"At about the same time", as used herein, means in particular simultaneous administration or that directly after administration of the first component, the second component is administered or directly after administration of the second component, the first component is administered. The skilled person understands that "directly after" includes the time necessary to prepare the second administration—in particular the time necessary for exposing and disinfecting the location for the second administration as well as appropriate preparation of the "administration device" (e.g., syringe, pump, etc.). Simultaneous administration also includes if the periods of administration of the first component and of the second component overlap or if, for example, one component is administered over a longer period of time, such as 30 min, 1 h, 2 h or even more, e.g. by infusion, and the other component is administered at some time during such a long period. Administration of the first component and of the second component at about the same time is in particular preferred if different routes of administration and/or different administration sites are used.

It is also preferred that the at least two distinct components of the combination for use according to the present invention are administered consecutively. In more general, it is preferred that the first component and the second component are administered consecutively, wherein the at least two distinct components of the combination for use according to the present invention are preferably administered in the same form (i.e., in the same type of formulation, e.g., as nanoparticles, as pharmaceutical compositions, etc.).

This means that the first component is administered before or after the second component. In consecutive administration, the time between administration of the first component and administration of the second component is preferably no more than one week, more preferably no more than 3 days, even more preferably no more than 2 days and most preferably no more than 24 h. It is particularly preferred that the first component and the second component are administered at the same day with the time between administration of the first component and administration of the second component being preferably no more than 6 hours, more preferably no more than 3 hours, even more preferably no more than 2 hours and most preferably no more than 1 h.

Preferably, the first component and the second component are administered via the same route of administration. In more general, it is preferred that the first component and the second component are administered via the same route of administration, wherein the at least two distinct components of the combination for use according to the present invention are preferably administered in the same form (i.e., in the same type of formulation, e.g., as nanoparticles, as pharmaceutical compositions, etc.).

It is also preferred that the at least two distinct components of the combination for use according to the present invention are administered via distinct routes of administration. In more general, it is preferred that the first component and the second component are administered via distinct routes of administration, wherein the at least two distinct components of the combination for use according to the present invention are preferably administered in the same form (i.e., in the same type of formulation, e.g., as nanoparticles, as pharmaceutical compositions, etc.).

Preferably, the at least two distinct components of the combination for use according to the present invention are comprised in the same composition. In more general, it is preferred that the first component and the second component are comprised in the same composition, wherein the at least two distinct components of the combination for use according to the present invention are preferably administered in the same form (i.e., in the same type of formulation, e.g., as nanoparticles, etc.).

It is also preferred that the at least two distinct components of the combination for use according to the present invention are comprised in distinct compositions. In more general, it is preferred that the first component and the second component are comprised in distinct compositions, wherein the at least two distinct components of the combination for use according to the present invention are preferably administered in the same form (i.e., in the same type of formulation, e.g., as nanoparticles, etc.).

In particular, the present invention provides a pharmaceutical composition comprising a first antigenic peptide according to the present invention, which comprises or consists of a sequence variant of a fragment of the human tumor antigen.

In particular, the present invention provides a combination, e.g. for use in the prevention and/or treatment of B-cell malignancy, comprising a first antigenic peptide according to the present invention, which comprises or consists of a microbiota sequence variant of a fragment of the human tumor antigen CD22, and a second antigenic peptide according to the present invention, which comprises or consists of a sequence variant of a fragment of the human tumor antigen TNFRSF13C. Preferably, the first antigenic peptide comprises or consists of a sequence variant of the CD22 fragment (human reference peptide) "WVFEHPETL" (SEQ ID NO: 270), such as an antigenic peptide comprising or consisting of an amino acid sequence as set forth in SEQ ID NO: 106-110, 316 and 387-390, and the second antigenic peptide comprises or consists of a sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 220, 325 and 450. More preferably, the first antigenic peptide comprises or consists of an amino acid sequence as set forth in SEQ ID NO: 110, 387 and 390 and the second antigenic peptide comprises or consists of an amino acid sequence as set forth in SEQ ID NO: 220, and 450. Even more preferably, the pharmaceutical composition comprises an antigenic peptide comprising or consisting of SEQ ID NO: 110 and an antigenic peptide comprising or consisting of SEQ ID NO: 220.

More preferably, the combination according to the present invention (e.g. for use in the prevention and/or treatment of B-cell malignancy) comprises at least three distinct components as described above, in particular at least three distinct antigenic peptides according to the present invention. The above description regarding the combination of two distinct components applies accordingly for three distinct components.

Most preferably, the combination according to the present invention (e.g. for use in the prevention and/or treatment of B-cell malignancy) comprises at least four distinct components as described above, in particular at least four distinct antigenic peptides according to the present invention. The above description regarding the combination of two distinct components applies accordingly for four distinct components.

It is understood that the combination, e.g. for use in the prevention and/or treatment of B-cell malignancy, may also contain—instead of the above-described preferred combinations of antigenic peptides—a respective combination of immunogenic compounds of the invention, a respective combination of nanoparticles of the invention or a respective combination of nucleic acids of the invention.

BRIEF DESCRIPTION OF THE FIGURES

In the following a brief description of the appended figures will be given. The figures are intended to illustrate the present invention in more detail. However, they are not intended to limit the subject matter of the invention in any way.

EXAMPLES

Figure 1:
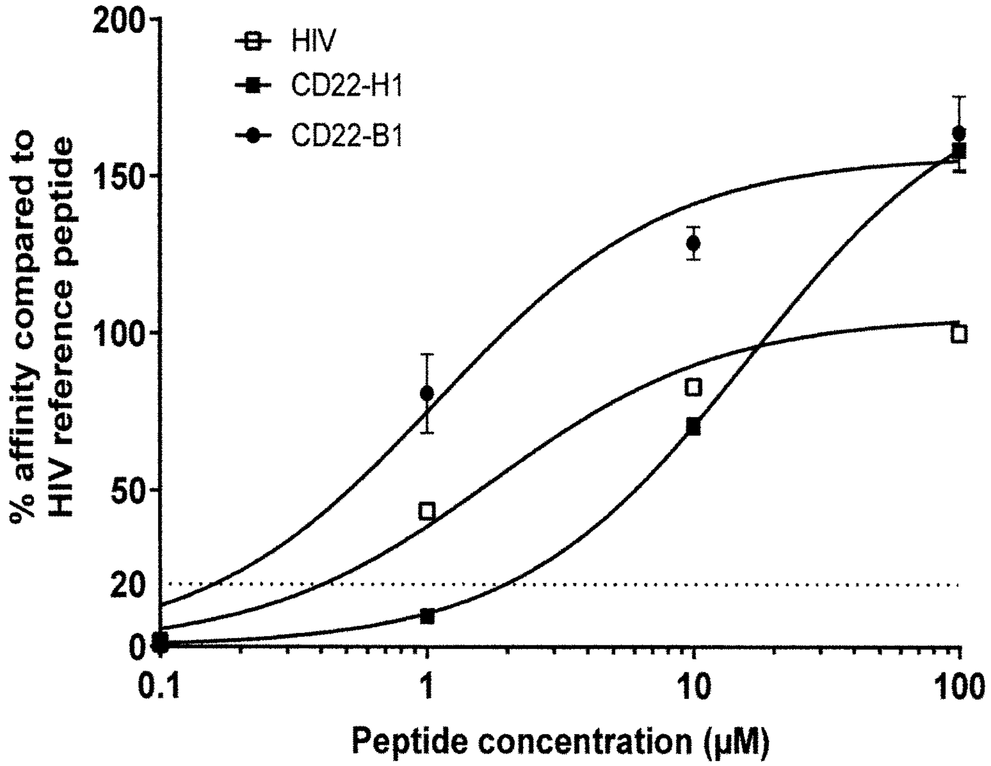
FIG. 1: shows for Example 1 in vitro affinity for the antigenic peptide CD22-B1 in comparison to the corresponding human CD22 epitope CD22-H1.
Figure 2:
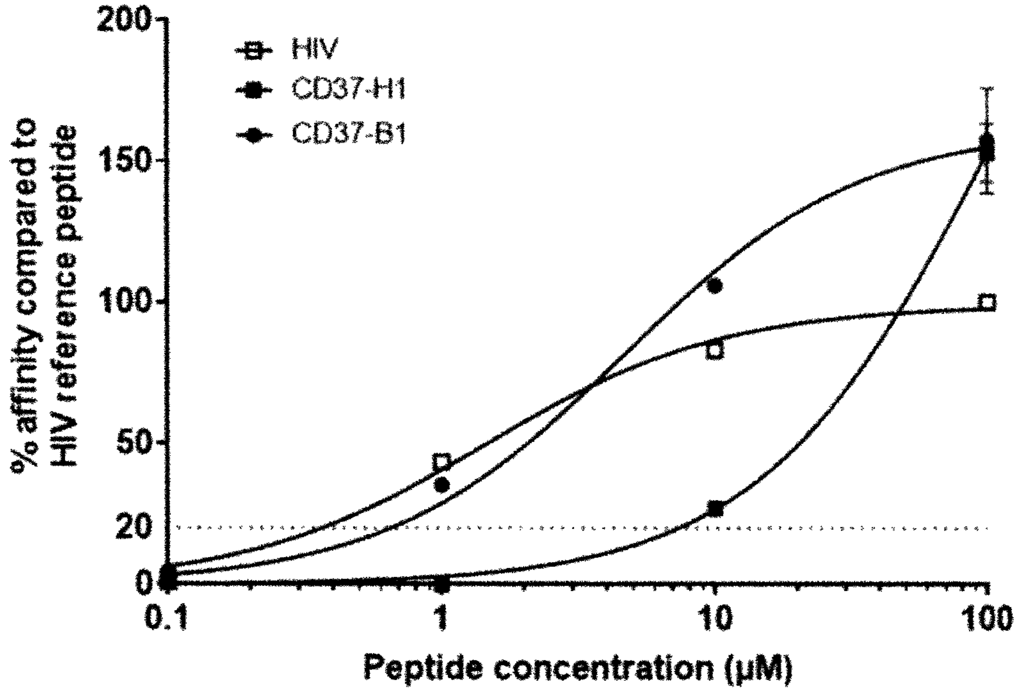
FIG. 2: shows for Example 1 in vitro affinity for the antigenic peptide CD37-B1 in comparison to the corresponding human CD37 epitope CD37-H1.
Figure 3:
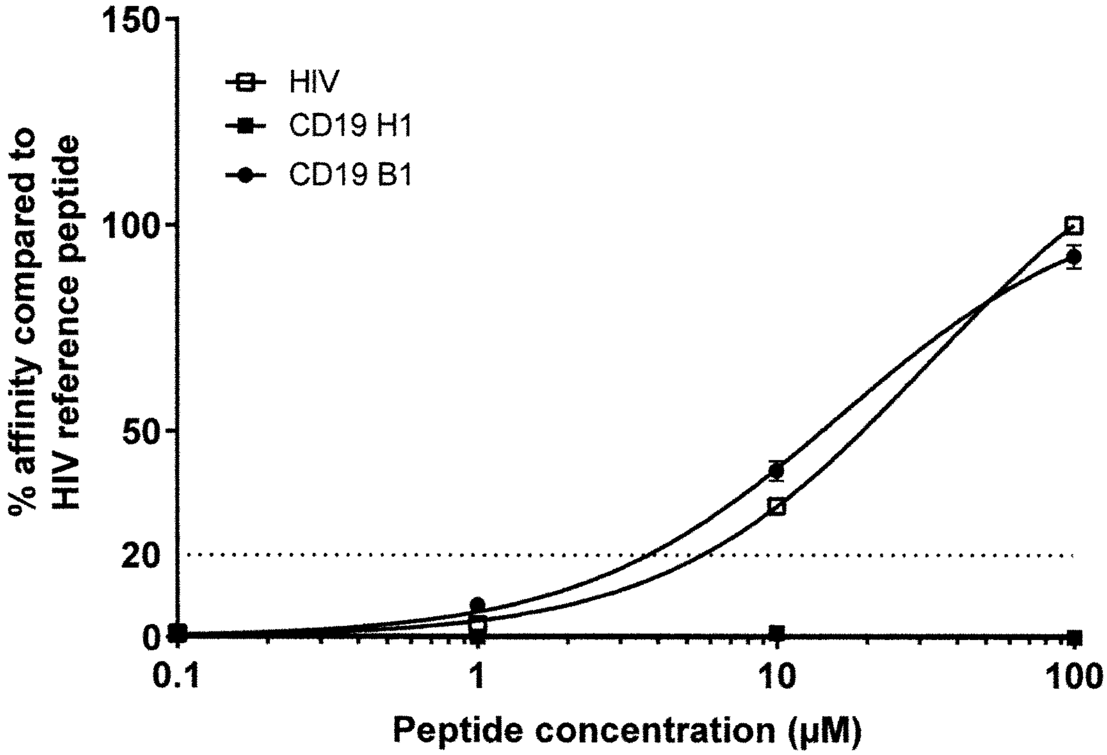
FIG. 3: shows for Example 1 in vitro affinity for the antigenic peptide CD19-B1 in comparison to the corresponding human CD19 epitope CD19-H1.
Figure 4:
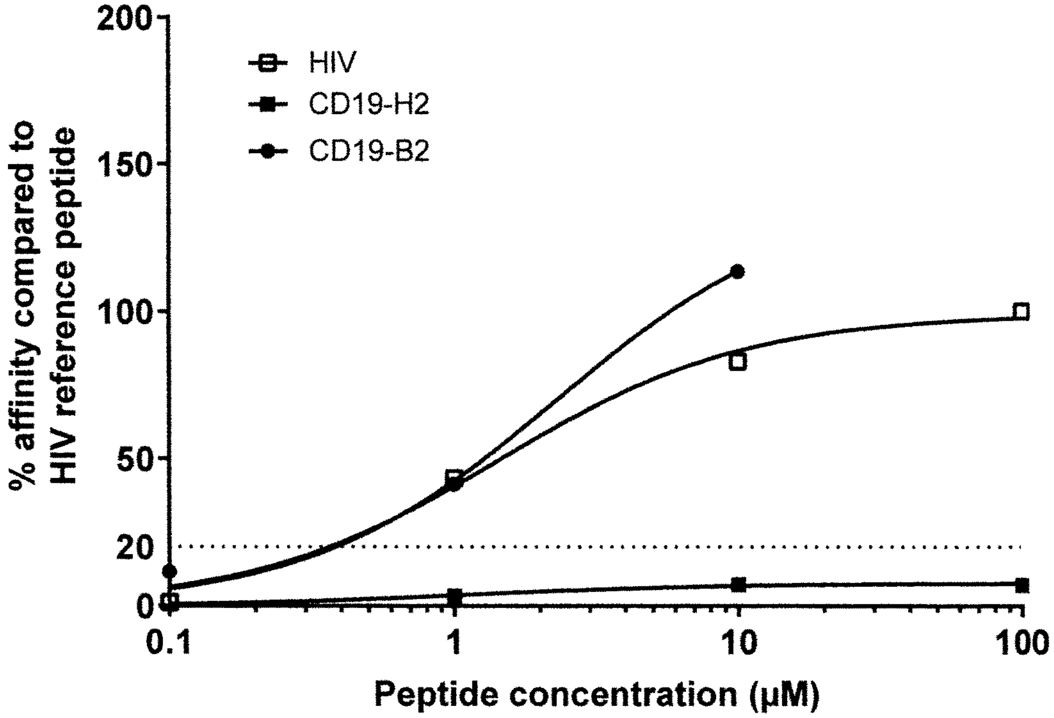
FIG. 4: shows for Example 1 in vitro affinity for the antigenic peptide CD19-B2 in comparison to the corresponding human CD19 epitope CD19-H2.
Figure 5:
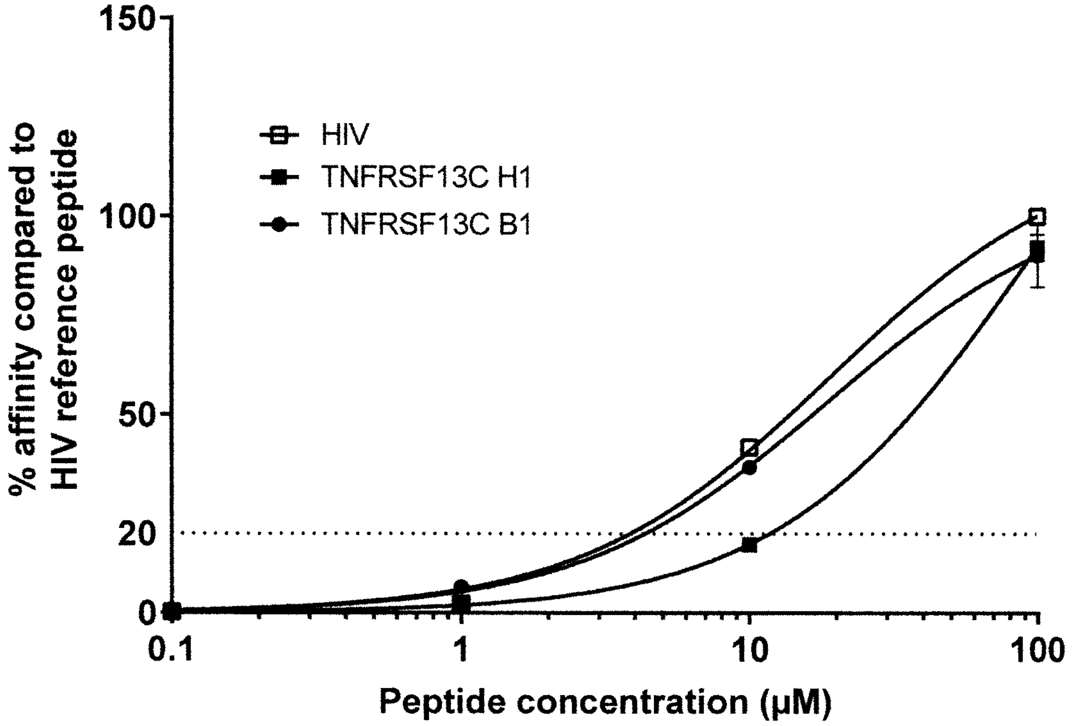
FIG. 5: shows for Example 1 in vitro affinity for the antigenic peptide TNFRSF13C-B1 in comparison to the corresponding human TNFRSF13C epitope TNFRSF13C-H1.
Figure 6:
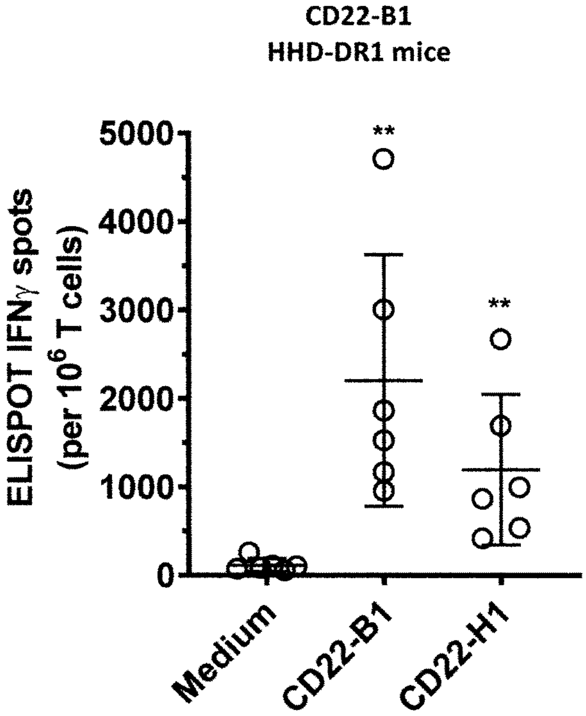
FIG. 6: shows for Example 2 ELISPOT results for HHD DR1 HLA-A2 transgenic mice vaccinated with the antigenic peptide CD22-B1 as indicated in the figure and cross-reactivity with the human corresponding peptide CD22-H1. The data were provided as a number of spots per $1 \cdot 10^6$ total T cells.
Figure 7:
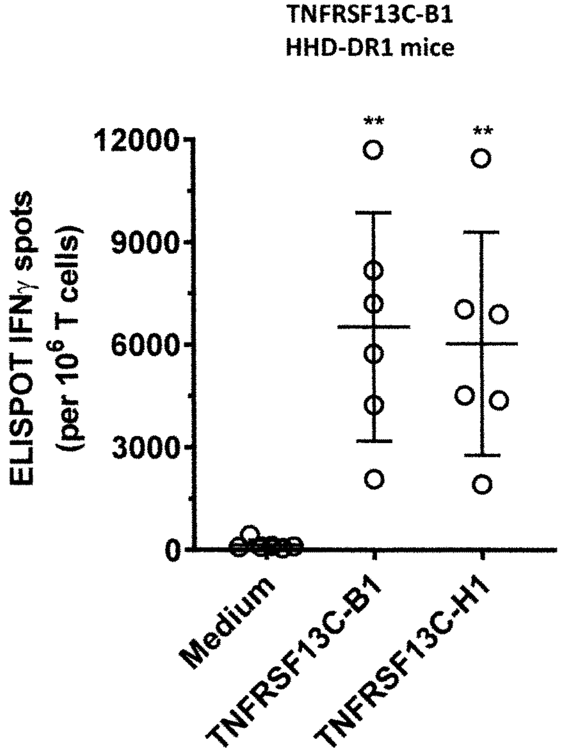
FIG. 7: shows for Example 2 ELISPOT results for HHD DR1 HLA-A2 transgenic mice vaccinated with the antigenic peptide TNFRSF13C-B1 as indicated in the figure and cross-reactivity with the human corresponding peptide TNFRSF13C-H1. The data were provided as a number of spots per $1 \cdot 10^6$ total T cells.
Figure 8:
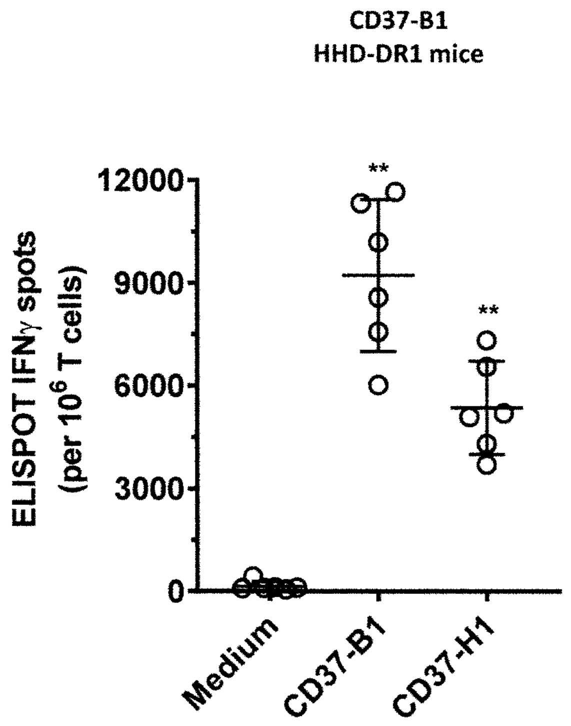
FIG. 8: shows for Example 2 ELISPOT results for HHD DR1 HLA-A2 transgenic mice vaccinated with the antigenic peptide CD37-B1 as indicated in the figure and cross-reactivity with the human corresponding peptide CD37-H1. The data were provided as a number of spots per $1 \cdot 10^6$ total T cells.
Figure 9:
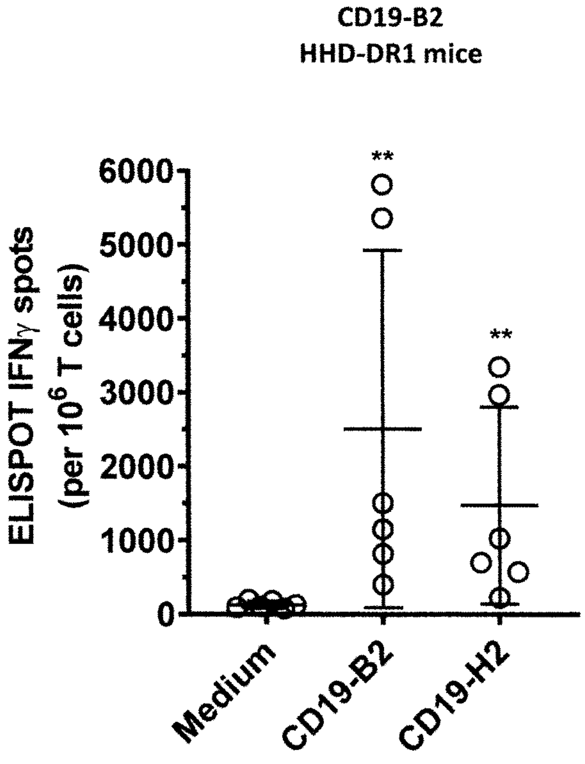
FIG. 9: shows for Example 2 ELISPOT results for HHD DR1 HLA-A2 transgenic mice vaccinated with the antigenic peptide CD19-B2 as indicated in the figure and cross-reactivity with the human corresponding peptide CD19-H2. The data were provided as a number of spots per $1 \cdot 10^6$ total T cells.
Figure 10:
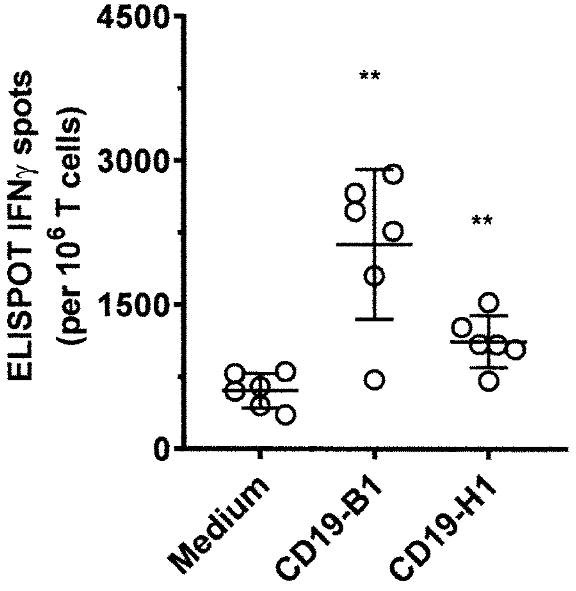
FIG. 10: shows for Example 2 ELISPOT results for HHD DR1 HLA-A2 transgenic mice vaccinated with the antigenic peptide CD19-B1 as indicated in the figure and cross-reactivity with the human corresponding peptide CD19-H1. The data were provided as a number of spots per $1 \cdot 10^6$ total T cells.

In the following, particular examples illustrating various embodiments and aspects of the invention are presented. However, the present invention shall not to be limited in scope by the specific embodiments described herein. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Example 1: Antigenic Peptides have Superior Affinity to the HLA-A*0201 Allele Next, binding affinity of various selected antigenic peptides and of the corresponding fragments of human tumor antigens (human reference peptides) to the HLA-A*0201 allele was confirmed in vitro. Namely, the antigenic peptide of sequence SEQ ID NO: 110 («YIFEHPELL» also referred herein as CD22-B1) was compared to the corresponding reference human peptides derived from CD22 («WVFEHPETL», SEQ ID NO: 270, also referred herein as CD22-H1). Moreover, the antigenic peptide of sequence SEQ ID NO: 109 («YVFEHPELL» also referred herein as CD22-B11) was compared to the corresponding reference human peptide derived from CD22 («WVFEHPETL», SEQ ID NO: 270, also referred herein as CD22-H1). Moreover, the antigenic peptide of sequence SEQ ID NO: 114 («FLAFVPLQL» also referred herein as CD37-B1) was compared to the corresponding reference human peptide derived from CD37 («GLAFVPLQI», SEQ ID NO: 271, also referred herein as CD37-H1). Moreover, the antigenic peptide of sequence SEQ ID NO: 117 («GMAFVPLLL» also referred herein as CD37-B11) was compared to the corresponding reference human peptide derived from CD37 («GLAFVPLQI», SEQ ID NO: 271, also referred herein as CD37-H1). Moreover, the antigenic peptide of sequence SEQ ID NO: 34 («LLVGILHLV» also referred herein as CD19-B1) was compared to the corresponding reference human peptide derived from CD19 («SLVGILHLQ», SEQ ID NO: 260, also referred herein as CD19-H1). Moreover, the antigenic peptide of sequence SEQ ID NO: 10 («TLLFLTPML» also referred herein as CD19-B2) was compared to the corresponding reference human peptide derived from CD19 («FLLFLTPME», SEQ ID NO: 258, also referred herein as CD19-H2). Moreover, the antigenic peptide of sequence SEQ ID NO: 39 («YLAYLIFEL» also referred herein as CD19-B6) was compared to the corresponding reference human peptide derived from CD19 («TLAYLIFCL», SEQ ID NO: 261, also referred herein as CD19-H6). Moreover, the antigenic peptide of sequence SEQ ID NO: 40 («LQMGGFYLL» also referred herein as CD19-B7) was compared to the corresponding reference human peptide derived from CD19 («QQMGGFYLC», SEQ ID NO: 262, also referred herein as CD19-H7). Moreover, the antigenic peptide of sequence SEQ ID NO: 220 («LMFGAPALV» also referred herein as TNFRSF13C-B1) was compared to the corresponding reference human peptide derived from TNFRSF13C («LLFGAPALL», SEQ ID NO: 279, also referred herein as TNFRSF13C-H1). Moreover, the antigenic peptide of sequence SEQ ID NO: 231 («ILPGLLFGL» also referred herein as TNFRSF13C-B31) was compared to the corresponding reference human peptide derived from TNFRSF13C («PLPGLLFGA», SEQ ID NO: 280, also referred herein as TNFRSF13C-H3). Moreover, the antigenic peptide of sequence SEQ ID NO: 227 («FMPGLLFGA» also referred herein as TNFRSF13C-B33) was compared to the corresponding reference human peptide derived from TNFRSF13C («PLPGLLFGA», SEQ ID NO: 280, also referred herein as TNFRSF13C-H3). Moreover, the antigenic peptide of sequence SEQ ID NO: 61 («YILGGLLMV» also referred herein as MS4A1-B12) was compared to the corresponding reference human peptide derived from MS4A1 (also known as CD20) («IALGGLLMI», SEQ ID NO: 263, also referred herein as MS4A1-H1). Moreover, the antigenic peptide of sequence SEQ ID NO: 72 («ILIPAGIYL» also referred herein as MS4A1-B3) was compared to the corresponding reference human peptide derived from MS4A1 (also known as CD20) («LMIPAGIYA», SEQ ID NO: 265, also referred herein as MS4A1-H3). Moreover, the antigenic peptide of sequence SEQ ID NO: 65 («AMNSLSLYI» also referred herein as MS4A1-B4) was compared to the corresponding reference human peptide derived from MS4A1 (also known as CD20) («IMNSLSLFA», SEQ ID NO: 264, also referred herein as MS4A1-H4). Moreover, the antigenic peptide of sequence SEQ ID NO: 86 («YLFLGILSL» also referred herein as MS4A1-B5) was compared to the corresponding reference human peptide derived from MS4A1 (also known as CD20) («SLFLGILSV», SEQ ID NO: 266, also referred herein as MS4A1-H5).

A. Materials and Methods

A1. Measuring the Affinity of the Peptide to T2 Cell Line.

The experimental protocol is similar to the one that was validated for peptides presented by the HLA-A*0201 (Tourdot et al., A general strategy to enhance immunogenicity of low-affinity HLA-A2.1-associated peptides: implication in the identification of cryptic tumor epitopes. Eur J Immunol. 2000 December; 30(12):3411-21). Affinity measurement of the peptides is achieved with the human tumoral cell T2 which expresses the HLA-A*0201 molecule, but which is TAP1/2 negative and incapable of presenting endogenous peptides.

T2 cells ($5\cdot10^4$ cells per well) are incubated with decreasing concentrations of peptides from 100 μM to 0.1 μM (4 points: 100 to 1 μM, 0.1 μM) in serum-free medium (TexMacs) supplemented with 100 ng/μl of (32 Microglobulin at 37° C. for 16 hours. Cells are then washed two times and marked with the anti-HLA-A2 antibody coupled to PE (clone BB7.2, BD Pharmagen).

The analysis is achieved by FACS (Macsquant analyzer 10—Miltenyi).

For each peptide concentration, the geometric mean of the labelling associated with the peptide of interest is subtracted from background noise and reported as a percentage of the geometric mean of the HLA-A*0202 labelling obtained for the reference peptide HIV pol 589-597 at a concentration of 100 μM. The relative affinity is then determined as follows:

relative affinity=concentration of each peptide inducing 20% of expression of HLA-*A**0201/concentration of the reference peptide inducing 20% of expression of HLA-*A**0201.

A2. Solubilisation of Peptides

Each peptide is solubilized by taking into account the amino acid composition. For peptides which do not include any Cystein, Methionin, or Tryptophane, the addition of DMSO is possible to up to 10% of the total volume. Other peptides are resuspended in water or PBS pH7.4.

B. Results

The mean relative fluorescence intensity values (data are normalized to the mean fluorescence of HIV peptide, i.e. a value of 100 is equal to the best binding observed with HIV peptide) of T2 cells obtained for the various concentrations of each peptide are shown in Table 2 below:

TABLE 2

| Peptide | | | | | |
|---|---|---|---|---|---|
| Name | SEQ ID NO. | 100 | 10 | 1 | 0.1 |
| CD22-B1 | 110 | 164 | 123 | 81 | 0 |
| CD22-B11 | 109 | 140.7 | 123.8 | 60.5 | 6.4 |
| CD22-H1 | 270 | 158 | 71 | 10 | 2 |
| CD37-B1 | 114 | 157 | 106 | 35 | 5 |
| CD37-B11 | 117 | 57.8 | 48.9 | 1.6 | 0.0 |
| CD37-H1 | 271 | 153 | 27 | 0 | 2 |
| CD19-B1 | 34 | 93 | 40 | 8 | ND |
| CD19-B11 | 35 | 108.5 | 30.5 | 5.2 | 0 |
| CD19-H1 | 260 | 0 | 1 | 0 | 1 |
| CD19-B2 | 10 | ND | 114 | 41 | 12 |
| CD19-H2 | 258 | 7 | 7 | 3 | ND |
| CD19-B6 | 39 | ND | 52.5 | 5.4 | 0 |
| CD19-H6 | 261 | ND | 39.6 | 4.1 | 0 |

TABLE 2-continued

| Peptide | | | | | |
|---|---|---|---|---|---|
| Name | SEQ ID NO. | 100 | 10 | 1 | 0.1 |
| CD19-B7 | 40 | 31.8 | 4.5 | 4.8 | 6 |
| CD19-H7 | 262 | 9.3 | 2 | 0.1 | 0 |
| TNFRSF13C-B1 | 220 | 90 | 37 | 7 | 1 |
| TNFRSF13C-H1 | 279 | 92 | 17 | 2 | 0 |
| TNFRSF13C-B31 | 231 | 104.3 | 71.9 | 1.5 | 0 |
| TNFRSF13C-B33 | 227 | 99.6 | 15.5 | 1.3 | 0 |
| TNFRSF13C-H3 | 280 | 8.4 | 0 | 0 | 0 |
| MS4A1-B12 | 61 | 42 | 7.6 | 1.1 | 1.2 |
| MS4A1-H1 | 263 | ND | 1.9 | 0.7 | 0 |
| MS4A1-B3 | 72 | 88.8 | 87.8 | 17.8 | 1.9 |
| MS4A1-H3 | 265 | 92.6 | 35.7 | 0.9 | 0 |
| MS4A1-B4 | 65 | 115.2 | 13.1 | 1.9 | 0.5 |
| MS4A1-H4 | 264 | 13.4 | 2.6 | 0.3 | 0 |
| MS4A1-B5 | 86 | ND | 29.8 | 0.2 | 0 |
| MS4A1-H5 | 266 | ND | 6.5 | 1.8 | 0 |

Table 3 below summarizes for each tested peptide the concentration required to induce 20% of HLA-A2 expression and the in vitro binding affinity (* normalized against HIV-pol concentration of peptide inducing 20% of HLA-A2 expression performed during the same experiment).

TABLE 3

| Peptide | SEQ ID NO | Concentration of peptide that induces 20% of HLA-A2 expression (μM) | In vitro binding affinity* |
|---|---|---|---|
| CD22-B1 | 110 | 0.16 | 0.4 |
| CD22-B11 | 109 | 0.2 | 0.5 |
| CD22-H1 | 270 | 1.97 | 5.3 |
| CD37-B1 | 114 | 0.65 | 1.6 |
| CD37-B11 | 117 | 2.30 | 3 |
| CD37-H1 | 271 | 7.35 | 17.5 |
| CD19-B1 | 34 | 3.7 | 0.7 |
| CD19-B11 | 35 | 5.97 | 0.8 |
| CD19-H1 | 260 | ND | ND |
| CD19-B2 | 10 | 0.38 | 1 |
| CD19-H2 | 258 | ND | ND |
| CD19-B6 | 39 | 3.76 | 0.4 |
| CD19-H6 | 261 | 4.98 | 0.5 |
| CD19-B7 | 40 | 49.63 | 6.8 |
| CD19-H7 | 262 | >100 | ND |
| TNFRSF13C-B1 | 220 | 4.35 | 1.1 |
| TNFRSF13C-H1 | 279 | 11.76 | 3.0 |
| TNFRSF13C-B31 | 231 | 1.60 | 0.40 |
| TNFRSF13C-B33 | 227 | 13.20 | 3.50 |
| TNFRSF13C-H3 | 280 | ND | ND |
| MS4A1-B12 | 61 | 31.20 | 3.50 |
| MS4A1-H1 | 263 | ND | ND |
| MS4A1-B3 | 72 | 0.70 | 0.10 |
| MS4A1-H3 | 265 | 4.83 | 0.50 |
| MS4A1-B4 | 65 | 12.3 | 2.1 |
| MS4A1-B41 | 68 | 2.45 | 0.30 |
| MS4A1-H4 | 264 | >100 | ND |
| MS4A1-B5 | 86 | 6.77 | 0.70 |
| MS4A1-H5 | 266 | ND | ND |

ND—Undeterminable

Figure 14:
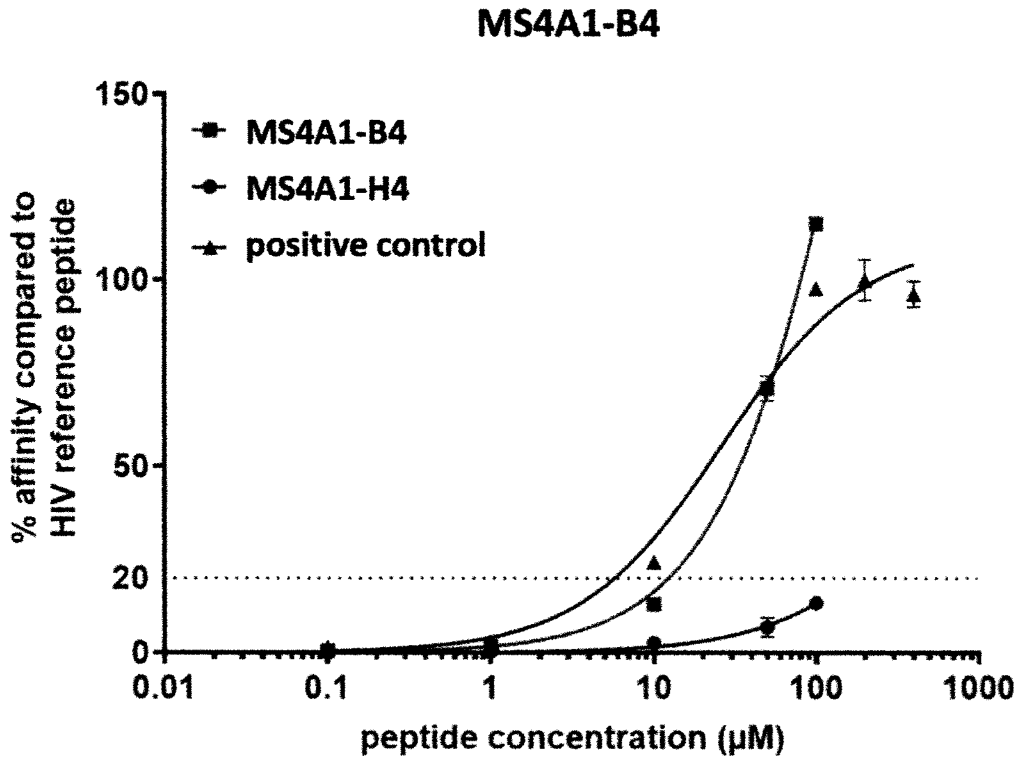
FIG. 14: shows for Example 1 in vitro affinity for the antigenic peptide MS4A1-B4 in comparison to the corresponding human MS4A1 epitope MS4A1-H4.

In addition, FIGS. 1-5 and 14 illustrate the results for selected examples, namely for the antigenic peptide CD22-B1 in comparison to the corresponding human CD22 fragment CD22-H1 (FIG. 1), for the antigenic peptide CD37-B1, in comparison to the corresponding human CD37 fragment CD37-H1 (FIG. 2), for the antigenic peptide CD19-B1 in comparison to the corresponding human CD19 fragment CD19-H1 (FIG. 3), for the antigenic peptide CD19-B2 in comparison to the corresponding human CD19 fragment CD19-H2 (FIG. 4), for the antigenic peptide TNFRSF13C-B1 in comparison to the corresponding human TNFRSF13C fragment TNFRSF13C-H1 (FIG. 5) and the antigenic peptide MS4A1-B4 in comparison to the corresponding human MS4A1 fragment MS4A1-B4 (FIG. 14).

In summary, the results show that the antigenic peptides according to the present invention show at least similar binding affinity to HLA-A*0201 as the corresponding human tumor antigen fragments. In most cases, the binding affinity observed for the antigenic peptides according to the present invention was stronger than that of the corresponding human epitopes. Without being bound to any theory it is assumed that such a strong binding affinity of the antigenic peptides according to the present invention reflects their ability to raise an immune response (i.e., their immunogenicity).

Example 2 Immunogenicity of CD22-B1, CD19B1, CD19-B2, CD37B1, TNFRSF13C-B1 and MS4A1-B4 in HLA-A2 Transgenic Mice and Cross-Reactivity with the Corresponding Human Peptide A. Materials and Methods A.1 Mouse Model Briefly, HLA-A2 HHD-DR1 humanized mice (C57BL/6JB2mtm1UncIAb-/-Tg(HLA-DRA,HLA-DRB1*0101)#GjhTg(HLA-A/H2-D/B2M)1Bpe) or HHD-DR3 humanized mice (C57BL/6JB2mtm1UncIAb-/-Tg(HLA-DRA, HLA-DRB1*0301) #GjhTg(HLA-A/H2-D/B2M)1Bpe) were assigned randomly (based on mouse sex and age) to experimental groups, wherein each group was immunized with a specific vaccination peptide (vacc-pAg) combined to a common helper peptide (h-pAg UCP2; sequence: KSVWSKLQSIGIRQH; SEQ ID NO: 475; for HHD DR1 mice or h-pAg DR3; sequence MAKTIAYDEEARRGLERGLN; SEQ ID n° 473; for HHD DR3 mice) (as outlined in Table 4 below).

TABLE 4

Experimental group composition. h-pAg: 'helper' peptide; vacc-pAg: vaccination peptide. The number of boost injections is indicated into brackets.

| Group | Peptide (vacc-pAg) | Helper (h-Ag) | Mice | Prime | Boost | Animal Number |
|---|---|---|---|---|---|---|
| 1 | CD22-B1 (60 nMole) | UCP2 (105 nMole) | HHD-DR1 | + | +(1X) | 6 |
| 2 | CD19-B1 (60 nMole) | UCP2 (105 nMole) | HHD-DR1 | + | +(1X) | 6 |
| 3 | CD19-B2 (60 nMole) | UCP2 (105 nMole) | HHD-DR1 | + | +(1X) | 6 |
| 4 | CD37-B1 (60 nMole) | UCP2 (105 nMole) | HHD-DR1 | + | +(1X) | 5 |
| 5 | TNFRSF13C-B1 (60 nMole) | UCP2 (105 nMole) | HHD-DR1 | + | +(1X) | 5 |
| 6 | CD22-B1 (95 nMole) | DR3 (65 nM) | HHD-DR3 | + | +(1X) | 5 |
| 7 | TNFRSF13C-B1 (95 nMole) | DR3 (65 nM) | HHD-DR3 | + | +(1X) | 5 |
| 8 | CD37-B1 (95 nMole) | DR3 (65 nM) | HHD-DR3 | + | +(1X) | 5 |
| 9 | MS4A1-B4 (60 nMole) | UCP2 (105 nMole) | HHD-DR1 | + | +(1X) | 6 |
| 10 | MS4A1-B4 95 nMole | DR3 (65 nM) | HHD-DR3 | + | +(1X) | 5 |

The peptides were provided as follows:

vacc-pAg: CD22-B1, CD19-B1, CD19-B2, CD37-B1, TNFRSF13C-B1 and MS4A1-B4 all produced and provided at a 4 mg/ml (4 mM) concentration;

h-pAg: DR3 or UCP2 re-suspended in pure distilled water at a 10 mg/mL concentration The peptide formulation to be injected (emulsion) was prepared freshly on each day of injection and for each group. A mix for 10 animals was prepared using 2 mL luer lock syringes (4606701V, B BRAUN) and luer connectors (Cole-Parmer, 45502-22): 500 μL of peptide mixture in syringe 1 was emulsified with 500 μL of IFA contained in syringe 2, at high speed as fast as possible until forming a thick (white foam) emulsion. Each emulsion was prepared in excess to compensate for the dead volumes at injection.

The animals were immunized on day 0 (do) with a prime injection, and on d14 with a boost injection. Each mouse was injected s.c. at tail base with 100 μL of an oil-based emulsion that contained:

60 nMole of vacc-pAg; 105 nMole of UCP2 helper peptide (for HHD-DR1 mice) or 65 nMole of DR3 helper peptide (for HHD-DR3 mice)

10 μL of PBS to reach a total volume of 50 μL (per mouse);

Incomplete Freund's Adjuvant (IFA) added at 1:1 (v:v) ratio (50 μL per mouse).

A.2 Analysis

Seven days after the boost injection (i.e. on d21), the animals were euthanized and the spleen was harvested. Splenocytes were prepared by mechanical disruption of the organ followed by 70 μm-filtering and Ficoll density gradient purification.

The cell suspensions were further used in an ELISPOT-IFNγ assay (Table 5). The cells were cultured in 200 μL of complete T cell medium. Experimental conditions (duplicates) were as follow: 2×105 total cells per well when cultured in presence of various pAg (10 μM) or medium-only; and 2×104 total cells when cultured in presence of CD3/CD28-loaded bead particles (T cell Activation/Expansion kit, 130-093-627, Miltenyi) (bead-to-cell ratio of 1:1). The cultures were assessed for their capacity to secrete IFNγ (Diaclone Kit Murine IFNγ ELISpot, 862.031-005PC), following the manufacturer's instructions (~16-18 h incubation time before performing the assay). The peptides used for restimulation are described in Table 5.

TABLE 5

Setup of the ELISPOT-IFNγ assay.

| Group | Stimulus | Wells | Animal | Total |
|---|---|---|---|---|
| 1 | CD22-H1 (10 μM) | 3 | 6 | 18 |
| | CD22-B1 (10 μM) | 3 | 6 | 18 |
| | CD3/CD28 bead | 3 | 6 | 18 |
| | Medium | 3 | 6 | 18 |
| 2 | CD19-H1 (10 μM) | 3 | 6 | 18 |
| | CD19-B1 (10 μM) | 3 | 6 | 18 |
| | CD3/CD28 bead | 3 | 6 | 18 |
| | Medium | 3 | 6 | 18 |
| 3 | CD19-H2 (10 μM) | 3 | 6 | 18 |
| | CD19-B2 (10 μM) | 3 | 6 | 18 |
| | CD3/CD28 bead | 3 | 6 | 18 |
| | Medium | 3 | 6 | 18 |
| 4 | CD37-H1 (10 μM) | 3 | 6 | 18 |
| | CD37-B1 (10 μM) | 3 | 6 | 18 |
| | CD3/CD28 bead | 3 | 6 | 18 |
| | Medium | 3 | 6 | 18 |
| 5 | TNFRSF13C-H1 (10 μM) | 3 | 6 | 18 |
| | TNFRSF13C-B1 (10 μM) | 3 | 6 | 18 |

TABLE 5-continued

Setup of the ELISPOT-IFNγ assay.

| Group | Stimulus | Wells | Animal | Total |
|---|---|---|---|---|
| | CD3/CD28 bead | 3 | 6 | 18 |
| | Medium | 3 | 6 | 18 |
| 6 | CD22-H1 (10 μM) | 3 | 6 | 18 |
| | CD22-B1 (10 μM) | 3 | 6 | 18 |
| | CD3/CD28 bead | 3 | 6 | 18 |
| | Medium | 3 | 6 | 18 |
| 7 | TNFRSF13C-H1 (10 μM) | 3 | 6 | 18 |
| | TNFRSF13C-B1 (10 μM) | 3 | 6 | 18 |
| | CD3/CD28 bead | 3 | 6 | 18 |
| | Medium | 3 | 6 | 18 |
| 8 | CD37-H1 (10 μM) | 3 | 6 | 18 |
| | CD37-B1 (10 μM) | 3 | 6 | 18 |
| | CD3/CD28 bead | 3 | 6 | 18 |
| | Medium | 3 | 6 | 18 |
| 9 | MS4A1-B4 (10 μM) | 3 | 6 | 18 |
| | MS4A1-H4 (10 μM) | 3 | 6 | 18 |
| | CD3/CD28 bead | 3 | 6 | 18 |
| | Medium | 3 | 6 | 18 |

Spots were counted on a CTL ELISpot reader. Data plotting and statistical analysis were performed with the Prism-5 software (GraphPad Software Inc.).

B. Results

All mice were aged of 8 to 13 weeks at the experiment starting date. Both males and females were used in the study. Animals have been housed in groups of 6 per cage at maximum. At time of sacrifice, the spleen T cell population was analysed by flow cytometry, showing that the large majority belonged to the CD4+ T cell subset.

After plating and incubation with the appropriate stimuli, the IFNγ-producing cells were revealed and counted. The data were provided as a number of spots per $1 \cdot 10^6$ total T cells. The individual average values (obtained from the triplicates) were next used to plot the group average values. Statistical analysis for comparison (to the medium condition) were performed using impaired non-parametric test (Mann Whitney) (**: $p<0.01$; *: $p<0.05$).

Figure 11:
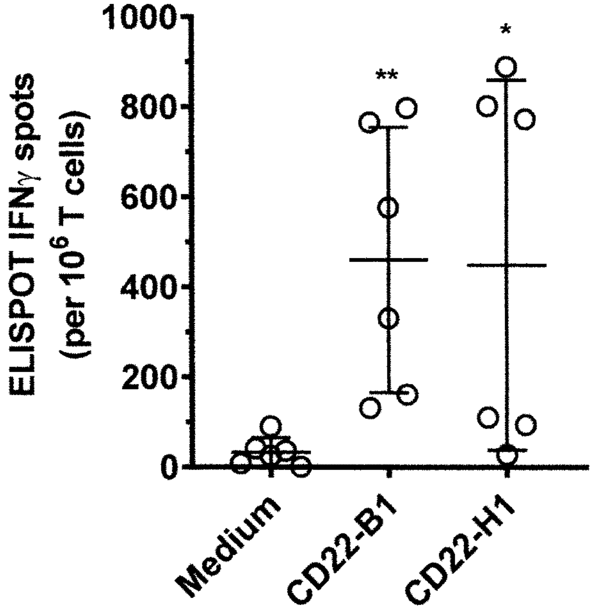
FIG. 11: shows for Example 2 ELISPOT results for HHD DR3 HLA-A2 transgenic mice vaccinated with the antigenic peptide CD22-B1 as indicated in the figure and cross-reactivity with the human corresponding peptide CD22-H1. The data were provided as a number of spots per $1 \cdot 10^6$ total T cells.
Figure 12:
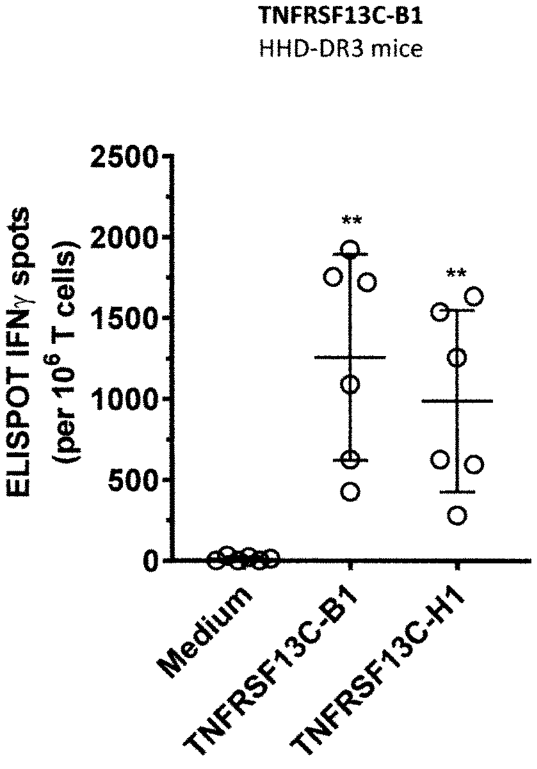
FIG. 12: shows for Example 2 ELISPOT results for HHD DR3 HLA-A2 transgenic mice vaccinated with the antigenic peptide TNFRSF13C-B1 as indicated in the figure and cross-reactivity with the human corresponding peptide TNFRSF13C-H1. The data were provided as a number of spots per $1 \cdot 10^6$ total T cells.
Figure 13:
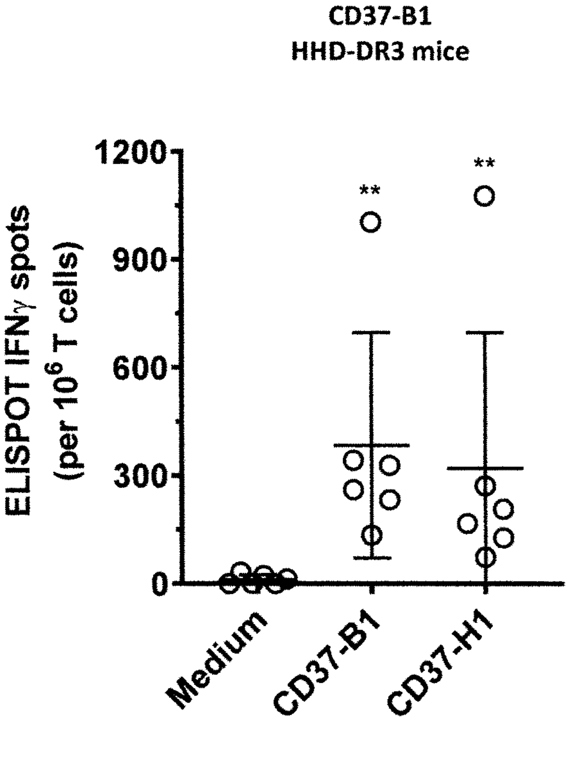
FIG. 13: shows for Example 2 ELISPOT results for HHD DR3 HLA-A2 transgenic mice vaccinated with the antigenic peptide CD37-B1 as indicated in the figure and cross-reactivity with the human corresponding peptide CD37-H1. The data were provided as a number of spots per $1 \cdot 10^6$ total T cells.

Overall, vaccination with the antigenic peptides according to the present invention (CD19-B1, CD19-B2, CD22-B1, CD37-B1, TNFRSF13C-B1 and MS4A1-B4) induced significant T cell responses in the ELISPOT-IFNγ assay in HHD DR1 mice (FIGS. 6-10) Immunogenicity of CD22-B1, CD37-B1, TNFRSF13C-B1 and MS4A1-B4 were confirmed in HHD DR1 mice (FIGS. 11-13).

The results (FIG. 6) show that immunization of HHD-DR1 mice with CD22-B1 allows to induce T-cells that are able to react strongly after challenge with either CD22-B1 or the human corresponding peptide CD22-H1. Thus, CD22-B2 is strongly immunogenic and is able to drive an effective immune response against the corresponding human peptide.

These results were confirmed in HHD DR3 mice expressing human HLA-A2 and HLA-DR3 MHC and lacking the murine H-2 class I and class II MHCs (Figure it).

The results (FIG. 7) show that immunization of HHD-DR1 mice with TNFRSF13C-B1 allows to induce T-cells that are able to react strongly after challenge with either TNFRSF13C-B1 or the human corresponding peptide TNFRSF13-H1. Thus, TNFRSF13C-B1 is strongly immunogenic and is able to drive an effective immune response against the corresponding human peptide.

These results were confirmed in HHD DR3 mice expressing human HLA-A2 and HLA-DR3 MHC and lacking the murine H-2 class I and class II MHCs (FIG. 12).

The results (FIG. 8) show that immunization of HHD-DR1 mice with CD37-B1 allows to induce T-cells that are able to react strongly after challenge with either CD37-B1 or the human corresponding peptide CD37-H1. Thus, CD37-B2 is strongly immunogenic and is able to drive an effective immune response against the corresponding human peptide.

These results were confirmed in HHD DR3 mice expressing human HLA-A2 and HLA-DR3 MHC and lacking the murine H-2 class I and class II MHCs (FIG. 13).

The results (FIG. 9) show that immunization of HHD-DR1 mice with CD19-B2 allows to induce T-cells that are able to react strongly after challenge with either CD19-B2 or the human corresponding peptide CD19-H2. Thus, CD19-B2 is strongly immunogenic and is able to drive an effective immune response against the corresponding human peptide.

The results (FIG. 10) show that immunization of HHD-DR1 mice with CD19-B1 allows to induce T-cells that are able to react strongly after challenge with either CD19-B1 or the human corresponding peptide CD19-H1. Thus, CD19-B1 is strongly immunogenic and is able to drive an effective immune response against the corresponding human peptide.

Figure 15:
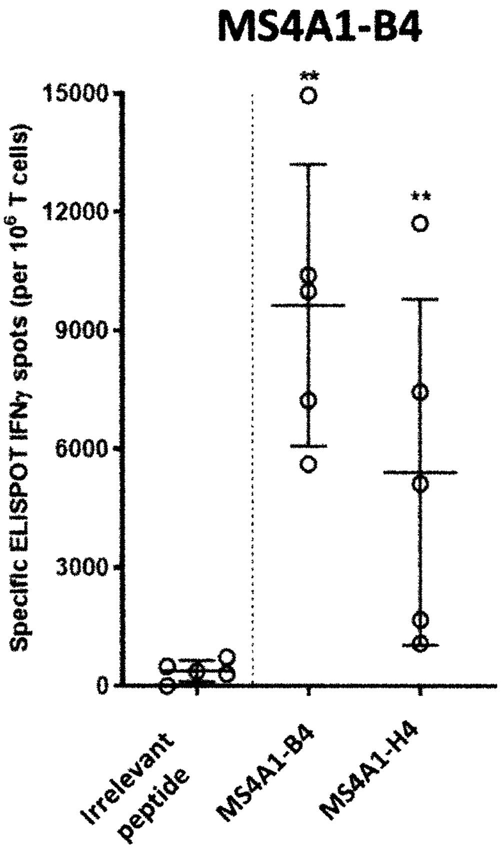
FIG. 15: shows for Example 2 ELISPOT results for HHD DR1 HLA-A2 transgenic mice vaccinated with the antigenic peptide MS4A1-B4 as indicated in the figure and cross-reactivity with the human corresponding peptide MS4A1-H4. The data were provided as a number of spots per $1 \cdot 10^6$ total T cells.

The results (FIG. 15) show that immunization of HHD-DR1 mice with MS4A1-B4 allows to induce T-cells that are able to react strongly after challenge with either MS4A1-B4 or the human corresponding peptide MS4A1-H4. Thus, MS4A1-B4 is strongly immunogenic and is able to drive an effective immune response against the corresponding human peptide.

Figure 16:
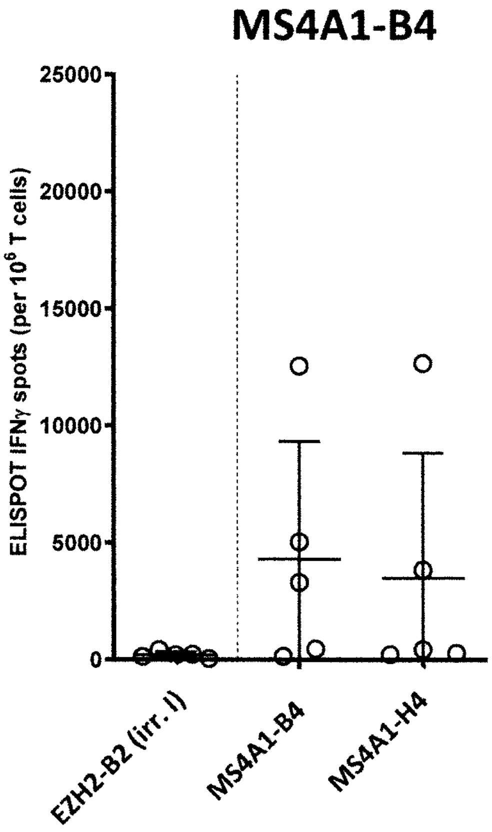
FIG. 16: shows for Example 2 ELISPOT results for HHD DR3 HLA-A2 transgenic mice vaccinated with the antigenic peptide MS4A1-B4 as indicated in the figure and cross-reactivity with the human corresponding peptide MS4A1-H4. The data were provided as a number of spots per $1 \cdot 10^6$ total T cells.

These results were confirmed in HHD DR3 mice expressing human HLA-A2 and HLA-DR3 MHC and lacking the murine H-2 class I and class II MHCs (FIG. 16).

Altogether, these immunogenicity studies described in Examples 2 performed in HHD DR3 and HHD DR1 mice showed that the 6 antigenic peptides of the invention, CD19-B1, CD19-B2, CD22-B1, CD37-B1, TNFRSF13C-B1 and MS4A1-B4 induced strong immune responses. Cross-reactivity of the T cells generated against CD19-B1, CD19-B2, CD22-B1, CD37-B1, TNFRSF13C-B1 and MS4A1-B4 for the corresponding human peptides was shown in HHD DR3 and HHD DR1 mice.

Accordingly, those results provide experimental evidence that antigen-based immunotherapy is able to improve T cell response in vivo and that the antigenic peptides according to the present invention are particularly efficient for that purpose.

Example 3: Ex Vivo Cytotoxic Effects of CD22-B1, CD37B1, TNFRSF13C-B1 and MS4A1-B4 Specific CD8 Human T Cells Multiple investigations support the notion of presence of a repertoire of specific T cells against microbial peptides. The number of microbial specific T-cells against peptides is expected to be low, but sufficient to be re-activated by a vaccine challenge.

To identify and functionally characterize circulating CD22-B1, CD37B1, TNFRSF13C-B1 and MS4A1-B4 specific T cells in humans, an in vitro amplification protocol has been developed in order to detect T cells specific for each antigenic peptide and investigate their cytotoxic capacity.

3.1 Identification of Antigenic Peptide-Specific CD8 T Cells in Human

In vitro amplification method and specific pMHC multimers have been used for identification of CD22-B1, CD37-B1, TNFRSF13C-B1 and MS4A1-B4 specific T cells. pMHC multimers were generated for all the bacteria peptides and their respective human counterpart. PBMCs from several HLA-A*02 healthy donors (up to 19 donors) were collected, enriched after CD137 and CD8 selection and subjected to multiple rounds of in vitro amplification with E02463 peptides loaded T2 cells to increase the number of specific T cell clones. Detection of OMP peptide specific CD8 T cells using cytometry analysis with the fluorescent multimer was performed on enriched CD8 T cell populations FIG. 17 exemplifies results obtained with one HLA-A2 healthy donor. For this donor, cell amplification allows detection of MS4A1-B4 specific cells (19.7%), TNFRSF13C-B1 specific cells (13%), CD22-B1 specific cells (4.6%) and CD37-B1 specific cells (2.5%).

In conclusion, these results demonstrate the presence of CD8 T cells in the blood of healthy HLA-A2 donors that can recognize the microbiome-derived peptides, and importantly also the human counterpart peptides.

3.2 Antigenic Peptide-Specific CD8 T Cytotoxicity Functions

CD8+ T cells expanded per above were used to perform cytotoxic assays in presence of different ratios of target and effector cells to assess their cytotoxic capacity, using flow cytometry readout.

Figure 17:
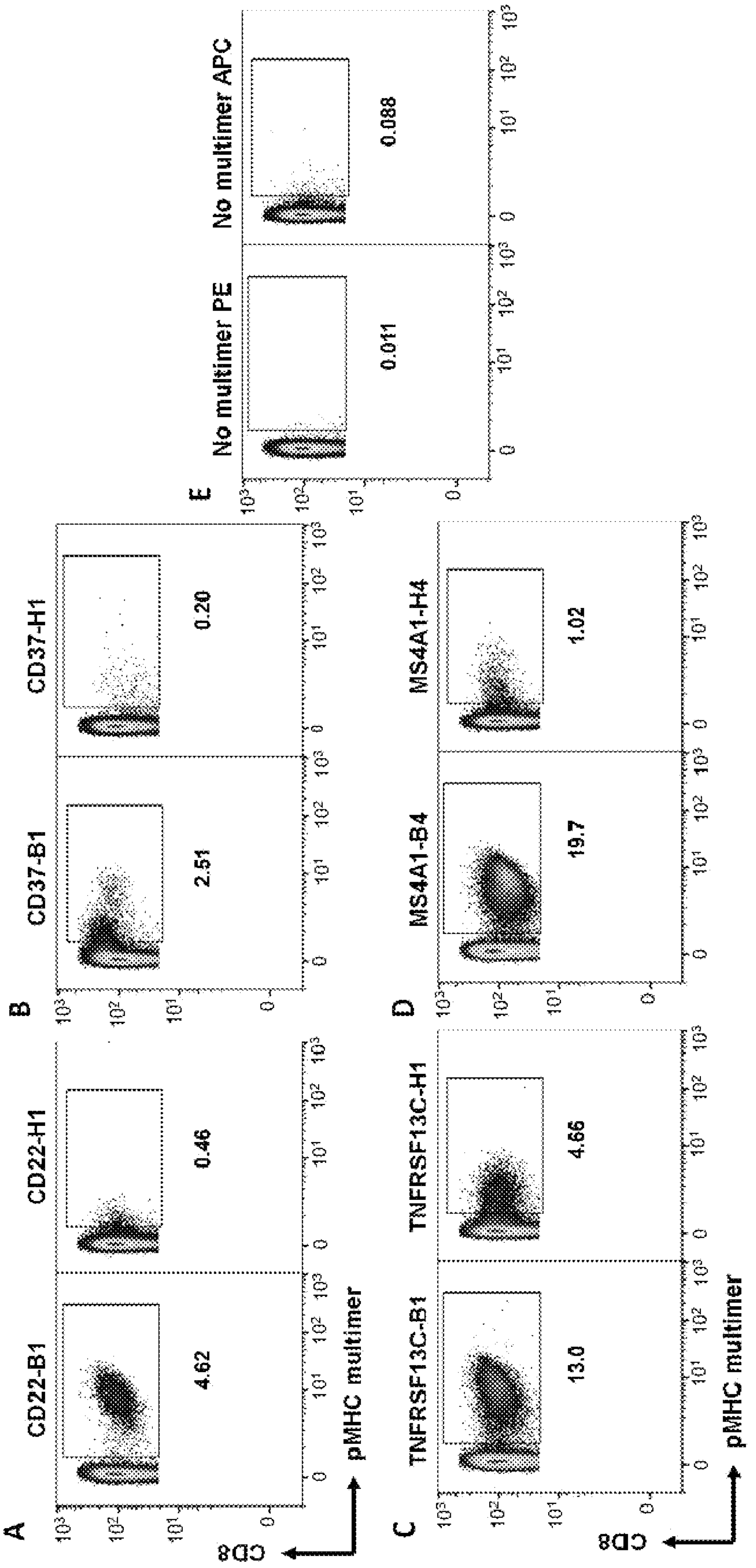
FIG. 17: shows for Example 3 the detection of CD22-B1, CD37B1, TNFRSF13C-B1 and MS4A1-B4 peptide-specific CD8+ T cells detected in peripheral blood from healthy donors (HLA-A2 positive).
Figure 18:
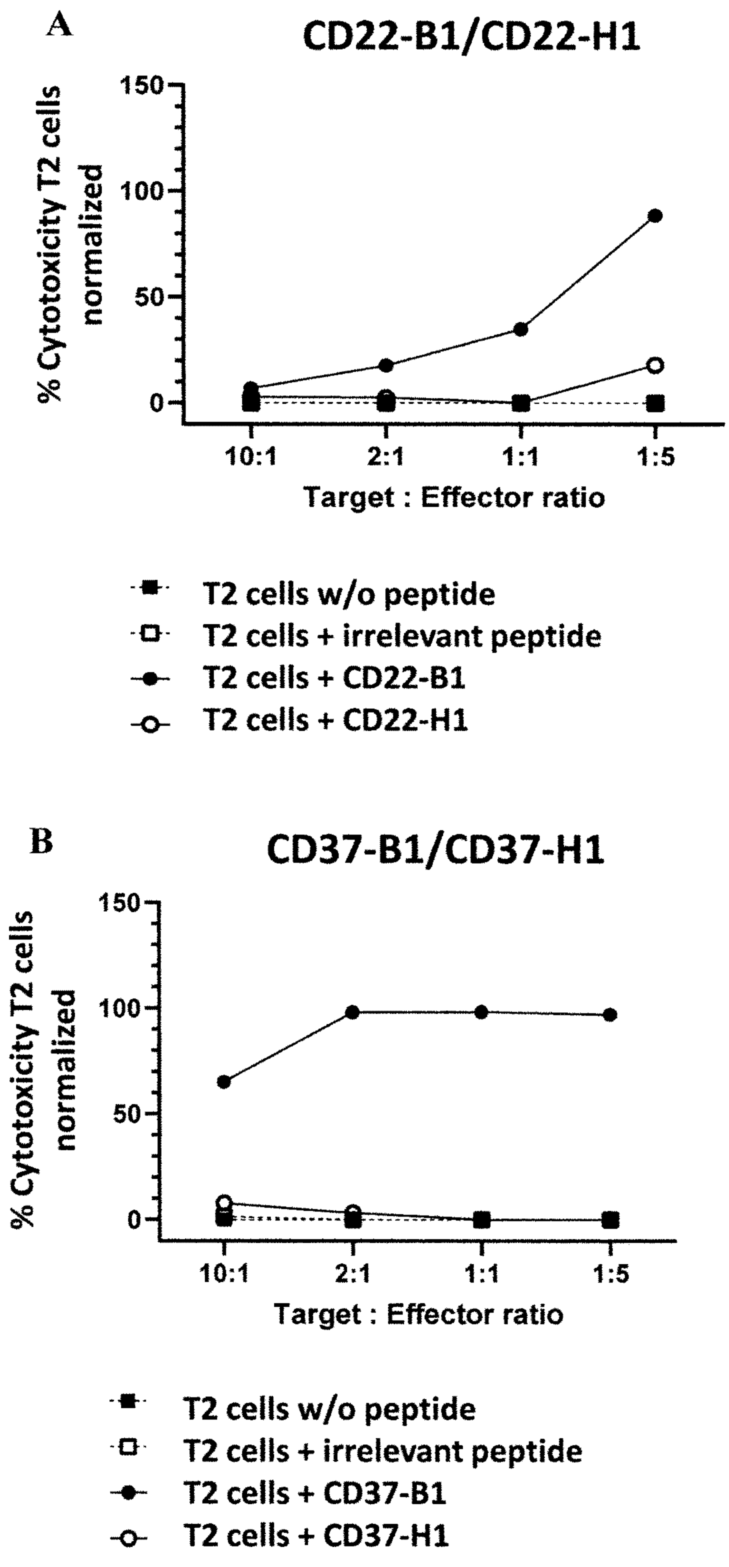
FIG. 18: shows for Example 3 the cytotoxic capacity of the CD22-B1, CD37B1, TNFRSF13C-B1 and MS4A1-B4 peptide-specific human T cells clone expanded in vitro by microbiome derived peptide stimulation. CD22-B1, CD37B1, TNFRSF13C-B1 and MS4A1-B4 peptide-specific T cells have the ability to kill T2 cells loaded with bacterial or human peptides.
Figure 18:
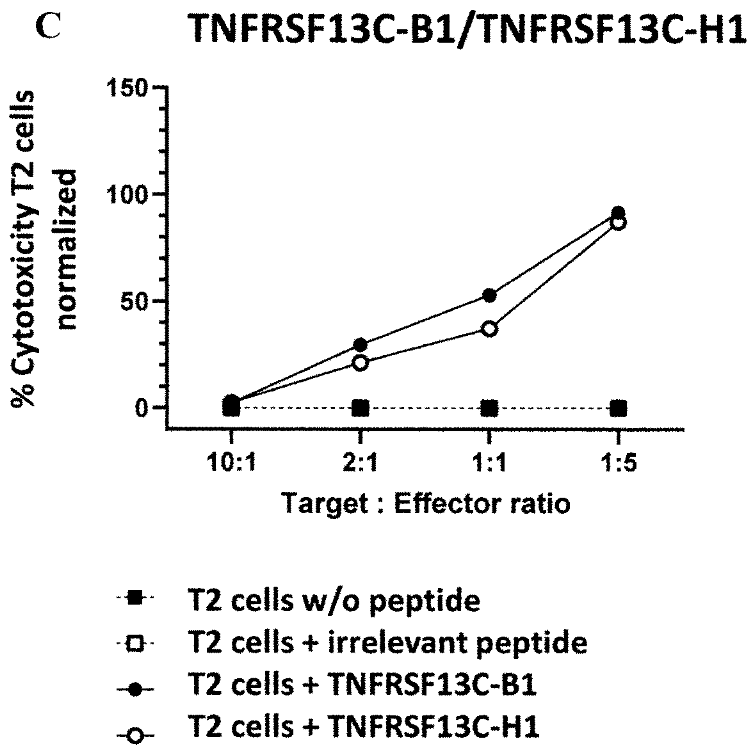
Figure 18:
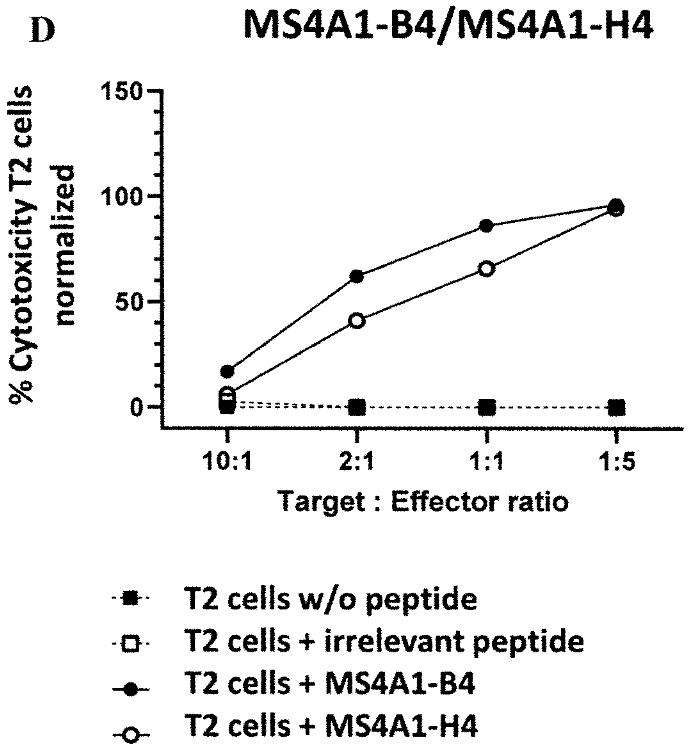
Figure 19:
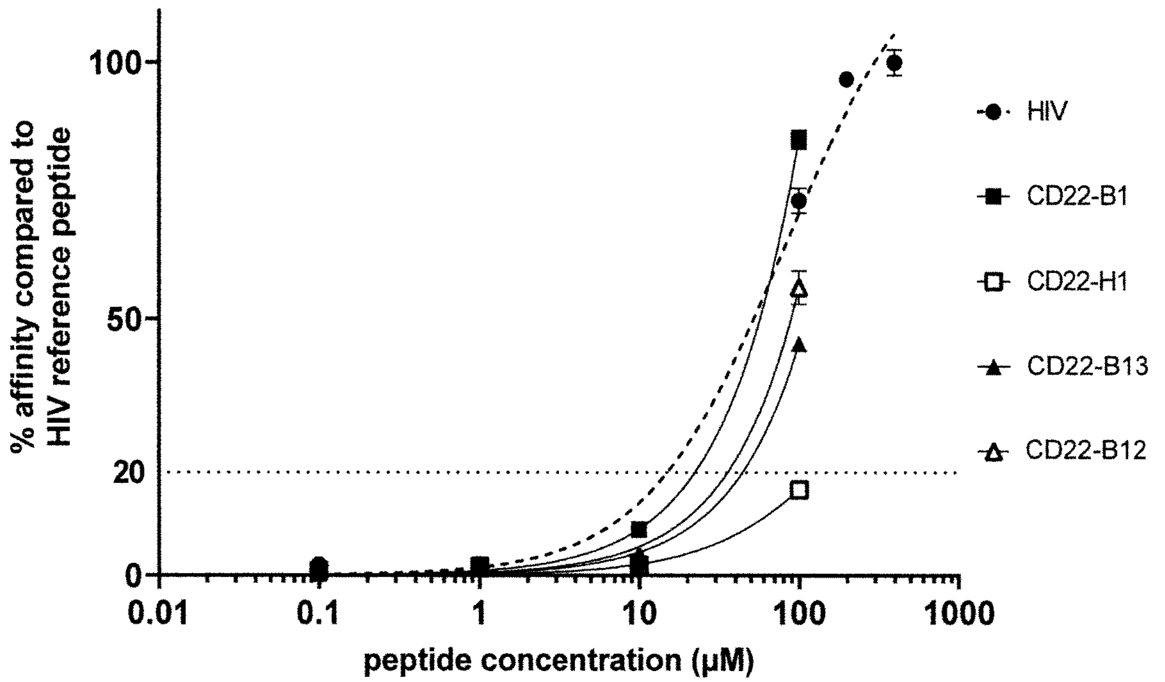
FIG. 19: shows for Example 4 in vitro affinity for the antigenic peptides CD22-B1, CD22-B12 and CD22-B13 in comparison to the corresponding human CD22 epitope CD22-H1.
Figure 20:
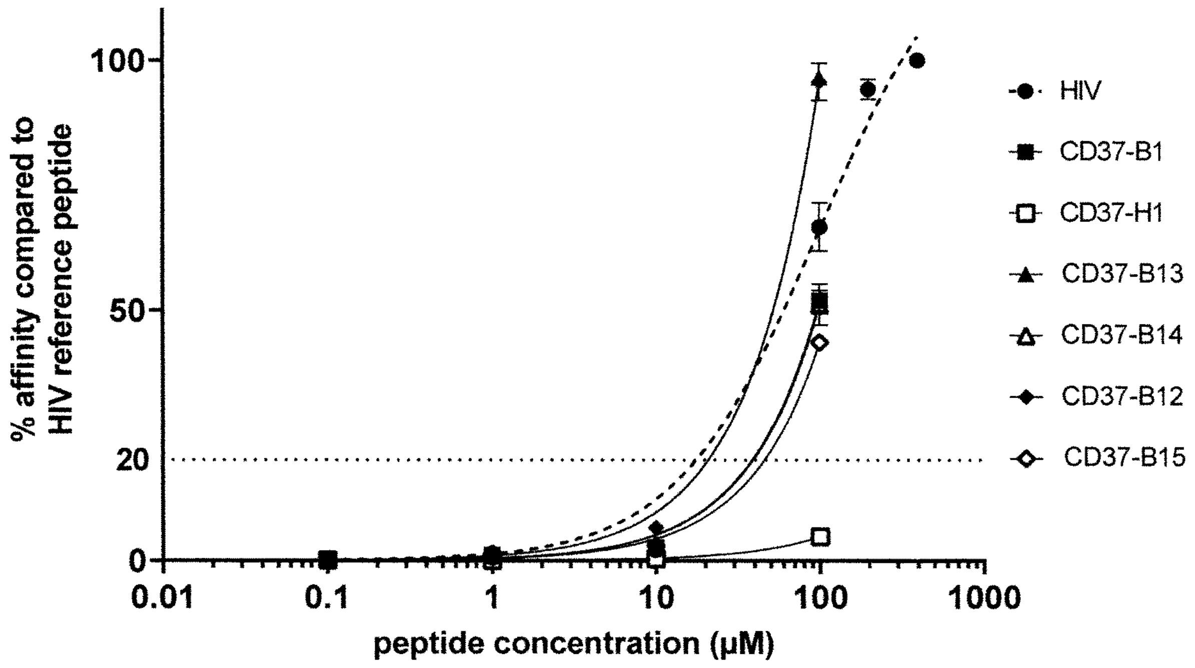
FIG. 20: shows for Example 4 in vitro affinity for the antigenic peptides CD37-B1, CD37-B12, CD37-B13, CD37-B14 and CD37-B15 in comparison to the corresponding human CD37 epitope CD37-H1.
Figure 21:
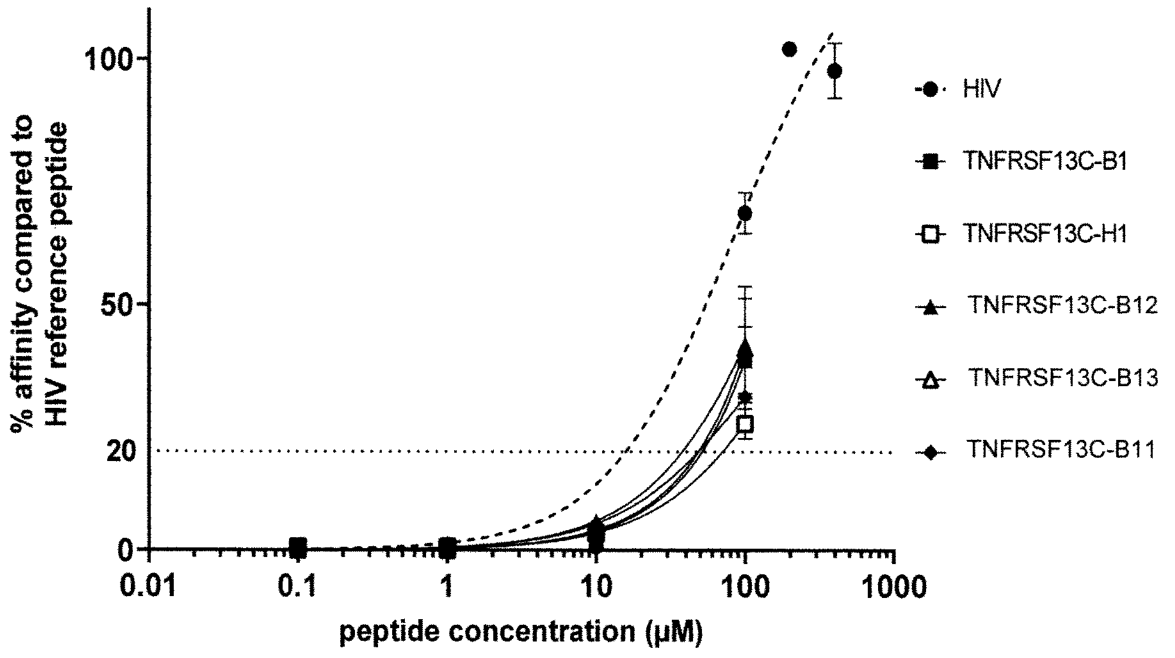
FIG. 21 shows for Example 4 in vitro affinity for the antigenic peptides TNFRSF13C-B1, TNFRSF13C-B11, TNFRSF13C-B12 and TNFRSF13C-B13 in comparison to the corresponding human TNFRSF13C epitope TNFRSF13C-H1.
Figure 22:
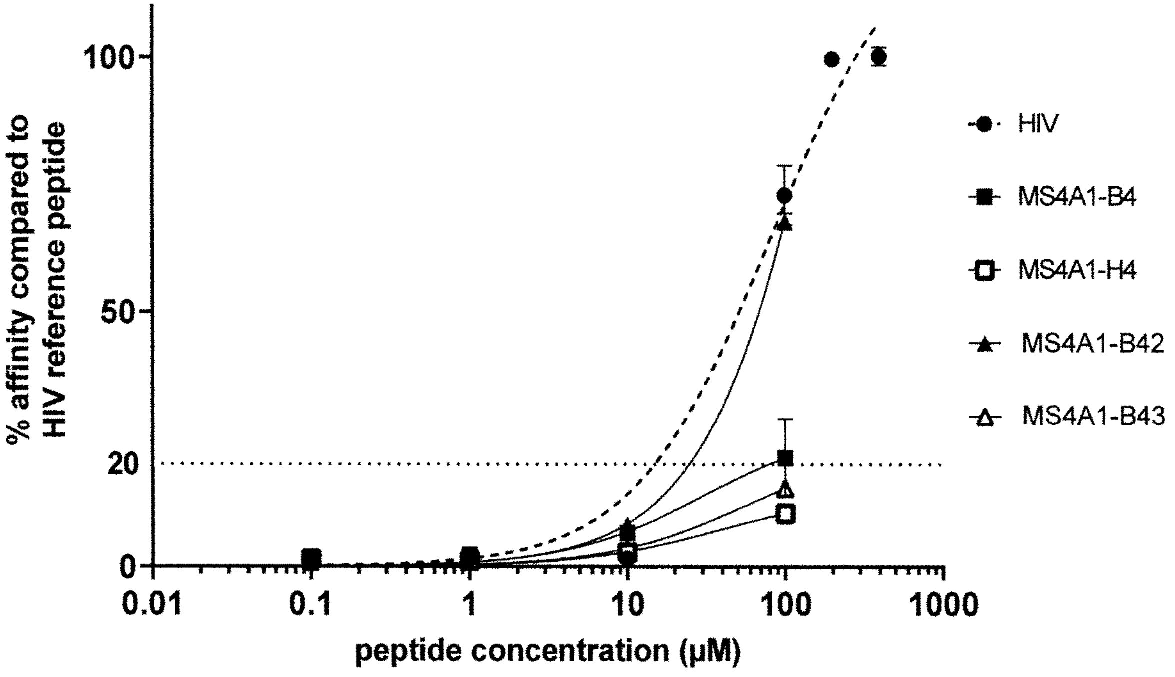
FIG. 22: shows for Example 4 in vitro affinity for the antigenic peptide MS4A1-B4, MS4A1-B42 and MS4A1-B43 in comparison to the corresponding human MS4A1 epitope MS4A1-H4.

Target cells were T2 cell lines loaded with bacterial peptide or human counterpart peptide. Negative control was T2 cells unloaded and T2 cells loaded with irrelevant peptide. As shown in FIG. 18, antigenic peptide-specific human T cells clone expanded in vitro have the capacity to kill T2 cells loaded with all the bacteria peptide, CD22-B1, CD37B1, TNFRSF13C-B1 and MS4A1-B4. More importantly, CD22-B1, CD37B1, TNFRSF13C-B1 and MS4A1-B4-specific human T cells clones expanded in vitro were able to kill T2 cells loaded with the human TNFR13C (BAFF-R) or MS4A1 (CD20) peptide when cross-reactivity is observed with the staining (FIG. 17).

Overall, these results demonstrate the presence of T cell clones in healthy volunteers able to recognize microbial peptide and to kill target with microbial peptides and human counterparts. These data are particularly encouraging as T cell clones have been obtained in healthy donors, therefore we could expect that specific T cell clones could be efficiently amplified in patients exposed to the immunization by antigenic peptides of the invention.

Example 4: Further Antigenic Peptides have Superior Affinity to the HLA-A*0201 Allele Next, binding affinity of further selected antigenic peptides and of the corresponding fragments of human tumor antigens (human reference peptides) to the HLA-A*0201 allele was confirmed in vitro.

Namely, the antigenic peptides of sequence SEQ ID NO: 110 («YIFEHPELL» also referred to herein as CD22-B1), of sequence SEQ ID NO: 107 («LIFEHPERV» also referred to herein as CD22-B12), and of sequence SEQ ID NO: 108 («RVFEHPELV» also referred to herein as CD22-B13) were compared to the corresponding reference human peptide derived from CD22 («WVFEHPETL», SEQ ID NO: 270, also referred herein as CD22-H1).

Moreover, the antigenic peptides of sequence SEQ ID NO: 114 («FLAFVPLQL» also referred herein as CD37-B1), of sequence SEQ ID NO: 119 («ILAFVPLYL» also referred to herein as CD37-B12), of sequence SEQ ID NO: 120 («IMAFVPLAV» also referred to herein as CD37-B13), of sequence SEQ ID NO: 491 («FLAFVPLDV» also referred to herein as CD37-B14) and of sequence SEQ ID NO: 493 («VLAFVPLGV» also referred to herein as CD37-B15) were compared to the corresponding reference human peptide derived from CD37 («GLAFVPLQI», SEQ ID NO: 271, also referred herein as CD37-H1).

Furthermore, the antigenic peptides of sequence SEQ ID NO: 220 («LMFGAPALV» also referred herein as TNFRSF13C-B1), of sequence SEQ ID NO: 212 («FLFGAPASA» also referred to herein as TNFRSF13C-B11), of sequence SEQ ID NO: 217 («LLFGAPAGV» also referred to herein as TNFRSF13C-B12), and of sequence SEQ ID NO: 224 («VLFGAPAYL» also referred to herein as TNFRSF13C-B13) were compared to the corresponding reference human peptide derived from TNFRSF13C («LLFGAPALL», SEQ ID NO: 279, also referred herein as TNFRSF13C-H1).

In addition, the antigenic peptides of sequence SEQ ID NO: 65 («AMNSLSLYI» also referred herein as MS4A1-B4), of sequence SEQ ID NO: 70 («YMNSLSLAL» also referred to herein as MS4A1-B42) and of sequence SEQ ID NO: 477 («AMNSLSLTV» also referred to herein as MS4A1-B43) were compared to the corresponding reference human peptide derived from MS4A1 (also known as CD20) («IMNSLSLFA», SEQ ID NO: 264, also referred herein as MS4A1-H4).

A. Materials and Methods

A1. Measuring the Affinity of the Peptide to T2 Cell Line

The experimental protocol is similar to the one that was validated for peptides presented by the HLA-A*0201 (Tourdot et al., A general strategy to enhance immunogenicity of low-affinity HLA-A2.1-associated peptides: implication in the identification of cryptic tumor epitopes. Eur J Immunol. 2000 December; 30(12):3411-21). Affinity measurement of the peptides is achieved with the human tumoral cell T2 which expresses the HLA-A*0201 molecule, but which is TAP1/2 negative and incapable of presenting endogenous peptides.

T2 cells ($5\cdot10^4$ cells per well) are incubated with decreasing concentrations of peptides from 100 to 0.1 μM (4 points: 100 μM, 10 μM, 1 μM, 0.1 μM) in serum-free medium (TexMacs) supplemented with 100 ng/μl of β2 Microglobulin at 37° C. for 16 hours. Cells are then washed two times and marked with the anti-HLA-A2 antibody coupled to PE (clone BB7.2, BD Pharmagen).

The analysis is achieved by FACS (Macsquant analyzer 10—Miltenyi).

For each peptide concentration, the geometric mean of the labelling associated with the peptide of interest is subtracted from background noise and reported as a percentage of the geometric mean of the HLA-A*0202 labelling obtained for the reference peptide HIV pol 589-597 at a concentration of 100 μM.

A2. Solubilisation of Peptides

Each peptide is solubilized by taking into account the amino acid composition. For peptides which do not include any Cystein, Methionin, or Tryptophane, the addition of DMSO is possible to up to 10% of the total volume. Other peptides are resuspended in water or PBS pH7.4.

B. Results

Results are shown in FIGS. 19-22. For each of the tested human reference epitopes CD22-H1 (FIG. 19), CD37-H1 (FIG. 20), TNFRSF13C-H1 (FIG. 21) and MS4A1-H4 (FIG. 22), the respective antigenic peptides according to the present invention show a stronger binding affinity to HLA-A*0201.

In summary, the results show that the antigenic peptides according to the present invention show stronger binding affinity to HLA-A*0201 than the corresponding human tumor antigen fragments. As outlined above, without being bound to any theory it is assumed that such a strong binding affinity of the antigenic peptides according to the present invention reflects their ability to raise an immune response (i.e., their immunogenicity).

SEQUENCE LISTING

```
Sequence total quantity: 509
SEQ ID NO: 1            moltype = AA  length = 9
FEATURE                 Location/Qualifiers
REGION                  1..9
                        note = peptide
source                  1..9
                        mol_type = protein
                        organism = synthetic construct
SEQUENCE: 1
FLLFLTPIL                                                         9

SEQ ID NO: 2            moltype = AA  length = 9
FEATURE                 Location/Qualifiers
REGION                  1..9
                        note = peptide
source                  1..9
                        mol_type = protein
                        organism = synthetic construct
SEQUENCE: 2
FLLFLTPLL                                                         9

SEQ ID NO: 3            moltype = AA  length = 9
FEATURE                 Location/Qualifiers
REGION                  1..9
                        note = peptide
source                  1..9
                        mol_type = protein
                        organism = synthetic construct
SEQUENCE: 3
FMLFLTPRI                                                         9

SEQ ID NO: 4            moltype = AA  length = 9
FEATURE                 Location/Qualifiers
REGION                  1..9
                        note = peptide
```

```
source                  1..9
                        mol_type = protein
                        organism = synthetic construct
SEQUENCE: 4
GLLFLTPLA                                                        9

SEQ ID NO: 5            moltype = AA  length = 9
FEATURE                 Location/Qualifiers
REGION                  1..9
                        note = peptide
source                  1..9
                        mol_type = protein
                        organism = synthetic construct
SEQUENCE: 5
GLLFLTPLL                                                        9

SEQ ID NO: 6            moltype = AA  length = 9
FEATURE                 Location/Qualifiers
REGION                  1..9
                        note = peptide
source                  1..9
                        mol_type = protein
                        organism = synthetic construct
SEQUENCE: 6
GLLFLTPLM                                                        9

SEQ ID NO: 7            moltype = AA  length = 9
FEATURE                 Location/Qualifiers
REGION                  1..9
                        note = peptide
source                  1..9
                        mol_type = protein
                        organism = synthetic construct
SEQUENCE: 7
ILLFLTPLL                                                        9

SEQ ID NO: 8            moltype = AA  length = 9
FEATURE                 Location/Qualifiers
REGION                  1..9
                        note = peptide
source                  1..9
                        mol_type = protein
                        organism = synthetic construct
SEQUENCE: 8
SLLFLTPLL                                                        9

SEQ ID NO: 9            moltype = AA  length = 9
FEATURE                 Location/Qualifiers
REGION                  1..9
                        note = peptide
source                  1..9
                        mol_type = protein
                        organism = synthetic construct
SEQUENCE: 9
TLLFLTPLI                                                        9

SEQ ID NO: 10           moltype = AA  length = 9
FEATURE                 Location/Qualifiers
REGION                  1..9
                        note = peptide
source                  1..9
                        mol_type = protein
                        organism = synthetic construct
SEQUENCE: 10
TLLFLTPML                                                        9

SEQ ID NO: 11           moltype = AA  length = 9
FEATURE                 Location/Qualifiers
REGION                  1..9
                        note = peptide
source                  1..9
                        mol_type = protein
                        organism = synthetic construct
SEQUENCE: 11
VLLFLTPML                                                        9

SEQ ID NO: 12           moltype = AA  length = 9
FEATURE                 Location/Qualifiers
```

```
REGION                  1..9
                        note = peptide
source                  1..9
                        mol_type = protein
                        organism = synthetic construct
SEQUENCE: 12
YLLFLTPVL                                                     9

SEQ ID NO: 13           moltype = AA  length = 9
FEATURE                 Location/Qualifiers
REGION                  1..9
                        note = peptide
source                  1..9
                        mol_type = protein
                        organism = synthetic construct
SEQUENCE: 13
ALSLGLPGL                                                     9

SEQ ID NO: 14           moltype = AA  length = 9
FEATURE                 Location/Qualifiers
REGION                  1..9
                        note = peptide
source                  1..9
                        mol_type = protein
                        organism = synthetic construct
SEQUENCE: 14
ALSLGLPLL                                                     9

SEQ ID NO: 15           moltype = AA  length = 9
FEATURE                 Location/Qualifiers
REGION                  1..9
                        note = peptide
source                  1..9
                        mol_type = protein
                        organism = synthetic construct
SEQUENCE: 15
ALSLGLPML                                                     9

SEQ ID NO: 16           moltype = AA  length = 9
FEATURE                 Location/Qualifiers
REGION                  1..9
                        note = peptide
source                  1..9
                        mol_type = protein
                        organism = synthetic construct
SEQUENCE: 16
ALSLGLPQL                                                     9

SEQ ID NO: 17           moltype = AA  length = 9
FEATURE                 Location/Qualifiers
REGION                  1..9
                        note = peptide
source                  1..9
                        mol_type = protein
                        organism = synthetic construct
SEQUENCE: 17
ALSLGLPRL                                                     9

SEQ ID NO: 18           moltype = AA  length = 9
FEATURE                 Location/Qualifiers
REGION                  1..9
                        note = peptide
source                  1..9
                        mol_type = protein
                        organism = synthetic construct
SEQUENCE: 18
AMSLGLPCL                                                     9

SEQ ID NO: 19           moltype = AA  length = 9
FEATURE                 Location/Qualifiers
REGION                  1..9
                        note = peptide
source                  1..9
                        mol_type = protein
                        organism = synthetic construct
SEQUENCE: 19
AMSLGLPML                                                     9

SEQ ID NO: 20           moltype = AA  length = 9
```

-continued

```
FEATURE                Location/Qualifiers
REGION                 1..9
                       note = peptide
source                 1..9
                       mol_type = protein
                       organism = synthetic construct
SEQUENCE: 20
FLSLGLPIL                                                            9

SEQ ID NO: 21          moltype = AA  length = 9
FEATURE                Location/Qualifiers
REGION                 1..9
                       note = peptide
source                 1..9
                       mol_type = protein
                       organism = synthetic construct
SEQUENCE: 21
FLSLGLPKL                                                            9

SEQ ID NO: 22          moltype = AA  length = 9
FEATURE                Location/Qualifiers
REGION                 1..9
                       note = peptide
source                 1..9
                       mol_type = protein
                       organism = synthetic construct
SEQUENCE: 22
ILSLGLPIL                                                            9

SEQ ID NO: 23          moltype = AA  length = 9
FEATURE                Location/Qualifiers
REGION                 1..9
                       note = peptide
source                 1..9
                       mol_type = protein
                       organism = synthetic construct
SEQUENCE: 23
KLSLGLPVL                                                            9

SEQ ID NO: 24          moltype = AA  length = 9
FEATURE                Location/Qualifiers
REGION                 1..9
                       note = peptide
source                 1..9
                       mol_type = protein
                       organism = synthetic construct
SEQUENCE: 24
LLSLGLPFL                                                            9

SEQ ID NO: 25          moltype = AA  length = 9
FEATURE                Location/Qualifiers
REGION                 1..9
                       note = peptide
source                 1..9
                       mol_type = protein
                       organism = synthetic construct
SEQUENCE: 25
LLSLGLPGL                                                            9

SEQ ID NO: 26          moltype = AA  length = 9
FEATURE                Location/Qualifiers
REGION                 1..9
                       note = peptide
source                 1..9
                       mol_type = protein
                       organism = synthetic construct
SEQUENCE: 26
MLSLGLPIL                                                            9

SEQ ID NO: 27          moltype = AA  length = 9
FEATURE                Location/Qualifiers
REGION                 1..9
                       note = peptide
source                 1..9
                       mol_type = protein
                       organism = synthetic construct
SEQUENCE: 27
RLSLGLPGL                                                            9
```

-continued

```
SEQ ID NO: 28           moltype = AA  length = 9
FEATURE                 Location/Qualifiers
REGION                  1..9
                        note = peptide
source                  1..9
                        mol_type = protein
                        organism = synthetic construct
SEQUENCE: 28
SLSLGLPIL                                                         9

SEQ ID NO: 29           moltype = AA  length = 9
FEATURE                 Location/Qualifiers
REGION                  1..9
                        note = peptide
source                  1..9
                        mol_type = protein
                        organism = synthetic construct
SEQUENCE: 29
SLSLGLPKL                                                         9

SEQ ID NO: 30           moltype = AA  length = 9
FEATURE                 Location/Qualifiers
REGION                  1..9
                        note = peptide
source                  1..9
                        mol_type = protein
                        organism = synthetic construct
SEQUENCE: 30
VLSLGLPLL                                                         9

SEQ ID NO: 31           moltype = AA  length = 9
FEATURE                 Location/Qualifiers
REGION                  1..9
                        note = peptide
source                  1..9
                        mol_type = protein
                        organism = synthetic construct
SEQUENCE: 31
VLSLGLPTA                                                         9

SEQ ID NO: 32           moltype = AA  length = 9
FEATURE                 Location/Qualifiers
REGION                  1..9
                        note = peptide
source                  1..9
                        mol_type = protein
                        organism = synthetic construct
SEQUENCE: 32
VLSLGLPTV                                                         9

SEQ ID NO: 33           moltype = AA  length = 9
FEATURE                 Location/Qualifiers
REGION                  1..9
                        note = peptide
source                  1..9
                        mol_type = protein
                        organism = synthetic construct
SEQUENCE: 33
YLSLGLPIL                                                         9

SEQ ID NO: 34           moltype = AA  length = 9
FEATURE                 Location/Qualifiers
REGION                  1..9
                        note = peptide
source                  1..9
                        mol_type = protein
                        organism = synthetic construct
SEQUENCE: 34
LLVGILHLV                                                         9

SEQ ID NO: 35           moltype = AA  length = 9
FEATURE                 Location/Qualifiers
REGION                  1..9
                        note = peptide
source                  1..9
                        mol_type = protein
                        organism = synthetic construct
SEQUENCE: 35
SLVGILHII                                                         9
```

```
SEQ ID NO: 36          moltype = AA  length = 9
FEATURE                Location/Qualifiers
REGION                 1..9
                       note = peptide
source                 1..9
                       mol_type = protein
                       organism = synthetic construct
SEQUENCE: 36
FLAYLIFGL                                                          9

SEQ ID NO: 37          moltype = AA  length = 9
FEATURE                Location/Qualifiers
REGION                 1..9
                       note = peptide
source                 1..9
                       mol_type = protein
                       organism = synthetic construct
SEQUENCE: 37
FLAYLIFTL                                                          9

SEQ ID NO: 38          moltype = AA  length = 9
FEATURE                Location/Qualifiers
REGION                 1..9
                       note = peptide
source                 1..9
                       mol_type = protein
                       organism = synthetic construct
SEQUENCE: 38
RLAYLIFLL                                                          9

SEQ ID NO: 39          moltype = AA  length = 9
FEATURE                Location/Qualifiers
REGION                 1..9
                       note = peptide
source                 1..9
                       mol_type = protein
                       organism = synthetic construct
SEQUENCE: 39
YLAYLIFEL                                                          9

SEQ ID NO: 40          moltype = AA  length = 9
FEATURE                Location/Qualifiers
REGION                 1..9
                       note = peptide
source                 1..9
                       mol_type = protein
                       organism = synthetic construct
SEQUENCE: 40
LQMGGFYLL                                                          9

SEQ ID NO: 41          moltype = AA  length = 9
FEATURE                Location/Qualifiers
REGION                 1..9
                       note = peptide
source                 1..9
                       mol_type = protein
                       organism = synthetic construct
SEQUENCE: 41
AILGGLLLI                                                          9

SEQ ID NO: 42          moltype = AA  length = 9
FEATURE                Location/Qualifiers
REGION                 1..9
                       note = peptide
source                 1..9
                       mol_type = protein
                       organism = synthetic construct
SEQUENCE: 42
ALLGGLLLI                                                          9

SEQ ID NO: 43          moltype = AA  length = 9
FEATURE                Location/Qualifiers
REGION                 1..9
                       note = peptide
source                 1..9
                       mol_type = protein
                       organism = synthetic construct
```

-continued

```
SEQUENCE: 43
ALLGGLLML                                                          9

SEQ ID NO: 44            moltype = AA  length = 9
FEATURE                  Location/Qualifiers
REGION                   1..9
                         note = peptide
source                   1..9
                         mol_type = protein
                         organism = synthetic construct
SEQUENCE: 44
FALGGLLTV                                                          9

SEQ ID NO: 45            moltype = AA  length = 9
FEATURE                  Location/Qualifiers
REGION                   1..9
                         note = peptide
source                   1..9
                         mol_type = protein
                         organism = synthetic construct
SEQUENCE: 45
FLLGGLLLI                                                          9

SEQ ID NO: 46            moltype = AA  length = 9
FEATURE                  Location/Qualifiers
REGION                   1..9
                         note = peptide
source                   1..9
                         mol_type = protein
                         organism = synthetic construct
SEQUENCE: 46
FLLGGLLMV                                                          9

SEQ ID NO: 47            moltype = AA  length = 9
FEATURE                  Location/Qualifiers
REGION                   1..9
                         note = peptide
source                   1..9
                         mol_type = protein
                         organism = synthetic construct
SEQUENCE: 47
GMLGGLLLI                                                          9

SEQ ID NO: 48            moltype = AA  length = 9
FEATURE                  Location/Qualifiers
REGION                   1..9
                         note = peptide
source                   1..9
                         mol_type = protein
                         organism = synthetic construct
SEQUENCE: 48
GMLGGLLML                                                          9

SEQ ID NO: 49            moltype = AA  length = 9
FEATURE                  Location/Qualifiers
REGION                   1..9
                         note = peptide
source                   1..9
                         mol_type = protein
                         organism = synthetic construct
SEQUENCE: 49
HILGGLLMV                                                          9

SEQ ID NO: 50            moltype = AA  length = 9
FEATURE                  Location/Qualifiers
REGION                   1..9
                         note = peptide
source                   1..9
                         mol_type = protein
                         organism = synthetic construct
SEQUENCE: 50
IILGGLLVV                                                          9

SEQ ID NO: 51            moltype = AA  length = 9
FEATURE                  Location/Qualifiers
REGION                   1..9
                         note = peptide
```

```
source                  1..9
                        mol_type = protein
                        organism = synthetic construct
SEQUENCE: 51
ILLGGLLLI                                                        9

SEQ ID NO: 52           moltype = AA  length = 9
FEATURE                 Location/Qualifiers
REGION                  1..9
                        note = peptide
source                  1..9
                        mol_type = protein
                        organism = synthetic construct
SEQUENCE: 52
LLLGGLLLI                                                        9

SEQ ID NO: 53           moltype = AA  length = 9
FEATURE                 Location/Qualifiers
REGION                  1..9
                        note = peptide
source                  1..9
                        mol_type = protein
                        organism = synthetic construct
SEQUENCE: 53
LLLGGLLMI                                                        9

SEQ ID NO: 54           moltype = AA  length = 9
FEATURE                 Location/Qualifiers
REGION                  1..9
                        note = peptide
source                  1..9
                        mol_type = protein
                        organism = synthetic construct
SEQUENCE: 54
NLLGGLLLI                                                        9

SEQ ID NO: 55           moltype = AA  length = 9
FEATURE                 Location/Qualifiers
REGION                  1..9
                        note = peptide
source                  1..9
                        mol_type = protein
                        organism = synthetic construct
SEQUENCE: 55
SILGGLLLI                                                        9

SEQ ID NO: 56           moltype = AA  length = 9
FEATURE                 Location/Qualifiers
REGION                  1..9
                        note = peptide
source                  1..9
                        mol_type = protein
                        organism = synthetic construct
SEQUENCE: 56
SLLGGLLLI                                                        9

SEQ ID NO: 57           moltype = AA  length = 9
FEATURE                 Location/Qualifiers
REGION                  1..9
                        note = peptide
source                  1..9
                        mol_type = protein
                        organism = synthetic construct
SEQUENCE: 57
SLLGGLLML                                                        9

SEQ ID NO: 58           moltype = AA  length = 9
FEATURE                 Location/Qualifiers
REGION                  1..9
                        note = peptide
source                  1..9
                        mol_type = protein
                        organism = synthetic construct
SEQUENCE: 58
SMLGGLLLI                                                        9

SEQ ID NO: 59           moltype = AA  length = 9
FEATURE                 Location/Qualifiers
```

```
REGION              1..9
                    note = peptide
source              1..9
                    mol_type = protein
                    organism = synthetic construct
SEQUENCE: 59
TLLGGLLMI                                                           9

SEQ ID NO: 60       moltype = AA  length = 9
FEATURE             Location/Qualifiers
REGION              1..9
                    note = peptide
source              1..9
                    mol_type = protein
                    organism = synthetic construct
SEQUENCE: 60
YALGGLLEV                                                           9

SEQ ID NO: 61       moltype = AA  length = 9
FEATURE             Location/Qualifiers
REGION              1..9
                    note = peptide
source              1..9
                    mol_type = protein
                    organism = synthetic construct
SEQUENCE: 61
YILGGLLMV                                                           9

SEQ ID NO: 62       moltype = AA  length = 9
FEATURE             Location/Qualifiers
REGION              1..9
                    note = peptide
source              1..9
                    mol_type = protein
                    organism = synthetic construct
SEQUENCE: 62
YMLGGLLLI                                                           9

SEQ ID NO: 63       moltype = AA  length = 9
FEATURE             Location/Qualifiers
REGION              1..9
                    note = peptide
source              1..9
                    mol_type = protein
                    organism = synthetic construct
SEQUENCE: 63
YVLGGLLMI                                                           9

SEQ ID NO: 64       moltype = AA  length = 9
FEATURE             Location/Qualifiers
REGION              1..9
                    note = peptide
source              1..9
                    mol_type = protein
                    organism = synthetic construct
SEQUENCE: 64
YVLGGLLMV                                                           9

SEQ ID NO: 65       moltype = AA  length = 9
FEATURE             Location/Qualifiers
REGION              1..9
                    note = peptide
source              1..9
                    mol_type = protein
                    organism = synthetic construct
SEQUENCE: 65
AMNSLSLYI                                                           9

SEQ ID NO: 66       moltype = AA  length = 9
FEATURE             Location/Qualifiers
REGION              1..9
                    note = peptide
source              1..9
                    mol_type = protein
                    organism = synthetic construct
SEQUENCE: 66
ILNSLSLKI                                                           9

SEQ ID NO: 67       moltype = AA  length = 9
```

```
FEATURE                 Location/Qualifiers
REGION                  1..9
                        note = peptide
source                  1..9
                        mol_type = protein
                        organism = synthetic construct
SEQUENCE: 67
ILNSLSLKL                                                                    9

SEQ ID NO: 68           moltype = AA  length = 9
FEATURE                 Location/Qualifiers
REGION                  1..9
                        note = peptide
source                  1..9
                        mol_type = protein
                        organism = synthetic construct
SEQUENCE: 68
ILNSLSLLL                                                                    9

SEQ ID NO: 69           moltype = AA  length = 9
FEATURE                 Location/Qualifiers
REGION                  1..9
                        note = Artificial
source                  1..9
                        mol_type = protein
                        organism = synthetic construct
SEQUENCE: 69
LLNSLSLFL                                                                    9

SEQ ID NO: 70           moltype = AA  length = 9
FEATURE                 Location/Qualifiers
REGION                  1..9
                        note = peptide
source                  1..9
                        mol_type = protein
                        organism = synthetic construct
SEQUENCE: 70
YMNSLSLAL                                                                    9

SEQ ID NO: 71           moltype = AA  length = 9
FEATURE                 Location/Qualifiers
REGION                  1..9
                        note = peptide
source                  1..9
                        mol_type = protein
                        organism = synthetic construct
SEQUENCE: 71
FLIPAGIFL                                                                    9

SEQ ID NO: 72           moltype = AA  length = 9
FEATURE                 Location/Qualifiers
REGION                  1..9
                        note = peptide
source                  1..9
                        mol_type = protein
                        organism = synthetic construct
SEQUENCE: 72
ILIPAGIYL                                                                    9

SEQ ID NO: 73           moltype = AA  length = 9
FEATURE                 Location/Qualifiers
REGION                  1..9
                        note = peptide
source                  1..9
                        mol_type = protein
                        organism = synthetic construct
SEQUENCE: 73
LLIPAGIAV                                                                    9

SEQ ID NO: 74           moltype = AA  length = 9
FEATURE                 Location/Qualifiers
REGION                  1..9
                        note = peptide
source                  1..9
                        mol_type = protein
                        organism = synthetic construct
SEQUENCE: 74
LLIPAGIEL                                                                    9
```

```
SEQ ID NO: 75           moltype = AA  length = 9
FEATURE                 Location/Qualifiers
REGION                  1..9
                        note = peptide
source                  1..9
                        mol_type = protein
                        organism = synthetic construct
SEQUENCE: 75
LLIPAGIGL                                                     9

SEQ ID NO: 76           moltype = AA  length = 9
FEATURE                 Location/Qualifiers
REGION                  1..9
                        note = peptide
source                  1..9
                        mol_type = protein
                        organism = synthetic construct
SEQUENCE: 76
LLIPAGILI                                                     9

SEQ ID NO: 77           moltype = AA  length = 9
FEATURE                 Location/Qualifiers
REGION                  1..9
                        note = peptide
source                  1..9
                        mol_type = protein
                        organism = synthetic construct
SEQUENCE: 77
LLIPAGILL                                                     9

SEQ ID NO: 78           moltype = AA  length = 9
FEATURE                 Location/Qualifiers
REGION                  1..9
                        note = peptide
source                  1..9
                        mol_type = protein
                        organism = synthetic construct
SEQUENCE: 78
MLIPAGIPA                                                     9

SEQ ID NO: 79           moltype = AA  length = 9
FEATURE                 Location/Qualifiers
REGION                  1..9
                        note = peptide
source                  1..9
                        mol_type = protein
                        organism = synthetic construct
SEQUENCE: 79
MMIPAGIAV                                                     9

SEQ ID NO: 80           moltype = AA  length = 9
FEATURE                 Location/Qualifiers
REGION                  1..9
                        note = peptide
source                  1..9
                        mol_type = protein
                        organism = synthetic construct
SEQUENCE: 80
VMIPAGIFL                                                     9

SEQ ID NO: 81           moltype = AA  length = 9
FEATURE                 Location/Qualifiers
REGION                  1..9
                        note = peptide
source                  1..9
                        mol_type = protein
                        organism = synthetic construct
SEQUENCE: 81
FLFLGILGL                                                     9

SEQ ID NO: 82           moltype = AA  length = 9
FEATURE                 Location/Qualifiers
REGION                  1..9
                        note = peptide
source                  1..9
                        mol_type = protein
                        organism = synthetic construct
SEQUENCE: 82
FLFLGILPL                                                     9
```

```
SEQ ID NO: 83           moltype = AA  length = 9
FEATURE                 Location/Qualifiers
REGION                  1..9
                        note = peptide
source                  1..9
                        mol_type = protein
                        organism = synthetic construct
SEQUENCE: 83
MLFLGILSV                                                          9

SEQ ID NO: 84           moltype = AA  length = 9
FEATURE                 Location/Qualifiers
REGION                  1..9
                        note = peptide
source                  1..9
                        mol_type = protein
                        organism = synthetic construct
SEQUENCE: 84
YLFLGILGI                                                          9

SEQ ID NO: 85           moltype = AA  length = 9
FEATURE                 Location/Qualifiers
REGION                  1..9
                        note = peptide
source                  1..9
                        mol_type = protein
                        organism = synthetic construct
SEQUENCE: 85
YLFLGILGL                                                          9

SEQ ID NO: 86           moltype = AA  length = 9
FEATURE                 Location/Qualifiers
REGION                  1..9
                        note = peptide
source                  1..9
                        mol_type = protein
                        organism = synthetic construct
SEQUENCE: 86
YLFLGILSL                                                          9

SEQ ID NO: 87           moltype = AA  length = 9
FEATURE                 Location/Qualifiers
REGION                  1..9
                        note = peptide
source                  1..9
                        mol_type = protein
                        organism = synthetic construct
SEQUENCE: 87
YLFLGILYL                                                          9

SEQ ID NO: 88           moltype = AA  length = 9
FEATURE                 Location/Qualifiers
REGION                  1..9
                        note = peptide
source                  1..9
                        mol_type = protein
                        organism = synthetic construct
SEQUENCE: 88
FLSNDTVLL                                                          9

SEQ ID NO: 89           moltype = AA  length = 9
FEATURE                 Location/Qualifiers
REGION                  1..9
                        note = peptide
source                  1..9
                        mol_type = protein
                        organism = synthetic construct
SEQUENCE: 89
FLSNDTVPL                                                          9

SEQ ID NO: 90           moltype = AA  length = 9
FEATURE                 Location/Qualifiers
REGION                  1..9
                        note = peptide
source                  1..9
                        mol_type = protein
                        organism = synthetic construct
```

-continued

```
SEQUENCE: 90
FLSNDTVSA                                                      9

SEQ ID NO: 91          moltype = AA  length = 9
FEATURE                Location/Qualifiers
REGION                 1..9
                       note = peptide
source                 1..9
                       mol_type = protein
                       organism = synthetic construct
SEQUENCE: 91
FMSNDTVKV                                                      9

SEQ ID NO: 92          moltype = AA  length = 9
FEATURE                Location/Qualifiers
REGION                 1..9
                       note = peptide
source                 1..9
                       mol_type = protein
                       organism = synthetic construct
SEQUENCE: 92
ILSNDTVWL                                                      9

SEQ ID NO: 93          moltype = AA  length = 9
FEATURE                Location/Qualifiers
REGION                 1..9
                       note = peptide
source                 1..9
                       mol_type = protein
                       organism = synthetic construct
SEQUENCE: 93
KMSNDTVVL                                                      9

SEQ ID NO: 94          moltype = AA  length = 9
FEATURE                Location/Qualifiers
REGION                 1..9
                       note = peptide
source                 1..9
                       mol_type = protein
                       organism = synthetic construct
SEQUENCE: 94
RLSNDTVGL                                                      9

SEQ ID NO: 95          moltype = AA  length = 9
FEATURE                Location/Qualifiers
REGION                 1..9
                       note = peptide
source                 1..9
                       mol_type = protein
                       organism = synthetic construct
SEQUENCE: 95
RMSNDTVEI                                                      9

SEQ ID NO: 96          moltype = AA  length = 9
FEATURE                Location/Qualifiers
REGION                 1..9
                       note = peptide
source                 1..9
                       mol_type = protein
                       organism = synthetic construct
SEQUENCE: 96
TLSNDTVWL                                                      9

SEQ ID NO: 97          moltype = AA  length = 9
FEATURE                Location/Qualifiers
REGION                 1..9
                       note = peptide
source                 1..9
                       mol_type = protein
                       organism = synthetic construct
SEQUENCE: 97
ALLGPWLIV                                                      9

SEQ ID NO: 98          moltype = AA  length = 9
FEATURE                Location/Qualifiers
REGION                 1..9
                       note = peptide
```

```
source                1..9
                      mol_type = protein
                      organism = synthetic construct
SEQUENCE: 98
FLLGPWLCL                                                     9

SEQ ID NO: 99         moltype = AA  length = 9
FEATURE               Location/Qualifiers
REGION                1..9
                      note = peptide
source                1..9
                      mol_type = protein
                      organism = synthetic construct
SEQUENCE: 99
KLLGPWLSV                                                     9

SEQ ID NO: 100        moltype = AA  length = 9
FEATURE               Location/Qualifiers
REGION                1..9
                      note = peptide
source                1..9
                      mol_type = protein
                      organism = synthetic construct
SEQUENCE: 100
LLLGPWLLL                                                     9

SEQ ID NO: 101        moltype = AA  length = 9
FEATURE               Location/Qualifiers
REGION                1..9
                      note = peptide
source                1..9
                      mol_type = protein
                      organism = synthetic construct
SEQUENCE: 101
YLLGPWLLV                                                     9

SEQ ID NO: 102        moltype = AA  length = 9
FEATURE               Location/Qualifiers
REGION                1..9
                      note = peptide
source                1..9
                      mol_type = protein
                      organism = synthetic construct
SEQUENCE: 102
ILILAICGV                                                     9

SEQ ID NO: 103        moltype = AA  length = 9
FEATURE               Location/Qualifiers
REGION                1..9
                      note = peptide
source                1..9
                      mol_type = protein
                      organism = synthetic construct
SEQUENCE: 103
IMILAICLV                                                     9

SEQ ID NO: 104        moltype = AA  length = 9
FEATURE               Location/Qualifiers
REGION                1..9
                      note = peptide
source                1..9
                      mol_type = protein
                      organism = synthetic construct
SEQUENCE: 104
RLILAICGL                                                     9

SEQ ID NO: 105        moltype = AA  length = 9
FEATURE               Location/Qualifiers
REGION                1..9
                      note = peptide
source                1..9
                      mol_type = protein
                      organism = synthetic construct
SEQUENCE: 105
YLILAICGV                                                     9

SEQ ID NO: 106        moltype = AA  length = 9
FEATURE               Location/Qualifiers
```

```
REGION                1..9
                      note = peptide
source                1..9
                      mol_type = protein
                      organism = synthetic construct
SEQUENCE: 106
KIFEHPELL                                                   9

SEQ ID NO: 107        moltype = AA  length = 9
FEATURE               Location/Qualifiers
REGION                1..9
                      note = peptide
source                1..9
                      mol_type = protein
                      organism = synthetic construct
SEQUENCE: 107
LIFEHPERV                                                   9

SEQ ID NO: 108        moltype = AA  length = 9
FEATURE               Location/Qualifiers
REGION                1..9
                      note = peptide
source                1..9
                      mol_type = protein
                      organism = synthetic construct
SEQUENCE: 108
RVFEHPELV                                                   9

SEQ ID NO: 109        moltype = AA  length = 9
FEATURE               Location/Qualifiers
REGION                1..9
                      note = peptide
source                1..9
                      mol_type = protein
                      organism = synthetic construct
SEQUENCE: 109
YVFEHPELL                                                   9

SEQ ID NO: 110        moltype = AA  length = 9
FEATURE               Location/Qualifiers
REGION                1..9
                      note = peptide
source                1..9
                      mol_type = protein
                      organism = synthetic construct
SEQUENCE: 110
YIFEHPETA                                                   9

SEQ ID NO: 111        moltype = AA  length = 9
FEATURE               Location/Qualifiers
REGION                1..9
                      note = peptide
source                1..9
                      mol_type = protein
                      organism = synthetic construct
SEQUENCE: 111
ALAFVPLAV                                                   9

SEQ ID NO: 112        moltype = AA  length = 9
FEATURE               Location/Qualifiers
REGION                1..9
                      note = peptide
source                1..9
                      mol_type = protein
                      organism = synthetic construct
SEQUENCE: 112
ALAFVPLSV                                                   9

SEQ ID NO: 113        moltype = AA  length = 9
FEATURE               Location/Qualifiers
REGION                1..9
                      note = peptide
source                1..9
                      mol_type = protein
                      organism = synthetic construct
SEQUENCE: 113
FLAFVPLIL                                                   9

SEQ ID NO: 114        moltype = AA  length = 9
```

```
FEATURE                 Location/Qualifiers
REGION                  1..9
                        note = peptide
source                  1..9
                        mol_type = protein
                        organism = synthetic construct
SEQUENCE: 114
FLAFVPLQL                                                                    9

SEQ ID NO: 115          moltype = AA  length = 9
FEATURE                 Location/Qualifiers
REGION                  1..9
                        note = peptide
source                  1..9
                        mol_type = protein
                        organism = synthetic construct
SEQUENCE: 115
FLAFVPLVL                                                                    9

SEQ ID NO: 116          moltype = AA  length = 9
FEATURE                 Location/Qualifiers
REGION                  1..9
                        note = peptide
source                  1..9
                        mol_type = protein
                        organism = synthetic construct
SEQUENCE: 116
FMAFVPLQL                                                                    9

SEQ ID NO: 117          moltype = AA  length = 9
FEATURE                 Location/Qualifiers
REGION                  1..9
                        note = peptide
source                  1..9
                        mol_type = protein
                        organism = synthetic construct
SEQUENCE: 117
GMAFVPLLL                                                                    9

SEQ ID NO: 118          moltype = AA  length = 9
FEATURE                 Location/Qualifiers
REGION                  1..9
                        note = peptide
source                  1..9
                        mol_type = protein
                        organism = synthetic construct
SEQUENCE: 118
HLAFVPLLV                                                                    9

SEQ ID NO: 119          moltype = AA  length = 9
FEATURE                 Location/Qualifiers
REGION                  1..9
                        note = peptide
source                  1..9
                        mol_type = protein
                        organism = synthetic construct
SEQUENCE: 119
ILAFVPLYL                                                                    9

SEQ ID NO: 120          moltype = AA  length = 9
FEATURE                 Location/Qualifiers
REGION                  1..9
                        note = peptide
source                  1..9
                        mol_type = protein
                        organism = synthetic construct
SEQUENCE: 120
IMAFVPLAV                                                                    9

SEQ ID NO: 121          moltype = AA  length = 9
FEATURE                 Location/Qualifiers
REGION                  1..9
                        note = peptide
source                  1..9
                        mol_type = protein
                        organism = synthetic construct
SEQUENCE: 121
IMAFVPLIV                                                                    9
```

-continued

```
SEQ ID NO: 122          moltype = AA  length = 9
FEATURE                 Location/Qualifiers
REGION                  1..9
                        note = peptide
source                  1..9
                        mol_type = protein
                        organism = synthetic construct
SEQUENCE: 122
IMAFVPLVV                                                          9

SEQ ID NO: 123          moltype = AA  length = 9
FEATURE                 Location/Qualifiers
REGION                  1..9
                        note = peptide
source                  1..9
                        mol_type = protein
                        organism = synthetic construct
SEQUENCE: 123
LLAFVPLAL                                                          9

SEQ ID NO: 124          moltype = AA  length = 9
FEATURE                 Location/Qualifiers
REGION                  1..9
                        note = peptide
source                  1..9
                        mol_type = protein
                        organism = synthetic construct
SEQUENCE: 124
LLAFVPLDV                                                          9

SEQ ID NO: 125          moltype = AA  length = 9
FEATURE                 Location/Qualifiers
REGION                  1..9
                        note = peptide
source                  1..9
                        mol_type = protein
                        organism = synthetic construct
SEQUENCE: 125
LLAFVPLML                                                          9

SEQ ID NO: 126          moltype = AA  length = 9
FEATURE                 Location/Qualifiers
REGION                  1..9
                        note = peptide
source                  1..9
                        mol_type = protein
                        organism = synthetic construct
SEQUENCE: 126
LLAFVPLSL                                                          9

SEQ ID NO: 127          moltype = AA  length = 9
FEATURE                 Location/Qualifiers
REGION                  1..9
                        note = peptide
source                  1..9
                        mol_type = protein
                        organism = synthetic construct
SEQUENCE: 127
LMAFVPLTL                                                          9

SEQ ID NO: 128          moltype = AA  length = 9
FEATURE                 Location/Qualifiers
REGION                  1..9
                        note = peptide
source                  1..9
                        mol_type = protein
                        organism = synthetic construct
SEQUENCE: 128
TLAFVPLAV                                                          9

SEQ ID NO: 129          moltype = AA  length = 9
FEATURE                 Location/Qualifiers
REGION                  1..9
                        note = peptide
source                  1..9
                        mol_type = protein
                        organism = synthetic construct
SEQUENCE: 129
VLAFVPLLV                                                          9
```

```
SEQ ID NO: 130          moltype = AA  length = 9
FEATURE                 Location/Qualifiers
REGION                  1..9
                        note = peptide
source                  1..9
                        mol_type = protein
                        organism = synthetic construct
SEQUENCE: 130
VMAFVPLVV                                                          9

SEQ ID NO: 131          moltype = AA  length = 9
FEATURE                 Location/Qualifiers
REGION                  1..9
                        note = peptide
source                  1..9
                        mol_type = protein
                        organism = synthetic construct
SEQUENCE: 131
FLYFGMLLL                                                          9

SEQ ID NO: 132          moltype = AA  length = 9
FEATURE                 Location/Qualifiers
REGION                  1..9
                        note = peptide
source                  1..9
                        mol_type = protein
                        organism = synthetic construct
SEQUENCE: 132
GLYFGMLHM                                                          9

SEQ ID NO: 133          moltype = AA  length = 9
FEATURE                 Location/Qualifiers
REGION                  1..9
                        note = peptide
source                  1..9
                        mol_type = protein
                        organism = synthetic construct
SEQUENCE: 133
LLYFGMLGL                                                          9

SEQ ID NO: 134          moltype = AA  length = 9
FEATURE                 Location/Qualifiers
REGION                  1..9
                        note = peptide
source                  1..9
                        mol_type = protein
                        organism = synthetic construct
SEQUENCE: 134
LLYFGMLLL                                                          9

SEQ ID NO: 135          moltype = AA  length = 9
FEATURE                 Location/Qualifiers
REGION                  1..9
                        note = peptide
source                  1..9
                        mol_type = protein
                        organism = synthetic construct
SEQUENCE: 135
TMYFGMLYL                                                          9

SEQ ID NO: 136          moltype = AA  length = 9
FEATURE                 Location/Qualifiers
REGION                  1..9
                        note = peptide
source                  1..9
                        mol_type = protein
                        organism = synthetic construct
SEQUENCE: 136
VLYFGMLLI                                                          9

SEQ ID NO: 137          moltype = AA  length = 9
FEATURE                 Location/Qualifiers
REGION                  1..9
                        note = peptide
source                  1..9
                        mol_type = protein
                        organism = synthetic construct
```

```
SEQUENCE: 137
CLIDKTSVV                                                          9

SEQ ID NO: 138          moltype = AA  length = 9
FEATURE                 Location/Qualifiers
REGION                  1..9
                        note = peptide
source                  1..9
                        mol_type = protein
                        organism = synthetic construct
SEQUENCE: 138
FLIDKTSAA                                                          9

SEQ ID NO: 139          moltype = AA  length = 9
FEATURE                 Location/Qualifiers
REGION                  1..9
                        note = peptide
source                  1..9
                        mol_type = protein
                        organism = synthetic construct
SEQUENCE: 139
ILIDKTSGA                                                          9

SEQ ID NO: 140          moltype = AA  length = 9
FEATURE                 Location/Qualifiers
REGION                  1..9
                        note = peptide
source                  1..9
                        mol_type = protein
                        organism = synthetic construct
SEQUENCE: 140
ILIDKTSGV                                                          9

SEQ ID NO: 141          moltype = AA  length = 9
FEATURE                 Location/Qualifiers
REGION                  1..9
                        note = peptide
source                  1..9
                        mol_type = protein
                        organism = synthetic construct
SEQUENCE: 141
IMIDKTSTV                                                          9

SEQ ID NO: 142          moltype = AA  length = 9
FEATURE                 Location/Qualifiers
REGION                  1..9
                        note = peptide
source                  1..9
                        mol_type = protein
                        organism = synthetic construct
SEQUENCE: 142
VIIDKTSSV                                                          9

SEQ ID NO: 143          moltype = AA  length = 9
FEATURE                 Location/Qualifiers
REGION                  1..9
                        note = peptide
source                  1..9
                        mol_type = protein
                        organism = synthetic construct
SEQUENCE: 143
VLIDKTSQL                                                          9

SEQ ID NO: 144          moltype = AA  length = 9
FEATURE                 Location/Qualifiers
REGION                  1..9
                        note = peptide
source                  1..9
                        mol_type = protein
                        organism = synthetic construct
SEQUENCE: 144
VLIDKTSSV                                                          9

SEQ ID NO: 145          moltype = AA  length = 9
FEATURE                 Location/Qualifiers
REGION                  1..9
                        note = peptide
```

```
source                  1..9
                        mol_type = protein
                        organism = synthetic construct
SEQUENCE: 145
YLIDKTSNI                                                                   9

SEQ ID NO: 146          moltype = AA  length = 9
FEATURE                 Location/Qualifiers
REGION                  1..9
                        note = peptide
source                  1..9
                        mol_type = protein
                        organism = synthetic construct
SEQUENCE: 146
YLIDKTSNL                                                                   9

SEQ ID NO: 147          moltype = AA  length = 9
FEATURE                 Location/Qualifiers
REGION                  1..9
                        note = peptide
source                  1..9
                        mol_type = protein
                        organism = synthetic construct
SEQUENCE: 147
YLIDKTSTV                                                                   9

SEQ ID NO: 148          moltype = AA  length = 9
FEATURE                 Location/Qualifiers
REGION                  1..9
                        note = peptide
source                  1..9
                        mol_type = protein
                        organism = synthetic construct
SEQUENCE: 148
FILLFATHV                                                                   9

SEQ ID NO: 149          moltype = AA  length = 9
FEATURE                 Location/Qualifiers
REGION                  1..9
                        note = peptide
source                  1..9
                        mol_type = protein
                        organism = synthetic construct
SEQUENCE: 149
FLLLFATSV                                                                   9

SEQ ID NO: 150          moltype = AA  length = 9
FEATURE                 Location/Qualifiers
REGION                  1..9
                        note = peptide
source                  1..9
                        mol_type = protein
                        organism = synthetic construct
SEQUENCE: 150
LLLLFATAV                                                                   9

SEQ ID NO: 151          moltype = AA  length = 9
FEATURE                 Location/Qualifiers
REGION                  1..9
                        note = peptide
source                  1..9
                        mol_type = protein
                        organism = synthetic construct
SEQUENCE: 151
LLLLFATSV                                                                   9

SEQ ID NO: 152          moltype = AA  length = 9
FEATURE                 Location/Qualifiers
REGION                  1..9
                        note = peptide
source                  1..9
                        mol_type = protein
                        organism = synthetic construct
SEQUENCE: 152
LMLLFATSV                                                                   9

SEQ ID NO: 153          moltype = AA  length = 9
FEATURE                 Location/Qualifiers
```

```
REGION              1..9
                    note = peptide
source              1..9
                    mol_type = protein
                    organism = synthetic construct
SEQUENCE: 153
MMLLFATLL                                                    9

SEQ ID NO: 154      moltype = AA  length = 9
FEATURE             Location/Qualifiers
REGION              1..9
                    note = peptide
source              1..9
                    mol_type = protein
                    organism = synthetic construct
SEQUENCE: 154
YLLLFATNV                                                    9

SEQ ID NO: 155      moltype = AA  length = 9
FEATURE             Location/Qualifiers
REGION              1..9
                    note = peptide
source              1..9
                    mol_type = protein
                    organism = synthetic construct
SEQUENCE: 155
YLLLFATYL                                                    9

SEQ ID NO: 156      moltype = AA  length = 9
FEATURE             Location/Qualifiers
REGION              1..9
                    note = peptide
source              1..9
                    mol_type = protein
                    organism = synthetic construct
SEQUENCE: 156
ILVGICLGV                                                    9

SEQ ID NO: 157      moltype = AA  length = 9
FEATURE             Location/Qualifiers
REGION              1..9
                    note = peptide
source              1..9
                    mol_type = protein
                    organism = synthetic construct
SEQUENCE: 157
SIVGICLNV                                                    9

SEQ ID NO: 158      moltype = AA  length = 9
FEATURE             Location/Qualifiers
REGION              1..9
                    note = peptide
source              1..9
                    mol_type = protein
                    organism = synthetic construct
SEQUENCE: 158
KLIKYFLKV                                                    9

SEQ ID NO: 159      moltype = AA  length = 9
FEATURE             Location/Qualifiers
REGION              1..9
                    note = peptide
source              1..9
                    mol_type = protein
                    organism = synthetic construct
SEQUENCE: 159
KLIKYFLVV                                                    9

SEQ ID NO: 160      moltype = AA  length = 9
FEATURE             Location/Qualifiers
REGION              1..9
                    note = peptide
source              1..9
                    mol_type = protein
                    organism = synthetic construct
SEQUENCE: 160
MMIKYFLCV                                                    9

SEQ ID NO: 161      moltype = AA  length = 9
```

```
FEATURE                Location/Qualifiers
REGION                 1..9
                       note = peptide
source                 1..9
                       mol_type = protein
                       organism = synthetic construct
SEQUENCE: 161
NLIKYFLYV                                                                   9

SEQ ID NO: 162         moltype = AA  length = 9
FEATURE                Location/Qualifiers
REGION                 1..9
                       note = peptide
source                 1..9
                       mol_type = protein
                       organism = synthetic construct
SEQUENCE: 162
SLIKYFLSI                                                                   9

SEQ ID NO: 163         moltype = AA  length = 9
FEATURE                Location/Qualifiers
REGION                 1..9
                       note = peptide
source                 1..9
                       mol_type = protein
                       organism = synthetic construct
SEQUENCE: 163
ALVLALVGV                                                                   9

SEQ ID NO: 164         moltype = AA  length = 9
FEATURE                Location/Qualifiers
REGION                 1..9
                       note = peptide
source                 1..9
                       mol_type = protein
                       organism = synthetic construct
SEQUENCE: 164
ALVLALVPV                                                                   9

SEQ ID NO: 165         moltype = AA  length = 9
FEATURE                Location/Qualifiers
REGION                 1..9
                       note = peptide
source                 1..9
                       mol_type = protein
                       organism = synthetic construct
SEQUENCE: 165
GLVLALVGV                                                                   9

SEQ ID NO: 166         moltype = AA  length = 9
FEATURE                Location/Qualifiers
REGION                 1..9
                       note = peptide
source                 1..9
                       mol_type = protein
                       organism = synthetic construct
SEQUENCE: 166
NLVLALVEV                                                                   9

SEQ ID NO: 167         moltype = AA  length = 9
FEATURE                Location/Qualifiers
REGION                 1..9
                       note = peptide
source                 1..9
                       mol_type = protein
                       organism = synthetic construct
SEQUENCE: 167
SLVLALVGV                                                                   9

SEQ ID NO: 168         moltype = AA  length = 9
FEATURE                Location/Qualifiers
REGION                 1..9
                       note = peptide
source                 1..9
                       mol_type = protein
                       organism = synthetic construct
SEQUENCE: 168
SLVLALVSV                                                                   9
```

```
SEQ ID NO: 169          moltype = AA  length = 9
FEATURE                 Location/Qualifiers
REGION                  1..9
                        note = peptide
source                  1..9
                        mol_type = protein
                        organism = synthetic construct
SEQUENCE: 169
SLVLALVYV                                                          9

SEQ ID NO: 170          moltype = AA  length = 9
FEATURE                 Location/Qualifiers
REGION                  1..9
                        note = peptide
source                  1..9
                        mol_type = protein
                        organism = synthetic construct
SEQUENCE: 170
TLVLALVSV                                                          9

SEQ ID NO: 171          moltype = AA  length = 9
FEATURE                 Location/Qualifiers
REGION                  1..9
                        note = peptide
source                  1..9
                        mol_type = protein
                        organism = synthetic construct
SEQUENCE: 171
ALALVLALL                                                          9

SEQ ID NO: 172          moltype = AA  length = 9
FEATURE                 Location/Qualifiers
REGION                  1..9
                        note = peptide
source                  1..9
                        mol_type = protein
                        organism = synthetic construct
SEQUENCE: 172
ALALVLAML                                                          9

SEQ ID NO: 173          moltype = AA  length = 9
FEATURE                 Location/Qualifiers
REGION                  1..9
                        note = peptide
source                  1..9
                        mol_type = protein
                        organism = synthetic construct
SEQUENCE: 173
ALALVLATV                                                          9

SEQ ID NO: 174          moltype = AA  length = 9
FEATURE                 Location/Qualifiers
REGION                  1..9
                        note = peptide
source                  1..9
                        mol_type = protein
                        organism = synthetic construct
SEQUENCE: 174
FLALVLAAA                                                          9

SEQ ID NO: 175          moltype = AA  length = 9
FEATURE                 Location/Qualifiers
REGION                  1..9
                        note = peptide
source                  1..9
                        mol_type = protein
                        organism = synthetic construct
SEQUENCE: 175
FLALVLAAL                                                          9

SEQ ID NO: 176          moltype = AA  length = 9
FEATURE                 Location/Qualifiers
REGION                  1..9
                        note = peptide
source                  1..9
                        mol_type = protein
                        organism = synthetic construct
SEQUENCE: 176
FLALVLAGL                                                          9
```

```
SEQ ID NO: 177          moltype = AA  length = 9
FEATURE                 Location/Qualifiers
REGION                  1..9
                        note = peptide
source                  1..9
                        mol_type = protein
                        organism = synthetic construct
SEQUENCE: 177
FLALVLAGV                                                          9

SEQ ID NO: 178          moltype = AA  length = 9
FEATURE                 Location/Qualifiers
REGION                  1..9
                        note = peptide
source                  1..9
                        mol_type = protein
                        organism = synthetic construct
SEQUENCE: 178
FLALVLALL                                                          9

SEQ ID NO: 179          moltype = AA  length = 9
FEATURE                 Location/Qualifiers
REGION                  1..9
                        note = peptide
source                  1..9
                        mol_type = protein
                        organism = synthetic construct
SEQUENCE: 179
FLALVLAML                                                          9

SEQ ID NO: 180          moltype = AA  length = 9
FEATURE                 Location/Qualifiers
REGION                  1..9
                        note = peptide
source                  1..9
                        mol_type = protein
                        organism = synthetic construct
SEQUENCE: 180
FLALVLATL                                                          9

SEQ ID NO: 181          moltype = AA  length = 9
FEATURE                 Location/Qualifiers
REGION                  1..9
                        note = peptide
source                  1..9
                        mol_type = protein
                        organism = synthetic construct
SEQUENCE: 181
GLALVLAAI                                                          9

SEQ ID NO: 182          moltype = AA  length = 9
FEATURE                 Location/Qualifiers
REGION                  1..9
                        note = peptide
source                  1..9
                        mol_type = protein
                        organism = synthetic construct
SEQUENCE: 182
GLALVLAAL                                                          9

SEQ ID NO: 183          moltype = AA  length = 9
FEATURE                 Location/Qualifiers
REGION                  1..9
                        note = peptide
source                  1..9
                        mol_type = protein
                        organism = synthetic construct
SEQUENCE: 183
GLALVLAAV                                                          9

SEQ ID NO: 184          moltype = AA  length = 9
FEATURE                 Location/Qualifiers
REGION                  1..9
                        note = peptide
source                  1..9
                        mol_type = protein
                        organism = synthetic construct
```

```
SEQUENCE: 184
GLALVLALL                                                          9

SEQ ID NO: 185          moltype = AA  length = 9
FEATURE                 Location/Qualifiers
REGION                  1..9
                        note = peptide
source                  1..9
                        mol_type = protein
                        organism = synthetic construct
SEQUENCE: 185
GLALVLALV                                                          9

SEQ ID NO: 186          moltype = AA  length = 9
FEATURE                 Location/Qualifiers
REGION                  1..9
                        note = peptide
source                  1..9
                        mol_type = protein
                        organism = synthetic construct
SEQUENCE: 186
GLALVLANI                                                          9

SEQ ID NO: 187          moltype = AA  length = 9
FEATURE                 Location/Qualifiers
REGION                  1..9
                        note = peptide
source                  1..9
                        mol_type = protein
                        organism = synthetic construct
SEQUENCE: 187
GLALVLATL                                                          9

SEQ ID NO: 188          moltype = AA  length = 9
FEATURE                 Location/Qualifiers
REGION                  1..9
                        note = peptide
source                  1..9
                        mol_type = protein
                        organism = synthetic construct
SEQUENCE: 188
GLALVLATV                                                          9

SEQ ID NO: 189          moltype = AA  length = 9
FEATURE                 Location/Qualifiers
REGION                  1..9
                        note = peptide
source                  1..9
                        mol_type = protein
                        organism = synthetic construct
SEQUENCE: 189
GLALVLAVV                                                          9

SEQ ID NO: 190          moltype = AA  length = 9
FEATURE                 Location/Qualifiers
REGION                  1..9
                        note = peptide
source                  1..9
                        mol_type = protein
                        organism = synthetic construct
SEQUENCE: 190
GMALVLAAV                                                          9

SEQ ID NO: 191          moltype = AA  length = 9
FEATURE                 Location/Qualifiers
REGION                  1..9
                        note = peptide
source                  1..9
                        mol_type = protein
                        organism = synthetic construct
SEQUENCE: 191
ILALVLAMV                                                          9

SEQ ID NO: 192          moltype = AA  length = 9
FEATURE                 Location/Qualifiers
REGION                  1..9
                        note = peptide
```

-continued

```
source                1..9
                      mol_type = protein
                      organism = synthetic construct
SEQUENCE: 192
ILALVLARV                                                                  9

SEQ ID NO: 193        moltype = AA  length = 9
FEATURE               Location/Qualifiers
REGION                1..9
                      note = peptide
source                1..9
                      mol_type = protein
                      organism = synthetic construct
SEQUENCE: 193
ILALVLAYL                                                                  9

SEQ ID NO: 194        moltype = AA  length = 9
FEATURE               Location/Qualifiers
REGION                1..9
                      note = peptide
source                1..9
                      mol_type = protein
                      organism = synthetic construct
SEQUENCE: 194
KLALVLAML                                                                  9

SEQ ID NO: 195        moltype = AA  length = 9
FEATURE               Location/Qualifiers
REGION                1..9
                      note = peptide
source                1..9
                      mol_type = protein
                      organism = synthetic construct
SEQUENCE: 195
LLALVLAEV                                                                  9

SEQ ID NO: 196        moltype = AA  length = 9
FEATURE               Location/Qualifiers
REGION                1..9
                      note = peptide
source                1..9
                      mol_type = protein
                      organism = synthetic construct
SEQUENCE: 196
MLALVLAGL                                                                  9

SEQ ID NO: 197        moltype = AA  length = 9
FEATURE               Location/Qualifiers
REGION                1..9
                      note = peptide
source                1..9
                      mol_type = protein
                      organism = synthetic construct
SEQUENCE: 197
SLALVLALL                                                                  9

SEQ ID NO: 198        moltype = AA  length = 9
FEATURE               Location/Qualifiers
REGION                1..9
                      note = peptide
source                1..9
                      mol_type = protein
                      organism = synthetic construct
SEQUENCE: 198
SLALVLALV                                                                  9

SEQ ID NO: 199        moltype = AA  length = 9
FEATURE               Location/Qualifiers
REGION                1..9
                      note = peptide
source                1..9
                      mol_type = protein
                      organism = synthetic construct
SEQUENCE: 199
SLALVLAML                                                                  9
```

```
SEQ ID NO: 200          moltype = AA  length = 9
FEATURE                 Location/Qualifiers
REGION                  1..9
                        note = peptide
source                  1..9
                        mol_type = protein
                        organism = synthetic construct
SEQUENCE: 200
VLALVLAEL                                                          9

SEQ ID NO: 201          moltype = AA  length = 9
FEATURE                 Location/Qualifiers
REGION                  1..9
                        note = peptide
source                  1..9
                        mol_type = protein
                        organism = synthetic construct
SEQUENCE: 201
VLALVLAEV                                                          9

SEQ ID NO: 202          moltype = AA  length = 9
FEATURE                 Location/Qualifiers
REGION                  1..9
                        note = peptide
source                  1..9
                        mol_type = protein
                        organism = synthetic construct
SEQUENCE: 202
VLALVLAGV                                                          9

SEQ ID NO: 203          moltype = AA  length = 9
FEATURE                 Location/Qualifiers
REGION                  1..9
                        note = peptide
source                  1..9
                        mol_type = protein
                        organism = synthetic construct
SEQUENCE: 203
VLALVLALV                                                          9

SEQ ID NO: 204          moltype = AA  length = 9
FEATURE                 Location/Qualifiers
REGION                  1..9
                        note = peptide
source                  1..9
                        mol_type = protein
                        organism = synthetic construct
SEQUENCE: 204
VLALVLAMV                                                          9

SEQ ID NO: 205          moltype = AA  length = 9
FEATURE                 Location/Qualifiers
REGION                  1..9
                        note = peptide
source                  1..9
                        mol_type = protein
                        organism = synthetic construct
SEQUENCE: 205
VLALVLATV                                                          9

SEQ ID NO: 206          moltype = AA  length = 9
FEATURE                 Location/Qualifiers
REGION                  1..9
                        note = peptide
source                  1..9
                        mol_type = protein
                        organism = synthetic construct
SEQUENCE: 206
YLALVLAFL                                                          9

SEQ ID NO: 207          moltype = AA  length = 9
FEATURE                 Location/Qualifiers
REGION                  1..9
                        note = peptide
source                  1..9
                        mol_type = protein
                        organism = synthetic construct
```

```
SEQUENCE: 207
YLALVLALI                                                         9

SEQ ID NO: 208          moltype = AA  length = 9
FEATURE                 Location/Qualifiers
REGION                  1..9
                        note = peptide
source                  1..9
                        mol_type = protein
                        organism = synthetic construct
SEQUENCE: 208
YLALVLALL                                                         9

SEQ ID NO: 209          moltype = AA  length = 9
FEATURE                 Location/Qualifiers
REGION                  1..9
                        note = peptide
source                  1..9
                        mol_type = protein
                        organism = synthetic construct
SEQUENCE: 209
YLALVLAML                                                         9

SEQ ID NO: 210          moltype = AA  length = 9
FEATURE                 Location/Qualifiers
REGION                  1..9
                        note = peptide
source                  1..9
                        mol_type = protein
                        organism = synthetic construct
SEQUENCE: 210
ALFGAPAAV                                                         9

SEQ ID NO: 211          moltype = AA  length = 9
FEATURE                 Location/Qualifiers
REGION                  1..9
                        note = peptide
source                  1..9
                        mol_type = protein
                        organism = synthetic construct
SEQUENCE: 211
ALFGAPAKL                                                         9

SEQ ID NO: 212          moltype = AA  length = 9
FEATURE                 Location/Qualifiers
REGION                  1..9
                        note = peptide
source                  1..9
                        mol_type = protein
                        organism = synthetic construct
SEQUENCE: 212
FLFGAPASA                                                         9

SEQ ID NO: 213          moltype = AA  length = 9
FEATURE                 Location/Qualifiers
REGION                  1..9
                        note = peptide
source                  1..9
                        mol_type = protein
                        organism = synthetic construct
SEQUENCE: 213
GLFGAPAFI                                                         9

SEQ ID NO: 214          moltype = AA  length = 9
FEATURE                 Location/Qualifiers
REGION                  1..9
                        note = peptide
source                  1..9
                        mol_type = protein
                        organism = synthetic construct
SEQUENCE: 214
LLFGAPAAL                                                         9

SEQ ID NO: 215          moltype = AA  length = 9
FEATURE                 Location/Qualifiers
REGION                  1..9
                        note = peptide
```

```
source                 1..9
                       mol_type = protein
                       organism = synthetic construct
SEQUENCE: 215
LLFGAPAGI                                                         9

SEQ ID NO: 216         moltype = AA  length = 9
FEATURE                Location/Qualifiers
REGION                 1..9
                       note = peptide
source                 1..9
                       mol_type = protein
                       organism = synthetic construct
SEQUENCE: 216
LLFGAPAGL                                                         9

SEQ ID NO: 217         moltype = AA  length = 9
FEATURE                Location/Qualifiers
REGION                 1..9
                       note = peptide
source                 1..9
                       mol_type = protein
                       organism = synthetic construct
SEQUENCE: 217
LLFGAPAGV                                                         9

SEQ ID NO: 218         moltype = AA  length = 9
FEATURE                Location/Qualifiers
REGION                 1..9
                       note = peptide
source                 1..9
                       mol_type = protein
                       organism = synthetic construct
SEQUENCE: 218
LLFGAPALL                                                         9

SEQ ID NO: 219         moltype = AA  length = 9
FEATURE                Location/Qualifiers
REGION                 1..9
                       note = peptide
source                 1..9
                       mol_type = protein
                       organism = synthetic construct
SEQUENCE: 219
LMFGAPAFV                                                         9

SEQ ID NO: 220         moltype = AA  length = 9
FEATURE                Location/Qualifiers
REGION                 1..9
                       note = peptide
source                 1..9
                       mol_type = protein
                       organism = synthetic construct
SEQUENCE: 220
LMFGAPALV                                                         9

SEQ ID NO: 221         moltype = AA  length = 9
FEATURE                Location/Qualifiers
REGION                 1..9
                       note = peptide
source                 1..9
                       mol_type = protein
                       organism = synthetic construct
SEQUENCE: 221
MLFGAPAEA                                                         9

SEQ ID NO: 222         moltype = AA  length = 9
FEATURE                Location/Qualifiers
REGION                 1..9
                       note = peptide
source                 1..9
                       mol_type = protein
                       organism = synthetic construct
SEQUENCE: 222
SMFGAPAHV                                                         9

SEQ ID NO: 223         moltype = AA  length = 9
FEATURE                Location/Qualifiers
```

```
REGION              1..9
                    note = peptide
source              1..9
                    mol_type = protein
                    organism = synthetic construct
SEQUENCE: 223
VLFGAPANL                                                      9

SEQ ID NO: 224      moltype = AA  length = 9
FEATURE             Location/Qualifiers
REGION              1..9
                    note = peptide
source              1..9
                    mol_type = protein
                    organism = synthetic construct
SEQUENCE: 224
VLFGAPAYL                                                      9

SEQ ID NO: 225      moltype = AA  length = 9
FEATURE             Location/Qualifiers
REGION              1..9
                    note = peptide
source              1..9
                    mol_type = protein
                    organism = synthetic construct
SEQUENCE: 225
YLFGAPAAA                                                      9

SEQ ID NO: 226      moltype = AA  length = 9
FEATURE             Location/Qualifiers
REGION              1..9
                    note = peptide
source              1..9
                    mol_type = protein
                    organism = synthetic construct
SEQUENCE: 226
FLPGLLFSV                                                      9

SEQ ID NO: 227      moltype = AA  length = 9
FEATURE             Location/Qualifiers
REGION              1..9
                    note = peptide
source              1..9
                    mol_type = protein
                    organism = synthetic construct
SEQUENCE: 227
FMPGLLFGA                                                      9

SEQ ID NO: 228      moltype = AA  length = 9
FEATURE             Location/Qualifiers
REGION              1..9
                    note = peptide
source              1..9
                    mol_type = protein
                    organism = synthetic construct
SEQUENCE: 228
FVPGLLFGV                                                      9

SEQ ID NO: 229      moltype = AA  length = 9
FEATURE             Location/Qualifiers
REGION              1..9
                    note = peptide
source              1..9
                    mol_type = protein
                    organism = synthetic construct
SEQUENCE: 229
GLPGLLFEL                                                      9

SEQ ID NO: 230      moltype = AA  length = 9
FEATURE             Location/Qualifiers
REGION              1..9
                    note = peptide
source              1..9
                    mol_type = protein
                    organism = synthetic construct
SEQUENCE: 230
ILPGLLFAI                                                      9

SEQ ID NO: 231      moltype = AA  length = 9
```

```
FEATURE                 Location/Qualifiers
REGION                  1..9
                        note = peptide
source                  1..9
                        mol_type = protein
                        organism = synthetic construct
SEQUENCE: 231
ILPGLLFGL                                                                    9

SEQ ID NO: 232          moltype = AA  length = 9
FEATURE                 Location/Qualifiers
REGION                  1..9
                        note = peptide
source                  1..9
                        mol_type = protein
                        organism = synthetic construct
SEQUENCE: 232
ILPGLLFLI                                                                    9

SEQ ID NO: 233          moltype = AA  length = 9
FEATURE                 Location/Qualifiers
REGION                  1..9
                        note = peptide
source                  1..9
                        mol_type = protein
                        organism = synthetic construct
SEQUENCE: 233
ILPGLLFSL                                                                    9

SEQ ID NO: 234          moltype = AA  length = 9
FEATURE                 Location/Qualifiers
REGION                  1..9
                        note = peptide
source                  1..9
                        mol_type = protein
                        organism = synthetic construct
SEQUENCE: 234
ILPGLLFYI                                                                    9

SEQ ID NO: 235          moltype = AA  length = 9
FEATURE                 Location/Qualifiers
REGION                  1..9
                        note = peptide
source                  1..9
                        mol_type = protein
                        organism = synthetic construct
SEQUENCE: 235
ILPGLLFYM                                                                    9

SEQ ID NO: 236          moltype = AA  length = 9
FEATURE                 Location/Qualifiers
REGION                  1..9
                        note = peptide
source                  1..9
                        mol_type = protein
                        organism = synthetic construct
SEQUENCE: 236
IMPGLLFHI                                                                    9

SEQ ID NO: 237          moltype = AA  length = 9
FEATURE                 Location/Qualifiers
REGION                  1..9
                        note = peptide
source                  1..9
                        mol_type = protein
                        organism = synthetic construct
SEQUENCE: 237
IMPGLLFQV                                                                    9

SEQ ID NO: 238          moltype = AA  length = 9
FEATURE                 Location/Qualifiers
REGION                  1..9
                        note = peptide
source                  1..9
                        mol_type = protein
                        organism = synthetic construct
SEQUENCE: 238
IMPGLLFYV                                                                    9
```

```
SEQ ID NO: 239          moltype = AA  length = 9
FEATURE                 Location/Qualifiers
REGION                  1..9
                        note = peptide
source                  1..9
                        mol_type = protein
                        organism = synthetic construct
SEQUENCE: 239
KLPGLLFHA                                                    9

SEQ ID NO: 240          moltype = AA  length = 9
FEATURE                 Location/Qualifiers
REGION                  1..9
                        note = peptide
source                  1..9
                        mol_type = protein
                        organism = synthetic construct
SEQUENCE: 240
KLPGLLFSV                                                    9

SEQ ID NO: 241          moltype = AA  length = 9
FEATURE                 Location/Qualifiers
REGION                  1..9
                        note = peptide
source                  1..9
                        mol_type = protein
                        organism = synthetic construct
SEQUENCE: 241
LLPGLLFGL                                                    9

SEQ ID NO: 242          moltype = AA  length = 9
FEATURE                 Location/Qualifiers
REGION                  1..9
                        note = peptide
source                  1..9
                        mol_type = protein
                        organism = synthetic construct
SEQUENCE: 242
LLPGLLFTL                                                    9

SEQ ID NO: 243          moltype = AA  length = 9
FEATURE                 Location/Qualifiers
REGION                  1..9
                        note = peptide
source                  1..9
                        mol_type = protein
                        organism = synthetic construct
SEQUENCE: 243
LLPGLLFVV                                                    9

SEQ ID NO: 244          moltype = AA  length = 9
FEATURE                 Location/Qualifiers
REGION                  1..9
                        note = peptide
source                  1..9
                        mol_type = protein
                        organism = synthetic construct
SEQUENCE: 244
MLPGLLFAL                                                    9

SEQ ID NO: 245          moltype = AA  length = 9
FEATURE                 Location/Qualifiers
REGION                  1..9
                        note = peptide
source                  1..9
                        mol_type = protein
                        organism = synthetic construct
SEQUENCE: 245
MLPGLLFGL                                                    9

SEQ ID NO: 246          moltype = AA  length = 9
FEATURE                 Location/Qualifiers
REGION                  1..9
                        note = peptide
source                  1..9
                        mol_type = protein
                        organism = synthetic construct
SEQUENCE: 246
MLPGLLFKV                                                    9
```

```
SEQ ID NO: 247          moltype = AA  length = 9
FEATURE                 Location/Qualifiers
REGION                  1..9
                        note = peptide
source                  1..9
                        mol_type = protein
                        organism = synthetic construct
SEQUENCE: 247
MLPGLLFVV                                                         9

SEQ ID NO: 248          moltype = AA  length = 9
FEATURE                 Location/Qualifiers
REGION                  1..9
                        note = peptide
source                  1..9
                        mol_type = protein
                        organism = synthetic construct
SEQUENCE: 248
PLPGLLFSV                                                         9

SEQ ID NO: 249          moltype = AA  length = 9
FEATURE                 Location/Qualifiers
REGION                  1..9
                        note = peptide
source                  1..9
                        mol_type = protein
                        organism = synthetic construct
SEQUENCE: 249
RMPGLLFKV                                                         9

SEQ ID NO: 250          moltype = AA  length = 9
FEATURE                 Location/Qualifiers
REGION                  1..9
                        note = peptide
source                  1..9
                        mol_type = protein
                        organism = synthetic construct
SEQUENCE: 250
SLPGLLFFL                                                         9

SEQ ID NO: 251          moltype = AA  length = 9
FEATURE                 Location/Qualifiers
REGION                  1..9
                        note = peptide
source                  1..9
                        mol_type = protein
                        organism = synthetic construct
SEQUENCE: 251
SLPGLLFTL                                                         9

SEQ ID NO: 252          moltype = AA  length = 9
FEATURE                 Location/Qualifiers
REGION                  1..9
                        note = peptide
source                  1..9
                        mol_type = protein
                        organism = synthetic construct
SEQUENCE: 252
SLPGLLFVV                                                         9

SEQ ID NO: 253          moltype = AA  length = 9
FEATURE                 Location/Qualifiers
REGION                  1..9
                        note = peptide
source                  1..9
                        mol_type = protein
                        organism = synthetic construct
SEQUENCE: 253
TLPGLLFPA                                                         9

SEQ ID NO: 254          moltype = AA  length = 9
FEATURE                 Location/Qualifiers
REGION                  1..9
                        note = peptide
source                  1..9
                        mol_type = protein
                        organism = synthetic construct
```

```
SEQUENCE: 254
TLPGLLFPV                                                          9

SEQ ID NO: 255          moltype = AA  length = 9
FEATURE                 Location/Qualifiers
REGION                  1..9
                        note = peptide
source                  1..9
                        mol_type = protein
                        organism = synthetic construct
SEQUENCE: 255
VLPGLLFGV                                                          9

SEQ ID NO: 256          moltype = AA  length = 9
FEATURE                 Location/Qualifiers
REGION                  1..9
                        note = peptide
source                  1..9
                        mol_type = protein
                        organism = synthetic construct
SEQUENCE: 256
VLPGLLFYV                                                          9

SEQ ID NO: 257          moltype = AA  length = 9
FEATURE                 Location/Qualifiers
REGION                  1..9
                        note = peptide
source                  1..9
                        mol_type = protein
                        organism = synthetic construct
SEQUENCE: 257
YLPGLLFLM                                                          9

SEQ ID NO: 258          moltype = AA  length = 9
FEATURE                 Location/Qualifiers
source                  1..9
                        mol_type = protein
                        organism = Homo sapiens
SEQUENCE: 258
FLLFLTPME                                                          9

SEQ ID NO: 259          moltype = AA  length = 9
FEATURE                 Location/Qualifiers
source                  1..9
                        mol_type = protein
                        organism = Homo sapiens
SEQUENCE: 259
KLSLGLPGL                                                          9

SEQ ID NO: 260          moltype = AA  length = 9
FEATURE                 Location/Qualifiers
source                  1..9
                        mol_type = protein
                        organism = Homo sapiens
SEQUENCE: 260
SLVGILHLQ                                                          9

SEQ ID NO: 261          moltype = AA  length = 9
FEATURE                 Location/Qualifiers
source                  1..9
                        mol_type = protein
                        organism = Homo sapiens
SEQUENCE: 261
TLAYLIFCL                                                          9

SEQ ID NO: 262          moltype = AA  length = 9
FEATURE                 Location/Qualifiers
source                  1..9
                        mol_type = protein
                        organism = Homo sapiens
SEQUENCE: 262
QQMGGFYLC                                                          9

SEQ ID NO: 263          moltype = AA  length = 9
FEATURE                 Location/Qualifiers
source                  1..9
                        mol_type = protein
                        organism = Homo sapiens
```

```
SEQUENCE: 263
IALGGLLMI                                                          9

SEQ ID NO: 264          moltype = AA  length = 9
FEATURE                 Location/Qualifiers
source                  1..9
                        mol_type = protein
                        organism = Homo sapiens
SEQUENCE: 264
IMNSLSLFA                                                          9

SEQ ID NO: 265          moltype = AA  length = 9
FEATURE                 Location/Qualifiers
source                  1..9
                        mol_type = protein
                        organism = Homo sapiens
SEQUENCE: 265
LMIPAGIYA                                                          9

SEQ ID NO: 266          moltype = AA  length = 9
FEATURE                 Location/Qualifiers
source                  1..9
                        mol_type = protein
                        organism = Homo sapiens
SEQUENCE: 266
SLFLGILSV                                                          9

SEQ ID NO: 267          moltype = AA  length = 9
FEATURE                 Location/Qualifiers
source                  1..9
                        mol_type = protein
                        organism = Homo sapiens
SEQUENCE: 267
FLSNDTVQL                                                          9

SEQ ID NO: 268          moltype = AA  length = 9
FEATURE                 Location/Qualifiers
source                  1..9
                        mol_type = protein
                        organism = Homo sapiens
SEQUENCE: 268
HLLGPWLLL                                                          9

SEQ ID NO: 269          moltype = AA  length = 9
FEATURE                 Location/Qualifiers
source                  1..9
                        mol_type = protein
                        organism = Homo sapiens
SEQUENCE: 269
ILILAICGL                                                          9

SEQ ID NO: 270          moltype = AA  length = 9
FEATURE                 Location/Qualifiers
source                  1..9
                        mol_type = protein
                        organism = Homo sapiens
SEQUENCE: 270
WVFEHPETL                                                          9

SEQ ID NO: 271          moltype = AA  length = 9
FEATURE                 Location/Qualifiers
source                  1..9
                        mol_type = protein
                        organism = Homo sapiens
SEQUENCE: 271
GLAFVPLQI                                                          9

SEQ ID NO: 272          moltype = AA  length = 9
FEATURE                 Location/Qualifiers
source                  1..9
                        mol_type = protein
                        organism = Homo sapiens
SEQUENCE: 272
GLYFGMLLL                                                          9

SEQ ID NO: 273          moltype = AA  length = 9
FEATURE                 Location/Qualifiers
```

```
source                 1..9
                       mol_type = protein
                       organism = Homo sapiens
SEQUENCE: 273
ILIDKTSFV                                                                  9

SEQ ID NO: 274         moltype = AA  length = 9
FEATURE                Location/Qualifiers
source                 1..9
                       mol_type = protein
                       organism = Homo sapiens
SEQUENCE: 274
LLLLFATQI                                                                  9

SEQ ID NO: 275         moltype = AA  length = 9
FEATURE                Location/Qualifiers
source                 1..9
                       mol_type = protein
                       organism = Homo sapiens
SEQUENCE: 275
SIVGICLGV                                                                  9

SEQ ID NO: 276         moltype = AA  length = 9
FEATURE                Location/Qualifiers
source                 1..9
                       mol_type = protein
                       organism = Homo sapiens
SEQUENCE: 276
SIVGICLGV                                                                  9

SEQ ID NO: 277         moltype = AA  length = 9
FEATURE                Location/Qualifiers
source                 1..9
                       mol_type = protein
                       organism = Homo sapiens
SEQUENCE: 277
ALVLALVLV                                                                  9

SEQ ID NO: 278         moltype = AA  length = 9
FEATURE                Location/Qualifiers
source                 1..9
                       mol_type = protein
                       organism = Homo sapiens
SEQUENCE: 278
GLALVLALV                                                                  9

SEQ ID NO: 279         moltype = AA  length = 9
FEATURE                Location/Qualifiers
source                 1..9
                       mol_type = protein
                       organism = Homo sapiens
SEQUENCE: 279
LLFGAPALL                                                                  9

SEQ ID NO: 280         moltype = AA  length = 9
FEATURE                Location/Qualifiers
source                 1..9
                       mol_type = protein
                       organism = Homo sapiens
SEQUENCE: 280
PLPGLLFGA                                                                  9

SEQ ID NO: 281         moltype = AA  length = 5
FEATURE                Location/Qualifiers
source                 1..5
                       mol_type = protein
                       organism = Homo sapiens
SEQUENCE: 281
LFLTP                                                                      5

SEQ ID NO: 282         moltype = AA  length = 5
FEATURE                Location/Qualifiers
source                 1..5
                       mol_type = protein
                       organism = Homo sapiens
SEQUENCE: 282
SLGLP                                                                      5

SEQ ID NO: 283         moltype = AA  length = 5
```

-continued

```
FEATURE                 Location/Qualifiers
source                  1..5
                        mol_type = protein
                        organism = Homo sapiens
SEQUENCE: 283
VGILH                                                                5

SEQ ID NO: 284          moltype = AA  length = 5
FEATURE                 Location/Qualifiers
source                  1..5
                        mol_type = protein
                        organism = Homo sapiens
SEQUENCE: 284
AYLIF                                                                5

SEQ ID NO: 285          moltype = AA  length = 5
FEATURE                 Location/Qualifiers
source                  1..5
                        mol_type = protein
                        organism = Homo sapiens
SEQUENCE: 285
MGGFY                                                                5

SEQ ID NO: 286          moltype = AA  length = 5
FEATURE                 Location/Qualifiers
source                  1..5
                        mol_type = protein
                        organism = Homo sapiens
SEQUENCE: 286
LGGLL                                                                5

SEQ ID NO: 287          moltype = AA  length = 5
FEATURE                 Location/Qualifiers
source                  1..5
                        mol_type = protein
                        organism = Homo sapiens
SEQUENCE: 287
NSLSL                                                                5

SEQ ID NO: 288          moltype = AA  length = 5
FEATURE                 Location/Qualifiers
source                  1..5
                        mol_type = protein
                        organism = Homo sapiens
SEQUENCE: 288
IPAGI                                                                5

SEQ ID NO: 289          moltype = AA  length = 5
FEATURE                 Location/Qualifiers
source                  1..5
                        mol_type = protein
                        organism = Homo sapiens
SEQUENCE: 289
FLGIL                                                                5

SEQ ID NO: 290          moltype = AA  length = 5
FEATURE                 Location/Qualifiers
source                  1..5
                        mol_type = protein
                        organism = Homo sapiens
SEQUENCE: 290
SNDTV                                                                5

SEQ ID NO: 291          moltype = AA  length = 5
FEATURE                 Location/Qualifiers
source                  1..5
                        mol_type = protein
                        organism = Homo sapiens
SEQUENCE: 291
LGPWL                                                                5

SEQ ID NO: 292          moltype = AA  length = 5
FEATURE                 Location/Qualifiers
source                  1..5
                        mol_type = protein
                        organism = Homo sapiens
SEQUENCE: 292
ILAIC                                                                5
```

-continued

```
SEQ ID NO: 293          moltype = AA  length = 5
FEATURE                 Location/Qualifiers
source                  1..5
                        mol_type = protein
                        organism = Homo sapiens
SEQUENCE: 293
FEHPE                                                           5

SEQ ID NO: 294          moltype = AA  length = 5
FEATURE                 Location/Qualifiers
source                  1..5
                        mol_type = protein
                        organism = Homo sapiens
SEQUENCE: 294
AFVPL                                                           5

SEQ ID NO: 295          moltype = AA  length = 5
FEATURE                 Location/Qualifiers
source                  1..5
                        mol_type = protein
                        organism = Homo sapiens
SEQUENCE: 295
YFGML                                                           5

SEQ ID NO: 296          moltype = AA  length = 5
FEATURE                 Location/Qualifiers
source                  1..5
                        mol_type = protein
                        organism = Homo sapiens
SEQUENCE: 296
IDKTS                                                           5

SEQ ID NO: 297          moltype = AA  length = 5
FEATURE                 Location/Qualifiers
source                  1..5
                        mol_type = protein
                        organism = Homo sapiens
SEQUENCE: 297
LLFAT                                                           5

SEQ ID NO: 298          moltype = AA  length = 5
FEATURE                 Location/Qualifiers
source                  1..5
                        mol_type = protein
                        organism = Homo sapiens
SEQUENCE: 298
VGICL                                                           5

SEQ ID NO: 299          moltype = AA  length = 5
FEATURE                 Location/Qualifiers
source                  1..5
                        mol_type = protein
                        organism = Homo sapiens
SEQUENCE: 299
IKYFL                                                           5

SEQ ID NO: 300          moltype = AA  length = 5
FEATURE                 Location/Qualifiers
source                  1..5
                        mol_type = protein
                        organism = Homo sapiens
SEQUENCE: 300
VLALV                                                           5

SEQ ID NO: 301          moltype = AA  length = 5
FEATURE                 Location/Qualifiers
source                  1..5
                        mol_type = protein
                        organism = Homo sapiens
SEQUENCE: 301
ALVLA                                                           5

SEQ ID NO: 302          moltype = AA  length = 5
FEATURE                 Location/Qualifiers
source                  1..5
                        mol_type = protein
                        organism = Homo sapiens
SEQUENCE: 302
FGAPA                                                           5
```

```
SEQ ID NO: 303          moltype = AA  length = 5
FEATURE                 Location/Qualifiers
source                  1..5
                        mol_type = protein
                        organism = Homo sapiens
SEQUENCE: 303
PGLLF                                                                5

SEQ ID NO: 304          moltype = AA  length = 9
FEATURE                 Location/Qualifiers
REGION                  1..9
                        note = peptide
VARIANT                 1..2
                        note = X can be any naturally occurring amino acid
VARIANT                 8..9
                        note = X can be any naturally occurring amino acid
source                  1..9
                        mol_type = protein
                        organism = synthetic construct
SEQUENCE: 304
XXLFLTPXX                                                            9

SEQ ID NO: 305          moltype = AA  length = 9
FEATURE                 Location/Qualifiers
REGION                  1..9
                        note = peptide
VARIANT                 1..2
                        note = X can be any naturally occurring amino acid
VARIANT                 8..9
                        note = X can be any naturally occurring amino acid
source                  1..9
                        mol_type = protein
                        organism = synthetic construct
SEQUENCE: 305
XXSLGLPXX                                                            9

SEQ ID NO: 306          moltype = AA  length = 9
FEATURE                 Location/Qualifiers
REGION                  1..9
                        note = peptide
VARIANT                 1..2
                        note = X can be any naturally occurring amino acid
VARIANT                 8..9
                        note = X can be any naturally occurring amino acid
source                  1..9
                        mol_type = protein
                        organism = synthetic construct
SEQUENCE: 306
XXVGILHXX                                                            9

SEQ ID NO: 307          moltype = AA  length = 9
FEATURE                 Location/Qualifiers
REGION                  1..9
                        note = peptide
VARIANT                 1..2
                        note = X can be any naturally occurring amino acid
VARIANT                 8..9
                        note = X can be any naturally occurring amino acid
source                  1..9
                        mol_type = protein
                        organism = synthetic construct
SEQUENCE: 307
XXAYLIFXX                                                            9

SEQ ID NO: 308          moltype = AA  length = 9
FEATURE                 Location/Qualifiers
REGION                  1..9
                        note = peptide
VARIANT                 1..2
                        note = X can be any naturally occurring amino acid
VARIANT                 8..9
                        note = X can be any naturally occurring amino acid
source                  1..9
                        mol_type = protein
                        organism = synthetic construct
SEQUENCE: 308
XXMGGFYXX                                                            9
```

-continued

```
SEQ ID NO: 309          moltype = AA  length = 9
FEATURE                 Location/Qualifiers
REGION                  1..9
                        note = peptide
VARIANT                 1..2
                        note = X can be any naturally occurring amino acid
VARIANT                 8..9
                        note = X can be any naturally occurring amino acid
source                  1..9
                        mol_type = protein
                        organism = synthetic construct
SEQUENCE: 309
XXLGGLLXX                                                                9

SEQ ID NO: 310          moltype = AA  length = 9
FEATURE                 Location/Qualifiers
REGION                  1..9
                        note = peptide
VARIANT                 1..2
                        note = X can be any naturally occurring amino acid
VARIANT                 8..9
                        note = X can be any naturally occurring amino acid
source                  1..9
                        mol_type = protein
                        organism = synthetic construct
SEQUENCE: 310
XXNSLSLXX                                                                9

SEQ ID NO: 311          moltype = AA  length = 9
FEATURE                 Location/Qualifiers
REGION                  1..9
                        note = peptide
VARIANT                 1..2
                        note = X can be any naturally occurring amino acid
VARIANT                 8..9
                        note = X can be any naturally occurring amino acid
source                  1..9
                        mol_type = protein
                        organism = synthetic construct
SEQUENCE: 311
XXIPAGIXX                                                                9

SEQ ID NO: 312          moltype = AA  length = 9
FEATURE                 Location/Qualifiers
REGION                  1..9
                        note = peptide
VARIANT                 1..2
                        note = X can be any naturally occurring amino acid
VARIANT                 8..9
                        note = X can be any naturally occurring amino acid
source                  1..9
                        mol_type = protein
                        organism = synthetic construct
SEQUENCE: 312
XXFLGILXX                                                                9

SEQ ID NO: 313          moltype = AA  length = 9
FEATURE                 Location/Qualifiers
REGION                  1..9
                        note = peptide
VARIANT                 1..2
                        note = X can be any naturally occurring amino acid
VARIANT                 8..9
                        note = X can be any naturally occurring amino acid
source                  1..9
                        mol_type = protein
                        organism = synthetic construct
SEQUENCE: 313
XXSNDTVXX                                                                9

SEQ ID NO: 314          moltype = AA  length = 9
FEATURE                 Location/Qualifiers
REGION                  1..9
                        note = XXLGPWLXX
VARIANT                 1..2
                        note = X can be any naturally occurring amino acid
VARIANT                 8..9
                        note = X can be any naturally occurring amino acid
```

-continued

```
source                1..9
                      mol_type = protein
                      organism = synthetic construct
SEQUENCE: 314
XXLGPWLXX                                                                9

SEQ ID NO: 315        moltype = AA  length = 9
FEATURE               Location/Qualifiers
REGION                1..9
                      note = peptide
VARIANT               1..2
                      note = X can be any naturally occurring amino acid
VARIANT               8..9
                      note = X can be any naturally occurring amino acid
source                1..9
                      mol_type = protein
                      organism = synthetic construct
SEQUENCE: 315
XXILAICXX                                                                9

SEQ ID NO: 316        moltype = AA  length = 9
FEATURE               Location/Qualifiers
REGION                1..9
                      note = peptide
VARIANT               1..2
                      note = X can be any naturally occurring amino acid
VARIANT               8..9
                      note = X can be any naturally occurring amino acid
source                1..9
                      mol_type = protein
                      organism = synthetic construct
SEQUENCE: 316
XXFEHPEXX                                                                9

SEQ ID NO: 317        moltype = AA  length = 9
FEATURE               Location/Qualifiers
REGION                1..9
                      note = peptide
VARIANT               1..2
                      note = X can be any naturally occurring amino acid
VARIANT               8..9
                      note = X can be any naturally occurring amino acid
source                1..9
                      mol_type = protein
                      organism = synthetic construct
SEQUENCE: 317
XXAFVPLXX                                                                9

SEQ ID NO: 318        moltype = AA  length = 9
FEATURE               Location/Qualifiers
REGION                1..9
                      note = peptide
VARIANT               1..2
                      note = X can be any naturally occurring amino acid
VARIANT               8..9
                      note = X can be any naturally occurring amino acid
source                1..9
                      mol_type = protein
                      organism = synthetic construct
SEQUENCE: 318
XXYFGMLXX                                                                9

SEQ ID NO: 319        moltype = AA  length = 9
FEATURE               Location/Qualifiers
REGION                1..9
                      note = peptide
VARIANT               1..2
                      note = X can be any naturally occurring amino acid
VARIANT               8..9
                      note = X can be any naturally occurring amino acid
source                1..9
                      mol_type = protein
                      organism = synthetic construct
SEQUENCE: 319
XXIDKTSXX                                                                9
```

```
SEQ ID NO: 320          moltype = AA  length = 9
FEATURE                 Location/Qualifiers
REGION                  1..9
                        note = peptide
VARIANT                 1..2
                        note = X can be any naturally occurring amino acid
VARIANT                 8..9
                        note = X can be any naturally occurring amino acid
source                  1..9
                        mol_type = protein
                        organism = synthetic construct
SEQUENCE: 320
XXLLFATXX                                                                  9

SEQ ID NO: 321          moltype = AA  length = 9
FEATURE                 Location/Qualifiers
REGION                  1..9
                        note = peptide
VARIANT                 1..2
                        note = X can be any naturally occurring amino acid
VARIANT                 8..9
                        note = X can be any naturally occurring amino acid
source                  1..9
                        mol_type = protein
                        organism = synthetic construct
SEQUENCE: 321
XXVGICLXX                                                                  9

SEQ ID NO: 322          moltype = AA  length = 9
FEATURE                 Location/Qualifiers
REGION                  1..9
                        note = peptide
VARIANT                 1..2
                        note = X can be any naturally occurring amino acid
VARIANT                 8..9
                        note = X can be any naturally occurring amino acid
source                  1..9
                        mol_type = protein
                        organism = synthetic construct
SEQUENCE: 322
XXIKYFLXX                                                                  9

SEQ ID NO: 323          moltype = AA  length = 9
FEATURE                 Location/Qualifiers
REGION                  1..9
                        note = peptide
VARIANT                 1..2
                        note = X can be any naturally occurring amino acid
VARIANT                 8..9
                        note = X can be any naturally occurring amino acid
source                  1..9
                        mol_type = protein
                        organism = synthetic construct
SEQUENCE: 323
XXVLALVXX                                                                  9

SEQ ID NO: 324          moltype = AA  length = 9
FEATURE                 Location/Qualifiers
REGION                  1..9
                        note = peptide
VARIANT                 1..2
                        note = X can be any naturally occurring amino acid
VARIANT                 8..9
                        note = X can be any naturally occurring amino acid
source                  1..9
                        mol_type = protein
                        organism = synthetic construct
SEQUENCE: 324
XXALVLAXX                                                                  9

SEQ ID NO: 325          moltype = AA  length = 9
FEATURE                 Location/Qualifiers
REGION                  1..9
                        note = peptide
VARIANT                 1..2
                        note = X can be any naturally occurring amino acid
VARIANT                 8..9
                        note = X can be any naturally occurring amino acid
```

```
source                  1..9
                        mol_type = protein
                        organism = synthetic construct
SEQUENCE: 325
XXFGAPAXX                                                                   9

SEQ ID NO: 326          moltype = AA  length = 9
FEATURE                 Location/Qualifiers
REGION                  1..9
                        note = peptide
VARIANT                 1..2
                        note = X can be any naturally occurring amino acid
VARIANT                 8..9
                        note = X can be any naturally occurring amino acid
source                  1..9
                        mol_type = protein
                        organism = synthetic construct
SEQUENCE: 326
XXPGLLFXX                                                                   9

SEQ ID NO: 327          moltype = AA  length = 9
FEATURE                 Location/Qualifiers
REGION                  1..9
                        note = peptide
VARIANT                 8
                        note = X can be any naturally occurring amino acid
source                  1..9
                        mol_type = protein
                        organism = synthetic construct
SEQUENCE: 327
FLLFLTPXL                                                                   9

SEQ ID NO: 328          moltype = AA  length = 9
FEATURE                 Location/Qualifiers
REGION                  1..9
                        note = peptide
VARIANT                 2
                        note = X can be any naturally occurring amino acid
VARIANT                 8..9
                        note = X can be any naturally occurring amino acid
source                  1..9
                        mol_type = protein
                        organism = synthetic construct
SEQUENCE: 328
FXLFLTPXX                                                                   9

SEQ ID NO: 329          moltype = AA  length = 9
FEATURE                 Location/Qualifiers
REGION                  1..9
                        note = peptide
VARIANT                 8..9
                        note = X can be any naturally occurring amino acid
source                  1..9
                        mol_type = protein
                        organism = synthetic construct
SEQUENCE: 329
GLLFLTPXX                                                                   9

SEQ ID NO: 330          moltype = AA  length = 9
FEATURE                 Location/Qualifiers
REGION                  1..9
                        note = peptide
VARIANT                 8..9
                        note = X can be any naturally occurring amino acid
source                  1..9
                        mol_type = protein
                        organism = synthetic construct
SEQUENCE: 330
TLLFLTPXX                                                                   9

SEQ ID NO: 331          moltype = AA  length = 9
FEATURE                 Location/Qualifiers
REGION                  1..9
                        note = peptide
VARIANT                 1
                        note = X can be any naturally occurring amino acid
source                  1..9
                        mol_type = protein
                        organism = synthetic construct
```

```
SEQUENCE: 331
XLLFLTPLL                                                       9

SEQ ID NO: 332          moltype = AA  length = 9
FEATURE                 Location/Qualifiers
REGION                  1..9
                        note = peptide
VARIANT                 1
                        note = X can be any naturally occurring amino acid
source                  1..9
                        mol_type = protein
                        organism = synthetic construct
SEQUENCE: 332
XLLFLTPML                                                       9

SEQ ID NO: 333          moltype = AA  length = 9
FEATURE                 Location/Qualifiers
REGION                  1..9
                        note = peptide
VARIANT                 1
                        note = X can be any naturally occurring amino acid
VARIANT                 8
                        note = X can be any naturally occurring amino acid
source                  1..9
                        mol_type = protein
                        organism = synthetic construct
SEQUENCE: 333
XLLFLTPXL                                                       9

SEQ ID NO: 334          moltype = AA  length = 9
FEATURE                 Location/Qualifiers
REGION                  1..9
                        note = peptide
VARIANT                 8
                        note = X can be any naturally occurring amino acid
source                  1..9
                        mol_type = protein
                        organism = synthetic construct
SEQUENCE: 334
ALSLGLPXL                                                       9

SEQ ID NO: 335          moltype = AA  length = 9
FEATURE                 Location/Qualifiers
REGION                  1..9
                        note = peptide
VARIANT                 8
                        note = X can be any naturally occurring amino acid
source                  1..9
                        mol_type = protein
                        organism = synthetic construct
SEQUENCE: 335
AMSLGLPXL                                                       9

SEQ ID NO: 336          moltype = AA  length = 9
FEATURE                 Location/Qualifiers
REGION                  1..9
                        note = peptide
VARIANT                 8
                        note = X can be any naturally occurring amino acid
source                  1..9
                        mol_type = protein
                        organism = synthetic construct
SEQUENCE: 336
FLSLGLPXL                                                       9

SEQ ID NO: 337          moltype = AA  length = 9
FEATURE                 Location/Qualifiers
REGION                  1..9
                        note = peptide
VARIANT                 8
                        note = X can be any naturally occurring amino acid
source                  1..9
                        mol_type = protein
                        organism = synthetic construct
SEQUENCE: 337
LLSLGLPXL                                                       9

SEQ ID NO: 338          moltype = AA  length = 9
FEATURE                 Location/Qualifiers
```

```
REGION                  1..9
                        note = peptide
VARIANT                 8
                        note = X can be any naturally occurring amino acid
source                  1..9
                        mol_type = protein
                        organism = synthetic construct
SEQUENCE: 338
SLSLGLPXL                                                                  9

SEQ ID NO: 339          moltype = AA  length = 9
FEATURE                 Location/Qualifiers
REGION                  1..9
                        note = peptide
VARIANT                 8..9
                        note = X can be any naturally occurring amino acid
source                  1..9
                        mol_type = protein
                        organism = synthetic construct
SEQUENCE: 339
VLSLGLPXX                                                                  9

SEQ ID NO: 340          moltype = AA  length = 9
FEATURE                 Location/Qualifiers
REGION                  1..9
                        note = peptide
VARIANT                 1
                        note = X can be any naturally occurring amino acid
source                  1..9
                        mol_type = protein
                        organism = synthetic construct
SEQUENCE: 340
XLSLGLPGL                                                                  9

SEQ ID NO: 341          moltype = AA  length = 9
FEATURE                 Location/Qualifiers
REGION                  1..9
                        note = peptide
VARIANT                 1
                        note = X can be any naturally occurring amino acid
source                  1..9
                        mol_type = protein
                        organism = synthetic construct
SEQUENCE: 341
XLSLGLPIL                                                                  9

SEQ ID NO: 342          moltype = AA  length = 9
FEATURE                 Location/Qualifiers
REGION                  1..9
                        note = peptide
VARIANT                 1
                        note = X can be any naturally occurring amino acid
source                  1..9
                        mol_type = protein
                        organism = synthetic construct
SEQUENCE: 342
XLSLGLPKL                                                                  9

SEQ ID NO: 343          moltype = AA  length = 9
FEATURE                 Location/Qualifiers
REGION                  1..9
                        note = peptide
VARIANT                 1
                        note = X can be any naturally occurring amino acid
VARIANT                 8
                        note = X can be any naturally occurring amino acid
source                  1..9
                        mol_type = protein
                        organism = synthetic construct
SEQUENCE: 343
XLSLGLPXL                                                                  9

SEQ ID NO: 344          moltype = AA  length = 9
FEATURE                 Location/Qualifiers
REGION                  1..9
                        note = peptide
VARIANT                 1
                        note = X can be any naturally occurring amino acid
```

```
VARIANT              8..9
                     note = X can be any naturally occurring amino acid
source               1..9
                     mol_type = protein
                     organism = synthetic construct
SEQUENCE: 344
XLVGILHXX                                                                    9

SEQ ID NO: 345       moltype = AA  length = 9
FEATURE              Location/Qualifiers
REGION               1..9
                     note = peptide
VARIANT              8
                     note = X can be any naturally occurring amino acid
source               1..9
                     mol_type = protein
                     organism = synthetic construct
SEQUENCE: 345
FLAYLIFXL                                                                    9

SEQ ID NO: 346       moltype = AA  length = 9
FEATURE              Location/Qualifiers
REGION               1..9
                     note = peptide
VARIANT              1
                     note = X can be any naturally occurring amino acid
VARIANT              8
                     note = X can be any naturally occurring amino acid
source               1..9
                     mol_type = protein
                     organism = synthetic construct
SEQUENCE: 346
XLAYLIFXL                                                                    9

SEQ ID NO: 347       moltype = AA  length = 9
FEATURE              Location/Qualifiers
REGION               1..9
                     note = peptide
VARIANT              8..9
                     note = X can be any naturally occurring amino acid
source               1..9
                     mol_type = protein
                     organism = synthetic construct
SEQUENCE: 347
ALLGGLLXX                                                                    9

SEQ ID NO: 348       moltype = AA  length = 9
FEATURE              Location/Qualifiers
REGION               1..9
                     note = peptide
VARIANT              2
                     note = X can be any naturally occurring amino acid
source               1..9
                     mol_type = protein
                     organism = synthetic construct
SEQUENCE: 348
AXLGGLLLI                                                                    9

SEQ ID NO: 349       moltype = AA  length = 9
FEATURE              Location/Qualifiers
REGION               1..9
                     note = peptide
VARIANT              2
                     note = X can be any naturally occurring amino acid
VARIANT              8
                     note = X can be any naturally occurring amino acid
source               1..9
                     mol_type = protein
                     organism = synthetic construct
SEQUENCE: 349
FXLGGLLXV                                                                    9

SEQ ID NO: 350       moltype = AA  length = 9
FEATURE              Location/Qualifiers
REGION               1..9
                     note = peptide
VARIANT              8..9
                     note = X can be any naturally occurring amino acid
```

```
source                  1..9
                        mol_type = protein
                        organism = synthetic construct
SEQUENCE: 350
GMLGGLLXX                                                     9

SEQ ID NO: 351          moltype = AA  length = 9
FEATURE                 Location/Qualifiers
REGION                  1..9
                        note = peptide
VARIANT                 1
                        note = X can be any naturally occurring amino acid
VARIANT                 8
                        note = X can be any naturally occurring amino acid
source                  1..9
                        mol_type = protein
                        organism = synthetic construct
SEQUENCE: 351
XLLGGLLXI                                                     9

SEQ ID NO: 352          moltype = AA  length = 9
FEATURE                 Location/Qualifiers
REGION                  1..9
                        note = peptide
VARIANT                 8..9
                        note = X can be any naturally occurring amino acid
source                  1..9
                        mol_type = protein
                        organism = synthetic construct
SEQUENCE: 352
SLLGGLLXX                                                     9

SEQ ID NO: 353          moltype = AA  length = 9
FEATURE                 Location/Qualifiers
REGION                  1..9
                        note = peptide
VARIANT                 2
                        note = X can be any naturally occurring amino acid
source                  1..9
                        mol_type = protein
                        organism = synthetic construct
SEQUENCE: 353
SXLGGLLLI                                                     9

SEQ ID NO: 354          moltype = AA  length = 9
FEATURE                 Location/Qualifiers
REGION                  1..9
                        note = peptide
VARIANT                 2
                        note = X can be any naturally occurring amino acid
source                  1..9
                        mol_type = protein
                        organism = synthetic construct
SEQUENCE: 354
YXLGGLLMV                                                     9

SEQ ID NO: 355          moltype = AA  length = 9
FEATURE                 Location/Qualifiers
REGION                  1..9
                        note = peptide
VARIANT                 2
                        note = X can be any naturally occurring amino acid
VARIANT                 8
                        note = X can be any naturally occurring amino acid
source                  1..9
                        mol_type = protein
                        organism = synthetic construct
SEQUENCE: 355
YXLGGLLXV                                                     9

SEQ ID NO: 356          moltype = AA  length = 9
FEATURE                 Location/Qualifiers
REGION                  1..9
                        note = peptide
VARIANT                 1
                        note = X can be any naturally occurring amino acid
source                  1..9
                        mol_type = protein
                        organism = synthetic construct
```

```
SEQUENCE: 356
XLLGGLLLI                                                  9

SEQ ID NO: 357         moltype = AA  length = 9
FEATURE                Location/Qualifiers
REGION                 1..9
                       note = peptide
VARIANT                1
                       note = X can be any naturally occurring amino acid
source                 1..9
                       mol_type = protein
                       organism = synthetic construct
SEQUENCE: 357
XMLGGLLLI                                                  9

SEQ ID NO: 358         moltype = AA  length = 9
FEATURE                Location/Qualifiers
REGION                 1..9
                       note = peptide
VARIANT                1..2
                       note = X can be any naturally occurring amino acid
source                 1..9
                       mol_type = protein
                       organism = synthetic construct
SEQUENCE: 358
XXLGGLLMI                                                  9

SEQ ID NO: 359         moltype = AA  length = 9
FEATURE                Location/Qualifiers
REGION                 1..9
                       note = peptide
VARIANT                1..2
                       note = X can be any naturally occurring amino acid
source                 1..9
                       mol_type = protein
                       organism = synthetic construct
SEQUENCE: 359
XXLGGLLML                                                  9

SEQ ID NO: 360         moltype = AA  length = 9
FEATURE                Location/Qualifiers
REGION                 1..9
                       note = peptide
VARIANT                1..2
                       note = X can be any naturally occurring amino acid
source                 1..9
                       mol_type = protein
                       organism = synthetic construct
SEQUENCE: 360
XXLGGLLMV                                                  9

SEQ ID NO: 361         moltype = AA  length = 9
FEATURE                Location/Qualifiers
REGION                 1..9
                       note = peptide
VARIANT                8..9
                       note = X can be any naturally occurring amino acid
source                 1..9
                       mol_type = protein
                       organism = synthetic construct
SEQUENCE: 361
ILNSLSLXX                                                  9

SEQ ID NO: 362         moltype = AA  length = 9
FEATURE                Location/Qualifiers
REGION                 1..9
                       note = peptide
VARIANT                1
                       note = X can be any naturally occurring amino acid
VARIANT                8
                       note = X can be any naturally occurring amino acid
source                 1..9
                       mol_type = protein
                       organism = synthetic construct
SEQUENCE: 362
XLNSLSLXL                                                  9

SEQ ID NO: 363         moltype = AA  length = 9
FEATURE                Location/Qualifiers
```

```
REGION                1..9
                      note = peptide
VARIANT               1
                      note = X can be any naturally occurring amino acid
VARIANT               8..9
                      note = X can be any naturally occurring amino acid
source                1..9
                      mol_type = protein
                      organism = synthetic construct
SEQUENCE: 363
XMNSLSLXX                                                   9

SEQ ID NO: 364        moltype = AA  length = 9
FEATURE               Location/Qualifiers
REGION                1..9
                      note = peptide
VARIANT               1..2
                      note = X can be any naturally occurring amino acid
VARIANT               8
                      note = X can be any naturally occurring amino acid
source                1..9
                      mol_type = protein
                      organism = synthetic construct
SEQUENCE: 364
XXNSLSLXI                                                   9

SEQ ID NO: 365        moltype = AA  length = 9
FEATURE               Location/Qualifiers
REGION                1..9
                      note = peptide
VARIANT               8..9
                      note = X can be any naturally occurring amino acid
source                1..9
                      mol_type = protein
                      organism = synthetic construct
SEQUENCE: 365
LLIPAGIXX                                                   9

SEQ ID NO: 366        moltype = AA  length = 9
FEATURE               Location/Qualifiers
REGION                1..9
                      note = peptide
VARIANT               2
                      note = X can be any naturally occurring amino acid
VARIANT               8..9
                      note = X can be any naturally occurring amino acid
source                1..9
                      mol_type = protein
                      organism = synthetic construct
SEQUENCE: 366
MXIPAGIXX                                                   9

SEQ ID NO: 367        moltype = AA  length = 9
FEATURE               Location/Qualifiers
REGION                1..9
                      note = peptide
VARIANT               1
                      note = X can be any naturally occurring amino acid
VARIANT               8
                      note = X can be any naturally occurring amino acid
source                1..9
                      mol_type = protein
                      organism = synthetic construct
SEQUENCE: 367
XLIPAGIXL                                                   9

SEQ ID NO: 368        moltype = AA  length = 9
FEATURE               Location/Qualifiers
REGION                1..9
                      note = peptide
VARIANT               1
                      note = X can be any naturally occurring amino acid
VARIANT               8..9
                      note = X can be any naturally occurring amino acid
source                1..9
                      mol_type = protein
                      organism = synthetic construct
SEQUENCE: 368
XMIPAGIXX                                                   9
```

```
SEQ ID NO: 369          moltype = AA  length = 9
FEATURE                 Location/Qualifiers
REGION                  1..9
                        note = peptide
VARIANT                 1..2
                        note = X can be any naturally occurring amino acid
source                  1..9
                        mol_type = protein
                        organism = synthetic construct
SEQUENCE: 369
XXIPAGIAV                                                                9

SEQ ID NO: 370          moltype = AA  length = 9
FEATURE                 Location/Qualifiers
REGION                  1..9
                        note = peptide
VARIANT                 8
                        note = X can be any naturally occurring amino acid
source                  1..9
                        mol_type = protein
                        organism = synthetic construct
SEQUENCE: 370
FLFLGILXL                                                                9

SEQ ID NO: 371          moltype = AA  length = 9
FEATURE                 Location/Qualifiers
REGION                  1..9
                        note = peptide
VARIANT                 8
                        note = X can be any naturally occurring amino acid
source                  1..9
                        mol_type = protein
                        organism = synthetic construct
SEQUENCE: 371
YLFLGILXL                                                                9

SEQ ID NO: 372          moltype = AA  length = 9
FEATURE                 Location/Qualifiers
REGION                  1..9
                        note = peptide
VARIANT                 8..9
                        note = X can be any naturally occurring amino acid
source                  1..9
                        mol_type = protein
                        organism = synthetic construct
SEQUENCE: 372
YLFLGILXX                                                                9

SEQ ID NO: 373          moltype = AA  length = 9
FEATURE                 Location/Qualifiers
REGION                  1..9
                        note = peptide
VARIANT                 1
                        note = X can be any naturally occurring amino acid
source                  1..9
                        mol_type = protein
                        organism = synthetic construct
SEQUENCE: 373
XLFLGILGL                                                                9

SEQ ID NO: 374          moltype = AA  length = 9
FEATURE                 Location/Qualifiers
REGION                  1..9
                        note = peptide
VARIANT                 1
                        note = X can be any naturally occurring amino acid
VARIANT                 9
                        note = X can be any naturally occurring amino acid
source                  1..9
                        mol_type = protein
                        organism = synthetic construct
SEQUENCE: 374
XLFLGILSX                                                                9

SEQ ID NO: 375          moltype = AA  length = 9
FEATURE                 Location/Qualifiers
REGION                  1..9
                        note = peptide
```

-continued

```
VARIANT             8
                    note = X can be any naturally occurring amino acid
source              1..9
                    mol_type = protein
                    organism = synthetic construct
SEQUENCE: 375
FLSNDTVXL                                                    9

SEQ ID NO: 376      moltype = AA  length = 9
FEATURE             Location/Qualifiers
REGION              1..9
                    note = peptide
VARIANT             8..9
                    note = X can be any naturally occurring amino acid
source              1..9
                    mol_type = protein
                    organism = synthetic construct
SEQUENCE: 376
FLSNDTVXX                                                    9

SEQ ID NO: 377      moltype = AA  length = 9
FEATURE             Location/Qualifiers
REGION              1..9
                    note = peptide
VARIANT             2
                    note = X can be any naturally occurring amino acid
VARIANT             8..9
                    note = X can be any naturally occurring amino acid
source              1..9
                    mol_type = protein
                    organism = synthetic construct
SEQUENCE: 377
FXSNDTVXX                                                    9

SEQ ID NO: 378      moltype = AA  length = 9
FEATURE             Location/Qualifiers
REGION              1..9
                    note = peptide
VARIANT             1
                    note = X can be any naturally occurring amino acid
VARIANT             8..9
                    note = X can be any naturally occurring amino acid
source              1..9
                    mol_type = protein
                    organism = synthetic construct
SEQUENCE: 378
XMSNDTVXX                                                    9

SEQ ID NO: 379      moltype = AA  length = 9
FEATURE             Location/Qualifiers
REGION              1..9
                    note = peptide
VARIANT             1
                    note = X can be any naturally occurring amino acid
source              1..9
                    mol_type = protein
                    organism = synthetic construct
SEQUENCE: 379
XLSNDTVWL                                                    9

SEQ ID NO: 380      moltype = AA  length = 9
FEATURE             Location/Qualifiers
REGION              1..9
                    note = peptide
VARIANT             1
                    note = X can be any naturally occurring amino acid
VARIANT             8
                    note = X can be any naturally occurring amino acid
source              1..9
                    mol_type = protein
                    organism = synthetic construct
SEQUENCE: 380
XLSNDTVXL                                                    9

SEQ ID NO: 381      moltype = AA  length = 9
FEATURE             Location/Qualifiers
REGION              1..9
                    note = peptide
```

```
VARIANT                 1
                        note = X can be any naturally occurring amino acid
VARIANT                 8
                        note = X can be any naturally occurring amino acid
source                  1..9
                        mol_type = protein
                        organism = synthetic construct
SEQUENCE: 381
XLLGPWLXL                                                                  9

SEQ ID NO: 382          moltype = AA  length = 9
FEATURE                 Location/Qualifiers
REGION                  1..9
                        note = peptide
VARIANT                 1
                        note = X can be any naturally occurring amino acid
VARIANT                 8
                        note = X can be any naturally occurring amino acid
source                  1..9
                        mol_type = protein
                        organism = synthetic construct
SEQUENCE: 382
XLLGPWLXV                                                                  9

SEQ ID NO: 383          moltype = AA  length = 9
FEATURE                 Location/Qualifiers
REGION                  1..9
                        note = peptide
VARIANT                 1
                        note = X can be any naturally occurring amino acid
VARIANT                 8..9
                        note = X can be any naturally occurring amino acid
source                  1..9
                        mol_type = protein
                        organism = synthetic construct
SEQUENCE: 383
XLLGPWLXX                                                                  9

SEQ ID NO: 384          moltype = AA  length = 9
FEATURE                 Location/Qualifiers
REGION                  1..9
                        note = peptide
VARIANT                 2
                        note = X can be any naturally occurring amino acid
VARIANT                 8
                        note = X can be any naturally occurring amino acid
source                  1..9
                        mol_type = protein
                        organism = synthetic construct
SEQUENCE: 384
IXILAICXV                                                                  9

SEQ ID NO: 385          moltype = AA  length = 9
FEATURE                 Location/Qualifiers
REGION                  1..9
                        note = peptide
VARIANT                 1
                        note = X can be any naturally occurring amino acid
source                  1..9
                        mol_type = protein
                        organism = synthetic construct
SEQUENCE: 385
XLILAICGV                                                                  9

SEQ ID NO: 386          moltype = AA  length = 9
FEATURE                 Location/Qualifiers
REGION                  1..9
                        note = peptide
VARIANT                 1
                        note = X can be any naturally occurring amino acid
VARIANT                 9
                        note = X can be any naturally occurring amino acid
source                  1..9
                        mol_type = protein
                        organism = synthetic construct
SEQUENCE: 386
XLILAICGX                                                                  9

SEQ ID NO: 387          moltype = AA  length = 9
```

-continued

```
FEATURE                Location/Qualifiers
REGION                 1..9
                       note = peptide
VARIANT                1
                       note = X can be any naturally occurring amino acid
VARIANT                8..9
                       note = X can be any naturally occurring amino acid
source                 1..9
                       mol_type = protein
                       organism = synthetic construct
SEQUENCE: 387
XIFEHPEXX                                                    9

SEQ ID NO: 388         moltype = AA  length = 9
FEATURE                Location/Qualifiers
REGION                 1..9
                       note = peptide
VARIANT                1..2
                       note = X can be any naturally occurring amino acid
source                 1..9
                       mol_type = protein
                       organism = synthetic construct
SEQUENCE: 388
XXFEHPELL                                                    9

SEQ ID NO: 389         moltype = AA  length = 9
FEATURE                Location/Qualifiers
REGION                 1..9
                       note = peptide
VARIANT                1..2
                       note = X can be any naturally occurring amino acid
VARIANT                9
                       note = X can be any naturally occurring amino acid
source                 1..9
                       mol_type = protein
                       organism = synthetic construct
SEQUENCE: 389
XXFEHPELX                                                    9

SEQ ID NO: 390         moltype = AA  length = 9
FEATURE                Location/Qualifiers
REGION                 1..9
                       note = peptide
VARIANT                1..2
                       note = X can be any naturally occurring amino acid
VARIANT                8..9
                       note = X can be any naturally occurring amino acid
source                 1..9
                       mol_type = protein
                       organism = synthetic construct
SEQUENCE: 390
XXFEHPEXX                                                    9

SEQ ID NO: 391         moltype = AA  length = 9
FEATURE                Location/Qualifiers
REGION                 1..9
                       note = peptide
VARIANT                8
                       note = X can be any naturally occurring amino acid
source                 1..9
                       mol_type = protein
                       organism = synthetic construct
SEQUENCE: 391
ALAFVPLXV                                                    9

SEQ ID NO: 392         moltype = AA  length = 9
FEATURE                Location/Qualifiers
REGION                 1..9
                       note = peptide
VARIANT                8
                       note = X can be any naturally occurring amino acid
source                 1..9
                       mol_type = protein
                       organism = synthetic construct
SEQUENCE: 392
FLAFVPLXL                                                    9

SEQ ID NO: 393         moltype = AA  length = 9
FEATURE                Location/Qualifiers
```

```
REGION              1..9
                    note = peptide
VARIANT             2
                    note = X can be any naturally occurring amino acid
source              1..9
                    mol_type = protein
                    organism = synthetic construct
SEQUENCE: 393
FXAFVPLQL                                                    9

SEQ ID NO: 394      moltype = AA  length = 9
FEATURE             Location/Qualifiers
REGION              1..9
                    note = peptide
VARIANT             8
                    note = X can be any naturally occurring amino acid
source              1..9
                    mol_type = protein
                    organism = synthetic construct
SEQUENCE: 394
IMAFVPLXV                                                    9

SEQ ID NO: 395      moltype = AA  length = 9
FEATURE             Location/Qualifiers
REGION              1..9
                    note = peptide
VARIANT             8
                    note = X can be any naturally occurring amino acid
source              1..9
                    mol_type = protein
                    organism = synthetic construct
SEQUENCE: 395
LLAFVPLXL                                                    9

SEQ ID NO: 396      moltype = AA  length = 9
FEATURE             Location/Qualifiers
REGION              1..9
                    note = peptide
VARIANT             8..9
                    note = X can be any naturally occurring amino acid
source              1..9
                    mol_type = protein
                    organism = synthetic construct
SEQUENCE: 396
LLAFVPLXX                                                    9

SEQ ID NO: 397      moltype = AA  length = 9
FEATURE             Location/Qualifiers
REGION              1..9
                    note = peptide
VARIANT             1
                    note = X can be any naturally occurring amino acid
VARIANT             8
                    note = X can be any naturally occurring amino acid
source              1..9
                    mol_type = protein
                    organism = synthetic construct
SEQUENCE: 397
XMAFVPLXV                                                    9

SEQ ID NO: 398      moltype = AA  length = 9
FEATURE             Location/Qualifiers
REGION              1..9
                    note = peptide
VARIANT             1
                    note = X can be any naturally occurring amino acid
VARIANT             8
                    note = X can be any naturally occurring amino acid
source              1..9
                    mol_type = protein
                    organism = synthetic construct
SEQUENCE: 398
XMAFVPLXL                                                    9

SEQ ID NO: 399      moltype = AA  length = 9
FEATURE             Location/Qualifiers
REGION              1..9
                    note = peptide
```

-continued

```
VARIANT              1
                     note = X can be any naturally occurring amino acid
source               1..9
                     mol_type = protein
                     organism = synthetic construct
SEQUENCE: 399
XLAFVPLAV                                                                  9

SEQ ID NO: 400       moltype = AA  length = 9
FEATURE              Location/Qualifiers
REGION               1..9
                     note = peptide
VARIANT              1
                     note = X can be any naturally occurring amino acid
VARIANT              8
                     note = X can be any naturally occurring amino acid
source               1..9
                     mol_type = protein
                     organism = synthetic construct
SEQUENCE: 400
XLAFVPLXV                                                                  9

SEQ ID NO: 401       moltype = AA  length = 9
FEATURE              Location/Qualifiers
REGION               1..9
                     note = peptide
VARIANT              1..2
                     note = X can be any naturally occurring amino acid
source               1..9
                     mol_type = protein
                     organism = synthetic construct
SEQUENCE: 401
XXAFVPLAV                                                                  9

SEQ ID NO: 402       moltype = AA  length = 9
FEATURE              Location/Qualifiers
REGION               1..9
                     note = peptide
VARIANT              1..2
                     note = X can be any naturally occurring amino acid
VARIANT              8
                     note = X can be any naturally occurring amino acid
source               1..9
                     mol_type = protein
                     organism = synthetic construct
SEQUENCE: 402
XXAFVPLXL                                                                  9

SEQ ID NO: 403       moltype = AA  length = 9
FEATURE              Location/Qualifiers
REGION               1..9
                     note = peptide
VARIANT              8
                     note = X can be any naturally occurring amino acid
source               1..9
                     mol_type = protein
                     organism = synthetic construct
SEQUENCE: 403
LLYFGMLXL                                                                  9

SEQ ID NO: 404       moltype = AA  length = 9
FEATURE              Location/Qualifiers
REGION               1..9
                     note = peptide
VARIANT              1
                     note = X can be any naturally occurring amino acid
VARIANT              8
                     note = X can be any naturally occurring amino acid
source               1..9
                     mol_type = protein
                     organism = synthetic construct
SEQUENCE: 404
XLYFGMLXL                                                                  9

SEQ ID NO: 405       moltype = AA  length = 9
FEATURE              Location/Qualifiers
REGION               1..9
                     note = peptide
```

VARIANT 1
note = X can be any naturally occurring amino acid
VARIANT 8..9
note = X can be any naturally occurring amino acid
source 1..9
mol_type = protein
organism = synthetic construct
SEQUENCE: 405
XLYFGMLXX 9

SEQ ID NO: 406 moltype = AA length = 10
FEATURE Location/Qualifiers
REGION 1..10
note = peptide
VARIANT 1..2
note = X can be any naturally occurring amino acid
VARIANT 9
note = X can be any naturally occurring amino acid
source 1..10
mol_type = protein
organism = synthetic construct
SEQUENCE: 406
XXLYFGMLXL 10

SEQ ID NO: 407 moltype = AA length = 9
FEATURE Location/Qualifiers
REGION 1..9
note = peptide
VARIANT 9
note = X can be any naturally occurring amino acid
source 1..9
mol_type = protein
organism = synthetic construct
SEQUENCE: 407
ILIDKTSGX 9

SEQ ID NO: 408 moltype = AA length = 9
FEATURE Location/Qualifiers
REGION 1..9
note = peptide
VARIANT 2
note = X can be any naturally occurring amino acid
VARIANT 8
note = X can be any naturally occurring amino acid
source 1..9
mol_type = protein
organism = synthetic construct
SEQUENCE: 408
IXIDKTSXV 9

SEQ ID NO: 409 moltype = AA length = 9
FEATURE Location/Qualifiers
REGION 1..9
note = peptide
VARIANT 8..9
note = X can be any naturally occurring amino acid
source 1..9
mol_type = protein
organism = synthetic construct
SEQUENCE: 409
VLIDKTSXX 9

SEQ ID NO: 410 moltype = AA length = 9
FEATURE Location/Qualifiers
VARIANT 2
note = X can be any naturally occurring amino acid
source 1..9
mol_type = protein
organism = synthetic construct
REGION 1..9
note = peptide
SEQUENCE: 410
VXIDKTSSV 9

SEQ ID NO: 411 moltype = AA length = 9
FEATURE Location/Qualifiers
REGION 1..9
note = peptide -continued

```
VARIANT                 8..9
                        note = X can be any naturally occurring amino acid
source                  1..9
                        mol_type = protein
                        organism = synthetic construct
SEQUENCE: 411
YLIDKTSXX                                                                9

SEQ ID NO: 412          moltype = AA  length = 9
FEATURE                 Location/Qualifiers
REGION                  1..9
                        note = peptide
VARIANT                 1
                        note = X can be any naturally occurring amino acid
VARIANT                 8
                        note = X can be any naturally occurring amino acid
source                  1..9
                        mol_type = protein
                        organism = synthetic construct
SEQUENCE: 412
XLIDKTSXA                                                                9

SEQ ID NO: 413          moltype = AA  length = 9
FEATURE                 Location/Qualifiers
REGION                  1..9
                        note = peptide
VARIANT                 1
                        note = X can be any naturally occurring amino acid
VARIANT                 8
                        note = X can be any naturally occurring amino acid
source                  1..9
                        mol_type = protein
                        organism = synthetic construct
SEQUENCE: 413
XLIDKTSXV                                                                9

SEQ ID NO: 414          moltype = AA  length = 9
FEATURE                 Location/Qualifiers
REGION                  1..9
                        note = peptide
VARIANT                 1
                        note = X can be any naturally occurring amino acid
VARIANT                 8..9
                        note = X can be any naturally occurring amino acid
source                  1..9
                        mol_type = protein
                        organism = synthetic construct
SEQUENCE: 414
XLIDKTSXX                                                                9

SEQ ID NO: 415          moltype = AA  length = 9
FEATURE                 Location/Qualifiers
REGION                  1..9
                        note = peptide
VARIANT                 2
                        note = X can be any naturally occurring amino acid
VARIANT                 8
                        note = X can be any naturally occurring amino acid
source                  1..9
                        mol_type = protein
                        organism = synthetic construct
SEQUENCE: 415
FXLLFATXV                                                                9

SEQ ID NO: 416          moltype = AA  length = 9
FEATURE                 Location/Qualifiers
REGION                  1..9
                        note = peptide
VARIANT                 8
                        note = X can be any naturally occurring amino acid
source                  1..9
                        mol_type = protein
                        organism = synthetic construct
SEQUENCE: 416
LLLLFATXV                                                                9

SEQ ID NO: 417          moltype = AA  length = 9
FEATURE                 Location/Qualifiers
```

-continued

```
REGION                 1..9
                       note = peptide
VARIANT                2
                       note = X can be any naturally occurring amino acid
VARIANT                8
                       note = X can be any naturally occurring amino acid
source                 1..9
                       mol_type = protein
                       organism = synthetic construct
SEQUENCE: 417
LXLLFATXV                                                   9

SEQ ID NO: 418         moltype = AA  length = 9
FEATURE                Location/Qualifiers
REGION                 1..9
                       note = peptide
VARIANT                8..9
                       note = X can be any naturally occurring amino acid
source                 1..9
                       mol_type = protein
                       organism = synthetic construct
SEQUENCE: 418
YLLLFATXX                                                   9

SEQ ID NO: 419         moltype = AA  length = 9
FEATURE                Location/Qualifiers
REGION                 1..9
                       note = peptide
VARIANT                1..2
                       note = X can be any naturally occurring amino acid
source                 1..9
                       mol_type = protein
                       organism = synthetic construct
SEQUENCE: 419
XXLLFATSV                                                   9

SEQ ID NO: 420         moltype = AA  length = 9
FEATURE                Location/Qualifiers
REGION                 1..9
                       note = peptide
VARIANT                1
                       note = X can be any naturally occurring amino acid
VARIANT                8..9
                       note = X can be any naturally occurring amino acid
source                 1..9
                       mol_type = protein
                       organism = synthetic construct
SEQUENCE: 420
XMLLFATXX                                                   9

SEQ ID NO: 421         moltype = AA  length = 9
FEATURE                Location/Qualifiers
REGION                 1..9
                       note = peptide
VARIANT                1..2
                       note = X can be any naturally occurring amino acid
VARIANT                8
                       note = X can be any naturally occurring amino acid
source                 1..9
                       mol_type = protein
                       organism = synthetic construct
SEQUENCE: 421
XXVGICLXV                                                   9

SEQ ID NO: 422         moltype = AA  length = 9
FEATURE                Location/Qualifiers
REGION                 1..9
                       note = peptide
VARIANT                8
                       note = X can be any naturally occurring amino acid
source                 1..9
                       mol_type = protein
                       organism = synthetic construct
SEQUENCE: 422
KLIKYFLXV                                                   9

SEQ ID NO: 423         moltype = AA  length = 9
FEATURE                Location/Qualifiers
```

```
REGION                  1..9
                        note = peptide
VARIANT                 1
                        note = X can be any naturally occurring amino acid
VARIANT                 8
                        note = X can be any naturally occurring amino acid
source                  1..9
                        mol_type = protein
                        organism = synthetic construct
SEQUENCE: 423
XLIKYFLXV                                                     9

SEQ ID NO: 424          moltype = AA  length = 9
FEATURE                 Location/Qualifiers
REGION                  1..9
                        note = peptide
VARIANT                 1
                        note = X can be any naturally occurring amino acid
VARIANT                 8..9
                        note = X can be any naturally occurring amino acid
source                  1..9
                        mol_type = protein
                        organism = synthetic construct
SEQUENCE: 424
XLIKYFLXX                                                     9

SEQ ID NO: 425          moltype = AA  length = 9
FEATURE                 Location/Qualifiers
REGION                  1..9
                        note = peptide
VARIANT                 1..2
                        note = X can be any naturally occurring amino acid
VARIANT                 8
                        note = X can be any naturally occurring amino acid
source                  1..9
                        mol_type = protein
                        organism = synthetic construct
SEQUENCE: 425
XXIKYFLXV                                                     9

SEQ ID NO: 426          moltype = AA  length = 9
FEATURE                 Location/Qualifiers
REGION                  1..9
                        note = peptide
VARIANT                 8
                        note = X can be any naturally occurring amino acid
source                  1..9
                        mol_type = protein
                        organism = synthetic construct
SEQUENCE: 426
ALVLALVXV                                                     9

SEQ ID NO: 427          moltype = AA  length = 9
FEATURE                 Location/Qualifiers
REGION                  1..9
                        note = peptide
VARIANT                 8
                        note = X can be any naturally occurring amino acid
source                  1..9
                        mol_type = protein
                        organism = synthetic construct
SEQUENCE: 427
SLVLALVXV                                                     9

SEQ ID NO: 428          moltype = AA  length = 9
FEATURE                 Location/Qualifiers
REGION                  1..9
                        note = peptide
VARIANT                 1
                        note = X can be any naturally occurring amino acid
VARIANT                 8
                        note = X can be any naturally occurring amino acid
source                  1..9
                        mol_type = protein
                        organism = synthetic construct
SEQUENCE: 428
XLVLALVXV                                                     9

SEQ ID NO: 429          moltype = AA  length = 9
```

-continued

```
FEATURE               Location/Qualifiers
REGION                1..9
                      note = peptide
VARIANT               8
                      note = X can be any naturally occurring amino acid
source                1..9
                      mol_type = protein
                      organism = synthetic construct
SEQUENCE: 429
ALALVLAXL                                                              9

SEQ ID NO: 430        moltype = AA  length = 9
FEATURE               Location/Qualifiers
REGION                1..9
                      note = peptide
VARIANT               8..9
                      note = X can be any naturally occurring amino acid
source                1..9
                      mol_type = protein
                      organism = synthetic construct
SEQUENCE: 430
ALALVLAXX                                                              9

SEQ ID NO: 431        moltype = AA  length = 9
FEATURE               Location/Qualifiers
REGION                1..9
                      note = peptide
VARIANT               9
                      note = X can be any naturally occurring amino acid
source                1..9
                      mol_type = protein
                      organism = synthetic construct
SEQUENCE: 431
FLALVLAAX                                                              9

SEQ ID NO: 432        moltype = AA  length = 9
FEATURE               Location/Qualifiers
REGION                1..9
                      note = peptide
VARIANT               8
                      note = X can be any naturally occurring amino acid
source                1..9
                      mol_type = protein
                      organism = synthetic construct
SEQUENCE: 432
FLALVLAXL                                                              9

SEQ ID NO: 433        moltype = AA  length = 9
FEATURE               Location/Qualifiers
REGION                1..9
                      note = peptide
VARIANT               8
                      note = X can be any naturally occurring amino acid
source                1..9
                      mol_type = protein
                      organism = synthetic construct
SEQUENCE: 433
GLALVLAXI                                                              9

SEQ ID NO: 434        moltype = AA  length = 9
FEATURE               Location/Qualifiers
REGION                1..9
                      note = peptide
VARIANT               8
                      note = X can be any naturally occurring amino acid
source                1..9
                      mol_type = protein
                      organism = synthetic construct
SEQUENCE: 434
GLALVLAXL                                                              9

SEQ ID NO: 435        moltype = AA  length = 9
FEATURE               Location/Qualifiers
REGION                1..9
                      note = peptide
VARIANT               8
                      note = X can be any naturally occurring amino acid
```

```
source                  1..9
                        mol_type = protein
                        organism = synthetic construct
SEQUENCE: 435
GLALVLAXV                                                                   9

SEQ ID NO: 436          moltype = AA  length = 9
FEATURE                 Location/Qualifiers
REGION                  1..9
                        note = peptide
VARIANT                 2
                        note = X can be any naturally occurring amino acid
source                  1..9
                        mol_type = protein
                        organism = synthetic construct
SEQUENCE: 436
GXALVLAVV                                                                   9

SEQ ID NO: 437          moltype = AA  length = 9
FEATURE                 Location/Qualifiers
REGION                  1..9
                        note = peptide
VARIANT                 9
                        note = X can be any naturally occurring amino acid
source                  1..9
                        mol_type = protein
                        organism = synthetic construct
SEQUENCE: 437
SLALVLALX                                                                   9

SEQ ID NO: 438          moltype = AA  length = 9
FEATURE                 Location/Qualifiers
REGION                  1..9
                        note = peptide
VARIANT                 9
                        note = X can be any naturally occurring amino acid
source                  1..9
                        mol_type = protein
                        organism = synthetic construct
SEQUENCE: 438
VLALVLAEX                                                                   9

SEQ ID NO: 439          moltype = AA  length = 9
FEATURE                 Location/Qualifiers
REGION                  1..9
                        note = peptide
VARIANT                 8
                        note = X can be any naturally occurring amino acid
source                  1..9
                        mol_type = protein
                        organism = synthetic construct
SEQUENCE: 439
VLALVLAXV                                                                   9

SEQ ID NO: 440          moltype = AA  length = 9
FEATURE                 Location/Qualifiers
REGION                  1..9
                        note = peptide
VARIANT                 8
                        note = X can be any naturally occurring amino acid
source                  1..9
                        mol_type = protein
                        organism = synthetic construct
SEQUENCE: 440
YLALVLAXL                                                                   9

SEQ ID NO: 441          moltype = AA  length = 9
FEATURE                 Location/Qualifiers
REGION                  1..9
                        note = peptide
VARIANT                 1
                        note = X can be any naturally occurring amino acid
source                  1..9
                        mol_type = protein
                        organism = synthetic construct
SEQUENCE: 441
XLALVLAEV                                                                   9

SEQ ID NO: 442          moltype = AA  length = 9
```

```
FEATURE                 Location/Qualifiers
REGION                  1..9
                        note = peptide
VARIANT                 1
                        note = X can be any naturally occurring amino acid
source                  1..9
                        mol_type = protein
                        organism = synthetic construct
SEQUENCE: 442
XLALVLALL                                                                  9

SEQ ID NO: 443          moltype = AA  length = 9
FEATURE                 Location/Qualifiers
REGION                  1..9
                        note = peptide
VARIANT                 1
                        note = X can be any naturally occurring amino acid
source                  1..9
                        mol_type = protein
                        organism = synthetic construct
SEQUENCE: 443
XLALVLAML                                                                  9

SEQ ID NO: 444          moltype = AA  length = 9
FEATURE                 Location/Qualifiers
REGION                  1..9
                        note = peptide
VARIANT                 1
                        note = X can be any naturally occurring amino acid
VARIANT                 8
                        note = X can be any naturally occurring amino acid
source                  1..9
                        mol_type = protein
                        organism = synthetic construct
SEQUENCE: 444
XLALVLAXL                                                                  9

SEQ ID NO: 445          moltype = AA  length = 9
FEATURE                 Location/Qualifiers
REGION                  1..9
                        note = peptide
VARIANT                 1
                        note = X can be any naturally occurring amino acid
VARIANT                 8
                        note = X can be any naturally occurring amino acid
source                  1..9
                        mol_type = protein
                        organism = synthetic construct
SEQUENCE: 445
XLALVLAXI                                                                  9

SEQ ID NO: 446          moltype = AA  length = 9
FEATURE                 Location/Qualifiers
REGION                  1..9
                        note = peptide
VARIANT                 1
                        note = X can be any naturally occurring amino acid
VARIANT                 8
                        note = X can be any naturally occurring amino acid
source                  1..9
                        mol_type = protein
                        organism = synthetic construct
SEQUENCE: 446
XLALVLAXV                                                                  9

SEQ ID NO: 447          moltype = AA  length = 9
FEATURE                 Location/Qualifiers
REGION                  1..9
                        note = peptide
VARIANT                 8..9
                        note = X can be any naturally occurring amino acid
source                  1..9
                        mol_type = protein
                        organism = synthetic construct
SEQUENCE: 447
ALFGAPAXX                                                                  9

SEQ ID NO: 448          moltype = AA  length = 9
FEATURE                 Location/Qualifiers
```

```
REGION                  1..9
                        note = peptide
VARIANT                 8
                        note = X can be any naturally occurring amino acid
source                  1..9
                        mol_type = protein
                        organism = synthetic construct
SEQUENCE: 448
LLFGAPAXL                                                                   9

SEQ ID NO: 449          moltype = AA  length = 9
FEATURE                 Location/Qualifiers
REGION                  1..9
                        note = peptide
VARIANT                 9
                        note = X can be any naturally occurring amino acid
source                  1..9
                        mol_type = protein
                        organism = synthetic construct
SEQUENCE: 449
LLFGAPAGX                                                                   9

SEQ ID NO: 450          moltype = AA  length = 9
FEATURE                 Location/Qualifiers
REGION                  1..9
                        note = peptide
VARIANT                 8
                        note = X can be any naturally occurring amino acid
source                  1..9
                        mol_type = protein
                        organism = synthetic construct
SEQUENCE: 450
LMFGAPAXV                                                                   9

SEQ ID NO: 451          moltype = AA  length = 9
FEATURE                 Location/Qualifiers
REGION                  1..9
                        note = peptide
VARIANT                 8
                        note = X can be any naturally occurring amino acid
source                  1..9
                        mol_type = protein
                        organism = synthetic construct
SEQUENCE: 451
VLFGAPAXL                                                                   9

SEQ ID NO: 452          moltype = AA  length = 9
FEATURE                 Location/Qualifiers
REGION                  1..9
                        note = peptide
VARIANT                 1
                        note = X can be any naturally occurring amino acid
VARIANT                 8
                        note = X can be any naturally occurring amino acid
source                  1..9
                        mol_type = protein
                        organism = synthetic construct
SEQUENCE: 452
XLFGAPAXA                                                                   9

SEQ ID NO: 453          moltype = AA  length = 9
FEATURE                 Location/Qualifiers
REGION                  1..9
                        note = peptide
VARIANT                 1
                        note = X can be any naturally occurring amino acid
VARIANT                 8
                        note = X can be any naturally occurring amino acid
source                  1..9
                        mol_type = protein
                        organism = synthetic construct
SEQUENCE: 453
XLFGAPAXI                                                                   9

SEQ ID NO: 454          moltype = AA  length = 9
FEATURE                 Location/Qualifiers
REGION                  1..9
                        note = peptide
```

```
VARIANT              1
                     note = X can be any naturally occurring amino acid
VARIANT              8
                     note = X can be any naturally occurring amino acid
source               1..9
                     mol_type = protein
                     organism = synthetic construct
SEQUENCE: 454
XMFGAPAXV                                                              9

SEQ ID NO: 455       moltype = AA  length = 9
FEATURE              Location/Qualifiers
REGION               1..9
                     note = peptide
VARIANT              1..2
                     note = X can be any naturally occurring amino acid
VARIANT              8
                     note = X can be any naturally occurring amino acid
source               1..9
                     mol_type = protein
                     organism = synthetic construct
SEQUENCE: 455
XXFGAPAXV                                                              9

SEQ ID NO: 456       moltype = AA  length = 9
FEATURE              Location/Qualifiers
REGION               1..9
                     note = peptide
VARIANT              2
                     note = X can be any naturally occurring amino acid
VARIANT              8
                     note = X can be any naturally occurring amino acid
source               1..9
                     mol_type = protein
                     organism = synthetic construct
SEQUENCE: 456
FXPGLLFXV                                                              9

SEQ ID NO: 457       moltype = AA  length = 9
FEATURE              Location/Qualifiers
REGION               1..9
                     note = peptide
VARIANT              9
                     note = X can be any naturally occurring amino acid
source               1..9
                     mol_type = protein
                     organism = synthetic construct
SEQUENCE: 457
ILPGLLFYX                                                              9

SEQ ID NO: 458       moltype = AA  length = 9
FEATURE              Location/Qualifiers
REGION               1..9
                     note = peptide
VARIANT              8
                     note = X can be any naturally occurring amino acid
source               1..9
                     mol_type = protein
                     organism = synthetic construct
SEQUENCE: 458
ILPGLLFXI                                                              9

SEQ ID NO: 459       moltype = AA  length = 9
FEATURE              Location/Qualifiers
REGION               1..9
                     note = peptide
VARIANT              8
                     note = X can be any naturally occurring amino acid
source               1..9
                     mol_type = protein
                     organism = synthetic construct
SEQUENCE: 459
ILPGLLFXL                                                              9

SEQ ID NO: 460       moltype = AA  length = 9
FEATURE              Location/Qualifiers
REGION               1..9
                     note = peptide
```

-continued

```
VARIANT                 8..9
                        note = X can be any naturally occurring amino acid
source                  1..9
                        mol_type = protein
                        organism = synthetic construct
SEQUENCE: 460
IMPGLLFXX                                                                    9

SEQ ID NO: 461          moltype = AA  length = 9
FEATURE                 Location/Qualifiers
REGION                  1..9
                        note = peptide
VARIANT                 8..9
                        note = X can be any naturally occurring amino acid
source                  1..9
                        mol_type = protein
                        organism = synthetic construct
SEQUENCE: 461
KLPGLLFXX                                                                    9

SEQ ID NO: 462          moltype = AA  length = 9
FEATURE                 Location/Qualifiers
REGION                  1..9
                        note = peptide
VARIANT                 8..9
                        note = X can be any naturally occurring amino acid
source                  1..9
                        mol_type = protein
                        organism = synthetic construct
SEQUENCE: 462
LLPGLLFXX                                                                    9

SEQ ID NO: 463          moltype = AA  length = 9
FEATURE                 Location/Qualifiers
REGION                  1..9
                        note = peptide
VARIANT                 8..9
                        note = X can be any naturally occurring amino acid
source                  1..9
                        mol_type = protein
                        organism = synthetic construct
SEQUENCE: 463
MLPGLLFXX                                                                    9

SEQ ID NO: 464          moltype = AA  length = 9
FEATURE                 Location/Qualifiers
REGION                  1..9
                        note = peptide
VARIANT                 8..9
                        note = X can be any naturally occurring amino acid
source                  1..9
                        mol_type = protein
                        organism = synthetic construct
SEQUENCE: 464
SLPGLLFXX                                                                    9

SEQ ID NO: 465          moltype = AA  length = 9
FEATURE                 Location/Qualifiers
REGION                  1..9
                        note = peptide
VARIANT                 9
                        note = X can be any naturally occurring amino acid
source                  1..9
                        mol_type = protein
                        organism = synthetic construct
SEQUENCE: 465
TLPGLLFPX                                                                    9

SEQ ID NO: 466          moltype = AA  length = 9
FEATURE                 Location/Qualifiers
REGION                  1..9
                        note = peptide
VARIANT                 8
                        note = X can be any naturally occurring amino acid
source                  1..9
                        mol_type = protein
                        organism = synthetic construct
SEQUENCE: 466
VLPGLLFXV                                                                    9
```

```
SEQ ID NO: 467          moltype = AA  length = 9
FEATURE                 Location/Qualifiers
REGION                  1..9
                        note = peptide
VARIANT                 1
                        note = X can be any naturally occurring amino acid
VARIANT                 8..9
                        note = X can be any naturally occurring amino acid
source                  1..9
                        mol_type = protein
                        organism = synthetic construct
SEQUENCE: 467
XMPGLLFXX                                                                   9

SEQ ID NO: 468          moltype = AA  length = 9
FEATURE                 Location/Qualifiers
REGION                  1..9
                        note = peptide
VARIANT                 1
                        note = X can be any naturally occurring amino acid
source                  1..9
                        mol_type = protein
                        organism = synthetic construct
SEQUENCE: 468
XLPGLLFSV                                                                   9

SEQ ID NO: 469          moltype = AA  length = 9
FEATURE                 Location/Qualifiers
REGION                  1..9
                        note = peptide
VARIANT                 1
                        note = X can be any naturally occurring amino acid
source                  1..9
                        mol_type = protein
                        organism = synthetic construct
SEQUENCE: 469
XLPGLLFVV                                                                   9

SEQ ID NO: 470          moltype = AA  length = 9
FEATURE                 Location/Qualifiers
REGION                  1..9
                        note = peptide
VARIANT                 1
                        note = X can be any naturally occurring amino acid
VARIANT                 8
                        note = X can be any naturally occurring amino acid
source                  1..9
                        mol_type = protein
                        organism = synthetic construct
SEQUENCE: 470
XLPGLLFXM                                                                   9

SEQ ID NO: 471          moltype = AA  length = 9
FEATURE                 Location/Qualifiers
REGION                  1..9
                        note = peptide
VARIANT                 1
                        note = X can be any naturally occurring amino acid
VARIANT                 8
                        note = X can be any naturally occurring amino acid
source                  1..9
                        mol_type = protein
                        organism = synthetic construct
SEQUENCE: 471
XLPGLLFXL                                                                   9

SEQ ID NO: 472          moltype = AA  length = 9
FEATURE                 Location/Qualifiers
REGION                  1..9
                        note = peptide
VARIANT                 1
                        note = X can be any naturally occurring amino acid
VARIANT                 8
                        note = X can be any naturally occurring amino acid
source                  1..9
                        mol_type = protein
                        organism = synthetic construct
```

```
SEQUENCE: 472
XLPGLLFXV                                                    9

SEQ ID NO: 473          moltype = AA  length = 20
FEATURE                 Location/Qualifiers
REGION                  1..20
                        note = peptide
source                  1..20
                        mol_type = protein
                        organism = synthetic construct
SEQUENCE: 473
MAKTIAYDEE ARRGLERGLN                                        20

SEQ ID NO: 474          moltype = AA  length = 13
FEATURE                 Location/Qualifiers
REGION                  1..13
                        note = peptide
source                  1..13
                        mol_type = protein
                        organism = synthetic construct
SEQUENCE: 474
TPPAYRPPNA PIL                                               13

SEQ ID NO: 475          moltype = AA  length = 15
FEATURE                 Location/Qualifiers
REGION                  1..15
                        note = peptide
source                  1..15
                        mol_type = protein
                        organism = synthetic construct
SEQUENCE: 475
KSVWSKLQSI GIRQH                                             15

SEQ ID NO: 476          moltype = AA  length = 9
FEATURE                 Location/Qualifiers
REGION                  1..9
                        note = peptide
source                  1..9
                        mol_type = protein
                        organism = synthetic construct
SEQUENCE: 476
AMNSLSLLL                                                    9

SEQ ID NO: 477          moltype = AA  length = 9
FEATURE                 Location/Qualifiers
REGION                  1..9
                        note = peptide
source                  1..9
                        mol_type = protein
                        organism = synthetic construct
SEQUENCE: 477
AMNSLSLTV                                                    9

SEQ ID NO: 478          moltype = AA  length = 9
FEATURE                 Location/Qualifiers
REGION                  1..9
                        note = peptide
source                  1..9
                        mol_type = protein
                        organism = synthetic construct
SEQUENCE: 478
GMNSLSLLV                                                    9

SEQ ID NO: 479          moltype = AA  length = 9
FEATURE                 Location/Qualifiers
REGION                  1..9
                        note = peptide
source                  1..9
                        mol_type = protein
                        organism = synthetic construct
SEQUENCE: 479
ILNSLSLDI                                                    9

SEQ ID NO: 480          moltype = AA  length = 9
FEATURE                 Location/Qualifiers
REGION                  1..9
                        note = peptide
```

-continued

```
source                  1..9
                        mol_type = protein
                        organism = synthetic construct
SEQUENCE: 480
ILNSLSLTA                                                          9

SEQ ID NO: 481          moltype = AA  length = 9
FEATURE                 Location/Qualifiers
REGION                  1..9
                        note = peptide
source                  1..9
                        mol_type = protein
                        organism = synthetic construct
SEQUENCE: 481
QMNSLSLFL                                                          9

SEQ ID NO: 482          moltype = AA  length = 9
FEATURE                 Location/Qualifiers
REGION                  1..9
                        note = peptide
source                  1..9
                        mol_type = protein
                        organism = synthetic construct
SEQUENCE: 482
VLNSLSLYA                                                          9

SEQ ID NO: 483          moltype = AA  length = 9
FEATURE                 Location/Qualifiers
REGION                  1..9
                        note = peptide
source                  1..9
                        mol_type = protein
                        organism = synthetic construct
SEQUENCE: 483
VMNSLSLLI                                                          9

SEQ ID NO: 484          moltype = AA  length = 9
FEATURE                 Location/Qualifiers
REGION                  1..9
                        note = peptide
source                  1..9
                        mol_type = protein
                        organism = synthetic construct
SEQUENCE: 484
YINSLSLFI                                                          9

SEQ ID NO: 485          moltype = AA  length = 9
FEATURE                 Location/Qualifiers
REGION                  1..9
                        note = peptide
source                  1..9
                        mol_type = protein
                        organism = synthetic construct
SEQUENCE: 485
FLFEHPETF                                                          9

SEQ ID NO: 486          moltype = AA  length = 9
FEATURE                 Location/Qualifiers
REGION                  1..9
                        note = peptide
source                  1..9
                        mol_type = protein
                        organism = synthetic construct
SEQUENCE: 486
HIFEHPEHL                                                          9

SEQ ID NO: 487          moltype = AA  length = 9
FEATURE                 Location/Qualifiers
REGION                  1..9
                        note = peptide
source                  1..9
                        mol_type = protein
                        organism = synthetic construct
SEQUENCE: 487
RVFEHPERV                                                          9

SEQ ID NO: 488          moltype = AA  length = 9
FEATURE                 Location/Qualifiers
```

-continued

```
REGION              1..9
                    note = peptide
source              1..9
                    mol_type = protein
                    organism = synthetic construct
SEQUENCE: 488
YTFEHPETI                                                      9

SEQ ID NO: 489      moltype = AA  length = 9
FEATURE             Location/Qualifiers
REGION              1..9
                    note = peptide
source              1..9
                    mol_type = protein
                    organism = synthetic construct
SEQUENCE: 489
ALAFVPLWL                                                      9

SEQ ID NO: 490      moltype = AA  length = 9
FEATURE             Location/Qualifiers
REGION              1..9
                    note = peptide
source              1..9
                    mol_type = protein
                    organism = synthetic construct
SEQUENCE: 490
AMAFVPLAL                                                      9

SEQ ID NO: 491      moltype = AA  length = 9
FEATURE             Location/Qualifiers
REGION              1..9
                    note = peptide
source              1..9
                    mol_type = protein
                    organism = synthetic construct
SEQUENCE: 491
FLAFVPLDV                                                      9

SEQ ID NO: 492      moltype = AA  length = 9
FEATURE             Location/Qualifiers
REGION              1..9
                    note = peptide
source              1..9
                    mol_type = protein
                    organism = synthetic construct
SEQUENCE: 492
LLAFVPLPL                                                      9

SEQ ID NO: 493      moltype = AA  length = 9
FEATURE             Location/Qualifiers
REGION              1..9
                    note = peptide
source              1..9
                    mol_type = protein
                    organism = synthetic construct
SEQUENCE: 493
VLAFVPLGV                                                      9

SEQ ID NO: 494      moltype = AA  length = 9
FEATURE             Location/Qualifiers
REGION              1..9
                    note = peptide
source              1..9
                    mol_type = protein
                    organism = synthetic construct
SEQUENCE: 494
ALFGAPAAA                                                      9

SEQ ID NO: 495      moltype = AA  length = 9
FEATURE             Location/Qualifiers
REGION              1..9
                    note = peptide
source              1..9
                    mol_type = protein
                    organism = synthetic construct
SEQUENCE: 495
ILFGAPAGA                                                      9

SEQ ID NO: 496      moltype = AA  length = 9
```

-continued

```
FEATURE                 Location/Qualifiers
REGION                  1..9
                        note = peptide
source                  1..9
                        mol_type = protein
                        organism = synthetic construct
SEQUENCE: 496
NMFGAPAQV                                                                  9

SEQ ID NO: 497          moltype = AA  length = 9
FEATURE                 Location/Qualifiers
REGION                  1..9
                        note = peptide
source                  1..9
                        mol_type = protein
                        organism = synthetic construct
SEQUENCE: 497
SLFGAPATA                                                                  9

SEQ ID NO: 498          moltype = AA  length = 9
FEATURE                 Location/Qualifiers
REGION                  1..9
                        note = peptide
source                  1..9
                        mol_type = protein
                        organism = synthetic construct
SEQUENCE: 498
TLFGAPAAA                                                                  9

SEQ ID NO: 499          moltype = AA  length = 9
FEATURE                 Location/Qualifiers
REGION                  1..9
                        note = peptide
source                  1..9
                        mol_type = protein
                        organism = synthetic construct
SEQUENCE: 499
VIFGAPALV                                                                  9

SEQ ID NO: 500          moltype = AA  length = 9
FEATURE                 Location/Qualifiers
REGION                  1..9
                        note = peptide
source                  1..9
                        mol_type = protein
                        organism = synthetic construct
SEQUENCE: 500
VLFGAPAGI                                                                  9

SEQ ID NO: 501          moltype = AA  length = 9
FEATURE                 Location/Qualifiers
REGION                  1..9
                        note = peptide
VARIANT                 8..9
                        note = X can be any naturally occurring amino acid
source                  1..9
                        mol_type = protein
                        organism = synthetic construct
SEQUENCE: 501
AMNSLSLXX                                                                  9

SEQ ID NO: 502          moltype = AA  length = 9
FEATURE                 Location/Qualifiers
REGION                  1..9
                        note = peptide
VARIANT                 1
                        note = X can be any naturally occurring amino acid
VARIANT                 9
                        note = X can be any naturally occurring amino acid
source                  1..9
                        mol_type = protein
                        organism = synthetic construct
SEQUENCE: 502
XMNSLSLLX                                                                  9

SEQ ID NO: 503          moltype = AA  length = 9
FEATURE                 Location/Qualifiers
```

```
REGION                  1..9
                        note = peptide
VARIANT                 1
                        note = X can be any naturally occurring amino acid
VARIANT                 8
                        note = X can be any naturally occurring amino acid
source                  1..9
                        mol_type = protein
                        organism = synthetic construct
SEQUENCE: 503
XMNSLSLXI                                                            9

SEQ ID NO: 504          moltype = AA  length = 9
FEATURE                 Location/Qualifiers
REGION                  1..9
                        note = peptide
VARIANT                 1
                        note = X can be any naturally occurring amino acid
VARIANT                 8
                        note = X can be any naturally occurring amino acid
source                  1..9
                        mol_type = protein
                        organism = synthetic construct
SEQUENCE: 504
XMNSLSLXL                                                            9

SEQ ID NO: 505          moltype = AA  length = 9
FEATURE                 Location/Qualifiers
REGION                  1..9
                        note = peptide
VARIANT                 2
                        note = X can be any naturally occurring amino acid
VARIANT                 9
                        note = X can be any naturally occurring amino acid
source                  1..9
                        mol_type = protein
                        organism = synthetic construct
SEQUENCE: 505
YXFEHPETX                                                            9

SEQ ID NO: 506          moltype = AA  length = 9
FEATURE                 Location/Qualifiers
REGION                  1..9
                        note = peptide
VARIANT                 9
                        note = X can be any naturally occurring amino acid
source                  1..9
                        mol_type = protein
                        organism = synthetic construct
SEQUENCE: 506
ALFGAPAAX                                                            9

SEQ ID NO: 507          moltype = AA  length = 9
FEATURE                 Location/Qualifiers
REGION                  1..9
                        note = peptide
VARIANT                 8..9
                        note = X can be any naturally occurring amino acid
source                  1..9
                        mol_type = protein
                        organism = synthetic construct
SEQUENCE: 507
VLFGAPAXX                                                            9

SEQ ID NO: 508          moltype = AA  length = 9
FEATURE                 Location/Qualifiers
REGION                  1..9
                        note = peptide
VARIANT                 1
                        note = X can be any naturally occurring amino acid
source                  1..9
                        mol_type = protein
                        organism = synthetic construct
SEQUENCE: 508
XLFGAPAAA                                                            9

SEQ ID NO: 509          moltype = AA  length = 9
FEATURE                 Location/Qualifiers
```

-continued

```
REGION                    1..9
                          note = peptide
VARIANT                   1
                          note = X can be any naturally occurring amino acid
source                    1..9
                          mol_type = protein
                          organism = synthetic construct
SEQUENCE: 509
XMFGAPALV                                                     9
```

The invention claimed is:

1. A method for treating a B-cell malignancy or initiating, enhancing or prolonging an anti-tumor-response against a B-cell malignancy in a subject in need thereof, the method comprising administering to the subject:

a first antigenic peptide comprising or consisting of an amino acid sequence as set forth in any one of SEQ ID NO: 65 and 114, an immunogenic compound comprising the first antigenic peptide, a nanoparticle comprising the first antigenic peptide, a pharmaceutical composition comprising the first antigenic peptide, or a combination comprising (1) the first antigenic peptide, and (2) a second antigenic peptide comprising or consisting of an amino acid sequence as set forth in any one of SEQ ID NO: 65, 70, 114, 119, 120, 477, 491, and 493.

2. The method according to claim 1, wherein the B-cell malignancy is a B-cell lymphoma selected from the group consisting of non-Hodgkin lymphoma (NHL), diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and follicular lymphoma (FL).

3. The method according to claim 1, comprising administering the combination to the subject.

4. The method according to claim 3, wherein the first antigenic peptide consists of the amino acid sequence as set forth in SEQ ID NO: 65 and the second antigenic peptide consists of the amino acid sequence as set forth in SEQ ID NO: 114.

5. The method according to claim 1, comprising administering to the subject the first antigenic peptide, the second antigenic peptide, and a third antigenic peptide comprising or consisting of an amino acid sequence as set forth in any one of SEQ ID NO: 107, 108, 109, and 110.

6. The method according to claim 1, comprising administering to the subject the first antigenic peptide, the second antigenic peptide, a third antigenic peptide comprising or consisting of an amino acid sequence as set forth in any one of SEQ ID NO: 212, 217, 220, 224, 325, and 450, and a fourth antigenic peptide comprising or consisting of an amino acid sequence as set forth in any one of SEQ ID NO: 107, 108, 109, and 110.

7. The method according to claim 6, wherein:

the first antigenic peptide consists of an amino acid sequence as set forth in SEQ ID NO: 65;

the second antigenic peptide consists of an amino acid sequence as set forth in SEQ ID NO: 114;

the third antigenic peptide consists of an amino acid sequence as set forth in SEQ ID NO: 220; and the fourth antigenic peptide consists of an amino acid sequence as set forth in SEQ ID NO: 110.

8. The method according to claim 1, further comprising administering to the subject a helper peptide.

9. The method according to claim 8, wherein the helper peptide is a peptide consisting of an amino acid sequence according to SEQ ID NO: 475.

10. The method according to claim 1, comprising administering to the subject:

the first antigenic peptide consisting of an amino acid sequence as set forth in SEQ ID NO: 65110;

the second antigenic peptide consisting of an amino acid sequence as set forth in SEQ ID NO: 114;

a third antigenic peptide consisting of an amino acid sequence as set forth in SEQ ID NO: 220; and a fourth antigenic peptide consisting of an amino acid sequence as set forth in SEQ ID NO: 110, and a further peptide consisting of an amino acid sequence as set forth in SEQ ID NO: 475.

11. The method according to claim 1, further comprising administering to the subject an adjuvant.

12. The method according to claim 11, wherein the adjuvant is Montanide.

13. The method according to claim 12, wherein the Montanide is Montanide ISA 51 VG.

* * * * *